United States Patent
Weng et al.

(10) Patent No.: US 10,724,088 B2
(45) Date of Patent: *Jul. 28, 2020

(54) COMPOSITIONS AND METHODS FOR DETECTING RARE SEQUENCE VARIANTS

(71) Applicant: ACCURAGEN HOLDINGS LIMITED, George Town (KY)

(72) Inventors: Li Weng, Fremont, CA (US); Zhaohui Sun, Albany, CA (US); Shengrong Lin, Fremont, CA (US)

(73) Assignee: ACCURAGEN HOLDINGS LIMITED, George Town (KY)

( * ) Notice: Subject to any disclaimer, the term of this patent is extended or adjusted under 35 U.S.C. 154(b) by 0 days.

This patent is subject to a terminal disclaimer.

(21) Appl. No.: 16/172,310

(22) Filed: Oct. 26, 2018

(65) Prior Publication Data

US 2019/0119743 A1    Apr. 25, 2019

Related U.S. Application Data

(63) Continuation of application No. 15/800,558, filed on Nov. 1, 2017, now Pat. No. 10,155,980, which is a
(Continued)

(51) Int. Cl.
*C12Q 1/6869*  (2018.01)
*C12Q 1/6806*  (2018.01)
(Continued)

(52) U.S. Cl.
CPC .......... *C12Q 1/6869* (2013.01); *C12P 19/34* (2013.01); *C12Q 1/6806* (2013.01);
(Continued)

(58) Field of Classification Search
CPC ..... C12P 19/34; C12Q 1/6806; C12Q 1/6816; C12Q 1/6827; C12Q 1/6858; C12Q 1/6869
See application file for complete search history.

(56) References Cited

U.S. PATENT DOCUMENTS 5,130,238 A    7/1992  Malek et al.
5,234,809 A    8/1993  Boom et al.
(Continued)

FOREIGN PATENT DOCUMENTS

AU    9057901 A    3/2002
CN    101985654 A    3/2011
(Continued)

OTHER PUBLICATIONS

Amado, et al. Wild-type KRAS is required for panitumumab efficacy in patients with metastic colorectal cancer. Journal of Clinical Oncology. Apr. 1, 2008; 26(10);1626-1634.
(Continued)

*Primary Examiner* — Jeremy C Flinders
(74) *Attorney, Agent, or Firm* — Wilson Sonsini Goodrich & Rosati

(57) ABSTRACT

In some aspects, the present disclosure provides methods for identifying sequence variants in a nucleic acid sample. In some embodiments, a method comprises identifying sequence differences between sequencing reads and a reference sequence, and calling a sequence difference that occurs in at least two different circular polynucleotides, such as two circular polynucleotides having different junctions, or two different sheared polynucleotides as the sequence variant. In some aspects, the present disclosure provides compositions and systems useful in the described method.

23 Claims, 50 Drawing Sheets

Specification includes a Sequence Listing.

Related U.S. Application Data continuation of application No. PCT/US2017/047029, filed on Aug. 15, 2017.

(60) Provisional application No. 62/375,396, filed on Aug. 15, 2016.

(51) Int. Cl.
  *C12P 19/34* (2006.01)
  *C12Q 1/6816* (2018.01)
  *C12Q 1/6827* (2018.01)
  *C12Q 1/6858* (2018.01)

(52) U.S. Cl.
  CPC ......... *C12Q 1/6816* (2013.01); *C12Q 1/6827* (2013.01); *C12Q 1/6858* (2013.01)

(56) References Cited

U.S. PATENT DOCUMENTS

| | | |
|---|---|---|
| 5,270,184 A | 12/1993 | Walker et al. |
| 5,310,652 A | 5/1994 | Gelfand et al. |
| 5,322,770 A | 6/1994 | Gelfand |
| 5,330,892 A | 7/1994 | Vogelstein et al. |
| 5,352,775 A | 10/1994 | Albertsen et al. |
| 5,362,623 A | 11/1994 | Vogelstein et al. |
| 5,399,491 A | 3/1995 | Kacian et al. |
| 5,455,166 A | 10/1995 | Walker |
| 5,480,784 A | 1/1996 | Kacian et al. |
| 5,492,808 A | 2/1996 | De La Chapelle et al. |
| 5,494,810 A | 2/1996 | Barany et al. |
| 5,527,670 A | 6/1996 | Stanley |
| 5,527,676 A | 6/1996 | Vogelstein et al. |
| 5,545,540 A | 8/1996 | Mian |
| 5,571,905 A | 11/1996 | Vogelstein et al. |
| 5,576,422 A | 11/1996 | Vogelstein et al. |
| 5,591,826 A | 1/1997 | De La Chapelle et al. |
| 5,648,212 A | 7/1997 | Albertsen et al. |
| 5,648,245 A | 7/1997 | Fire et al. |
| 5,691,454 A | 11/1997 | Albertsen et al. |
| 5,693,470 A | 12/1997 | De La Chapelle et al. |
| 5,693,536 A | 12/1997 | Vogelstein et al. |
| 5,705,365 A | 1/1998 | Ryder et al. |
| 5,705,628 A | 1/1998 | Hawkins et al. |
| 5,710,029 A | 1/1998 | Ryder et al. |
| 5,783,666 A | 7/1998 | Albertsen et al. |
| 5,807,692 A | 9/1998 | Kinzler et al. |
| 5,830,676 A | 11/1998 | Vogelstein et al. |
| 5,830,711 A | 11/1998 | Barany et al. |
| 5,837,443 A | 11/1998 | De La Chapelle et al. |
| 5,854,033 A | 12/1998 | Lizardi |
| 5,871,925 A | 2/1999 | De La Chapelle et al. |
| 5,871,968 A | 2/1999 | Kinzler et al. |
| 5,888,779 A | 3/1999 | Kacian et al. |
| 5,939,291 A | 8/1999 | Loewy et al. |
| 5,955,263 A | 9/1999 | Vogelstein et al. |
| 6,033,850 A | 3/2000 | Purvis |
| RE36,713 E | 5/2000 | Vogelstein et al. |
| 6,090,566 A | 7/2000 | Vogelstein et al. |
| 6,114,124 A | 9/2000 | Albertsen et al. |
| 6,156,504 A | 12/2000 | Gocke et al. |
| 6,210,891 B1 | 4/2001 | Nyren et al. |
| 6,245,515 B1 | 6/2001 | Vogelstein et al. |
| 6,251,639 B1 | 6/2001 | Kurn |
| 6,277,605 B1 | 8/2001 | Wijnhoven et al. |
| 6,300,059 B1 | 10/2001 | Vogelstein et al. |
| 6,333,157 B1 | 12/2001 | Miller-Jones et al. |
| 6,380,369 B1 | 4/2002 | Adams et al. |
| 6,410,278 B1 | 6/2002 | Notomi et al. |
| 6,413,727 B1 | 7/2002 | Albertsen et al. |
| 6,416,984 B1 | 7/2002 | Haseltine et al. |
| 6,482,606 B1 | 11/2002 | Adams et al. |
| 6,511,805 B1 | 1/2003 | Gocke et al. |
| 6,521,409 B1 | 2/2003 | Gocke et al. |
| 6,610,477 B1 | 8/2003 | Haseltine et al. |
| 6,620,619 B2 | 9/2003 | Haseltine et al. |
| 6,677,312 B1 | 1/2004 | Vogelstein et al. |
| 6,800,617 B1 | 10/2004 | Vogelstein et al. |
| 6,833,246 B2 | 12/2004 | Balasubramanian |
| 6,917,726 B2 | 7/2005 | Levene et al. |
| 6,939,675 B2 | 9/2005 | Gocke et al. |
| 6,946,251 B2 | 9/2005 | Kurn |
| RE38,916 E | 12/2005 | Vogelstein et al. |
| 6,977,148 B2 | 12/2005 | Dean et al. |
| 7,001,724 B1 | 2/2006 | Greenfield et al. |
| 7,033,764 B2 | 4/2006 | Korlach et al. |
| 7,052,847 B2 | 5/2006 | Korlach et al. |
| 7,056,676 B2 | 6/2006 | Korlach et al. |
| 7,087,583 B2 | 8/2006 | Vogelstein et al. |
| 7,170,050 B2 | 1/2007 | Turner et al. |
| 7,183,053 B2 | 2/2007 | Gocke et al. |
| 7,208,275 B2 | 4/2007 | Gocke et al. |
| 7,267,955 B2 | 9/2007 | Vogelstein et al. |
| 7,282,335 B2 | 10/2007 | Gocke et al. |
| 7,288,380 B1 | 10/2007 | Gocke et al. |
| 7,326,778 B1 | 2/2008 | De La Chapelle et al. |
| 7,361,466 B2 | 4/2008 | Korlach et al. |
| 7,387,874 B2 | 6/2008 | Gocke et al. |
| 7,399,592 B2 | 7/2008 | Gocke et al. |
| 7,410,764 B2 | 8/2008 | Gocke et al. |
| 7,416,844 B2 | 8/2008 | Korlach et al. |
| 7,569,349 B2 | 8/2009 | Gocke et al. |
| 7,569,350 B2 | 8/2009 | Gocke et al. |
| RE40,948 E | 10/2009 | Vogelstein et al. |
| 7,700,286 B2 | 4/2010 | Stroun et al. |
| RE41,327 E | 5/2010 | Gocke et al. |
| 7,790,395 B2 | 9/2010 | Gocke et al. |
| 7,824,890 B2 | 11/2010 | Hoser et al. |
| 7,935,484 B2 | 5/2011 | Gocke et al. |
| 7,935,487 B2 | 5/2011 | Gocke et al. |
| 7,972,817 B2 | 7/2011 | Kopreski et al. |
| 8,048,629 B2 | 11/2011 | Gocke et al. |
| 8,209,130 B1 | 6/2012 | Kennedy et al. |
| 8,361,726 B2 | 1/2013 | Gocke et al. |
| RE44,596 E | 11/2013 | Stroun et al. |
| 8,835,358 B2 | 9/2014 | Fodor et al. |
| 9,217,167 B2 | 12/2015 | Heller et al. |
| 1,015,598 A1 | 12/2018 | Weng et al. |
| 2003/0032024 A1 | 2/2003 | Lizardi |
| 2004/0058378 A1 | 3/2004 | Kong et al. |
| 2006/0228721 A1 | 10/2006 | Leamon et al. |
| 2007/0087362 A1 | 4/2007 | Church et al. |
| 2007/0134128 A1 | 6/2007 | Korlach |
| 2008/0039417 A1 | 2/2008 | Wang et al. |
| 2008/0160511 A1 | 7/2008 | Dawson et al. |
| 2010/0075384 A1 | 3/2010 | Kong et al. |
| 2010/0115744 A1 | 5/2010 | Fong |
| 2010/0291548 A1 | 11/2010 | Sharaf et al. |
| 2010/0304989 A1 | 12/2010 | Von Hoff et al. |
| 2011/0003705 A1 | 1/2011 | Lowe et al. |
| 2011/0151438 A9 | 6/2011 | Nautiyal et al. |
| 2011/0237444 A1 | 9/2011 | Clancy et al. |
| 2011/0319299 A1 | 12/2011 | Osborne et al. |
| 2012/0115744 A1 | 5/2012 | Raymond et al. |
| 2013/0217023 A1 | 8/2013 | Godwin et al. |
| 2013/0224740 A1 | 8/2013 | Thierry et al. |
| 2014/0051154 A1 | 2/2014 | Hyland et al. |
| 2014/0066317 A1 | 3/2014 | Talasaz et al. |
| 2014/0121116 A1 | 5/2014 | Richards et al. |
| 2014/0154683 A1 | 6/2014 | Vogelstein et al. |
| 2014/0221329 A1 | 8/2014 | Cronin et al. |
| 2014/0227705 A1 | 8/2014 | Vogelstein et al. |
| 2014/0234850 A1 | 8/2014 | Zhang et al. |
| 2014/0274740 A1 | 9/2014 | Srinivasan et al. |
| 2014/0295498 A1 | 10/2014 | Turner et al. |
| 2014/0296081 A1 | 10/2014 | Diehn et al. |
| 2014/0336236 A1 | 11/2014 | Cronin et al. |
| 2015/0031035 A1 | 1/2015 | Kvam et al. |
| 2015/0044687 A1 | 2/2015 | Schmitt et al. |
| 2015/0141292 A1 | 5/2015 | Fodor et al. |
| 2015/0147815 A1 | 5/2015 | Babiarz et al. |
| 2015/0315636 A1 | 11/2015 | Nadeau et al. |
| 2015/0361492 A1 | 12/2015 | Vogelstein et al. |
| 2015/0366866 A1 | 12/2015 | Ali et al. |
| 2016/0040229 A1 | 2/2016 | Talasaz et al. |

(56) References Cited

U.S. PATENT DOCUMENTS

| | | | |
|---|---|---|---|
| 2016/0145691 A1 | 5/2016 | Cronin et al. | |
| 2016/0201135 A1 | 7/2016 | Cronin et al. | |
| 2016/0304954 A1 | 10/2016 | Lin et al. | |
| 2018/0298434 A1 | 10/2018 | Weng et al. | |
| 2018/0363039 A1 | 12/2018 | Weng et al. | |

FOREIGN PATENT DOCUMENTS

| | | | | |
|---|---|---|---|---|
| CN | 102625850 | A | 8/2012 | |
| CN | 104745679 | A | 7/2015 | |
| EP | 0684315 | A1 | 11/1995 | |
| EP | 0518650 | B1 | 1/1997 | |
| EP | 0390323 | B1 | 12/1998 | |
| EP | 0929694 | A1 | 7/1999 | |
| EP | 0580596 | B1 | 7/2000 | |
| EP | 0569527 | B1 | 3/2001 | |
| EP | 0730648 | B1 | 8/2004 | |
| EP | 2396430 | B1 | 5/2013 | |
| EP | 2828218 | A1 | 1/2015 | |
| WO | WO-9844151 | A1 | 10/1998 | |
| WO | WO-0049176 | A1 | 8/2000 | |
| WO | WO-0118230 | A1 * | 3/2001 | ............... C12N 9/52 |
| WO | WO-0120035 | A2 | 3/2001 | |
| WO | WO-0138580 | A2 | 5/2001 | |
| WO | WO-2007133703 | A2 | 11/2007 | |
| WO | WO-2007140417 | A2 | 12/2007 | |
| WO | WO-2013142389 | A1 | 9/2013 | |
| WO | WO-2014014498 | A1 | 1/2014 | |
| WO | WO-2014015084 | A2 | 1/2014 | |
| WO | WO-2014145128 | A2 | 9/2014 | |
| WO | WO-2015079042 | A1 | 6/2015 | |
| WO | WO-2015089333 | A1 | 6/2015 | |
| WO | WO-2016053638 | A1 | 4/2016 | |
| WO | WO-2017062863 | A1 | 4/2017 | |
| WO | WO-2017096322 | A1 | 6/2017 | |
| WO | WO-2017201102 | A1 | 11/2017 | |
| WO | WO-2017223366 | A1 | 12/2017 | |
| WO | WO-2018035170 | A1 | 2/2018 | |

OTHER PUBLICATIONS

Awuah, et al. Thermal inactivation kinetics of trypsin at aseptic processing temperatures. Journal of food process engineering 1993 v. 16 No. 4 pp. 315-328 (abstract).
Blast. Basic local alignment search tool. Available at http://blast.ncbi.nlm.nih.gov/Blast.cgi. Accessed on Oct. 10, 2016.
Bokemeyer, et al. Fluorouracil, leucovorin, and oxaliplatin with and without cetuximab in the first-line treatment of metastatic colorectal cancer. Journal of Clinical Oncology. Feb. 10, 2009; 27(5).: 663-671.
Brenner. A cultivated taste for yeast. Genome Biol. 2000;1(1):REVIEWS103. Epub Apr. 27, 2000.
Brenner, C. Chemical genomics in yeast. Genome Biology. 2004; 5:240.
Brietbach et al. Direct Quantification of Cell-Free, Circulating DNA from Unpurified Plasma. PLoS One 9(3):1-11 (2014).
Co-pending U.S. Appl. No. 16/368,355, filed Mar. 28, 2019.
Creating Standard Curves with Genomic DNA or Plasmid DNA Templates for Use in Quantitative PCR. Applied Biosystems 2003. Downloaded Oct. 17, 2017. URL:<http://www6.appliedbiosystems.com/support/tutorials/pdf/quant_pcr.pdf>.
Dawson, et al., Analysis of circulating tumor DNA to monitor metastatic breast cancer. The New England Journal of Medicine. Mar. 28, 2013. 368(13); 1199-1209.
Delcher, et al. Alignment of whole genomes. Nucleic Acids Research. Feb. 2, 1999; 27(11): 2369-2376.
Devonshire, Alison S. et al. Towards standardisation of cell-free DNA measurement in plasma: controls for extraction efficiency, fragment size bias and quantification, Analytical and Bioanalytical Chemistry, 406(26): 6499-6512 (2014).
Dicker, et al. The detection of TP53 mutations in chronic lymphocytic leukemia independently predicts rapid disease progression and is highly correlated with a complex aberrant karyotype. Leukemia. Jan. 2009; 23(1):117-124.:.
Eason, et al. Characterization of synthetic DNA bar codes in *Saccharomyces cerevisiae* gene-deletion strains. Proc Natl Acad Sci U S A. Jul. 27, 2004; 101(30): 11046-11051.
Emboss. Emboss Water: Pairwise Sequence Alignment (Nucleotide). Available at http://www.ebi.ac.uk/Tools/psa/emboss_water/nucleotide.html. Accessed on Oct. 10, 2016.
Enari et al. A caspase-activated DNase that degrades DNA during apoptosis, and its inhibitor ICAD. Nature 391:43-50 (1998).
Florsheim, et al. Integrated Innate Mechanisms Involved in Airway Allergic Inflammation to the Serine Protease Subtilisin. J Immunol. May 15, 2015; 194(10): 4621-4630.
Foss et al. Effects of fixative and fixation time on the extraction and polymerase chain reaction amplification of RNA from paraffin-embedded tissue. Comparison of two housekeeping gene mRNA controls. Diagn Mol Path 3:148-155 (1994).
Freshney. Culture of Animal Cells: A Manual of Basic Technique and Specialized Applications. 6th Edition. 2010.
Giacona, et al. Cell-free DNA in human blood plasma: length measurements in patients with pancreatic cancer and healthy controls. Pancreas. Jul. 1998;17(1):89-97.
Giaever, et al. Chemogenomic profiling: identifying the functional interactions of small molecules in yeast. Proc Natl Acad Sci U S A. Jan. 20, 2004;101(3):793-8. Epub Jan. 12, 2004.
Guatelli et al. Isothermal, in vitro amplification of nucleic acids by a multienzyme reaction modeled after retroviral replication. PNAS USA 87(5):1874-1878 (1990).
Harkins, et al., Replicating fetal trisomy patient-like reference material for use in non-invasive prenatal screening tests. Sera Care. AMP 2015. Nov. 5-7, 2015.
Harlow, et al. Antibodies: A Laboratory manual. Cold Spring Harbor Laboratory. 1988.
Heinrich. et al. Kinase mutations and imatinib response in patients with metastatic gastrointestinal stromal tumor. Journal of Clinical Oncology. Dec. 1, 2003; 21(23): 4342-4349.
Horizon Product Specification. cfDNA Reference Standard Set. 6068PSS-01(V-01). 2015.
Hussmann, et al. Reply to Schmitt et al.: Data-filtering schemes for avoiding double-counting in circle sequencing. PNAS. Apr. 22, 2014; 111(16).
Illumina. Genome Analyzer System. Available at http://support.illumina.com/content/dam/illumina-marketing/documents/products/datasheets/datasheet_genome_analyzeriix.pdf. Accessed onOct. 10, 2016.
Jahr, et al. DNA fragments in the blood plasma of cancer patients: quantitations and evidence for their origin from apoptotic and necrotic cells. Cancer Res. Feb. 15, 2001;61(4):1659-65.
Jeffreys et al. DNA Enrichment by Allele-Specific Hybridization (DEASH): A Novel Method for Haplotyping and for Detecting Low-Frequency Base Substitutional Variants and Recombinant DNA Molecules. Genome Research 13:2316-2324 (2003).
Jiang et al. The Long and Short of Circulating Cell-Free DNA and the Ins and Outs of Molecular Diagnostics. Trends Genet 32(6):360-371 (2016).
Katayama, et al. Mechanisms of acquired crizotinib resistance in ALK-rearranged lung cancers. Sci. Transl Med. Feb. 8, 2012; 8(4).
Kent, W.J. Blat—The Blast-like alignment tool. Genome Research. 2012: 656-664.
Kumar, et al. Emerging technologies in yeast genomics. Nat Rev Genet. Apr. 2001;2(4):302-12.
Kurtz, et al. Versatile and open software for comparing large genomes. Biomed central. Jan. 30, 2004.
Landegren, U. Molecular mechanics of nucleic acid sequence amplification. Elsevier Science. Jun. 9, 1993(6). 199-204.
Langmead et al. Ultrafast and memory-efficient alignment of short DNA sequences to the human genome. Genome biology 10:R25 (10 pgs) (2009).
Larking, et al. Clustal W and Clustal X version 2.0. Bioinformatics applications note. 2007. 2947-2948; 23(21).

(56) References Cited

OTHER PUBLICATIONS

Lee, et al. Nucleic acid amplification technologies: application to disease diagnosis. Biotechniques books. 1997.
Li, et al. Fast and accurate long-read alignment with burrows-wheeler transform. Bioinformatics. Mar. 1, 2010;26(5):589-95.
Li et al. Fast and accurate short read alignment with burrows-wheeler transform. Bioinformatics 25(14):1754-1760 (2009).
Li, et al. Technical advance: Whole genome amplification of plasma-circulating DNA enables expanded screening for allelic imbalance in plasma. Journal of Molecular Diagnostics. Feb. 8, 2006(1); 22-30.
Lin, et al. Rolling Circle Enzymatic Replication of a Complex Multi-Crossover DNA Nanostructure. J Am Chem Soc. Nov. 21, 2007; 129(46): 14475-14481.
Lipman, et al. Rapid and sensitive protein similarity searches. Science. Mar. 22, 1985; 227(4693):1435-41.
Lizardi, et al. Exponential amplification of recombinant-RNA hybridization probes. Biotechnology. 1988. 6:1197-1202.
Lou, et al. High-throughput DNA sequencing errors are reduced by orders of magnitude using circle sequencing. Proc Natl Acad Sci U S A. Dec. 3, 2013;110(49):19872-7. doi: 10.1073/pnas.1319590110. Epub Nov. 15, 2013.
Lou et al., Supporting Information for "High-throughput DNA sequencing errors are reduced by orders of magnitude using circle sequencing," Proc Natl Acad Sci U S A., 110(49):19872-7. doi: 10.1073/pnas.1319590110 (14 pages) (2013).
Lou et al. BioTechniques, pp. 1-14 [Support Information to Lou et al. BioTechniques 110(49) publication] (2013).
Maldonado, et al. Determinants of BRAF mutations in primary melanomas. Journal of the National Cancer Institute. Dec. 17, 2003; 95(24):1878-1880.
Matta, et al. Isolation and partial characterization of a thermostable extracellular protease of Bacillus polymyxa B-17. Int J Food Microbiol. Jul. 21, 1998;42(3):139-45 (abstract).
McLendon, et al. Survival analysis of presumptive prognostic markers among oligodendrogliomas. John Wiley & Sons. Oct. 15, 2005; 104(8):1693-1699.
McPherson, et al. eds. PCR 2: a practical approach. Oxford University Press. 1995.
Miller, et al. A simple salting out procedure for extracting DNA from human nucleated cells. Nucleic Acid Research. 1988; 16(3).
Misale, et al. Emergence of KRAS mutations and acquired resistance to anti-EGFR therapy in colorectal cancer. Nature. Jun. 13, 2012; 486(7404):532-536.
Neumann, et al., Frequency and type of KRAS mutations in routine diagnostic analysis of metastatic colorectal cancer. Pathol Res Pract. 2009;205(12):858-62.
Novocraft Technologies SDN BHD. NovoAlign. Available at http://www.novocraft.com/products/novoalign/. Accessed on Oct. 10, 2016.
Olivier, et al., TP53 mutations in human cancers: origins, consequences, and clinical use. Cold Spring Harb. Perspect Biology. 2010;1-17.
Pao, et al., EGF receptor gene mutations are common in lung cancers from "never smokers" and are associated with sensitivity of tumors to gefitinib and erlotinib. Proc. Natl. Acad. Sci. USA. Sep. 7, 2004; 101(36):13306-13311.
Paska et al. Effect of formalin, acetone, and RNAlater fixatives on tissue preservation and different size amplicons by real-time PCR from paraffin-embedded tissue. Diagn Mol Path 13(4): 234-240 (2004).
PCT/US2017/047029 International search Report and Written Opinion dated Jan. 18, 2018.
Pearson, et al. Improved Tools for Biological Sequence Comparison. Proc. Nat'l Acad. Sci. USA. 85 (1988): 2444-48.
Polidoros et al. Rolling circle amplification-RACE: a method for simultaneous isolation of 5' and 3' cDNA ends from amplified cDNA templates. BioTechniques 41:35-42 (2006).

Promega. Thermolysin—Thermostable Proteinase with High Digest Temperature; Better Denaturation, Digestion of Proteolytically Resistant Proteins. Available at https://www.promega.com/products/mass-spectrometry/proteases-and-surfactants/thermolysin/. Accessed Apr. 11, 2018.
Qiagen. How can QIAGEN Protease and Proteinase K be inactivated? Available at https://www.qiagen.com/ca/resources/faq?id=d24681d7-88e7-421a-84d9-27bfd5141103&lang=en. Accessed Apr. 11, 2018.
Remacle, et al. Substrate Cleavage Analysis of Furin and Related Proprotein Convertases—A Comparative Study. J Biol Chem. Jul. 25, 2008; 283(30): 20897-20906.
Samuels, et al. High Frequency of Mutations of the PIK3CA Gene in Human Cancers. Science Mag. Apr. 23, 2004; 304.
Schmitt, et al. Risks of double-counting in deep sequencing. PNAS. Apr. 22, 2014;111(16).
SeraCare and NIST Partner on Development of Circulating Tumor DNA Reference Standards for Diagnostics (Press Release). SeraCare Life Sciences, Inc. Jul. 14, 2016 (2 pages).
Seraseq(TM) ctDNA: A Breakthrough QC Technology. SeraCare Life Sciences, Inc. (2017) 6 pages.
Shaw, et al. Clinical Features and Outcome of Patients With Non-Small-Cell Lung Cancer Who Harbor EML4-ALK. Journal of Clinical Oncology. Sep. 10, 2009; 27(26):4247-4253.
Sievers, et al. Fast, Scalable generation of high-quality protein multiple sequence alignments using clustal omega. Molecular systems biology. 2011.
Sigma-Alorich. Protease from Streptomyces griseus. Available at https://www.sigmaaldrich.com/catalog/product/sigma/p6911?lang=en&region=US#. Accessed Apr. 11, 2018.
Slater, et al. Automated generation of heuristics for biological sequence comparison. BMC Bioinformatics. Feb. 15, 2005; 6(31): 1-11.
SOAP.Short Oligonucleotide Analysis Package. Available at http://soap.genomics.org.cn/. Accessed on Oct. 10, 2016.
SOURCEFORGE-Maq-Mapping-and-Assembly-with-Qualities. Available at http://maq.sourceforge.net/. Accessed on Oct. 10, 2016.
Spargo, et al. Detection of *M. tuberculosis* DNA using thermophilic strand displacement amplification. Mol Cell Probes. Aug. 1996;10(4):247-56.
Stanford. HIV Drug resistance database. Available at https://hivdb.stanford.edu/pages/genotype-rx.html. Accessed on Oct. 10, 2016.
Tissen, P. Laboratory techniques in biochemistry and molecular biology:Hybridization with nucleic acid probes. Elsevier Science. 1993.
U.S. Appl. No. 15/102,241 Office Action dated Oct. 12, 2018.
U.S. Appl. No. 15/800,558 Office Action dated Jan. 26, 2018.
U.S. Appl. No. 15/800,558 Final Office Action dated Jul. 6, 2018.
Walsh, et al. Chelex 100 as a medium for simple extraction of DNA for PCR-based typing from forensic material. BioTechniques. 1991;10(4):506-513.
Wang, et al., Using ultra-sensitive next generation sequencing to dissect DNA damage-induced mutagenesis. Nature:Scientific Report. Dec. 2015.6:25310.
Wharam, et al. Specific detection of DNA and RNA targets using a novel isothermal nucleic acid amplification assay based on the formation of a three-way junction structure. Nucleic Acids Res. Jun. 1, 2001; 29(11): e54.
Widlak et al. Cleavage Preferences of the Apoptotic Endonuclease DFF40 (Caspase-activated DNase or Nuclease) on Naked DNA and Chromatin Substrates. The Journal of Biological Chemistry 275:8226-8232 (2000).
Winzeler, et al. Functional Characterization of the *S. cerevisiae* Genome by Gene Deletion and Parallel Analysis. Science. Aug. 6, 1999: vol. 285, Issue 5429, pp. 901-906.

\* cited by examiner

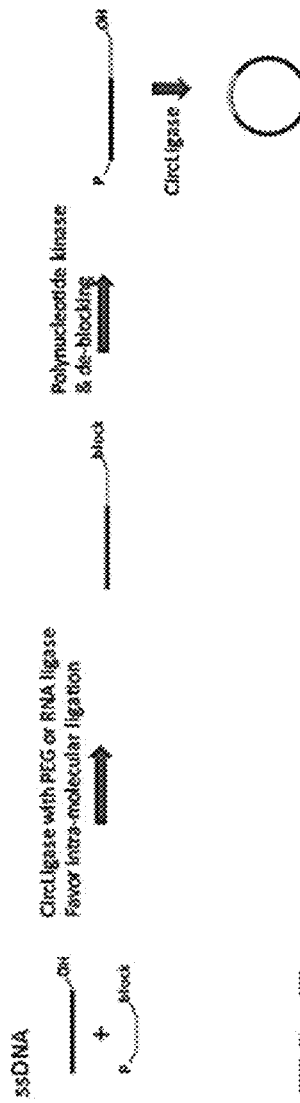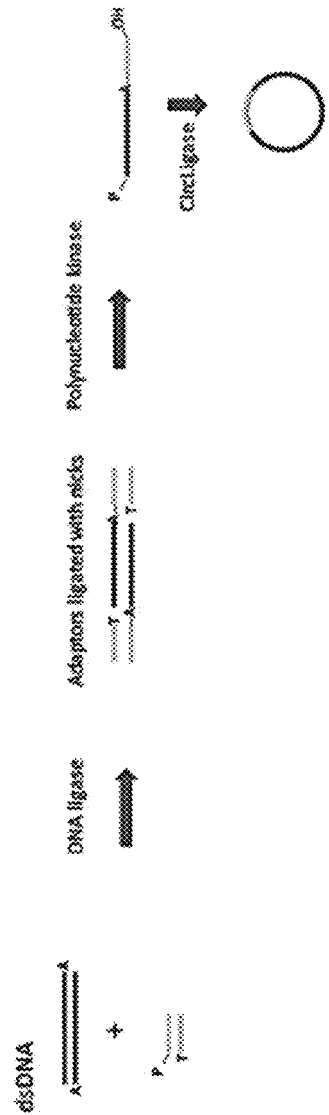

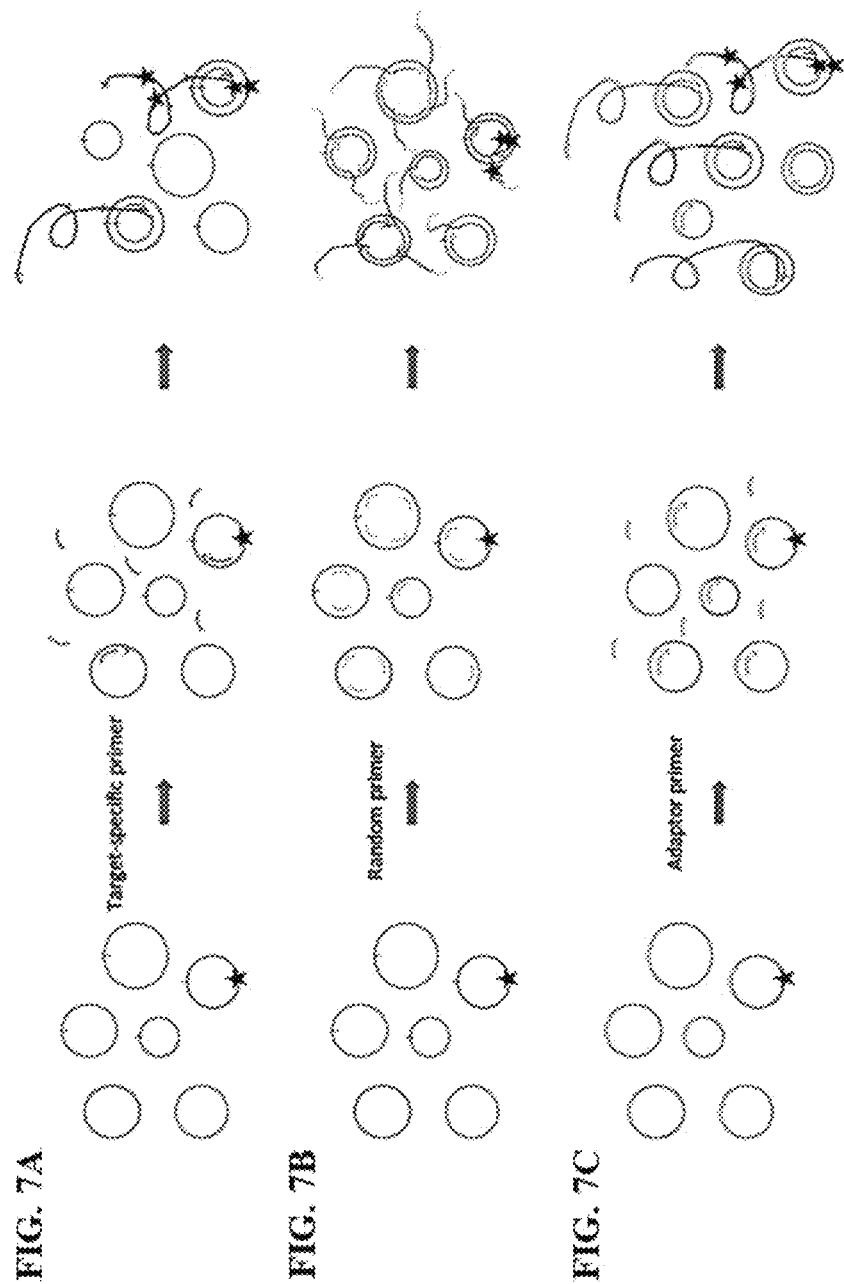

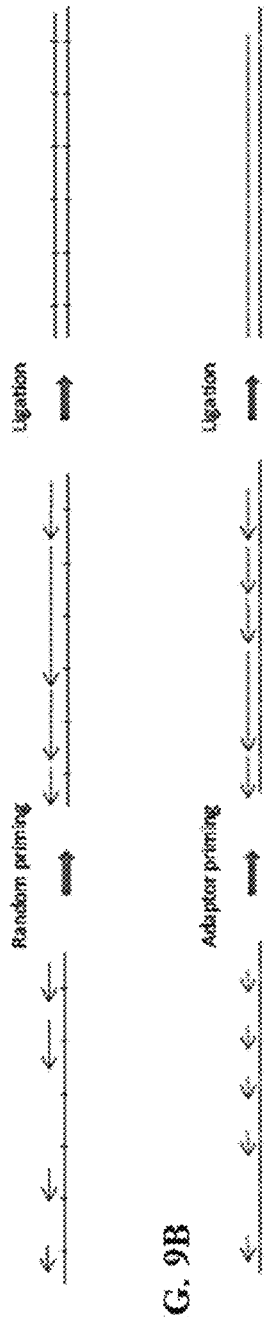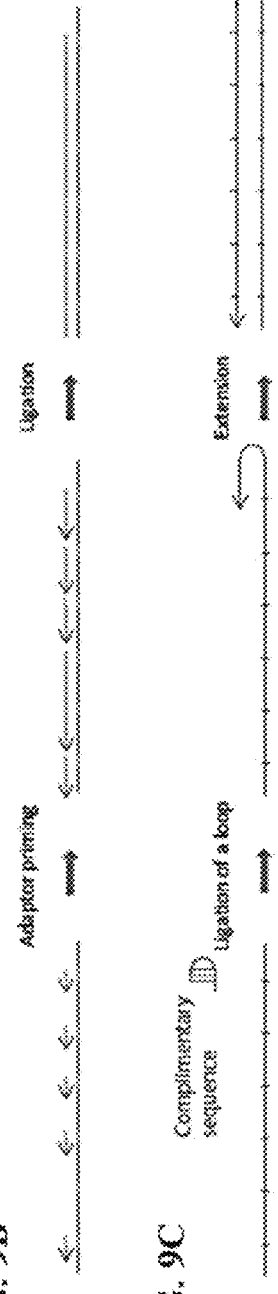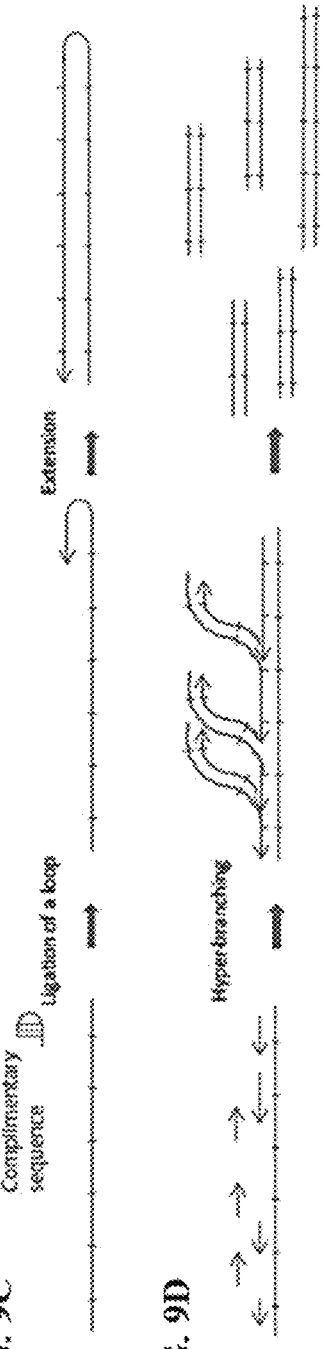
FIG. 9A
FIG. 9B
FIG. 9C
FIG. 9D

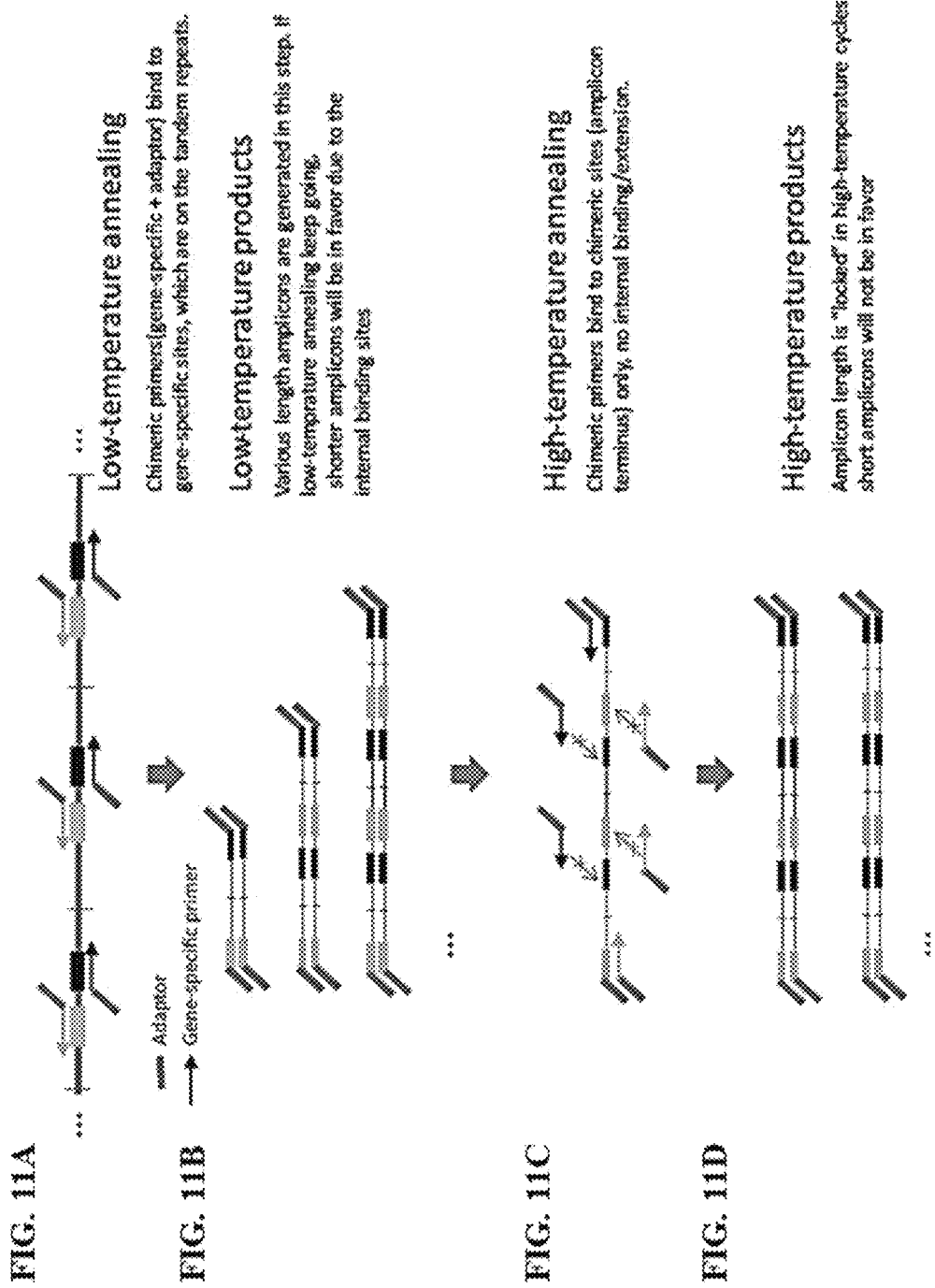

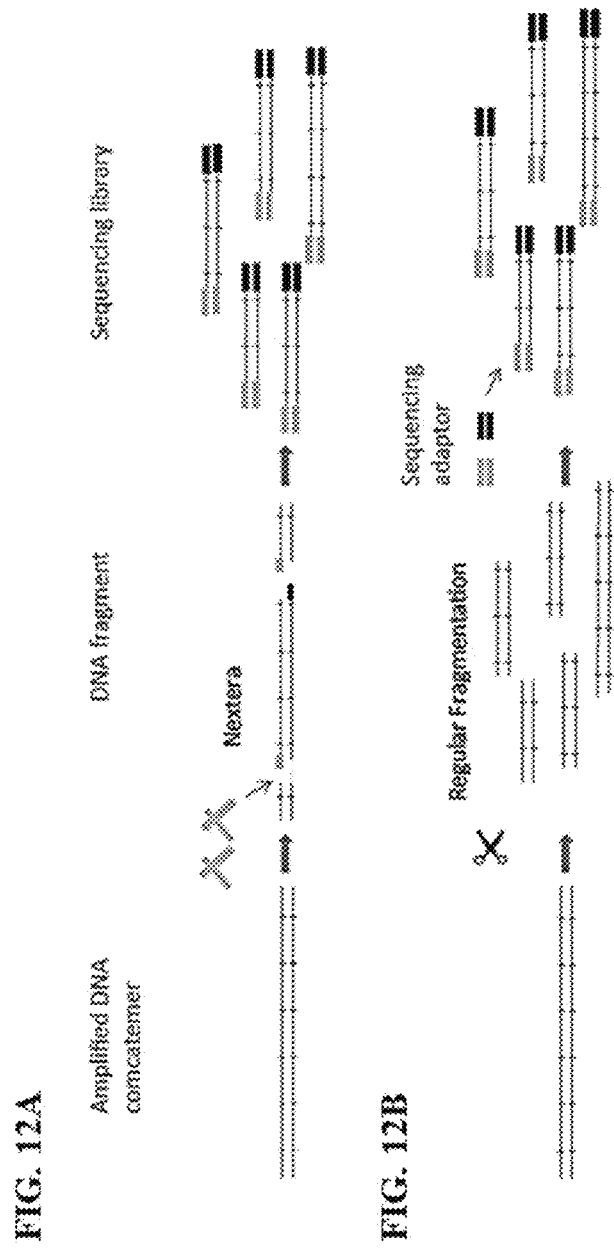

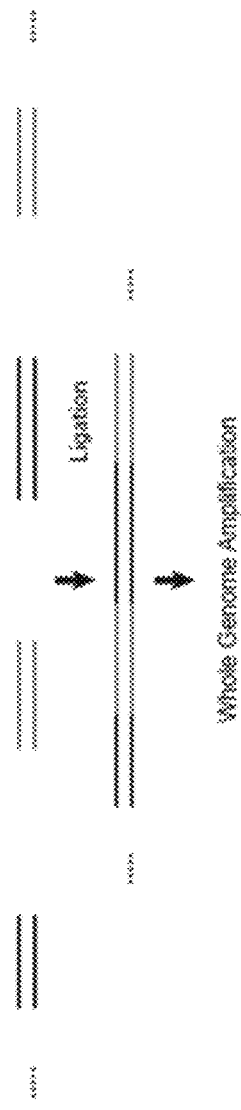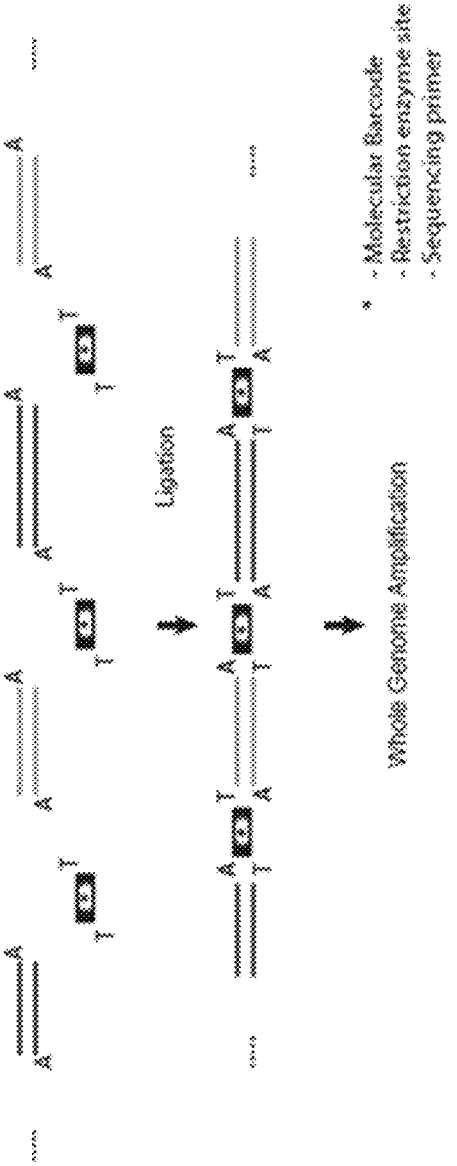
FIG. 25A Blunt end ligation (auto tag)
FIG. 25B Adaptor (barcode) ligation

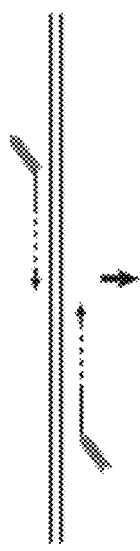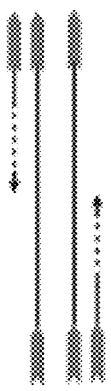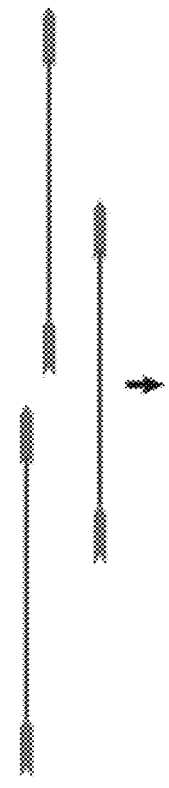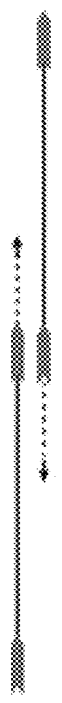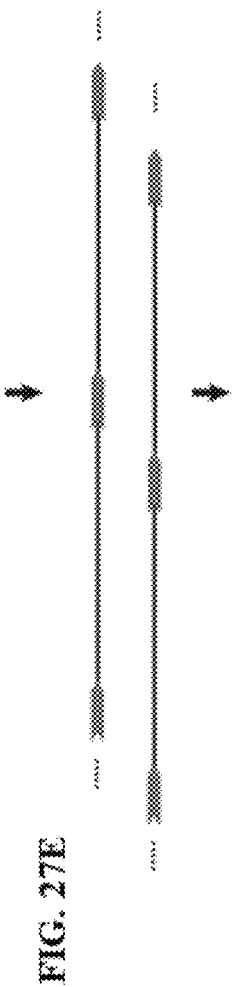
FIG. 27A  FIG. 27B  FIG. 27C  FIG. 27D  FIG. 27E  High-throughput sequencing

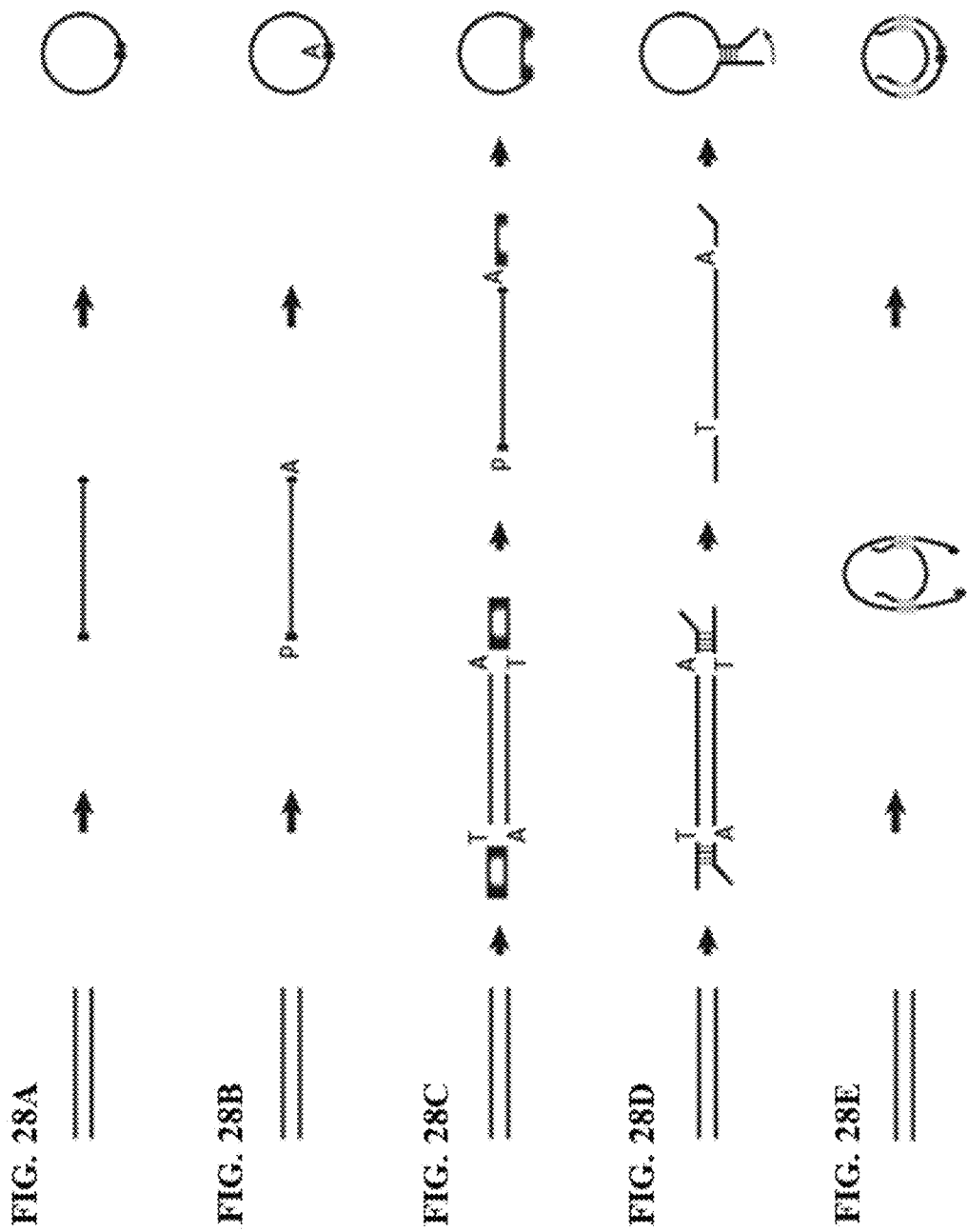

COMPOSITIONS AND METHODS FOR DETECTING RARE SEQUENCE VARIANTS

CROSS-REFERENCE

This application is a continuation of U.S. patent application Ser. No. 15/800,558, filed Nov. 1, 2017, which is a continuation application of International Patent Application No. PCT/US2017/047029, filed Aug. 15, 2017, which claims the benefit of U.S. Provisional Patent Application No. 62/375,396, filed Aug. 15, 2016, each of which are incorporated by reference in their entirety.

SEQUENCE LISTING

The instant application contains a Sequence Listing which has been submitted electronically in ASCII format and is hereby incorporated by reference in its entirety. Said ASCII copy, created on Oct. 26, 2018, is named 47608-707-302-SEQ.txt and is 39,405 bytes in size.

BACKGROUND

Identifying sequence variation within complex populations is an actively growing field, particularly with the advent of large scale parallel nucleic acid sequencing. However, large scale parallel sequencing has significant limitations in that the inherent error frequency in commonly-used techniques is larger than the frequency of many of the actual sequence variations in the population. For example, error rates of 0.1-1% have been reported in standard high throughput sequencing. Detection of rare sequence variants has high false positive rates when the frequency of variants is low, such as at or below the error rate.

There often exists a pressing need for detecting rare sequence variants. For example, detecting rare characteristic sequences can be used to identify and distinguish the presence of a harmful environmental contaminant, such as bacterial taxa. A common way of characterizing bacterial taxa is to identify differences in a highly conserved sequence, such as rRNA sequences. However, typical sequencing-based approaches to this are faced with challenges relating to the sheer number of different genomes in a given sample and the degree of homology between members, presenting a complex problem for already laborious procedures. Improved procedures would have the potential to enhance contamination detection in a variety of settings. For example, the clean rooms used to assemble components of satellites and other space craft can be surveyed with the present systems and methods to understand what microbial communities are present and to develop better decontamination and cleaning techniques to prevent the introduction of terrestrial microbes to other planets or samples thereof or to develop methodologies to distinguish data generated by putative extraterrestrial microorganisms from that generated by contaminating terrestrial microorganisms. Food monitoring applications include the periodic testing of production lines at food processing plants, surveying slaughter houses, inspecting the kitchens and food storage areas of restaurants, hospitals, schools, correctional facilities and other institutions for food borne pathogens. Water reserves and processing plants may also be similarly monitored.

Rare variant detection can also be important for the early detection of pathological mutations. For instance, detection of cancer-associated point mutations in clinical samples can improve the identification of minimal residual disease during chemotherapy and detect the appearance of tumor cells in relapsing patients. The detection of rare point mutations is also important for the assessment of exposure to environmental mutagens, to monitor endogenous DNA repair, and to study the accumulation of somatic mutations in aging individuals. Additionally, more sensitive methods to detect rare variants can enhance prenatal diagnosis, enabling the characterization of fetal cells present in maternal blood.

SUMMARY

In view of the foregoing, there is a need for improved methods of detecting rare sequence variants. The compositions and methods of the present disclosure address this need, and provide additional advantages as well. In particular, the various aspects of the disclosure provide for highly sensitive detection of rare or low frequency nucleic acid sequence variants (sometimes referred to as mutations). This includes identification and elucidation of low frequency nucleic acid variations (including substitutions, insertions and deletions) in samples that may contain low amounts of variant sequences in a background of normal sequences, as well as the identification of low frequency variations in a background of sequencing errors.

In one aspect, the disclosure provides a method of performing rolling circle amplification, the method comprising (a) circularizing individual polynucleotides in a plurality of polynucleotides to form a plurality of circular polynucleotides using a ligase enzyme, wherein each polynucleotide of the plurality of polynucleotides has a 5' end and a 3' end prior to ligation; (b) degrading the ligase enzyme; and (c) amplifying the circular polynucleotides after degrading the ligase enzyme to produce amplified polynucleotides; wherein polynucleotides are not purified or isolated between steps (a) and (c). In some embodiments, the method further comprises degrading linear polynucleotides between steps (a) and (c). In some embodiments, the plurality of polynucleotides comprises single-stranded polynucleotides. In some embodiments, an individual circular polynucleotide has a junction that is distinct among the circularized polynucleotides. In some embodiments, circularizing comprises the step of joining an adapter polynucleotide to the 5' end, the 3' end, or both the 5' end and the 3' end of a polynucleotide in the plurality of polynucleotides. In some embodiments, amplifying comprises subjecting the circular polynucleotides to an amplification reaction mixture comprising random primers. In some embodiments, amplifying comprises subjecting the circular polynucleotides to an amplification reaction mixture comprising one or more primers, each of which specifically hybridizes to a different target sequence via sequence complementarity. In some embodiments, the sample is a sample from a subject. In some embodiments, the sample is urine, stool, blood, saliva, tissue, or bodily fluid. In some embodiments, the sample comprises tumor cells. In some embodiments, the sample is a formalin-fixed paraffin embedded (FFPE) sample. In some embodiments, the method further comprises diagnosing, and optionally treating, said subject based on the calling step. In some embodiments, the sequence variant is a causal genetic variant. In some embodiments, the sequence variant is associated with a type or stage of cancer. In some embodiments, the plurality of polynucleotides comprises cell-free polynucleotides. In some embodiments, the cell-free polynucleotides comprise circulating tumor DNA. In some embodiments, the cell-free polynucleotides comprise circulating tumor RNA. In some embodiments, the method further comprises sequencing the amplified polynucleotides to produce a plurality of sequencing reads. In some embodiments, the method further comprises identifying sequence differences between the sequencing reads and a reference sequence. In some embodiments, the method further comprises calling a sequence difference as a sequence variant in the plurality of polynucleotides only when: (i) the sequence difference is identified on both strands of a double-stranded input molecule; (ii) the sequence difference occurs in a consensus sequence for a concatemer formed by rolling circle amplification; and/or (iii) the sequence difference occurs in two different molecules. In some embodiments, a sequence difference is identified as occurring in two different molecules when the sequence difference occurs in at least two circular polynucleotides having a different junction formed between the 5' end and 3' end. In some embodiments, a sequence difference is identified as occurring in two different molecules when reads corresponding to the two different molecules have a different 5' end and a different 3' end.

In another aspect, the disclosure provides a method of identifying a sequence variant in a nucleic acid sample comprising a plurality of polynucleotides, each polynucleotide of the plurality having a 5' end and a 3' end, the method comprising: (a) circularizing individual polynucleotides of said plurality to form a plurality of circular polynucleotides, each of which having a junction between the 5' end and 3' end; (b) amplifying the circular polynucleotides of (a) to produce amplified polynucleotides; (c) shearing the amplified polynucleotides to produce sheared polynucleotides, each sheared polynucleotide comprising one or more shear points at a 5' end and/or a 3' end; (d) sequencing the sheared polynucleotides to produce a plurality of sequencing reads; (e) identifying sequence differences between sequencing reads and a reference sequence; and (f) calling a sequence difference as the sequence variant when the sequence difference occurs in at least two different sheared polynucleotides. In some embodiments, calling the sequence difference as the sequence variant occurs further when (i) the sequence difference occurs in at least two circular polynucleotides having different junctions; (ii) the sequence difference is identified on both strands of a double-stranded input molecule; and/or (iii) the sequence difference occurs in a consensus sequence for a concatemer formed by amplification comprising rolling circle amplification. In some embodiments, the plurality of polynucleotides comprises single-stranded polynucleotides. In some embodiments, circularizing is effected by subjecting the plurality of polynucleotides to a ligation reaction. In some embodiments, the sequence variant is a single nucleotide polymorphism. In some embodiments, the reference sequence is a consensus sequence formed by aligning the sequencing reads with one another. In some embodiments, the reference sequence is a sequencing read. In some embodiments, circularizing comprises the step of joining an adapter polynucleotide to the 5' end, the 3' end, or both the 5' end and the 3' end of a polynucleotide in the plurality of polynucleotides. In some embodiments, amplifying is effected by using a polymerase having strand-displacement activity. In some embodiments, amplifying comprises subjecting the circular polynucleotides to an amplification reaction mixture comprising random primers. In some embodiments, amplifying comprises subjecting the circular polynucleotides to an amplification reaction mixture comprising one or more primers, each of which specifically hybridizes to a different target sequence via sequence complementarity. In some embodiments, the amplified polynucleotides are subjected to the sequencing step without enrichment. In some embodiments, the method further comprises enriching one or more target polynucleotides among the amplified polynucleotides by performing an enrichment step prior to sequencing. In some embodiments, a microbial contaminant is identified based on the calling step. In some embodiments, the sample is a sample from a subject. In some embodiments, the sample is urine, stool, blood, saliva, tissue, or bodily fluid. In some embodiments, the sample comprises tumor cells. In some embodiments, the sample is a formalin-fixed paraffin embedded (FFPE) sample. In some embodiments, the method further comprises diagnosing, and optionally treating, said subject based on the calling step. In some embodiments, the sequence variant is a causal genetic variant. In some embodiments, the sequence variant is associated with a type or stage of cancer. In some embodiments, the plurality of polynucleotides comprises cell-free polynucleotides. In some embodiments, the cell-free polynucleotides comprise circulating tumor DNA. FIG. 14 provides an illustrative schematic of an exemplary work-flow.

In another aspect, the disclosure provides a reaction mixture for performing a method according to any of the methods herein, wherein the reaction mixture comprises (a) a plurality of concatemers, wherein individual concatemers in the plurality comprise different junctions formed by circularizing individual polynucleotides having a 5' end and a 3' end; (b) a first primer comprising sequence A', wherein the first primer specifically hybridizes to sequence A of the target sequence via sequence complementarity between sequence A and sequence A'; (c) a second primer comprising sequence B, wherein the second primer specifically hybridizes to sequence B' present in a complementary polynucleotide comprising a complement of the target sequence via sequence complementarity between B and B'; and; (d) a polymerase that extends the first primer and the second primer to produce amplified polynucleotides; wherein the distance between the 5' end of sequence A and the 3' end of sequence B of the target sequence is 75 nt or less. In some embodiments, the first primer comprises sequence C 5' with respect to sequence A', the second primer comprises sequence D 5' with respect to sequence B, and neither sequence C nor sequence D hybridizes to the two or more concatemers during a first amplification step in an amplification reaction.

In another aspect, the disclosure provides a system for detecting a sequence variant comprising (a) a computer configured to receive a user request to perform a detection reaction on a sample; (b) an amplification system that performs a nucleic acid amplification reaction on the sample or a portion thereof in response to the user request, wherein the amplification reaction comprises the steps of (i) circularizing individual polynucleotides in a plurality of polynucleotides to form a plurality of circular polynucleotides using a ligase enzyme, wherein each polynucleotide of the plurality of polynucleotides has 5' end and 3' end prior to ligation; (ii) degrading the ligase enzyme; and (iii) amplifying the circular polynucleotides after degrading the ligase enzyme to produce amplified polynucleotides; wherein polynucleotides are not purified or isolated between steps (i) and (iii); (c) a sequencing system that generates sequencing reads for polynucleotides amplified by the amplification system, identifies sequence differences between sequencing reads and a reference sequence, and calls a sequence difference that occurs in at least two circular polynucleotides having different junctions as the sequence variant; and (d) a report generator that sends a report to a recipient, wherein the report contains results for detection of the sequence variant. In some embodiments, the recipient is the user.

In another aspect, the disclosure provides a computer-readable medium comprising codes that, upon execution by one or more processors, implement a method of detecting a sequence variant, the implemented method comprising: (a) receiving a customer request to perform a detection reaction on a sample; (b) performing a nucleic acid amplification reaction on the sample or a portion thereof in response to the customer request, wherein the amplification reaction comprises the steps of (i) circularizing individual polynucleotides in a plurality of polynucleotides to form a plurality of circular polynucleotides using a ligase enzyme, wherein each polynucleotide of the plurality of polynucleotides has a 5' end and 3' end prior to ligation; (ii) degrading the ligase enzyme; and (iii) amplifying the circular polynucleotides after degrading the ligase enzyme to produce amplified polynucleotides; wherein polynucleotides are not purified or isolated between steps (i) and (iii); (c) performing a sequencing analysis comprising the steps of (i) generating sequencing reads for polynucleotides amplified in the amplification reaction; (ii) identifying sequence differences between sequencing reads and a reference sequence; and (iii) calling a sequence difference that occurs in at least two circular polynucleotides having different junctions as the sequence variant; and (d) generating a report that contains results for detection of the sequence variant.

In another aspect, the disclosure provides a method of identifying a sequence variant in a nucleic acid sample comprising a plurality of polynucleotides, each polynucleotide of the plurality having a 5' end and a 3' end, the method comprising: (a) circularizing individual polynucleotides of said plurality to form a plurality of circular polynucleotides, each of which having a junction between the 5' end and 3' end; (b) degrading the ligase enzyme; (c) amplifying the circular polynucleotides of (a) using random primers to produce amplified polynucleotides; (d) shearing the amplified polynucleotides; (e) sequencing the sheared polynucleotides to produce a plurality of sequencing reads; (f) identifying sequence differences between sequencing reads and a reference sequence; and (g) calling a sequence difference as the sequence variant when: (i) the sequence difference is identified on both strands of a double-stranded input molecule; (ii) the sequence difference occurs in a consensus sequence for a concatemer formed by rolling circle amplification; (iii) calling a sequence difference as the sequence variant when the sequence difference occurs in at least two different sheared polynucleotides; and/or (iv) the sequence difference occurs in two different molecules; wherein a sequence difference is identified as occurring in two different molecules when the sequence difference occurs in at least two circular polynucleotides having a different junction formed between the 5' end and 3' end.

In another aspect, the disclosure provides a method of identifying a sequence variant in a nucleic acid sample comprising a plurality of polynucleotides, each polynucleotide of the plurality having a 5' end and a 3' end, the method comprising: (a) circularizing individual polynucleotides of said plurality to form a plurality of circular polynucleotides, each of which having a junction between the 5' end and 3' end; (b) degrading the ligase enzyme; (c) amplifying the circular polynucleotides of (a) using one or more primers, each of which specifically hybridizes to a different target sequence via sequence complementarity to produce amplified polynucleotides; (d) shearing the amplified polynucleotides; (e) sequencing the sheared polynucleotides to produce a plurality of sequencing reads; (f) identifying sequence differences between sequencing reads and a reference sequence; and (g) calling a sequence difference as the sequence variant when: (i) the sequence difference is identified on both strands of a double-stranded input molecule; (ii) the sequence difference occurs in a consensus sequence for a concatemer formed by rolling circle amplification; and/or (iii) the sequence difference occurs in two different molecules; wherein a sequence difference is identified as occurring in two different molecules when the sequence difference occurs in at least two circular polynucleotides having a different junction formed between the 5' end and 3' end.

In an aspect, the disclosure provides a method of identifying a sequence variant in a nucleic acid sample comprising a plurality of polynucleotides, each polynucleotide of the plurality having a 5' end and a 3' end, the method comprising (a) circularizing individual polynucleotides of the plurality to form a plurality of circular polynucleotides, wherein a given circular polynucleotide of the plurality has a junction sequence resulting from the circularization; (b) amplifying the circular polynucleotides of (a) to produce a plurality of amplified polynucleotides, wherein a first amplified polynucleotide of the plurality and a second amplified polynucleotide of the plurality comprise the junction sequence but comprise different sequences at their respective 5' and/or 3' ends; (c) sequencing the plurality of amplified polynucleotides or amplification products thereof to produce a plurality of sequencing reads corresponding to the first amplified polynucleotide and the second amplified polynucleotide; and (d) calling a sequence difference detected in the sequencing reads as the sequence variant when the sequence difference occurs in sequencing reads corresponding to both the first amplified polynucleotide and the second amplified polynucleotide.

In some embodiments, circularizing individual polynucleotides in (a) is effected by a ligase enzyme. In some embodiments, prior to (b), the ligase enzyme is degraded. In some embodiments, uncircularized polynucleotides are degraded prior to (b). In some embodiments, the plurality of circular polynucleotides is not purified or isolated prior to (b).

In some embodiments, circularizing in (a) comprises the step of joining an adapter polynucleotide to the 5' end, the 3' end, or both the 5' end and the 3' end of a polynucleotide in the plurality of polynucleotides.

In some embodiments, amplifying the circular polynucleotides in (b) is effected by a polymerase having strand-displacement activity. In some embodiments, amplifying the circular polynucleotides in (b) comprises rolling circle amplification (RCA). In some embodiments, amplifying in (b) comprises subjecting the circular polynucleotides to an amplification reaction mixture comprising random primers. In some embodiments, individual random primers comprise sequences at their respective 5' and/or 3 ends distinct from each other. In some embodiments, amplifying in (b) comprises subjecting the circular polynucleotides to an amplification reaction mixture comprising target specific primers. In some embodiments, amplifying comprises multiple cycles of denaturation, primer binding, and primer extension.

In some embodiments, the amplified polynucleotides are subjected to the sequencing of (c) without enrichment. In some embodiments, the method further comprises enriching one or more target polynucleotides among the amplified polynucleotides or amplification products thereof by performing an enrichment step prior to the sequencing of (c).

In some embodiments, the plurality of polynucleotides comprises single-stranded polynucleotides. In some embodiments, the sequence variant is a single nucleotide polymorphism. In some embodiments, the sample is a sample from a subject. In some embodiments, the sample comprises urine, stool, blood, saliva, tissue, or bodily fluid. In some embodiments, the sample comprises tumor cells. In some embodiments, the sample comprises a formalin-fixed paraffin embedded (FFPE) sample. In some embodiments, the plurality of polynucleotides comprises cell-free polynucleotides. In some embodiments, the cell-free polynucleotides comprise cell-free DNA. In some embodiments, the cell-free polynucleotides comprise cell-free RNA. In some embodiments, the cell-free polynucleotides comprise circulating tumor DNA. In some embodiments, the cell-free polynucleotides comprise circulating tumor RNA.

In some embodiments, in (d), the method comprises calling a sequence difference detected in the sequencing reads as the sequence variant when the sequence difference occurs in at least 50% of the sequencing reads from the first amplified polynucleotide and at least 50% of sequencing reads from the second amplified polynucleotide.

In an aspect, the present disclosure provides a method of identifying a sequence variant in a nucleic acid sample comprising a plurality of polynucleotides, each polynucleotide of the plurality having a 5' end and a 3' end, the method comprising (a) circularizing individual polynucleotides of the plurality to form a plurality of circular polynucleotides, wherein a given circular polynucleotide of the plurality has a junction sequence resulting from the circularization; (b) amplifying the circular polynucleotides of (a) to produce a plurality of amplified polynucleotides; (c) shearing the amplified polynucleotides to produce sheared polynucleotides, each sheared polynucleotide comprising one or more shear points at a 5' end and/or a 3' end; (d) sequencing amplification products of the sheared polynucleotides to produce a plurality of sequencing reads; and (e) calling a sequence difference detected in the sequencing reads as the sequence variant when the sequence difference occurs in sequencing reads corresponding to a first sheared polynucleotide and sequencing reads corresponding to a second sheared polynucleotide.

In some embodiments, circularizing individual polynucleotides in (a) is effected by a ligase enzyme. In some embodiments, prior to (b), the ligase enzyme is degraded. In some embodiments, uncircularized polynucleotides are degraded prior to (b). In some embodiments, the plurality of circular polynucleotides is not purified or isolated prior to (b).

In some embodiments, circularizing in (a) comprises the step of joining an adapter polynucleotide to the 5' end, the 3' end, or both the 5' end and the 3' end of a polynucleotide in the plurality of polynucleotides.

In some embodiments, amplifying the circular polynucleotides in (b) is effected by a polymerase having strand-displacement activity. In some embodiments, amplifying the circular polynucleotides in (b) comprises rolling circle amplification (RCA). In some embodiments, amplifying in (b) comprises subjecting the circular polynucleotides to an amplification reaction mixture comprising random primers. In some embodiments, individual random primers comprise sequences at their respective 5' and/or 3 ends distinct from each other. In some embodiments, amplifying in (b) comprises subjecting the circular polynucleotides to an amplification reaction mixture comprising target specific primers.

In some embodiments, the amplification products of the sheared polynucleotides are subjected to sequencing without enrichment. In some embodiments, the method further comprises enriching one or more target polynucleotides among the amplification products of the sheared polynucleotides by performing an enrichment step prior to the sequencing of (d). In some embodiments, shearing in (c) comprises subjecting the amplified polynucleotides to sonication. In some embodiments, shearing in (c) comprises subjecting the amplified polynucleotides to enzymatic cleavage.

In some embodiments, the plurality of polynucleotides comprises single-stranded polynucleotides. In some embodiments, the sequence variant is a single nucleotide polymorphism. In some embodiments, the sample is a sample from a subject. In some embodiments, the sample comprises urine, stool, blood, saliva, tissue, or bodily fluid. In some embodiments, the sample comprises tumor cells. In some embodiments, the sample comprises a formalin-fixed paraffin embedded (FFPE) sample. In some embodiments, the plurality of polynucleotides comprises cell-free polynucleotides. In some embodiments, the cell-free polynucleotides comprise cell-free DNA. In some embodiments, the cell-free polynucleotides comprise cell-free RNA. In some embodiments, the cell-free polynucleotides comprise circulating tumor DNA. In some embodiments, the cell-free polynucleotides comprise circulating tumor RNA.

In some embodiments, in (e), the method comprises calling a sequence difference detected in the sequencing reads as the sequence variant when the sequence difference occurs in at least 50% of the sequencing reads from the first sheared polynucleotide and at least 50% of the sequencing reads from the second sheared polynucleotide.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 also shows the use of target specific primers.

FIGS. 6A and 6B depict two schemes for the addition of adapters using blocked ends of the nucleic acids.

FIGS. 7A-7C depict three different ways to prime a rolling circle amplification (RCA) reaction. FIG. 7A shows the use of target specific primers, e.g. the particular target genes or target sequences of interest. This generally results in only target sequences being amplified. FIG. 7B depicts the use of random primers to perform whole genome amplification (WGA), which will generally amplify all sample sequences, which then are bioinformatically sorted out during processing. FIG. 7C depicts the use of adapter primers when adapters are used, also resulting in general non-target-specific amplification.

FIGS. 9A-9D depict a variety of schemes to achieve complementary strand synthesis for subsequent sequencing. FIG. 9A depicts the use of random priming of the target strand, followed by ligation. FIG. 9B depicts the use of adapter priming of the target strand, similarly followed by ligation. FIG. 9C depicts the use of a "loop" adapter, wherein the adapter has two sections of sequences that are complementary, such that they hybridize with each other to create a loop (e.g. stem-loop structures). Upon ligation to the end of the concatamer, the free end of the loop serves as the primer for the complementary strand. FIG. 9D shows the use of hyper-branching random primers to achieve second strand synthesis.

FIGS. 11A-11D depicts an embodiment in which back to back (B2B) primers are used with a "touch up" PCR step, such that amplification of short products (such as monomers) are less favored. In this case, the primers have two domains; a first domain that hybridizes to the target sequence (grey or black arrow) and a second domain that is a "universal primer" binding domain (bent rectangles; also sometimes referred to as an adapter) which does not hybridize to the original target sequence. In some embodiments, the first rounds of PCR are done with a low temperature annealing step (FIG. 11A), such that gene specific sequences bind. The low temperature run results in PCR products of various lengths, including short products (FIG. 11B). After a low number of rounds, the annealing temperature is raised, such that hybridization of the entire primer, both domains, is favored (FIG. 11C); as depicted these are found at the ends of the templates, while internal binding is less stable. Shorter products are thus less favored at the higher temperature with both domains than at the lower temperature or only a single domain (FIG. 11D).

FIGS. 12A and 12B depict two different methods of sequencing library construction. FIG. 12A illustrates an example of the Illumina® Nextera sample preparation system, by which DNA can be simultaneously fragmented and tagged with sequencing adapters in a single step. In FIG. 12B, concatemers are fragmented by sonication, followed by adding adapters to both ends (e.g. by use of kits by KAPA Biosystems), and PCR amplification. Other methods are available.

FIGS. 25A and 25B illustrate embodiments for the formation of polynucleotide multimers having identifiable junctions, in the absence of circularization. Polynucleotides (such as polynucleotide fragments, or cell-free DNA) are joined to form multimers having non-natural junctions useful in distinguishing independent polynucleotides in accordance with embodiments of the disclosure (also referred to herein as "auto-tag"). In FIG. 25A, polynucleotides are joined directly to one another by blunt-end ligation. In FIG. 25B, polynucleotides are joined via one or more intervening adapter oligonucleotides, which may further comprise a barcode sequence. Multimers are then subjected to amplification by any of a variety of methods, such as by random primers (whole genome amplification), adapter primers, or one or more target specific primers or primer pairs.

FIGS. 27A-27E illustrates an example variation on the process of FIG. 25. Target specific amplification primers comprise a common 5' "tail" that functions as an adapter (grey arrow). Initial amplification (e.g. by PCR) proceeds for a few cycles (e.g. at least about 5, 10, or more cycles). PCR products can serve as primers as well, annealing to other PCR products (e.g. when annealing temperature is reduced in a second phase) to produce concatemers having identifiable junctions. The second phase can comprise a number of cycles (e.g. 5, 10, 15, 20, or more cycles), and may include a selection or variation of conditions that favor concatemer formation and amplification. Methods according to this schematic are also referred to as "Relay Amp Seq", which may find particular use in a compartmentalized setting (e.g. in a droplet).

FIGS. 28A-28E illustrate non-limiting examples of methods for circularizing polynucleotides. In FIG. 28A, double-stranded polynucleotides (e.g. dsDNA) are denatured into single-strands, followed by direct circularization (e.g. self-joining ligation by CircLigase). In FIG. 28B, polynucleotides (e.g. DNA fragments) are end-repaired and A-tailed (adding single-based extension of adenosine to 3' ends) to improve ligation efficiency, followed by denaturation to single-strands, and circularization. In FIG. 28C, polynucleotides are end-repaired and A-tailed (if double-stranded), joined to adapters having a thymidine (T) extension, denatured into single-strands, and circularized. In FIG. 28D, polynucleotides are end-repaired and A-tailed (if double-stranded), both ends are ligated to an adapter having three elements (T extension for ligation, complementarity between adapters, and a 3' tail), strands are denatured, and single-stranded polynucleotides are circularized (facilitated by complementarity between the adapter sequences). In FIG. 28E, double-stranded polynucleotides are denatured to single-stranded form, and circularized in the presence of a molecular clamp that brings the ends of the polynucleotide closer together to facilitate joining.

FIGS. 36A-36I illustrate steps of various embodiments of the invention.

In FIG. 41A, the group is counted as 'variant' because all reads in the group show the variant ('x') with concatemer confirmation. In FIG. 41B, the variant is rejected and the consensus of the read family is classified as wild-type because a majority of the reads in the family do not show the variant ('x'). In FIG. 41C, a variant is called when the same sequence difference ('x') is detected in at least two different read families. A sequence difference (circle) that is not detected in at least two different read families is not called a variant.

DETAILED DESCRIPTION

Figure 1:
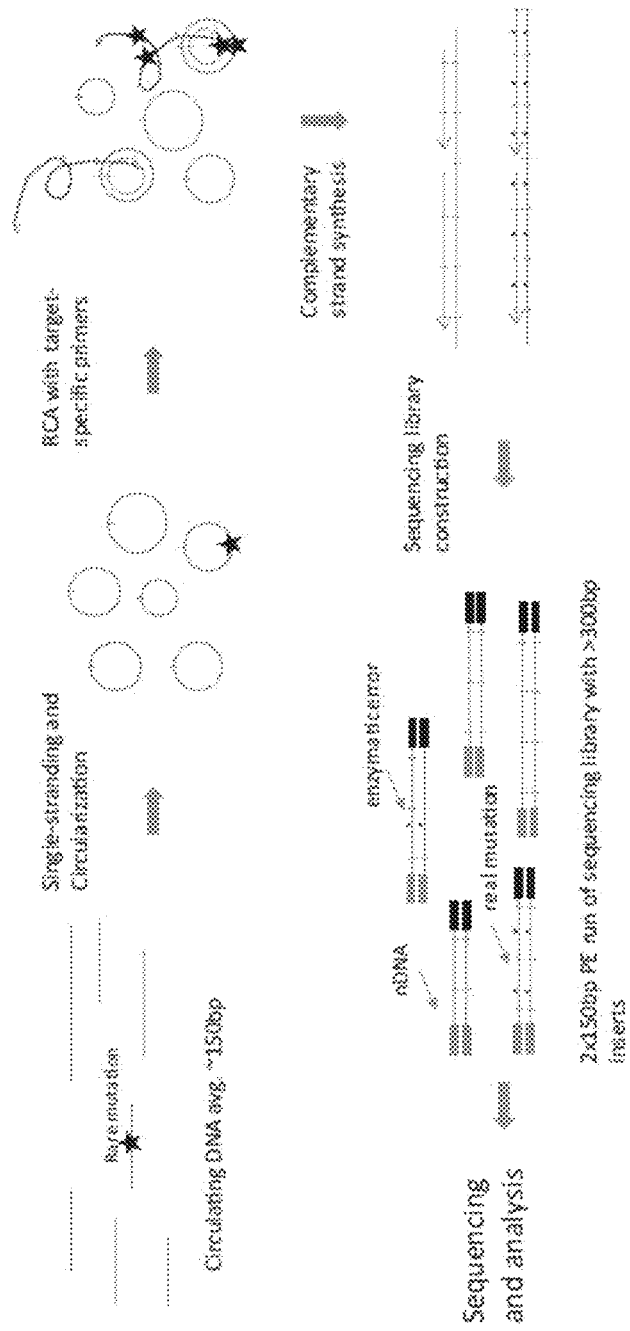
FIG. 1 depicts the schematic of one embodiment of methods according to the present disclosure. DNA strands are circularized and target specific primers corresponding to genes under investigation are added, along with polymerase, dNTPs, buffers, etc., such that rolling circle amplification (RCA) occurs to form concatamers (e.g. "multimers") of the template DNA (e.g. a "monomer"). The concatamers are treated to synthesize the corresponding complementary strand, and then adapters are added to make sequencing libraries. This resulting library, which is then sequenced using standard technologies, will generally contain three species: nDNA ("normal" DNA) that does not contain a rare sequence variant (e.g. a mutation); nDNA that contains enzymatic sequencing errors, and DNA that contains multimers of "real" or actual sequence variants that were pre-existing in the sample polynucleotides before amplification. The presence of multiple copies of the effectively rare mutation allows the detection and identification of the sequence variant.

The practice of some embodiments disclosed herein employ, unless otherwise indicated, conventional techniques of immunology, biochemistry, chemistry, molecular biology, microbiology, cell biology, genomics and recombinant DNA, which are within the skill of the art. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. In general, the term "target sequence" refers to a nucleic acid sequence on a single strand of nucleic acid. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner according to base complementarity. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the enzymatic cleavage of a polynucleotide by an endonuclease. A second sequence that is complementary to a first sequence is referred to as the "complement" of the first sequence. The term "hybridizable" as applied to a polynucleotide refers to the ability of the polynucleotide to form a complex that is stabilized via hydrogen bonding between the bases of the nucleotide residues in a hybridization reaction.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary, respectively). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. Sequence identity, such as for the purpose of assessing percent complementarity, may be measured by any suitable alignment algorithm, including but not limited to the Needleman-Wunsch algorithm (see e.g. the EMBOSS Needle aligner available at www.ebi.ac.uk/Tools/psa/emboss_needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss_water/nucleotide.html, optionally with default settings). Optimal alignment may be assessed using any suitable parameters of a chosen algorithm, including default parameters.

In general, "stringent conditions" for hybridization refer to conditions under which a nucleic acid having complementarity to a target sequence predominantly hybridizes with a target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Technniques In Biochemistry And Molecular Biology-Hybridization With Nucleic Acid Probes Part I, Second Chapter "Overview of principles of hybridization and the strategy of nucleic acid probe assay", Elsevier, N.Y.

In one aspect, the disclosure provides a method of identifying a sequence variant in a nucleic acid sample comprising a plurality of polynucleotides, each polynucleotide of the plurality having a 5' end and a 3' end. In some cases, the method comprises (a) circularizing individual polynucleotides of the plurality to form a plurality of circular polynucleotides, wherein a given circular polynucleotide of the plurality has a junction sequence resulting from said circularization; (b) amplifying the circularized polynucleotides of (a) to produce a plurality of amplified polynucleotides; (c) shearing the amplified polynucleotides to produce sheared polynucleotides, each sheared polynucleotide comprising one or more shear points at a 5' end and/or a 3' end; (d) sequencing the sheared polynucleotides and/or amplification products of the sheared polynucleotides to produce a plurality of sequencing reads; and (d) calling a sequence difference detected in the sequencing reads as the sequence variant when the sequence difference occurs in sequencing reads corresponding to a first sheared polynucleotide and a second sheared polynucleotide.

In some cases, the method comprises (a) circularizing individual polynucleotides of said plurality to form a plurality of circular polynucleotides, each of which having a junction between the 5' end and the 3' end; (b) amplifying the circular polynucleotides of (a) to produce amplified polynucleotides; (c) shearing the amplified polynucleotides to produce sheared polynucleotides, each sheared polynucleotide comprising one or more shear points at a 5' end and/or 3' end; (d) sequencing the sheared polynucleotides to produce a plurality of sequencing reads; (e) identifying sequencing differences between sequencing reads and a reference sequence; and (f) calling a sequence difference as the sequence variant when the sequence difference occurs in at least two different sheared polynucleotides.

In general, joining ends of a polynucleotide to one-another to form a circular polynucleotide (either directly, or with one or more intermediate adapter oligonucleotides) produces a junction having a junction sequence. Where the 5' end and 3' end of a polynucleotide are joined via an adapter polynucleotide, the term "junction" can refer to a junction between the polynucleotide and the adapter (e.g. one of the 5' end junction or the 3' end junction), or to the junction between the 5' end and the 3' end of the polynucleotide as formed by and including the adapter polynucleotide. Where the 5' end and the 3' end of a polynucleotide are joined without an intervening adapter (e.g. the 5' end and 3' end of a single-stranded DNA), the term "junction" refers to the point at which these two ends are joined. A junction may be identified by the sequence of nucleotides comprising the junction (also referred to as the "junction sequence").

In some embodiments, samples comprise polynucleotides having a mixture of ends formed by natural degradation processes (such as cell lysis, cell death, and other processes by which polynucleotides such as DNA and RNA are released from a cell to its surrounding environment in which it may be further degraded, e.g., cell-free polynucleotides, e.g., cell-free DNA and cell-free RNA), fragmentation that is a byproduct of sample processing (such as fixing, staining, and/or storage procedures), and fragmentation by methods that cleave DNA without restriction to specific target sequences (e.g. mechanical fragmentation, such as by sonication; non-sequence specific nuclease treatment, such as DNase I, fragmentase). Where samples comprise polynucleotides having a mixture of ends, the likelihood of two polynucleotides having the same 5' end or 3' end is low, and the likelihood that two polynucleotides will independently have both the same 5' end and 3' end is lower. Accordingly, in some embodiments, junctions may be used to distinguish different polynucleotides, even where the two polynucleotides comprise a portion having the same target sequence. Where polynucleotide ends are joined without an intervening adapter, a junction sequence may be identified by alignment to a reference sequence. For example, where the order of two component sequences appears to be reversed with respect to the reference sequence, the point at which the reversal appears to occur may be an indication of a junction at that point. Where polynucleotide ends are joined via one or more adapter sequences, a junction may be identified by proximity to the known adapter sequence, or by alignment as above if a sequencing read is of sufficient length to obtain sequence from both the 5' and 3' ends of the circularized polynucleotide. In some embodiments, the formation of a particular junction is a sufficiently rare event such that it is unique among the circularized polynucleotides of a sample.

In some embodiments, circularizing individual polynucleotides in (a) is effected by subjected the plurality of polynucleotides to a ligation reaction. The ligation reaction may comprise a ligase enzyme. In some embodiments, the ligase enzyme is degraded prior to amplifying in (b). Degradation of ligase prior to amplifying in (b) can increase the recovery rate of amplifiable polynucleotides. In some embodiments, the plurality of circularized polynucleotides are not purified or isolated prior to (b). In some embodiments, uncircularized, linear polynucleotides are degraded prior to amplifying.

In some cases, circularizing in (a) comprises the step of joining and adapter polynucleotide to the 5' end, the 3' end, or both the 5' end and the 3' end of a polynucleotide in the plurality of polynucleotides. As previously described, where the 5' end and/or 3' end of a polynucleotide are joined via an adapter polynucleotide, the term "junction" can refer to the junction between the polynucleotide and the adapter (e.g., one of the 5' end junction or the 3' end junction), or to the junction between the 5' end and the 3' end of the polynucleotide as formed by and including the adapter polynucleotide.

The circularized polynucleotides can be amplified, for example, after degradation of the ligase enzyme, to yield amplified polynucleotides. Amplifying the circular polynucleotides in (b) can be effected by a polymerase having strand-displacement activity. In some cases, the polymerase is a Phi29 DNA polymerase. In some cases, amplification comprises rolling circle amplification (RCA). The amplified polynucleotides resulting from RCA can comprise linear concatemers, or polynucleotides comprising two or more copies of a target sequence (e.g., subunit sequence) from a template polynucleotide. In some embodiments, amplifying comprises subjecting the circular polynucleotides to an amplification reaction mixture comprising random primers. In some cases, amplifying comprises subjecting the circular polynucleotides to an amplification reaction mixture comprising one or more primers, each of which specifically hybridizes to a different target sequence via sequence complementarity.

The amplified polynucleotides are sheared, in some cases, to produce sheared polynucleotides that are shorter in length relative to the unsheared polynucleotides. Two or more sheared polynucleotides originating from the same linear concatemer may have the same junction sequence but can have different 5' and/or 3' ends (e.g., shear ends).

Amplified polynucleotides can be sheared using any variety of methods, such as, but not limited to, physical fragmentation, enzymatic methods, and chemical fragmentation. Non-limiting examples of physical fragmentation methods that can be employed for the fragmentation of amplified polynucleotides include acoustic shearing, sonication, and hydrodynamic shearing. In some cases, acoustic shearing and sonication may be preferred. Non-limiting examples of enzymatic fragmentation methods that can be employed for the fragmentation of amplified polynucleotides include use of enzymes such as DNase I and other restriction endonucleases, including non-specific nucleases, and transposases. Non-limiting examples of chemical fragmentation methods that can be employed for the fragmentation of amplified polynucleotides include use of heat and divalent metal cations.

Sheared polynucleotides (also referred to as fragmented polynucleotides) which are shorter in length compared to the unsheared polynucleotides may be desired to match the capabilities of the sequencing instrument used for producing sequencing reads, also referred to as sequence reads. For example, amplified polynucleotides may be fragmented, for example sheared, to the optimal length determined by the downstream sequencing platform. Various sequencing instruments, further described herein, can accommodate nucleic acids of different lengths. In some cases, amplified polynucleotides are sheared in the process of attaching adaptors useful in downstream sequencing platforms, for example in flow cell attachment or sequencing primer binding. In some cases, sheared polynucleotides are subject to amplification to produce amplification products of the sheared polynucleotides prior to sequencing. Additional amplification can be desirable, for example, to generate a sufficient amount of polynucleotides for downstream analysis, for example, sequencing analysis. The resulting amplification products can comprise multiple copies of individual sheared polynucleotides.

During sequencing, sheared polynucleotides or amplification products thereof originating from the same amplified polynucleotide can be sequenced. Sequencing reads resulting from sequencing can be grouped into read families. A read family can comprise any suitable number of sequence reads. In some cases, a read family comprises at least 5, 10, 15, 20, 25, 50, 75, or 100 sequences reads. In some cases, a group of sequence reads may not be identified as a read family unless a minimum number of sequence reads are present. For example, a read family can comprise at least 2, 3, 4, 5, 7, 8, 9, or 10 sequence reads. In some cases, a read family comprises at least 25 read sequences. In some cases, sequence reads which may be classified as a read family based on a shared junction sequence and shared sequences of the 5' and 3' ends. In some embodiments, the sequence reads of a read family have the same junction sequence. In some embodiments, the sequence reads of a read family have the same sequences at the 5' and 3' end, for example, the sequences may be identical over at least 5 bases, 6 bases, 7 bases, 8 bases, 9 bases, or 10 bases at each of the 5' and 3' ends. In some cases, the sequences at the 5' and 3' ends are not identical amongst all sequence reads of a read family due to errors resulting from amplification and/or sequencing error. The sequencing reads of a read family may exhibit overlap when compared, for example by alignment. In some cases, the sequencing reads of a read family exhibit at least 75% identity, when optimally aligned. The term "percent (%) identity" refers to the percentage of identical residues shared between two sequences, e.g., a candidate sequence and a reference sequence, after aligning the sequences and introducing gaps, if necessary, to achieve the maximum percent identity (i.e., gaps can be introduced in one or both of the candidate and reference sequences for optimal alignment and, in some cases, non-homologous sequences can be disregarded for comparison purposes). Alignment, for purposes of determining percent identity, can be achieved in various ways, for instance, using publicly available computer software such as BLAST, ALIGN, or Megalign (DNASTAR) software. Percent identity of two sequences can be calculated by aligning a test sequence with a comparison sequence using BLAST, determining the number of amino acids or nucleotides in the aligned test sequence that are identical to amino acids or nucleotides in the same position of the comparison sequence, and dividing the number of identical amino acids or nucleotides by the number of amino acids or nucleotides in the comparison sequence. Two sequencing reads of a family can exhibit at least 75% identity (e.g., at least 80%, 85%, 90%, or 95% identity) over any suitable length of bases, when optimally aligned. A first pair of sequencing reads in a read family can exhibit a % identity that is different from a second pair of sequencing reads. In some cases, the % identity is determined for an alignment over a length of at least 50 bases (e.g., at least 60 bases, 70 bases, 80 bases, 90 bases, 100 bases, 110 bases, 120 bases, 130 bases, 140 bases, or 150 bases). In some cases, the alignment is over a length of between about 25-250 bases, between about 50-200 bases, between about 75-175 bases, or between about 100-150 bases. In some cases, the alignment is over the entire length of the test sequence or the comparison sequence. In some embodiments, two sequencing reads of a read family exhibit at least 75% identity (e.g., at least 80%, 85%, 90%, or 95% identity) over a length of at least 50 bases (e.g., at least 60 bases, 70 bases, 80 bases, 90 bases, 100 bases, 110 bases, 120 bases, 130 bases, 140 bases, or 150 bases) when optimally aligned.

Amplified polynucleotides comprising linear concatemers of a circular polynucleotide template can comprise multiples repeats or copies of the circular polynucleotide template sequence. Sheared polynucleotides produced from an amplified polynucleotide can have various copies of the circular polynucleotide template sequence. A sheared polynucleotide can have less than one copy of the repeat sequence, at least one copy of the repeat sequence, at least two copies of the repeat sequence, or at least three copies of the repeat sequence. The number of repeats in sheared polynucleotides can depend on the length of the repeat sequence. For example, for sheared fragments of approximately the same size, a concatemer having repeats of relatively shorter length can yield sheared fragments having more copies of the repeat sequence compared a concatemer having repeats of longer length.

A sequencing read of a sheared polynucleotide or amplification product thereof can in some cases comprise at least one copy of the repeat sequence. In some cases, the sequencing read comprises at least two copies of the repeat sequence (e.g., at least three copies, four copies, or five copies). The average number of copies of the repeat sequence from sequence reads of a read family can depend on the length of the polynucleotides of the nucleic acid sample.

Sequencing reads can be grouped into read families by first identifying the length and/or sequence of the repeated segment in the concatemer, which corresponds to the sequence of the circular polynucleotide template. In some cases, identifying the length and/or sequence of the repeated segment comprises alignment of reads to other reads or alignment to reference sequences. Next, the junction sequence can be identified, for example by alignment to a reference sequence. The sequences of the 5' and 3' ends of the polynucleotide and their relative distances (e.g., in bases) from the junction can be determined. Reads having the same junction sequence and shared sequences at the 5' and 3' ends can be grouped into a read family, representing the sequencing reads of amplification products originating from the same sheared polynucleotide.

A sequence difference observed in a read family can be called a true sequence difference as opposed to a result of amplification and/or sequencing error, in some cases, by confirming that the sequence difference occurs in a second read family having the same junction sequence but different sequences at respective 5' and 3' ends (e.g., at least two sheared polynucleotides). Two read families having the same junction sequence but different 5' and/or 3' ends can correspond to two sheared polynucleotides of the same linear concatemer. Observing the sequence difference in two read families corresponding to the two sheared polynucleotides of the same amplified polynucleotide can be one way to confirm that the sequence difference is truly present on other circular polynucleotide and not the result of amplification and/or sequencing error in one of the sheared polynucleotides.

In some cases, a sequence difference observed in sequence reads of a read family is considered a sequence difference if the sequence difference occurs in a majority of the sequencing reads of the read family. In some cases, the sequence difference observed in sequence reads of the read family is considered a sequence difference if the sequence difference occurs in at least 50% of sequencing reads of the read family (e.g., at least 60%, 70%, 80%, 90%, or 95% of sequencing reads). In some cases, the sequence difference observed in sequence reads of the read family is considered a sequence difference if the sequence difference occurs in 100% of sequencing reads of the read family. In some cases, a sequence difference detected in the sequencing reads is called as the sequence variant when the sequence difference occurs in a majority of the sequencing reads from a first sheared polynucleotide and a majority of sequencing reads from a second sheared polynucleotide. In some cases, a sequence difference detected in the sequencing reads is called as the sequence variant when the sequence difference occurs in at least 50% of the sequencing reads (e.g., at least 60%, 70%, 80%, 90%, or 95% of sequencing reads) from the first sheared polynucleotide and at least 50% of sequencing reads (e.g., at least 60%, 70%, 80%, 90%, of 95% or sequencing reads) from the second sheared polynucleotide. In some cases, a sequence difference detected in the sequencing reads is called as the sequence variant when the sequence difference occurs in 100% of the sequencing reads from the first sheared polynucleotide and 100% of sequencing reads from the second sheared polynucleotide.

By using two different sheared polynucleotides, that is two sheared polynucleotides having the same junction sequence but different shear ends, to confirm the presence of a sequence difference identified from sequencing reads in a sample, sequence variant detection can be improved. True sequence variants are expected to be found in at least two sheared polynucleotides originating from the same amplified polynucleotide whereas errors are expected to be found in less than two sheared polynucleotides. In some cases, the error rate of variant detection is reduced. In some embodiments, the error rate of variant detection is reduced by at least 5%, 10%, 15%, 20%, 25%, 30%, 35%, 40%, 45%, or 50%. In some cases, the sensitivity and/or specificity of variant detection is increased. In some embodiments, the sensitivity of variant detection is increased by at least 5%, 10%, 15%, 20%, 25%, 30%, 35%, 40%, 45%, or 50%. In some embodiments, the specificity of variant detection is increased by at least 5%, 10%, 15%, 20%, 25%, 30%, 35%, 40%, 45%, or 50%. In some cases, the false positive rate is decreased.

In some cases, calling the sequence different as the sequence variant occurs further when (i) the sequence difference occurs in at least two circular polynucleotides having different junctions; (ii) the sequence difference is identified on both strands of a double-stranded input molecule; and/or (iii) the sequence difference occurs in a consensus sequence for a concatemer formed by amplification comprising rolling circle amplification (RCA). In some cases, the reference sequence is a sequencing read. In some cases, the reference sequence is a consensus sequence formed by aligning the sequencing reads with one another.

In some cases, the sheared polynucleotides are subjected to sequencing without enrichment. However, if desired, enriching one or more target polynucleotides among the amplified polynucleotides and/or sheared polynucleotides can be performed in an enrichment step prior to sequencing. Exemplary enrichment steps may include the use of nucleic acids with sequence complementary to a target sequence.

The sequence variant, as described further herein, can be any variation with respect to the reference sequence. Non-limiting examples of sequence variants that can be detected using methods herein include single nucleotide polymorphisms (SNP), deletion/insertion polymorphisms (DIP), copy number variants (CNV), short tandem repeats (STR), simple sequence repeats (SSR), variable number of tandem repeats (VNTR), amplified fragment length polymorphisms (AFLP), retrotransposon-based insertion polymorphisms, sequence specific amplified polymorphism, and differences in epigenetic marks that can be detected as sequence variants (e.g. methylation differences). In some cases, the sequence variant is a polymorphism, such as a single-nucleotide polymorphism. In some cases, the sequence variant is a causal genetic variant. In some cases, the sequence variant is associated with a type or stage of cancer.

The nucleic acid sample can be a sample from a subject. In some cases, the sample is from a human subject. In some cases, the sample comprises urine, stool, blood, saliva, tissue, or bodily fluid from a subject, such as a human subject. In some cases, the sample comprises tumor cells. In some cases, the sample comprises a formalin-fixed paraffin embedded sample. In some cases, the plurality of polynucleotides of the sample comprises cell-free polynucleotides. The cell-free polynucleotides may comprise cell-free DNA, and in some cases, circulating tumor DNA and/or circulating tumor RNA. The cell-free polynucleotides may comprise cell-free RNA. In some embodiments, the method further comprises diagnosing, and optionally treating, the subject based on calling of the sequence variant. In some cases, a microbial contaminant in a sample is identified based on calling of the sequence variant. In such cases, the sample can be from a subject but may also be from a non-subject sample such as a soil sample or food sample.

The plurality of polynucleotides can be single-stranded. In some cases, the polynucleotides are in double-stranded form and are treated, for example by denaturation, to yield single-strands before proceeding with the circularization. In some cases, double-stranded polynucleotides are circularized to yield double-stranded circles and the double-stranded circles are treated, for example by denaturation, to yield single-stranded circles.

In another aspect, the disclosure provides a method of identifying a sequence variant in a nucleic acid sample comprising a plurality of polynucleotides, each polynucleotide of the plurality having a 5' end and a 3' end. In some embodiments, the method comprises: (a) circularizing individual polynucleotides of the plurality to form a plurality of circular polynucleotides, wherein a given circular polynucleotide has a junction sequence resulting from said circularization; (b) amplifying the circular polynucleotides of (a) to produce a plurality of amplified polynucleotides, wherein a first amplified polynucleotide of the plurality and a second amplified polynucleotide of the plurality comprise the junction sequence but comprise different sequences at their respective 5' and/or 3' ends; (c) sequencing the plurality of amplified polynucleotides and/or amplification products thereof to produce a plurality of sequencing reads corresponding to the first amplified polynucleotide and the second amplified polynucleotide; and (d) calling a sequence difference detected in the sequencing reads as the sequence variant when the sequence difference occurs in sequencing reads corresponding to both the first amplified polynucleotide and the second amplified polynucleotide. In some embodiments, circularizing individual polynucleotides in (a) is effected by a ligase enzyme. In some embodiments, the ligase enzyme is degraded prior to amplifying in (b). Degradation of ligase prior to amplifying in (b) can increase the recovery rate of amplifiable polynucleotides. In some embodiments, the plurality of circularized polynucleotides is not purified or isolated prior to (b).

In some cases, circularizing in (a) comprises the step of joining an adapter polynucleotide to the 5' end, the 3' end, or both the 5' end and the 3' end of a polynucleotide in the plurality of polynucleotides. As previously described, where the 5' end and/or 3' end of a polynucleotide are joined via an adapter polynucleotide, the term "junction" can refer to the junction between the polynucleotide and the adapter (e.g., one of the 5' end junction or the 3' end junction), or to the junction between the 5' end and the 3' end of the polynucleotide as formed by and including the adapter polynucleotide.

Following circularization, the circular polynucleotides are amplified. Amplifying the circular polynucleotides in (b) can be effected by a polymerase having strand-displacement activity. In some cases, the polymerase is a Phi29 DNA polymerase. In some cases, amplifying the circular polynucleotides in (b) comprises rolling circle amplification (RCA). Rolling circle amplification can result in amplification polynucleotides comprising linear concatemers of the template circular polynucleotide sequence. In some cases, amplifying in (b) comprises subjecting the circular polynucleotides to an amplification reaction mixture using random primers. Random primers which can non-specifically (e.g., randomly) hybridize to the circular polynucleotides during the amplifying of (b). Random primers which can non-specifically hybridize to circular polynucleotides can hybridize to a common circular polynucleotide, a plurality of circular polynucleotides, or both. In some cases, two or more random primers hybridize to the same circular polynucleotide (e.g., different regions of the same circular polynucleotide) and yield amplified polynucleotides having repeats of the same target sequence (or subunit sequence). Amplified polynucleotides of the same template (e.g., circular polynucleotide) can have the same junction sequence. In some embodiments, individual random primers comprise sequences at their respective 5' and/or 3' ends distinct from each other, and the resulting amplified polynucleotides can have sequences at 5' and/or 3' ends distinct from each other. Amplified polynucleotides of the same template, in some cases, have different 5' and/or 3' ends, depending on where the primer initially bound and where nucleotide incorporation was terminated. In some cases, amplifying in (b) comprises subjecting the circular polynucleotides to an amplification reaction mixture comprising target specific primers. Target specific primers can refer to primers targeting particular gene sequences, or in some cases refers to primers targeting adapter polynucleotide sequences. Amplified polynucleotides resulting from the use of target specific primers can share a common first end (e.g., primer) and may not share a second end, depending on where nucleotide incorporation was terminated. Amplifying can comprise multiple cycles of denaturation, primer binding, and primer extension. In some cases, the amplified polynucleotides can be subjected to further amplification to yield amplification products of the amplified polynucleotides. Additional amplification can be desirable, for example, to generate a sufficient amount of polynucleotides for downstream analysis, for example, sequencing analysis. The resulting amplification products can comprise multiple copies of individual amplified polynucleotides.

The amplified polynucleotides and/or amplification products thereof can be subsequently sequenced to yield sequencing reads. In some cases, the amplified polynucleotides and/or amplification products are subjected to sequencing without enrichment. However, if desired, enriching one or more target polynucleotides among the amplified polynucleotides and/or amplification products can be performed in an enrichment step prior to sequencing.

Sequencing reads can be grouped into read families. A read family can comprise any suitable number of sequence reads. In some cases, a read family comprises at least 5, 10, 15, 20, 25, 50, 75, or 100 sequence reads. In some cases, a group of sequence reads may not be identified as a read family unless a minimum number of sequence reads are present. For example, a read family comprises at least 2, 3, 4, 5, 6, 7, 8, 9, or 10 sequence reads. In some cases, a read family comprises at least 25 read sequences. In some embodiments, the sequence reads of a read family have the same junction sequence. In some embodiments, the sequence reads of a read family have the same sequences at the 5' and 3' ends, for example, the sequences may be identical over at least 5 bases, 6 bases, 7 bases, 8 bases, 9 bases, or 10 bases at each of the 5' and 3' ends. In some cases, the sequences at the 5' and 3' ends are not identical amongst all sequence reads of a read family due to errors resulting from amplification and/or sequencing. The sequencing reads of a read family may exhibit overlap when compared, for example by alignment. In some cases, the sequencing reads of a read family exhibit at least 75% identity, when optimally aligned. Two sequencing reads of a family can exhibit at least 75% identity (e.g., at least 80%, 85%, 90%, or 95% identity) over any suitable length of bases, when optimally aligned. A first pair of sequencing reads in a read family can exhibit a % identity that is different from a second pair of sequencing reads in the read family. In some cases, the % identity is determined for an alignment over a length of at least 50 bases (e.g., at least 60 bases, 70 bases, 80 bases, 90 bases, 100 bases, 110 bases, 120 bases, 130 bases, 140 bases, or 150 bases). In some cases, the alignment is over a length of between about 25-250 bases, between about 50-200 bases, between about 75-175 bases, or between about 100-150 bases. In some cases, the alignment is over the entire length of the test sequence or the comparison sequence. In some embodiments, two sequencing reads of a read family exhibit at least 75% identity (e.g., at least 80%, 85%, 90%, or 95% identity) over a length of at least 50 bases (e.g., at least 60 bases, 70 bases, 80 bases, 90 bases, 100 bases, 110 bases, 120 bases, 130 bases, 140 bases, or 150 bases) when optimally aligned.

Amplified polynucleotides comprising linear concatemers of a shared circular polynucleotide template can yield multiple linear concatemers of the same circular polynucleotide sequence but on multiple, individual molecules. A sequencing read of an amplified polynucleotide or amplification product thereof can in some cases comprise at least one copy of the repeat sequence. In some cases, the sequencing read comprises at least two copies of the repeat sequence (e.g., at least three copies, four copies, or five copies). The average number of copies of the repeat sequence from sequence reads of a read family can depend on the length of the polynucleotides of the nucleic acid sample. For example, a sample comprising relatively longer polynucleotides may result in concatemers with fewer repeats compared to a sample comprising relatively shorter polynucleotides if the concatemers are similar in length.

Sequencing reads can be grouped into read families by first identifying the length and/or sequence of the repeated segment in the concatemer, which corresponds to the sequence of the circular polynucleotide template. In some cases, identifying the length and/or sequence of the repeated segment comprises alignment of reads to other reads or alignment to reference sequences. Next, the junction sequence can be identified, for example by alignment to a reference sequence. The sequences of the 5' and 3' ends of the polynucleotide and their relative distances (e.g., in bases) from the junction can be determined. Reads having the same junction sequence and shared sequences at the 5' and 3' ends can be grouped into a read family, representing the sequencing reads of amplification products originating from the same amplified polynucleotide, or the same molecular copy of the circular polynucleotide.

A sequence difference observed in a read family can be called a true sequence difference as opposed to a result of amplification and/or sequencing error, in some cases, by confirming that the sequence difference occurs in a second read family having the same junction sequence but different sequences at respective 5' and 3' ends. Two read families having the same junction sequence but different 5' and/or 3' ends can correspond to two amplified polynucleotides of the same circular polynucleotide. Observing the sequence difference in two read families corresponding to the same circular polynucleotide can be one way to confirm that the sequence difference is truly present on the circular polynucleotide and not the result of amplification and/or sequencing error in one of the amplified polynucleotides.

In some cases, a sequence difference observed in sequence reads of a read family is considered a sequence difference if the sequence difference occurs in a majority of the sequencing reads of the read family. In some cases, the sequence difference observed in sequence reads of the read family is considered a sequence difference if the sequence difference occurs in at least 50% of sequencing reads of the read family (e.g., at least 60%, 70%, 80%, 90%, or 95% of sequencing reads). In some cases, the sequence difference observed in sequence reads of the read family is considered a sequence difference if the sequence difference occurs in 100% of sequencing reads of the read family. In some cases, a sequence difference detected in the sequencing reads is called as the sequence variant when the sequence difference occurs in a majority of the sequencing reads from a first amplified polynucleotide and a majority of sequencing reads from a second amplified polynucleotide. In some cases, a sequence difference detected in the sequencing reads is called as the sequence variant when the sequence difference occurs in at least 50% of the sequencing reads (e.g., at least 60%, 70%, 80%, 90%, or 95% of sequencing reads) from the first amplified polynucleotide and at least 50% of sequencing reads (e.g., at least 60%, 70%, 80%, 90%, or 95% of sequencing reads) from the second amplified polynucleotide. In some cases, a sequence difference detected in the sequencing reads is called as the sequence variant when the sequence difference occurs in 100% of the sequencing reads from the first amplified polynucleotide and 100% of sequencing reads from the second amplified polynucleotide.

In practicing the methods described herein, variant detection in a sample comprising a plurality of polynucleotides can be improved. In some cases, the error rate of variant detection is reduced. In some embodiments, the error rate of variant detection is reduced by at least 5%, 10%, 15%, 20%, 25%, 30%, 35%, 40%, 45%, or 50%. In some cases, the sensitivity and/or specificity of variant detection is increased. In some embodiments, the sensitivity of variant detection is increased by at least 5%, 10%, 15%, 20%, 25%, 30%, 35%, 40%, 45%, or 50%. In some embodiments, the specificity of variant detection is increased by at least 5%, 10%, 15%, 20%, 25%, 30%, 35%, 40%, 45%, or 50%. In some cases, the false positive rate is decreased.

The sequence variant, as described further herein, can be any variation with respect to the reference sequence. Non-limiting examples of sequence variants that can be detected using methods herein include single nucleotide polymorphisms (SNP), deletion/insertion polymorphisms (DIP), copy number variants (CNV), short tandem repeats (STR), simple sequence repeats (SSR), variable number of tandem repeats (VNTR), amplified fragment length polymorphisms (AFLP), retrotransposon-based insertion polymorphisms, sequence specific amplified polymorphism, and differences in epigenetic marks that can be detected as sequence variants (e.g. methylation differences). In some cases, the sequence variant is a polymorphism, such as a single-nucleotide polymorphism.

The nucleic acid sample can be a sample from a subject. In some cases, the sample is from a human subject. In some cases, the sample comprises urine, stool, blood, saliva, tissue, or bodily fluid from a subject, such as a human subject. In some cases, the sample comprises tumor cells. In some cases, the sample comprises a formalin-fixed paraffin embedded sample. In some cases, the plurality of polynucleotides of the sample comprises cell-free polynucleotides. The cell-free polynucleotides may comprise cell-free DNA, and in some cases, circulating tumor DNA. The cell-free polynucleotides may comprise cell-free RNA, and in some cases, circulating tumor RNA.

As previously described, the plurality of polynucleotides can be single-stranded. In some cases, the polynucleotides are in double-stranded form and are treated, for example by denaturation, to yield single-strands before proceeding with the circularization. In some cases, double-stranded polynucleotides are circularized to yield double-stranded circles and the double-stranded circles are treated, for example by denaturation, to yield single-stranded circles.

In another aspect, the disclosure provides a method of performing rolling circle amplification, such as in a nucleic acid sample comprising a plurality of polynucleotides. In some embodiments, each polynucleotide of the plurality has a 5' end and a 3' end, and the method comprises: (a) circularizing individual polynucleotides of the plurality to form a plurality of circular polynucleotides using a ligase enzyme, each polynucleotide having a junction between the 5' end and 3' end; (b) degrading the ligase enzyme; and (c) amplifying the circular polynucleotides of (a) after degrading the ligase enzyme, wherein polynucleotides are not purified or isolated between steps (a) and (c). In some embodiments, the method comprises additional steps of (d) sequencing the amplified polynucleotides to produce a plurality of sequencing reads; (e) identifying sequence differences between sequencing reads and a reference sequence; and (f) calling a sequence difference that occurs in at least two circular polynucleotides having different junctions as the sequence variant. In some embodiments, the method comprises identifying sequence differences between sequencing reads and a reference sequence, and calling a sequence difference that occurs in at least two circular polynucleotides having different junctions as the sequence variant, wherein: (a) the sequencing reads correspond to amplification products of the at least two circular polynucleotides; and (b) each of the at least two circular polynucleotides comprises a different junction formed by ligating a 5'end and 3'end of the respective polynucleotides.

In another aspect, the disclosure provides a method of performing rolling circle amplification, such as in a nucleic acid sample comprising a plurality of polynucleotides. In some embodiments, each polynucleotide of the plurality has a 5' end and a 3' end, and the method comprises: (a) circularizing individual polynucleotides of the plurality using a ligase enzyme to form a plurality of circular polynucleotides, each polynucleotide having a junction between the 5' end and 3' end; (b) degrading the ligase enzyme; (c) amplifying the circular polynucleotides of (a) after degrading the ligase enzyme to produce amplified polynucleotides, wherein polynucleotides are not purified or isolated between steps (a) and (c); (d) shearing the amplified polynucleotides to produce sheared polynucleotides, each sheared polynucleotide comprising one or more shear points at a 5' end and/or a 3' end. In some embodiments, the method comprises additional steps of (e) sequencing the sheared polynucleotides to produce a plurality of sequencing reads; (f) identifying sequence differences between sequencing reads and a reference sequence; and (g) calling a sequence difference as the sequence variant when the sequence difference occurs in at least two different sheared polynucleotides. Degradation of ligase prior to amplifying in (c) can increase the recovery rate of amplifiable polynucleotides.

In some embodiments, the method comprises identifying sequence differences between sequencing reads and a reference sequence, and calling a sequence difference that occurs in at least two circular polynucleotides having different junctions as the sequence variant, wherein: (a) the sequencing reads correspond to amplification products of the at least two circular polynucleotides; and (b) each of the at least two circular polynucleotides comprises a different junction formed by ligating a 5' end and 3' end of the respective polynucleotides. In some embodiments, the method comprises calling the sequence difference as the sequence variant occurs further when (i) the sequence difference occurs in at least two circular polynucleotides having different junctions; (ii) the sequence difference is identified on both strands of a double-stranded input molecule; and/or (iii) the sequence difference occurs in a consensus sequence for a concatemer formed by amplification comprising rolling circle amplification.

In general, the term "sequence variant" refers to any variation in sequence relative to one or more reference sequences. Typically, the sequence variant occurs with a lower frequency than the reference sequence for a given population of individuals for whom the reference sequence is known. For example, a particular bacterial genus may have a consensus reference sequence for the 16S rRNA gene, but individual species within that genus may have one or more sequence variants within the gene (or a portion thereof) that are useful in identifying that species in a population of bacteria. As a further example, sequences for multiple individuals of the same species (or multiple sequencing reads for the same individual) may produce a consensus sequence when optimally aligned, and sequence variants with respect to that consensus may be used to identify mutants in the population indicative of dangerous contamination. In general, a "consensus sequence" refers to a nucleotide sequence that reflects the most common choice of base at each position in the sequence where the series of related nucleic acids has been subjected to intensive mathematical and/or sequence analysis, such as optimal sequence alignment according to any of a variety of sequence alignment algorithms. A variety of alignment algorithms are available, some of which are described herein. In some embodiments, the reference sequence is a single known reference sequence, such as the genomic sequence of a single individual. In some embodiments, the reference sequence is a consensus sequence formed by aligning multiple known sequences, such as the genomic sequence of multiple individuals serving as a reference population, or multiple sequencing reads of polynucleotides from the same individual. In some embodiments, the reference sequence is a consensus sequence formed by optimally aligning the sequences from a sample under analysis, such that a sequence variant represents a variation relative to corresponding sequences in the same sample. In some embodiments, the sequence variant occurs with a low frequency in the population (also referred to as a "rare" sequence variant). For example, the sequence variant may occur with a frequency of about or less than about 5%, 4%, 3%, 2%, 1.5%, 1%, 0.75%, 0.5%, 0.25%, 0.1%, 0.075%, 0.05%, 0.04%, 0.03%, 0.02%, 0.01%, 0.005%, 0.001%, or lower. In some embodiments, the sequence variant occurs with a frequency of about or less than about 0.1%.

A sequence variant can be any variation with respect to a reference sequence. A sequence variation may consist of a change in, insertion of, or deletion of a single nucleotide, or of a plurality of nucleotides (e.g. 2, 3, 4, 5, 6, 7, 8, 9, 10, or more nucleotides). Where a sequence variant comprises two or more nucleotide differences, the nucleotides that are different may be contiguous with one another, or discontinuous. Non-limiting examples of types of sequence variants include single nucleotide polymorphisms (SNP), deletion/insertion polymorphisms (DIP), copy number variants (CNV), short tandem repeats (STR), simple sequence repeats (SSR), variable number of tandem repeats (VNTR), amplified fragment length polymorphisms (AFLP), retrotransposon-based insertion polymorphisms, sequence specific amplified polymorphism, and differences in epigenetic marks that can be detected as sequence variants (e.g. methylation differences).

Nucleic acid samples that may be subjected to methods described herein can be derived from any suitable source. In some embodiments, the samples used are environmental samples. Environmental sample may be from any environmental source, for example, naturally occurring or artificial atmosphere, water systems, soil, or any other sample of interest. In some embodiments, the environmental samples may be obtained from, for example, atmospheric pathogen collection systems, sub-surface sediments, groundwater, ancient water deep within the ground, plant root-soil interface of grassland, coastal water and sewage treatment plants.

Polynucleotides from a sample may be any of a variety of polynucleotides, including but not limited to, DNA, RNA, ribosomal RNA (rRNA), transfer RNA (tRNA), micro RNA (miRNA), messenger RNA (mRNA), fragments of any of these, or combinations of any two or more of these. In some embodiments, samples comprise DNA. In some embodiments, samples comprise genomic DNA. In some embodiments, samples comprise mitochondrial DNA, chloroplast DNA, plasmid DNA, bacterial artificial chromosomes, yeast artificial chromosomes, oligonucleotide tags, or combinations thereof. In some embodiments, the samples comprise DNA generated by amplification, such as by primer extension reactions using any suitable combination of primers and a DNA polymerase, including but not limited to polymerase chain reaction (PCR), reverse transcription, and combinations thereof. Where the template for the primer extension reaction is RNA, the product of reverse transcription is referred to as complementary DNA (cDNA). Primers useful in primer extension reactions can comprise sequences specific to one or more targets, random sequences, partially random sequences, and combinations thereof. In general, sample polynucleotides comprise any polynucleotide present in a sample, which may or may not include target polynucleotides. The polynucleotides may be single-stranded, double-stranded, or a combination of these. In some embodiments, polynucleotides subjected to a method of the disclosure are single-stranded polynucleotides, which may or may not be in the presence of double-stranded polynucleotides. In some embodiments, the polynucleotides are single-stranded DNA. Single-stranded DNA (ssDNA) may be ssDNA that is isolated in a single-stranded form, or DNA that is isolated in double-stranded form and subsequently made single-stranded for the purpose of one or more steps in a method of the disclosure.

In some embodiments, polynucleotides are subjected to subsequent steps (e.g. circularization and amplification) without an extraction step, and/or without a purification step. For example, a fluid sample may be treated to remove cells without an extraction step to produce a purified liquid sample and a cell sample, followed by isolation of DNA from the purified fluid sample. A variety of procedures for isolation of polynucleotides are available, such as by precipitation or non-specific binding to a substrate followed by washing the substrate to release bound polynucleotides. Where polynucleotides are isolated from a sample without a cellular extraction step, polynucleotides will largely be extracellular or "cell-free" polynucleotides, such as cell-free DNA and cell-free RNA, which may correspond to dead or damaged cells. The identity of such cells may be used to characterize the cells or population of cells from which they are derived, such as tumor cells (e.g. in cancer detection), fetal cells (e.g. in prenatal diagnostic), cells from transplanted tissue (e.g. in early detection of transplant failure), or members of a microbial community.

If a sample is treated to extract polynucleotides, such as from cells in a sample, a variety of extraction methods are available. For example, nucleic acids can be purified by organic extraction with phenol, phenol/chloroform/isoamyl alcohol, or similar formulations, including TRIzol and Tri-Reagent. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, Calif.); (2) stationary phase adsorption methods (U.S. Pat. No. 5,234,809; Walsh et al., 1991); and (3) salt-induced nucleic acid precipitation methods (Miller et al., (1988), such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads (see e.g. U.S. Pat. No. 5,705,628). In some embodiments, the above isolation methods may be preceded by an enzyme digestion step to help eliminate unwanted protein from the sample, e.g., digestion with proteinase K, or other like proteases. See, e.g., U.S. Pat. No. 7,001,724. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic acid isolation step, purification of nucleic acids can be performed after any step in the disclosed methods, such as to remove excess or unwanted reagents, reactants, or products. A variety of methods for determining the amount and/or purity of nucleic acids in a sample are available, such as by absorbance (e.g. absorbance of light at 260 nm, 280 nm, and a ratio of these) and detection of a label (e.g. fluorescent dyes and intercalating agents, such as SYBR green, SYBR blue, DAPI, propidium iodine, Hoechst stain, SYBR gold, ethidium bromide).

Where desired, polynucleotides from a sample may be fragmented prior to further processing. Fragmentation may be accomplished by any of a variety of methods, including chemical, enzymatic, and mechanical fragmentation. In some embodiments, the fragments have an average or median length from about 10 to about 1,000 nucleotides in length, such as between 10-800, 10-500, 50-500, 90-200, or 50-150 nucleotides. In some embodiments, the fragments have an average or median length of about or less than about 100, 200, 300, 500, 600, 800, 1000, or 1500 nucleotides. In some embodiments, the fragments range from about 90-200 nucleotides, and/or have an average length of about 150 nucleotides. In some embodiments, the fragmentation is accomplished mechanically comprising subjecting sample polynucleotides to acoustic sonication. In some embodiments, the fragmentation comprises treating the sample polynucleotides with one or more enzymes under conditions suitable for the one or more enzymes to generate double-stranded nucleic acid breaks. Examples of enzymes useful in the generation of polynucleotide fragments include sequence specific and non-sequence specific nucleases. Non-limiting examples of nucleases include DNase I, Fragmentase, restriction endonucleases, variants thereof, and combinations thereof. For example, digestion with DNase I can induce random double-stranded breaks in DNA in the absence of Mg++ and in the presence of Mn++. In some embodiments, fragmentation comprises treating the sample polynucleotides with one or more restriction endonucleases. Fragmentation can produce fragments having 5' overhangs, 3' overhangs, blunt ends, or a combination thereof. In some embodiments, such as when fragmentation comprises the use of one or more restriction endonucleases, cleavage of sample polynucleotides leaves overhangs having a predictable sequence. Fragmented polynucleotides may be subjected to a step of size selecting the fragments via standard methods such as column purification or isolation from an agarose gel.

According to some embodiments, polynucleotides among the plurality of polynucleotides from a sample are circularized. Circularization can include joining the 5' end of a polynucleotide to the 3' end of the same polynucleotide, to the 3' end of another polynucleotide in the sample, or to the 3' end of a polynucleotide from a different source (e.g. an artificial polynucleotide, such as an oligonucleotide adapter). In some embodiments, the 5' end of a polynucleotide is joined to the 3' end of the same polynucleotide (also referred to as "self-joining"). In some embodiment, conditions of the circularization reaction are selected to favor self-joining of polynucleotides within a particular range of lengths, so as to produce a population of circularized polynucleotides of a particular average length. For example, circularization reaction conditions may be selected to favor self-joining of polynucleotides shorter than about 5000, 2500, 1000, 750, 500, 400, 300, 200, 150, 100, 50, or fewer nucleotides in length. In some embodiments, fragments having lengths between 50-5000 nucleotides, 100-2500 nucleotides, or 150-500 nucleotides are favored, such that the average length of circularized polynucleotides falls within the respective range. In some embodiments, 80% or more of the circularized fragments are between 50-500 nucleotides in length, such as between 50-200 nucleotides in length. Reaction conditions that may be optimized include the length of time allotted for a joining reaction, the concentration of various reagents, and the concentration of polynucleotides to be joined. In some embodiments, a circularization reaction preserves the distribution of fragment lengths present in a sample prior to circularization. For example, one or more of the mean, median, mode, and standard deviation of fragment lengths in a sample before circularization and of circularized polynucleotides are within 75%, 80%, 85%, 90%, 95%, or more of one another.

In some cases, rather than preferentially forming self-joining circularization products, one or more adapter oligonucleotides are used, such that the 5' end and 3' end of a polynucleotide in the sample are joined by way of one or more intervening adapter oligonucleotides to form a circular polynucleotide. For example, the 5' end of a polynucleotide can be joined to the 3' end of an adapter, and the 5' end of the same adapter can be joined to the 3' end of the same polynucleotide. An adapter oligonucleotide includes any oligonucleotide having a sequence, at least a portion of which is known, that can be joined to a sample polynucleotide. Adapter oligonucleotides can comprise DNA, RNA, nucleotide analogues, non-canonical nucleotides, labeled nucleotides, modified nucleotides, or combinations thereof. Adapter oligonucleotides can be single-stranded, double-stranded, or partial duplex. In general, a partial-duplex adapter comprises one or more single-stranded regions and one or more double-stranded regions. Double-stranded adapters can comprise two separate oligonucleotides hybridized to one another (also referred to as an "oligonucleotide duplex"), and hybridization may leave one or more blunt ends, one or more 3' overhangs, one or more 5' overhangs, one or more bulges resulting from mismatched and/or unpaired nucleotides, or any combination of these. When two hybridized regions of an adapter are separated from one another by a non-hybridized region, a "bubble" structure results. Adapters of different kinds can be used in combination, such as adapters of different sequences. Different adapters can be joined to sample polynucleotides in sequential reactions or simultaneously. In some embodiments, identical adapters are added to both ends of a target polynucleotide. For example, first and second adapters can be added to the same reaction. Adapters can be manipulated prior to combining with sample polynucleotides. For example, terminal phosphates can be added or removed.

Where adapter oligonucleotides are used, the adapter oligonucleotides can contain one or more of a variety of sequence elements, including but not limited to, one or more amplification primer annealing sequences or complements thereof, one or more sequencing primer annealing sequences or complements thereof, one or more barcode sequences, one or more common sequences shared among multiple different adapters or subsets of different adapters, one or more restriction enzyme recognition sites, one or more overhangs complementary to one or more target polynucleotide overhangs, one or more probe binding sites (e.g. for attachment to a sequencing platform, such as a flow cell for massive parallel sequencing, such as flow cells as developed by Illumina, Inc.), one or more random or near-random sequences (e.g. one or more nucleotides selected at random from a set of two or more different nucleotides at one or more positions, with each of the different nucleotides selected at one or more positions represented in a pool of adapters comprising the random sequence), and combinations thereof. In some cases, the adapters may be used to purify those circles that contain the adapters, for example by using beads (particularly magnetic beads for ease of handling) that are coated with oligonucleotides comprising a complementary sequence to the adapter, that can "capture" the closed circles with the correct adapters by hybridization thereto, wash away those circles that do not contain the adapters and any unligated components, and then release the captured circles from the beads. In addition, in some cases, the complex of the hybridized capture probe and the target circle can be directly used to generate concatamers, such as by direct rolling circle amplification (RCA). In some embodiments, the adapters in the circles can also be used as a sequencing primer. Two or more sequence elements can be non-adjacent to one another (e.g. separated by one or more nucleotides), adjacent to one another, partially overlapping, or completely overlapping. For example, an amplification primer annealing sequence can also serve as a sequencing primer annealing sequence. Sequence elements can be located at or near the 3' end, at or near the 5' end, or in the interior of the adapter oligonucleotide. A sequence element may be of any suitable length, such as about or less than about 3, 4, 5, 6, 7, 8, 9, 10, 15, 20, 25, 30, 35, 40, 45, 50 or more nucleotides in length. Adapter oligonucleotides can have any suitable length, at least sufficient to accommodate the one or more sequence elements of which they are comprised. In some embodiments, adapters are about or less than about 10, 15, 20, 25, 30, 35, 40, 45, 50, 55, 60, 65, 70, 75, 80, 90, 100, 200, or more nucleotides in length. In some embodiments, an adapter oligonucleotide is in the range of about 12 to 40 nucleotides in length, such as about 15 to 35 nucleotides in length.

In some embodiments, the adapter oligonucleotides joined to fragmented polynucleotides from one sample comprise one or more sequences common to all adapter oligonucleotides and a barcode that is unique to the adapters joined to polynucleotides of that particular sample, such that the barcode sequence can be used to distinguish polynucleotides originating from one sample or adapter joining reaction from polynucleotides originating from another sample or adapter joining reaction. In some embodiments, an adapter oligonucleotide comprises a 5' overhang, a 3' overhang, or both that is complementary to one or more target polynucleotide overhangs. Complementary overhangs can be one or more nucleotides in length, including but not limited to 1, 2, 3, 4, 5, 6, 7, 8, 9, 10, 11, 12, 13, 14, 15, or more nucleotides in length. Complementary overhangs may comprise a fixed sequence. Complementary overhangs of an adapter oligonucleotide may comprise a random sequence of one or more nucleotides, such that one or more nucleotides are selected at random from a set of two or more different nucleotides at one or more positions, with each of the different nucleotides selected at one or more positions represented in a pool of adapters with complementary overhangs comprising the random sequence. In some embodiments, an adapter overhang is complementary to a target polynucleotide overhang produced by restriction endonuclease digestion. In some embodiments, an adapter overhang consists of an adenine or a thymine.

A variety of methods for circularizing polynucleotides are available. FIGS. 28A-28E illustrate non-limiting examples of methods for circularizing polynucleotides. In some embodiments, circularization comprises an enzymatic reaction, such as use of a ligase (e.g. an RNA or DNA ligase). A variety of ligases are available, including, but not limited to, Circligase™ (Epicentre; Madison, Wis.), RNA ligase, T4 RNA Ligase 1 (ssRNA Ligase, which works on both DNA and RNA). In addition, T4 DNA ligase can also ligate ssDNA if no dsDNA templates are present, although this is generally a slow reaction. Other non-limiting examples of ligases include NAD-dependent ligases including Taq DNA ligase, *Thermus filiformis* DNA ligase, *Escherichia coli* DNA ligase, Tth DNA ligase, *Thermus scotoductus* DNA ligase (I and II), thermostable ligase, Ampligase thermostable DNA ligase, VanC-type ligase, 9° N DNA Ligase, Tsp DNA ligase, and novel ligases discovered by bioprospecting; ATP-dependent ligases including T4 RNA ligase, T4 DNA ligase, T3 DNA ligase, T7 DNA ligase, Pfu DNA ligase, DNA ligase 1, DNA ligase III, DNA ligase IV, and novel ligases discovered by bioprospecting; and wild-type, mutant isoforms, and genetically engineered variants thereof. Where self-joining is desired, the concentration of polynucleotides and enzyme can be adjusted to facilitate the formation of intramolecular circles rather than intermolecular structures. Reaction temperatures and times can be adjusted as well. In some embodiments, 60° C. is used to facilitate intramolecular circles. In some embodiments, reaction times are between 12-16 hours. Reaction conditions may be those specified by the manufacturer of the selected enzyme. In some embodiments, an exonuclease step can be included to digest any unligated nucleic acids after the circularization reaction. That is, closed circles do not contain a free 5' or 3' end, and thus the introduction of a 5' or 3' exonuclease will not digest the closed circles but will digest the unligated components. This may find particular use in multiplex systems.

In general, joining ends of a polynucleotide to one-another to form a circular polynucleotide (either directly, or with one or more intermediate adapter oligonucleotides) produces a junction having a junction sequence. Where the 5' end and 3' end of a polynucleotide are joined via an adapter polynucleotide, the term "junction" can refer to a junction between the polynucleotide and the adapter (e.g. one of the 5' end junction or the 3' end junction), or to the junction between the 5' end and the 3' end of the polynucleotide as formed by and including the adapter polynucleotide. Where the 5' end and the 3' end of a polynucleotide are joined without an intervening adapter (e.g. the 5' end and 3' end of a single-stranded DNA), the term "junction" refers to the point at which these two ends are joined. A junction may be identified by the sequence of nucleotides comprising the junction (also referred to as the "junction sequence"). In some embodiments, samples comprise polynucleotides having a mixture of ends formed by natural degradation processes (such as cell lysis, cell death, and other processes by which DNA is released from a cell to its surrounding environment in which it may be further degraded, such as in cell-free polynucleotides, such as cell-free DNA and cell-free RNA), fragmentation that is a byproduct of sample processing (such as fixing, staining, and/or storage procedures), and fragmentation by methods that cleave DNA without restriction to specific target sequences (e.g. mechanical fragmentation, such as by sonication; non-sequence specific nuclease treatment, such as DNase I, fragmentase). Where samples comprise polynucleotides having a mixture of ends, the likelihood that two polynucleotides will have the same 5' end or 3' end is low, and the likelihood that two polynucleotides will independently have both the same 5' end and 3' end is extremely low. Accordingly, in some embodiments, junctions may be used to distinguish different polynucleotides, even where the two polynucleotides comprise a portion having the same target sequence. Where polynucleotide ends are joined without an intervening adapter, a junction sequence may be identified by alignment to a reference sequence. For example, where the order of two component sequences appears to be reversed with respect to the reference sequence, the point at which the reversal appears to occur may be an indication of a junction at that point. Where polynucleotide ends are joined via one or more adapter sequences, a junction may be identified by proximity to the known adapter sequence, or by alignment as above if a sequencing read is of sufficient length to obtain sequence from both the 5' and 3' ends of the circularized polynucleotide. In some embodiments, the formation of a particular junction is a sufficiently rare event such that it is unique among the circularized polynucleotides of a sample.

Figure 2:
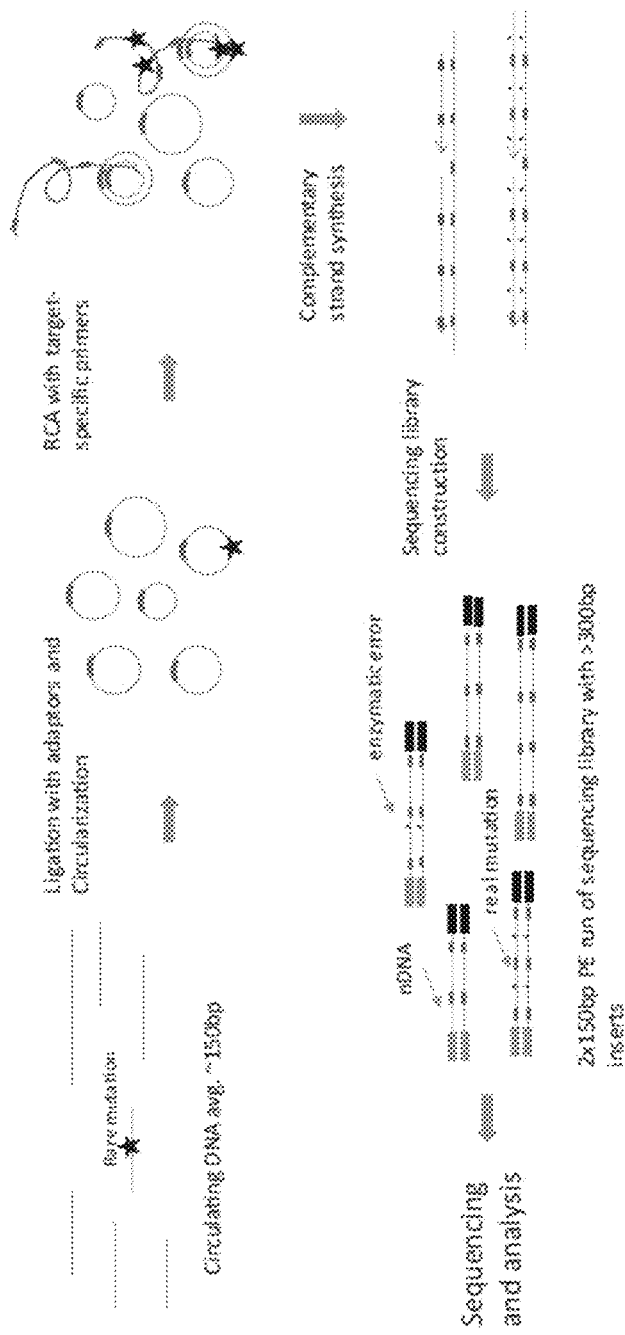
FIG. 2 depicts a similar strategy as FIG. 1 but with the addition of adapters to facilitate polynucleotide circularization.
Figure 3:
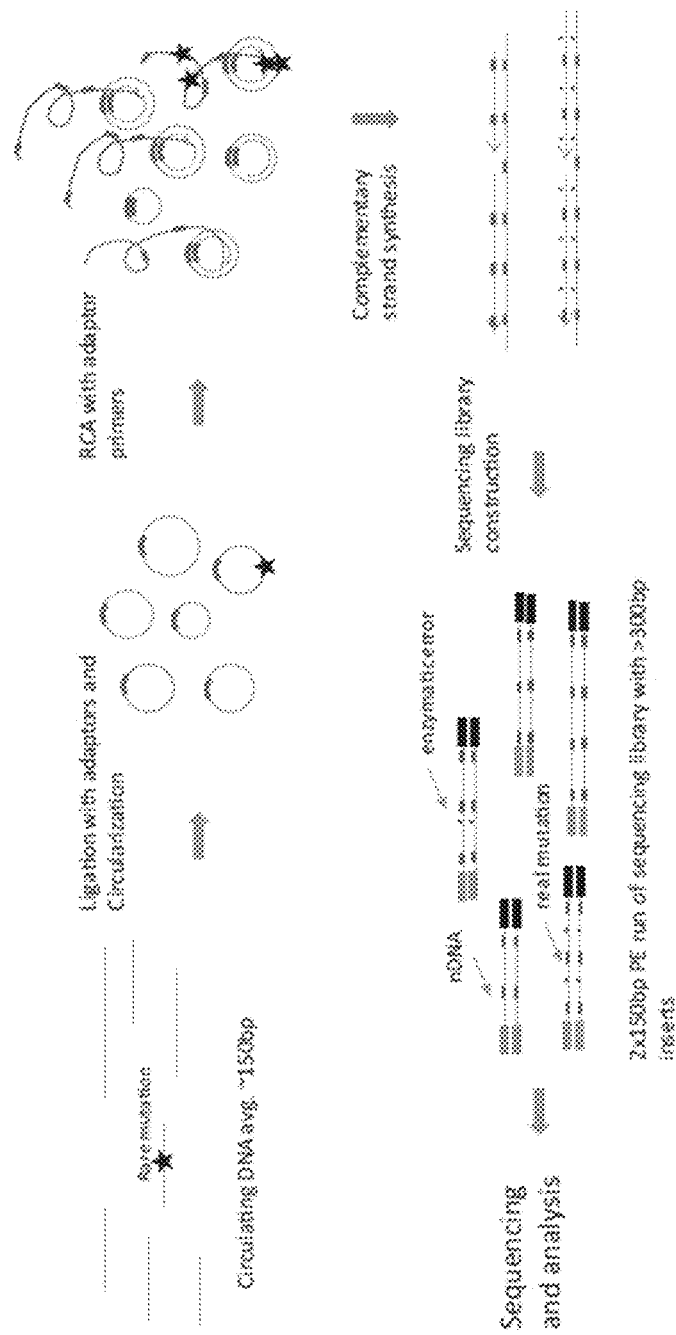
FIG. 3 is similar to FIG. 2 except adapter primers are used in amplification.
Figure 4A:
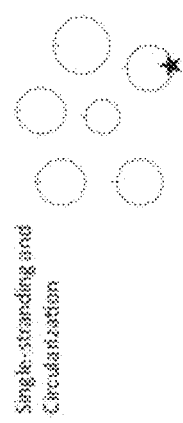
FIGS. 4A-4C depict three embodiments associated with the formation of circularized single-stranded (ss) DNA. At the top, single-stranded DNA (ssDNA) is circularized in the absence of adapters, while the middle scheme depicts the use of adapters, and the bottom scheme utilizes two adapter oligos (yielding different sequences on each end) and may further include a splint oligo that hybridizes to both adapters to bring the two ends in proximity.
Figure 4B:
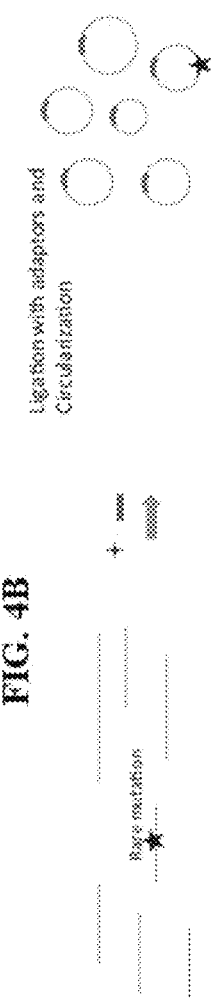
Figure 4C:
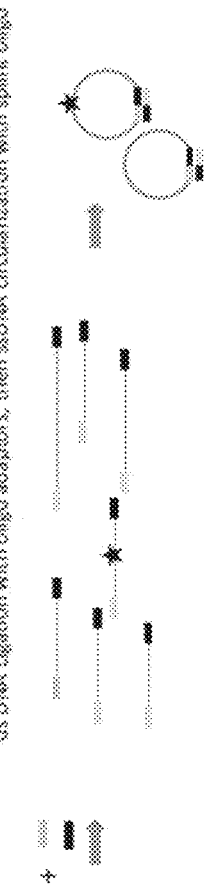

FIGS. 4A-4C illustrate three non-limiting examples of methods of circularizing polynucleotides. At the top (FIG. 4A), the polynucleotides are circularized in the absence of adapters, while the middle scheme (FIG. 4B) depicts the use of adapters, and the bottom scheme (FIG. 4C) utilizes two adapters. Where two adapters are used, one can be joined to the 5' end of the polynucleotide while the second adapter can be joined to the 3' end of the same polynucleotide. In some embodiments, adapter ligation may comprise use of two different adapters along with a "splint" nucleic acid that is complementary to the two adapters to facilitate ligation. Forked or "Y" adapters may also be used. Where two adapters are used, polynucleotides having the same adapter at both ends may be removed in subsequent steps due to self-annealing. FIGS. 1-3 depict embodiments of methods according to the present disclosure wherein polynucleotides are circularized in the absence of adaptors (FIG. 1) and in the presence of adaptors (FIGS. 2 and 3). Circularized polynucleotides with adaptors (FIGS. 2 and 3) can be amplified by rolling circle amplification (RCA) using target specific primers (FIG. 2) or primers which hybridize to the adaptor sequences (FIG. 3).

Figure 8:
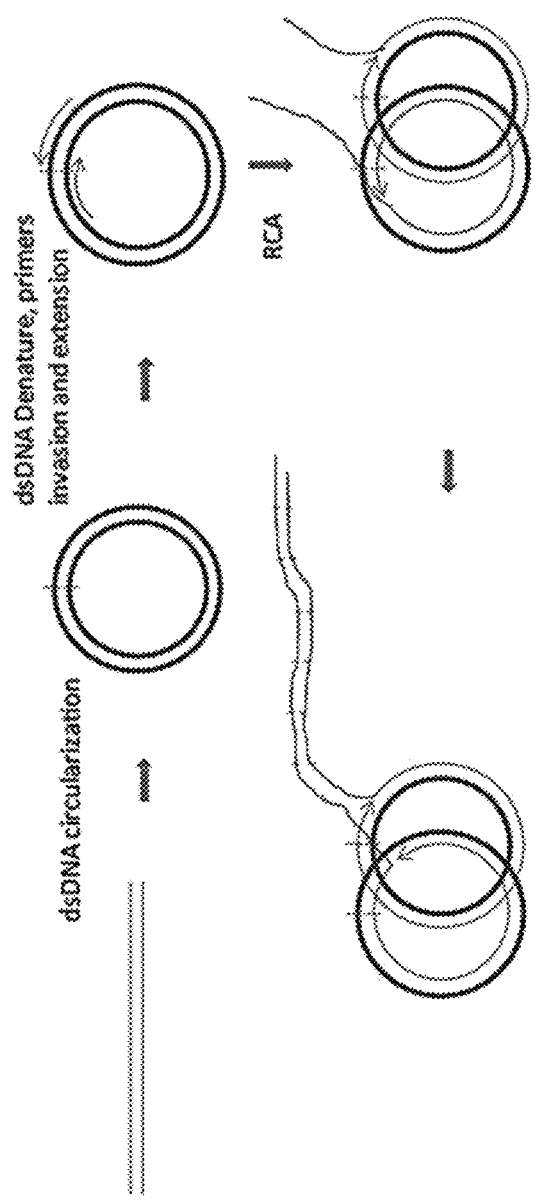
FIG. 8 depicts an example of double stranded DNA circularization and amplification, such that both strands are amplified, in accordance with an embodiment.

FIGS. 6A-6B illustrate further non-limiting example methods of circularizing polynucleotides, such as single-stranded DNA. The adapter can be asymmetrically added to either the 5' or 3' end of a polynucleotide. As shown in FIG. 6A, the single-stranded DNA (ssDNA) can have a free hydroxyl group at the 3' end, and the adapter can have a blocked 3' end such that in the presence of a ligase, a preferred reaction joins the 3' end of the ssDNA to the 5' end of the adapter. In this embodiment, it can be useful to use agents such as polyethylene glycols (PEGs) to drive the intermolecular ligation of a single ssDNA fragment and a single adapter, prior to an intramolecular ligation to form a circle. The reverse order of ends can also be done (blocked 3', free 5', etc.). Once the linear ligation is accomplished, the ligated pieces can be treated with an enzyme to remove the blocking moiety, such as through the use of a kinase or other suitable enzymes or chemistries. Once the blocking moiety is removed, the addition of a circularization enzyme, such as CircLigase, allows an intramolecular reaction to form the circularized polynucleotide. As shown in FIG. 6B, by using a double-stranded adapter with one strand having a 5' or 3' end blocked, a double stranded structure can be formed, which upon ligation produces a double-stranded fragment with nicks. The two strands can then be separated, the blocking moiety removed, and the single-stranded fragment circularized to form a circularized polynucleotide. In some cases, as illustrated in FIG. 8, double-stranded DNA (dsDNA) is circularized to yield a circularized, double-stranded circle. The double-stranded circle can be denatured to allow for primer binding and amplification of both strands.

Figure 5:
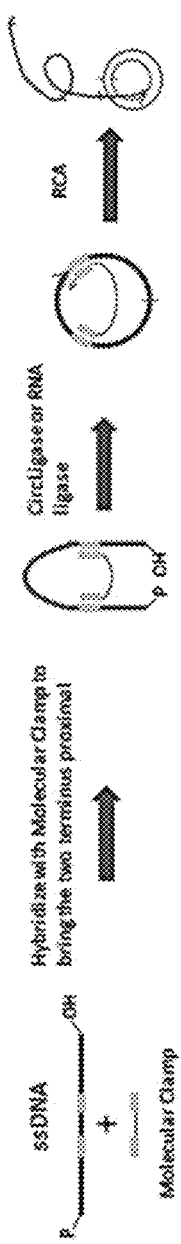
FIG. 5 depicts an embodiment for circularizing specific targets through the use of a "molecular clamp" to bring the two ends of the single stranded DNA into spatial proximity for ligation.

In some embodiments, molecular clamps are used to bring two ends of a polynucleotide (e.g. a single-stranded DNA) together in order to enhance the rate of intramolecular circularization. An example illustration of one such process is provided in FIG. 5. This can be done with or without adapters. The use of molecular clamps may be particularly useful in cases where the average polynucleotide fragment is greater than about 100 nucleotides in length. In some embodiments, the molecular clamp probe comprises three domains: a first domain, an intervening domain, and a second domain. The first and second domains will hybridize to corresponding sequences in a target polynucleotide via sequence complementarity. The intervening domain of the molecular clamp probe may not significantly hybridize with the target sequence. The hybridization of the clamp with the target polynucleotide thus can bring the two ends of the target sequence into closer proximity, which facilitates the intramolecular circularization of the target sequence in the presence of a circularization enzyme. In some embodiments, this is additionally useful as the molecular clamp can serve as an amplification primer as well.

After circularization, ligation enzymes are removed from reaction products using a protein degradation step. In some embodiments, protein degradation comprises treatment to remove or degrade ligase used in the circularization reaction. In some embodiments, treatment to degrade ligase comprises treatment with a protease, such as proteinase K. Proteinase K treatment may follow manufacturer protocols or standard protocols (e.g. as provided in Sambrook and Green, Molecular Cloning: A Laboratory Manual, 4th Edition (2012)). In some embodiments, protein degradation comprises treatment with a low pH or acidic solution or buffer. In some embodiments, protein degradation comprises heating the reaction, for example heating the reaction above 55° C., above 60° C., above 65° C., above 70° C., or greater. In some embodiments, linear polynucleotides are degraded, after circularization. In some embodiments, linear polynucleotides are degraded using an exonuclease. In some embodiments, the exonuclease comprises a lambda exonuclease. In some embodiments, the exonuclease comprises a RecJf nuclease. In some embodiments, an exonuclease is selected from at least one of ExoI, ExoIII, ExoV, ExoVII, and ExoT.

Circularization may be followed directly by sequencing the circularized polynucleotides. Alternatively, sequencing may be preceded by one or more amplification reactions. In general, "amplification" refers to a process by which one or more copies are made of a target polynucleotide or a portion thereof. A variety of methods of amplifying polynucleotides (e.g. DNA and/or RNA) are available. Amplification may be linear, exponential, or involve both linear and exponential phases in a multi-phase amplification process. Amplification methods may involve changes in temperature, such as a heat denaturation step, or may be isothermal processes that do not require heat denaturation. The polymerase chain reaction (PCR) uses multiple cycles of denaturation, annealing of primer pairs to opposite strands, and primer extension to exponentially increase copy numbers of the target sequence. Denaturation of annealed nucleic acid strands may be achieved by the application of heat, increasing local metal ion concentrations (e.g. U.S. Pat. No. 6,277,605), ultrasound radiation (e.g. WO/2000/049176), application of voltage (e.g. U.S. Pat. Nos. 5,527,670, 6,033,850, 5,939,291, and 6,333,157), and application of an electromagnetic field in combination with primers bound to a magnetically-responsive material (e.g. U.S. Pat. No. 5,545,540). In a variation called RT-PCR, reverse transcriptase (RT) is used to make a complementary DNA (cDNA) from RNA, and the cDNA is then amplified by PCR to produce multiple copies of DNA (e.g. U.S. Pat. Nos. 5,322,770 and 5,310,652). One example of an isothermal amplification method is strand displacement amplification, commonly referred to as SDA, which uses cycles of annealing pairs of primer sequences to opposite strands of a target sequence, primer extension in the presence of a dNTP to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product (e.g. U.S. Pat. Nos. 5,270,184 and 5,455,166). Thermophilic SDA (tSDA) uses thermophilic endonucleases and polymerases at higher temperatures in essentially the same method (European Pat. No. 0 684 315). Other amplification methods include rolling circle amplification (RCA) (e.g., Lizardi, "Rolling Circle Replication Reporter Systems," U.S. Pat. No. 5,854,033); helicase dependent amplification (HDA) (e.g., Kong et al., "Helicase Dependent Amplification Nucleic Acids," U.S. Pat. Appln. Pub. No. US 2004-0058378 A1); and loop-mediated isothermal amplification (LAMP) (e.g., Notomi et al., "Process for Synthesizing Nucleic Acid," U.S. Pat. No. 6,410,278). In some cases, isothermal amplification utilizes transcription by an RNA polymerase from a promoter sequence, such as may be incorporated into an oligonucleotide primer. Transcription-based amplification methods include nucleic acid sequence based amplification, also referred to as NASBA (e.g. U.S. Pat. No. 5,130,238); methods which rely on the use of an RNA replicase to amplify the probe molecule itself, commonly referred to as Qβ replicase (e.g., Lizardi, P. et al. (1988) BioTechnol. 6, 1197-1202); self-sustained sequence replication (e.g., Guatelli, J. et al. (1990) Proc. Natl. Acad. Sci. USA 87, 1874-1878; Landgren (1993) Trends in Genetics 9, 199-202; and HELEN H. LEE et al., NUCLEIC ACID AMPLIFICATION TECHNOLOGIES (1997)); and methods for generating additional transcription templates (e.g. U.S. Pat. Nos. 5,480,784 and 5,399,491). Further methods of isothermal nucleic acid amplification include the use of primers containing non-canonical nucleotides (e.g. uracil or RNA nucleotides) in combination with an enzyme that cleaves nucleic acids at the non-canonical nucleotides (e.g. DNA glycosylase or RNaseH) to expose binding sites for additional primers (e.g. U.S. Pat. Nos. 6,251,639, 6,946,251, and 7,824,890). Isothermal amplification processes can be linear or exponential.

In some embodiments, amplification comprises rolling circle amplification (RCA). A typical RCA reaction mixture comprises one or more primers, a polymerase, and dNTPs, and produces concatemers. Typically, the polymerase in an RCA reaction is a polymerase having strand-displacement activity. A variety of such polymerases are available, non-limiting examples of which include exonuclease minus DNA Polymerase I large (Klenow) Fragment, Phi29 DNA polymerase, Taq DNA Polymerase and the like. In general, a concatemer is a polynucleotide amplification product comprising two or more copies of a target sequence from a template polynucleotide (e.g. about or more than about 2, 3, 4, 5, 6, 7, 8, 9, 10, or more copies of the target sequence; in some embodiments, about or more than about 2 copies). Amplification primers may be of any suitable length, such as about or at least about 5, 10, 15, 20, 25, 30, 35, 40, 45, 50, 55, 60, 65, 70, 75, 80, 90, 100, or more nucleotides, any portion or all of which may be complementary to the corresponding target sequence to which the primer hybridizes (e.g. about, or at least about 5, 10, 15, 20, 25, 30, 35, 40, 45, 50, or more nucleotides). FIGS. 7A-7C depicts three non-limiting examples of suitable primers. FIG. 7A shows the use of no adapters and a target specific primer, which can be used for the detection of the presence or absence of a sequence variant within specific target sequences. In some embodiments, multiple target-specific primers for a plurality of targets are used in the same reaction. For example, target-specific primers for about or at least about 10, 50, 100, 150, 200, 250, 300, 400, 500, 1000, 2500, 5000, 10000, 15000, or more different target sequences may be used in a single amplification reaction in order to amplify a corresponding number of target sequences (if present) in parallel. Multiple target sequences may correspond to different portions of the same gene, different genes, or non-gene sequences. Where multiple primers target multiple target sequences in a single gene, primers may be spaced along the gene sequence (e.g. spaced apart by about or at least about 50 nucleotides, every 50-150 nucleotides, or every 50-100 nucleotides) in order to cover all or a specified portion of a target gene. FIG. 7C illustrates use of a primer that hybridizes to an adapter sequence (which in some cases may be an adapter oligonucleotide itself).

FIG. 7B illustrates an example of amplification by random primers. In general, a random primer comprises one or more random or near-random sequences (e.g. one or more nucleotides selected at random from a set of two or more different nucleotides at one or more positions, with each of the different nucleotides selected at one or more positions represented in a pool of adapters comprising the random sequence). In this way, polynucleotides (e.g. all or substantially all circularized polynucleotides) can be amplified in a sequence non-specific fashion. Such procedures may be referred to as "whole genome amplification" (WGA); however, typical WGA protocols (which do not involve a circularization step) do not efficiently amplify short polynucleotides, such as polynucleotide fragments contemplated by the present disclosure. For further illustrative discussion of WGA procedures, see for example Li et al (2006) J Mol. Diagn. 8(1):22-30.

Where circularized polynucleotides are amplified prior to sequencing, amplified products may be subjected to sequencing directly without enrichment, or subsequent to one or more enrichment steps. Enrichment may comprise purifying one or more reaction components, such as by retention of amplification products or removal of one or more reagents. For example, amplification products may be purified by hybridization to a plurality of probes attached to a substrate, followed by release of captured polynucleotides, such as by a washing step. Alternatively, amplification products can be labeled with a member of a binding pair followed by binding to the other member of the binding pair attached to a substrate, and washing to release the amplification product. Possible substrates include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, ceramics, resins, silica or silica-based materials including silicon and modified silicon, carbon, metals, inorganic glasses, plastics, optical fiber bundles, and a variety of other polymers. In some embodiments, the substrate is in the form of a bead or other small, discrete particle, which may be a magnetic or paramagnetic bead to facilitate isolation through application of a magnetic field. In general, "binding pair" refers to one of a first and a second moiety, wherein the first and the second moiety have a specific binding affinity for each other. Suitable binding pairs include, but are not limited to, antigens/antibodies (for example, digoxigenin/anti-digoxigenin, dinitrophenyl (DNP)/anti-DNP, dansyl-X-anti-dansyl, Fluorescein/anti-fluorescein, lucifer yellow/anti-lucifer yellow, and rhodamine anti-rhodamine); biotin/avidin (or biotin/streptavidin); calmodulin binding protein (CBP)/calmodulin; hormone/hormone receptor; lectin/carbohydrate; peptide/cell membrane receptor; protein A/antibody; hapten/antihapten; enzyme/cofactor; and enzyme/substrate.

Figure 10:
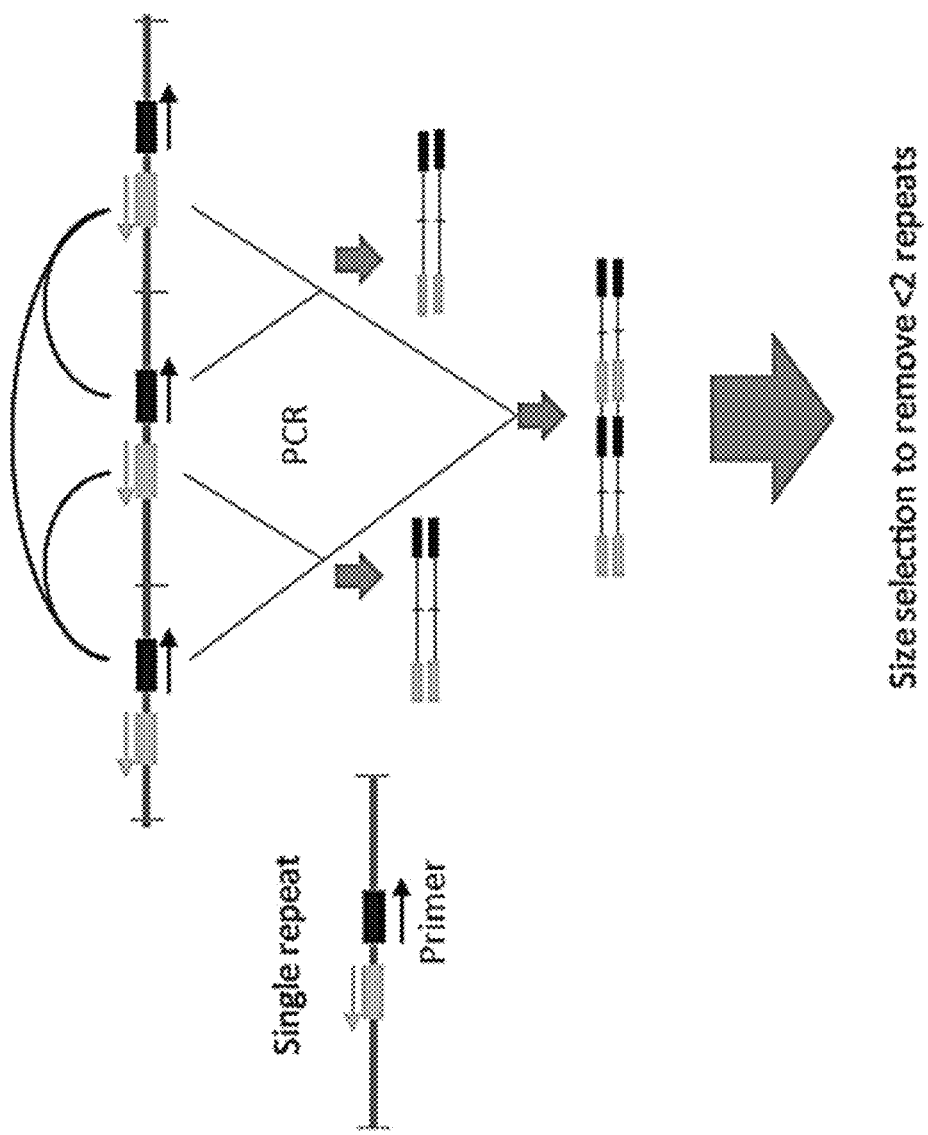
FIG. 10 shows a PCR method in accordance with an embodiment that promotes sequencing of circular polynucleotides or strands containing at least two copies of a target nucleic acid sequence, using a pair of primers that are oriented away from one another when aligned within a monomer of the target sequence (also referred to as "back to back," e.g. oriented in two directions but not on the ends of the domain to be amplified). In some embodiments, these primer sets are used after concatamers are formed to promote amplicons to be higher multimers, e.g. dimers, timers, etc., of the target sequence. Optionally, the method can further include a size selection to remove amplicons that are smaller than dimers.
Figures 13A, 13B, 13C:
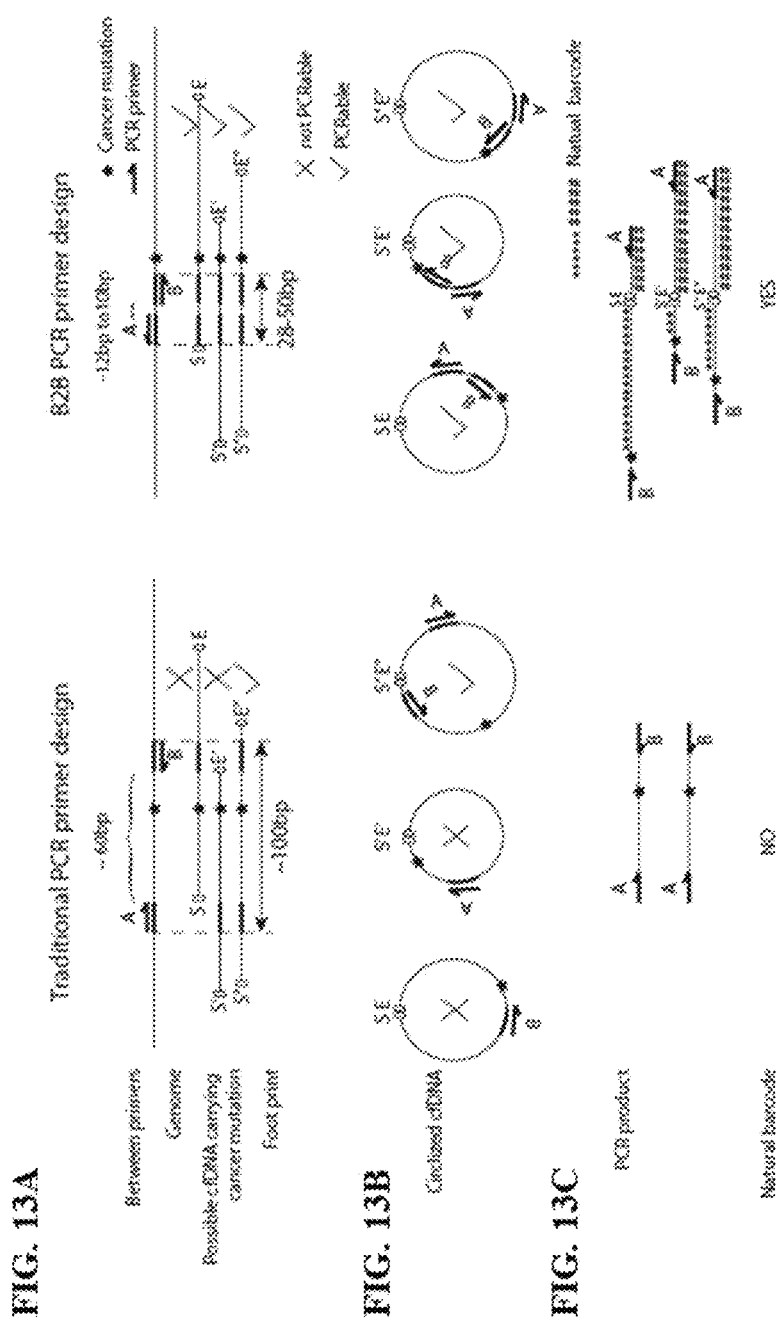
FIGS. 13A-C provide an illustration of example advantages of back-to-back (B2B) primer design compared to traditional PCR primer design. Traditional PCR primer design (left) places the primers (arrows, A and B) in the region flanking a target sequence, which may be a hotspot for mutations (black stars), and they are typically at least 60 base pairs (bp) apart, resulting a typical footprint of about 100 bp. In this illustration, the B2B primer design (right) places primers on one side of the target sequence. The two B2B primers are facing to the opposite directions, any may overlap (e.g. about or less than about 12 bp, 10 bp, 5 bp, or less). Depending on B2B primer lengths, the total footprint in this illustration can be between 28-50 bp. Due to the larger footprint, fragmentation events are more likely to disrupt primer binding in the traditional design, leading to loss of sequence information, whether for linear fragments (FIG. 13A), circularized DNA (FIG. 13B), or amplification products (FIG. 13C). Moreover, as illustrated in FIG. 13C, the B2B primer design captures junction sequences (also referred to as a "natural barcode") which can be used to distinguish different polynucleotides.
Figure 14:
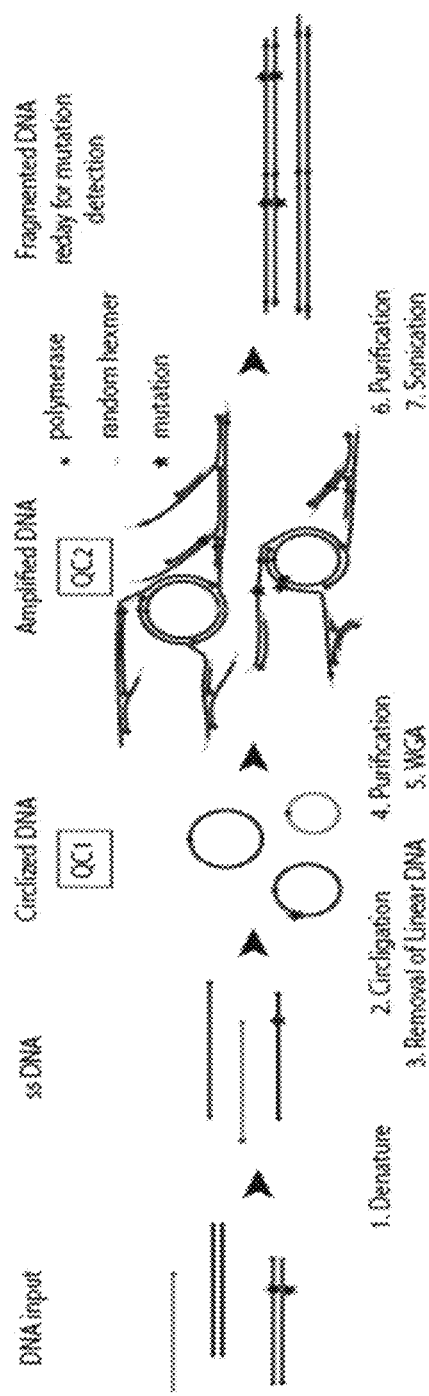
FIG. 14 Illustrates a method for generating templates for detecting sequence variants, in accordance with an embodiment (e.g. an example implementation of a process using circularized polynucleotides). DNA input is denatured into ssDNA, circularized by ligation, and non-circularized DNA is degraded by exonuclease digestion. Ligation efficiency is quantified by quantitative PCR (qPCR), comparing input DNA and circularized DNA amounts, typically yielding a ligation efficiency of at least about 80%. Circularized DNA is purified to exchange buffer, followed by whole genome amplification (WGA) with random primers and Phi29 polymerase. WGA products are purified, and products are fragmented (e.g. by sonication) into short fragments of about or less than about 400 bp. The on-target rate of amplified DNA is quantified by qPCR comparing the same amount of reference genome DNA to amplified DNA, typically showing an average on-target rate of about or more than about 95%.

In some embodiments, enrichment following amplification of circularized polynucleotides comprises one or more additional amplification reactions. In some embodiments, enrichment comprises amplifying a target sequence comprising sequence A and sequence B (oriented in a 5' to 3' direction) in an amplification reaction mixture comprising (a) the amplified polynucleotide; (b) a first primer comprising sequence A', wherein the first primer specifically hybridizes to sequence A of the target sequence via sequence complementarity between sequence A and sequence A'; (c) a second primer comprising sequence B, wherein the second primer specifically hybridizes to sequence B' present in a complementary polynucleotide comprising a complement of the target sequence via sequence complementarity between B and B'; and (d) a polymerase that extends the first primer and the second primer to produce amplified polynucleotides; wherein the distance between the 5' end of sequence A and the 3' end of sequence B of the target sequence is 75 nt or less. FIG. 10 illustrates an example arrangement of the first and second primer with respect to a target sequence in the context of a single repeat (which will typically not be amplified unless circular) and concatemers comprising multiple copies of the target sequence. Given the orientation of the primers with respect to a monomer of the target sequence, this arrangement may be referred to as "back to back" (B2B) or "inverted" primers. Amplification with B2B primers facilitates enrichment of circular and/or concatemeric amplification products. Moreover, this orientation combined with a relatively smaller footprint (total distance spanned by a pair of primers) permits amplification of a wider variety of fragmentation events around a target sequence, as a junction is less likely to occur between primers than in the arrangement of primers found in a typical amplification reaction (facing one another, spanning a target sequence). Additional embodiments and advantages of back to back primers are illustrated in FIGS. 13A-13C.

In some embodiments, the distance between the 5' end of sequence A and the 3' end of sequence B is about or less than about 200, 150, 100, 75, 50, 40, 30, 25, 20, 15, or fewer nucleotides. In some embodiments, sequence A is the complement of sequence B. In some embodiments, multiple pairs of B2B primers directed to a plurality of different target sequences are used in the same reaction to amplify a plurality of different target sequences in parallel (e.g. about or at least about 10, 50, 100, 150, 200, 250, 300, 400, 500, 1000, 2500, 5000, 10000, 15000, or more different target sequences). Primers can be of any suitable length, such as described elsewhere herein. Amplification may comprise any suitable amplification reaction under appropriate conditions, such as an amplification reaction described herein. In some embodiments, amplification is a polymerase chain reaction.

In some embodiments, B2B primers comprise at least two sequence elements, a first element that hybridizes to a target sequence via sequence complementarity, and a 5' "tail" that does not hybridize to the target sequence during a first amplification phase at a first hybridization temperature during which the first element hybridizes (e.g. due to lack of sequence complementarity between the tail and the portion of the target sequence immediately 3' with respect to where the first element binds). For example, the first primer comprises sequence C 5' with respect to sequence A', the second primer comprises sequence D 5' with respect to sequence B, and neither sequence C nor sequence D hybridize to the plurality of concatemers during a first amplification phase at a first hybridization temperature. In some embodiments in which such tailed primers are used, amplification can comprise a first phase and a second phase; the first phase comprises a hybridization step at a first temperature, during which the first and second primers hybridize to the concatemers (or circularized polynucleotides) and primer extension; and the second phase comprises a hybridization step at a second temperature that is higher than the first temperature, during which the first and second primers hybridize to amplification products comprising extended first or second primers, or complements thereof, and primer extension. The higher temperature favors hybridization between the first element and tail element of the primer in primer extension products over shorter fragments formed by hybridization between only the first element in a primer and an internal target sequence within a concatemer. Accordingly, the two-phase amplification may be used to reduce the extent to which short amplification products might otherwise be favored, thereby maintaining a relatively higher proportion of amplification products having two or more copies of a target sequence. For example, after 5 cycles (e.g. at least 5, 6, 7, 8, 9, 10, 15, 20, or more cycles) of hybridization at the second temperature and primer extension, at least 5% (e.g. at least 5%, 6%, 7%, 8%, 9%, 10%, 15%, 20%, 25%, 30%, or more) of amplified polynucleotides in the reaction mixture comprise two or more copies of the target sequence. An illustration of an embodiment in accordance with this two-phase, tailed B2B primer amplification process is illustrated in FIGS. 11A-11D.

In some embodiments, enrichment comprise amplification under conditions that are skewed to increase the length of amplicons from concatemers. For example, the primer concentration can be lowered, such that not every priming site will hybridize a primer, thus making the PCR products longer. Similarly, decreasing the primer hybridization time during the cycles will similarly allow fewer primers to hybridize, thus also making the average PCR amplicon size increase. Furthermore, increasing the temperature and/or extension time of the cycles may similarly increase the average length of the PCR amplicons. Any combination of these techniques can be used.

In some embodiments, particularly where an amplification with B2B primers has been performed, amplification products are treated to filter the resulting amplicons on the basis of size to reduce and/or eliminate the number of monomers a mixture comprising concatemers. This can be done using a variety of available techniques, including, but not limited to, fragment excision from gels and gel filtration (e.g. to enrich for fragments larger than about 300, 400, 500, or more nucleotides in length); as well as SPRI beads (Agencourt AMPure XP) for size selection by fine-tuning the binding buffer concentration. For example, the use of 0.6× binding buffer during mixing with DNA fragments may be used to preferentially bind DNA fragments larger than about 500 base pairs (bp).

In some embodiments, where amplification result in single-stranded concatamers, the single strands are converted to double-stranded constructs either prior to or as part of the formation of sequencing libraries that are generated for sequencing reactions. A variety of suitable methods to generate a double-stranded construct from a single-stranded nucleic acid are available. A number of possible methods are depicted in FIGS. 9A-9D, although a number of other methods can be used as well. As shown in FIG. 9A, for example, the use of random primers, polymerase, dNTPs and a ligase will result in double strands. FIG. 9B depicts the second strand synthesis when the concatamer contains adapter sequences, which can be used as the primers in the reaction. FIG. 9C depicts the use of a "loop," where one terminus of the loop adapter is added to the terminus of the concatamers, wherein the loop adapter has a small section of self-hybridizing nucleic acids. In this case, the ligation of the loop adapter results in the loop that is self hybridized and serves as the polymerase primer template. FIG. 9D shows the use of hyper-branching primers, generally of the most use in cases where the target sequence is known, where multiple strands are formed, particularly when a polymerase with a strong strand displacement function is used.

According to some embodiments, circularized polynucleotides (or amplification products thereof, which may have optionally been enriched) are subjected to a sequencing reaction to generate sequencing reads. Sequencing reads produced by such methods may be used in accordance with other methods disclosed herein. A variety of sequencing methodologies are available, particularly high-throughput sequencing methodologies. Examples include, without limitation, sequencing systems manufactured by Illumina (sequencing systems such as HiSeq® and MiSeq®), Life Technologies (Ion Torrent®, SOLiD®, etc.), Roche's 454 Life Sciences systems, Pacific Biosciences systems, etc. In some embodiments, sequencing comprises use of HiSeq® and MiSeq® systems to produce reads of about or more than about 50, 75, 100, 125, 150, 175, 200, 250, 300, or more nucleotides in length. In some embodiments, sequencing comprises a sequencing by synthesis process, where individual nucleotides are identified iteratively, as they are added to the growing primer extension product. Pyrosequencing is an example of a sequence by synthesis process that identifies the incorporation of a nucleotide by assaying the resulting synthesis mixture for the presence of by-products of the sequencing reaction, namely pyrophosphate. In particular, a primer/template/polymerase complex is contacted with a single type of nucleotide. If that nucleotide is incorporated, the polymerization reaction cleaves the nucleoside triphosphate between the $\alpha$ and $\beta$ phosphates of the triphosphate chain, releasing pyrophosphate. The presence of released pyrophosphate is then identified using a chemiluminescent enzyme reporter system that converts the pyrophosphate, with AMP, into ATP, then measures ATP using a luciferase enzyme to produce measurable light signals. Where light is detected, the base is incorporated, where no light is detected, the base is not incorporated. Following appropriate washing steps, the various bases are cyclically contacted with the complex to sequentially identify subsequent bases in the template sequence. See, e.g., U.S. Pat. No. 6,210,891.

In related sequencing processes, the primer/template/polymerase complex is immobilized upon a substrate and the complex is contacted with labeled nucleotides. The immobilization of the complex may be through the primer sequence, the template sequence and/or the polymerase enzyme, and may be covalent or noncovalent. For example, immobilization of the complex can be via a linkage between the polymerase or the primer and the substrate surface. In alternate configurations, the nucleotides are provided with and without removable terminator groups. Upon incorporation, the label is coupled with the complex and is thus detectable. In the case of terminator bearing nucleotides, all four different nucleotides, bearing individually identifiable labels, are contacted with the complex. Incorporation of the labeled nucleotide arrests extension, by virtue of the presence of the terminator, and adds the label to the complex, allowing identification of the incorporated nucleotide. The label and terminator are then removed from the incorporated nucleotide, and following appropriate washing steps, the process is repeated. In the case of non-terminated nucleotides, a single type of labeled nucleotide is added to the complex to determine whether it will be incorporated, as with pyrosequencing. Following removal of the label group on the nucleotide and appropriate washing steps, the various different nucleotides are cycled through the reaction mixture in the same process. See, e.g., U.S. Pat. No. 6,833,246, incorporated herein by reference in its entirety for all purposes. For example, the Illumina Genome Analyzer System is based on technology described in WO 98/44151, wherein DNA molecules are bound to a sequencing platform (flow cell) via an anchor probe binding site (otherwise referred to as a flow cell binding site) and amplified in situ on a glass slide. A solid surface on which DNA molecules are amplified typically comprise a plurality of first and second bound oligonucleotides, the first complementary to a sequence near or at one end of a target polynucleotide and the second complementary to a sequence near or at the other end of a target polynucleotide. This arrangement permits bridge amplification, such as described in US20140121116. The DNA molecules are then annealed to a sequencing primer and sequenced in parallel base-by-base using a reversible terminator approach. Hybridization of a sequencing primer may be preceded by cleavage of one strand of a double-stranded bridge polynucleotide at a cleavage site in one of the bound oligonucleotides anchoring the bridge, thus leaving one single strand not bound to the solid substrate that may be removed by denaturing, and the other strand bound and available for hybridization to a sequencing primer. Typically, the Illumina Genome Analyzer System utilizes flow-cells with 8 channels, generating sequencing reads of 18 to 36 bases in length, generating >1.3 Gbp of high quality data per run (see www.illumina.com).

In yet a further sequence by synthesis process, the incorporation of differently labeled nucleotides is observed in real time as template dependent synthesis is carried out. In particular, an individual immobilized primer/template/polymerase complex is observed as fluorescently labeled nucleotides are incorporated, permitting real time identification of each added base as it is added. In this process, label groups are attached to a portion of the nucleotide that is cleaved during incorporation. For example, by attaching the label group to a portion of the phosphate chain removed during incorporation, i.e., a $\beta$, $\gamma$, or other terminal phosphate group on a nucleoside polyphosphate, the label is not incorporated into the nascent strand, and instead, natural DNA is produced. Observation of individual molecules typically involves the optical confinement of the complex within a very small illumination volume. By optically confining the complex, one creates a monitored region in which randomly diffusing nucleotides are present for a very short period of time, while incorporated nucleotides are retained within the observation volume for longer as they are being incorporated. This results in a characteristic signal associated with the incorporation event, which is also characterized by a signal profile that is characteristic of the base being added. In related aspects, interacting label components, such as fluorescent resonant energy transfer (FRET) dye pairs, are provided upon the polymerase or other portion of the complex and the incorporating nucleotide, such that the incorporation event puts the labeling components in interactive proximity, and a characteristic signal results, that is again, also characteristic of the base being incorporated (See, e.g., U.S. Pat. Nos. 6,917,726, 7,033,764, 7,052,847, 7,056,676, 7,170,050, 7,361,466, and 7,416,844; and US 20070134128).

In some embodiments, the nucleic acids in the sample can be sequenced by ligation. This method typically uses a DNA ligase enzyme to identify the target sequence, for example, as used in the polony method and in the SOLiD technology (Applied Biosystems, now Invitrogen). In general, a pool of all possible oligonucleotides of a fixed length is provided, labeled according to the sequenced position. Oligonucleotides are annealed and ligated; the preferential ligation by DNA ligase for matching sequences results in a signal corresponding to the complementary sequence at that position.

In some embodiments, sequencing libraries are constructed from the amplified DNA concatemers prior to sequencing analysis. The amplified DNA concatemers can be simultaneously fragmented and tagged with sequencing adapters as illustrated in FIG. 12A. In some cases, the amplified DNA concatemers are fragmented, for example by sonication, and adaptors are added to both ends of the fragments as illustrated in FIG. 12B.

According to some embodiments, a sequence difference between sequencing reads and a reference sequence are called as a genuine sequence variant (e.g. existing in the sample prior to amplification or sequencing, and not a result of either of these processes) if it occurs in at least two different polynucleotides (e.g. two different circular polynucleotides, which can be distinguished as a result of having different junctions). Because sequence variants that are the result of amplification or sequencing errors are unlikely to be duplicated exactly (e.g. position and type) on two different polynucleotides comprising the same target sequence, adding this validation parameter greatly reduces the background of erroneous sequence variants, with a concurrent increase in the sensitivity and accuracy of detecting actual sequence variation in a sample. In some embodiments, a sequence variant having a frequency of about or less than about 5%, 4%, 3%, 2%, 1.5%, 1%, 0.75%, 0.5%, 0.25%, 0.1%, 0.075%, 0.05%, 0.04%, 0.03%, 0.02%, 0.01%, 0.005%, 0.001%, or lower is sufficiently above background to permit an accurate call. In some embodiments, the sequence variant occurs with a frequency of about or less than about 0.1%. In some embodiments, the frequency of a sequence variant is sufficiently above background when such frequency is statistically significantly above the background error rate (e.g. with a p-value of about or less than about 0.05, 0.01, 0.001, 0.0001, or lower). In some embodiments, the frequency of a sequence variant is sufficiently above background when such frequency is about or at least about 2-fold, 3-fold, 4-fold, 5-fold, 6-fold, 7-fold, 8-fold, 9-fold, 10-fold, 25-fold, 50-fold, 100-fold, or more above the background error rate (e.g. at least 5-fold higher). In some embodiments, the background error rate in accurately determining the sequence at a given position is about or less than about 1%, 0.5%, 0.1%, 0.05%, 0.01%, 0.005%, 0.001%, 0.0005%, or lower. In some embodiments, the error rate is lower than 0.001%.

In some embodiments, identifying a genuine sequence variant (also referred to as "calling" or "making a call") comprises optimally aligning one or more sequencing reads with a reference sequence to identify differences between the two, as well as to identify junctions. In general, alignment involves placing one sequence along another sequence, iteratively introducing gaps along each sequence, scoring how well the two sequences match, and preferably repeating for various positions along the reference. The best-scoring match is deemed to be the alignment and represents an inference about the degree of relationship between the sequences. In some embodiments, a reference sequence to which sequencing reads are compared is a reference genome, such as the genome of a member of the same species as the subject. A reference genome may be complete or incomplete. In some embodiments, a reference genome consists only of regions containing target polynucleotides, such as from a reference genome or from a consensus generated from sequencing reads under analysis. In some embodiments, a reference sequence comprises or consists of sequences of polynucleotides of one or more organisms, such as sequences from one or more bacteria, archaea, viruses, protists, fungi, or other organism. In some embodiments, the reference sequence consists of only a portion of a reference genome, such as regions corresponding to one or more target sequences under analysis (e.g. one or more genes, or portions thereof). For example, for detection of a pathogen (such as in the case of contamination detection), the reference genome is the entire genome of the pathogen (e.g. HIV, HPV, or a harmful bacterial strain, e.g. *E. coli*), or a portion thereof useful in identification, such as of a particular strain or serotype. In some embodiments, sequencing reads are aligned to multiple different reference sequences, such as to screen for multiple different organisms or strains.

In a typical alignment, a base in a sequencing read alongside a non-matching base in the reference indicates that a substitution mutation has occurred at that point. Similarly, where one sequence includes a gap alongside a base in the other sequence, an insertion or deletion mutation (an "indel") is inferred to have occurred. When it is desired to specify that one sequence is being aligned to one other, the alignment is sometimes called a pairwise alignment. Multiple sequence alignment generally refers to the alignment of two or more sequences, including, for example, by a series of pairwise alignments. In some embodiments, scoring an alignment involves setting values for the probabilities of substitutions and indels. When individual bases are aligned, a match or mismatch contributes to the alignment score by a substitution probability, which could be, for example, 1 for a match and 0.33 for a mismatch. An indel deducts from an alignment score by a gap penalty, which could be, for example, −1. Gap penalties and substitution probabilities can be based on empirical knowledge or a priori assumptions about how sequences mutate. Their values affect the resulting alignment. Examples of algorithms for performing alignments include, without limitation, the Smith-Waterman (SW) algorithm, the Needleman-Wunsch (NW) algorithm, algorithms based on the Burrows-Wheeler Transform (BWT), and hash function aligners such as Novoalign (Novocraft Technologies; available at www.novocraft.com), ELAND (Illumina, San Diego, Calif.), SOAP (available at soap.genomics.org.cn), and Maq (available at maq.sourceforge.net). One exemplary alignment program, which implements a BWT approach, is Burrows-Wheeler Aligner (BWA) available from the SourceForge web site maintained by Geeknet (Fairfax, Va.). BWT typically occupies 2 bits of memory per nucleotide, making it possible to index nucleotide sequences as long as 4G base pairs with a typical desktop or laptop computer. The pre-processing includes the construction of BWT (i.e., indexing the reference) and the supporting auxiliary data structures. BWA includes two different algorithms, both based on BWT. Alignment by BWA can proceed using the algorithm bwa-short, designed for short queries up to about 200 by with low error rate (<3%) (Li H. and Durbin R. Bioinformatics, 25:1754-60 (2009)). The second algorithm, BWA-SW, is designed for long reads with more errors (Li H. and Durbin R. (2010). Fast and accurate long-read alignment with Burrows-Wheeler Transform. Bioinformatics, Epub.). The bwa-sw aligner is sometimes referred to as "bwa-long", "bwa long algorithm", or similar. An alignment program that implements a version of the Smith-Waterman algorithm is MUMmer, available from the SourceForge web site maintained by Geeknet (Fairfax, Va.). MUMmer is a system for rapidly aligning entire genomes, whether in complete or draft form (Kurtz, S., et al., Genome Biology, 5:R12 (2004); Delcher, A. L., et al., Nucl. Acids Res., 27:11 (1999)). For example, MUMmer 3.0 can find all 20-basepair or longer exact matches between a pair of 5-megabase genomes in 13.7 seconds, using 78 MB of memory, on a 2.4 GHz Linux desktop computer. MUMmer can also align incomplete genomes; it can easily handle the 100s or 1000s of contigs from a shotgun sequencing project, and will align them to another set of contigs or a genome using the NUCmer program included with the system. Other non-limiting examples of alignment programs include: BLAT from Kent Informatics (Santa Cruz, Calif.) (Kent, W. J., Genome Research 4: 656-664 (2002)); SOAP2, from Beijing Genomics Institute (Beijing, Conn.) or BGI Americas Corporation (Cambridge, Mass.); Bowtie (Langmead, et al., Genome Biology, 10:R25 (2009)); Efficient Large-Scale Alignment of Nucleotide Databases (ELAND) or the ELANDv2 component of the Consensus Assessment of Sequence and Variation (CASAVA) software (Illumina, San Diego, Calif.); RTG Investigator from Real Time Genomics, Inc. (San Francisco, Calif.); Novoalign from Novocraft (Selangor, Malaysia); Exonerate, European Bioinformatics Institute (Hinxton, UK) (Slater, G., and Birney, E., BMC Bioinformatics 6:31(2005)), Clustal Omega, from University College Dublin (Dublin, Ireland) (Sievers F., et al., Mol Syst Biol 7, article 539 (2011)); ClustalW or ClustalX from University College Dublin (Dublin, Ireland) (Larkin M. A., et al., Bioinformatics, 23, 2947-2948 (2007)); and FASTA, European Bioinformatics Institute (Hinxton, UK) (Pearson W. R., et al., PNAS 85(8):2444-8 (1988); Lipman, D. J., Science 227(4693):1435-41 (1985)).

Figure 36A:
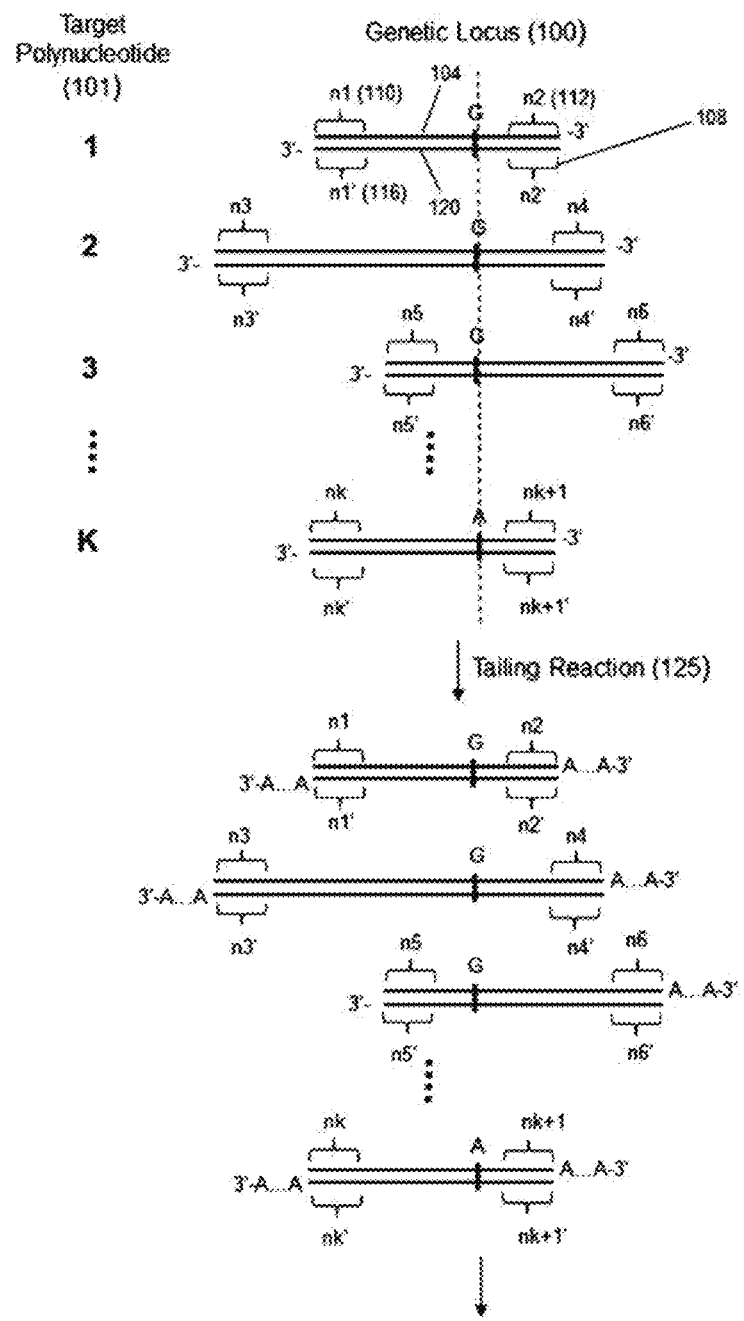

Illustrations of processes in accordance with some embodiments are provided in FIGS. 36A-36H, and in particular for embodiments employing 3' tailing reactions. FIG. 36A shows cell-free double stranded polynucleotides 1, 2, 3 . . . K (101), of a sample, which each contain a genetic locus (100) consisting of a single nucleotide, which may be occupied by a "G" or a rare variant "A". A sample containing such polynucleotides may be a patient tissue sample, such as a blood or plasma sample, or the like. Typically, reference sequences (e.g. in human genome databases) are available to compare the polynucleotide sequences to. Each polynucleotide has four sequence regions corresponding to the sequences of the two complementary strands at each end. Thus, for example, target polynucleotide 1 of FIG. 36A has sequence regions n1 (110) and n2 (112) at each end of strand and has complementary sequence regions n1' (116) and n2' (108) at the ends of complementary strand (120). Although sequence regions of the various polynucleotide strands are illustrated as small portions of strands, the sequence regions may comprise the entire segments from the end of a strand to genetic locus (100).

In some embodiments, to the target polynucleotides of the sample is added a 3' tailing activity along with nucleic acid monomers and/or other reaction components to implement tailing reaction (125) that extends the 3' ends with one or more A's. In this embodiment, the extension of predetermined nucleotides is shown as "A . . . A" to indicate that one or more nucleotides are added, but that the exact number added to each strand may be undetermined (unless an exo⁻ polymerase is used, as noted below). The representation of the added nucleotide by "A . . . A" is not intended to limit the kind of added nucleotides to only A's. The added nucleotides are predetermined in the sense that the kind of nucleotide precursors used in a tailing reaction are known and selected as an assay design choice. For example, a factor in the selection of a kind of predetermined nucleotide for a particular embodiment may be the efficiency of the circularization step in view of the kind of nucleotide selected. In some embodiments, nucleotide precursors may be nucleoside triphosphates of any of the four nucleotides, either separately, so that homopolymer tails are produced, or in mixtures, so that bi- or tri-nucleotide tails are produced. In some cases, uracil, and/or nucleotide analogues may be used in addition to or in place of the four natural DNA bases. In some embodiments in which a CircLigase™ enzyme is used, predetermined nucleotides may be A's and/or T's. In some embodiments, an exo⁻ polymerase is used in a tailing reaction, and only a single deoxyadenylate is added to a 3' end.

Figure 36B:
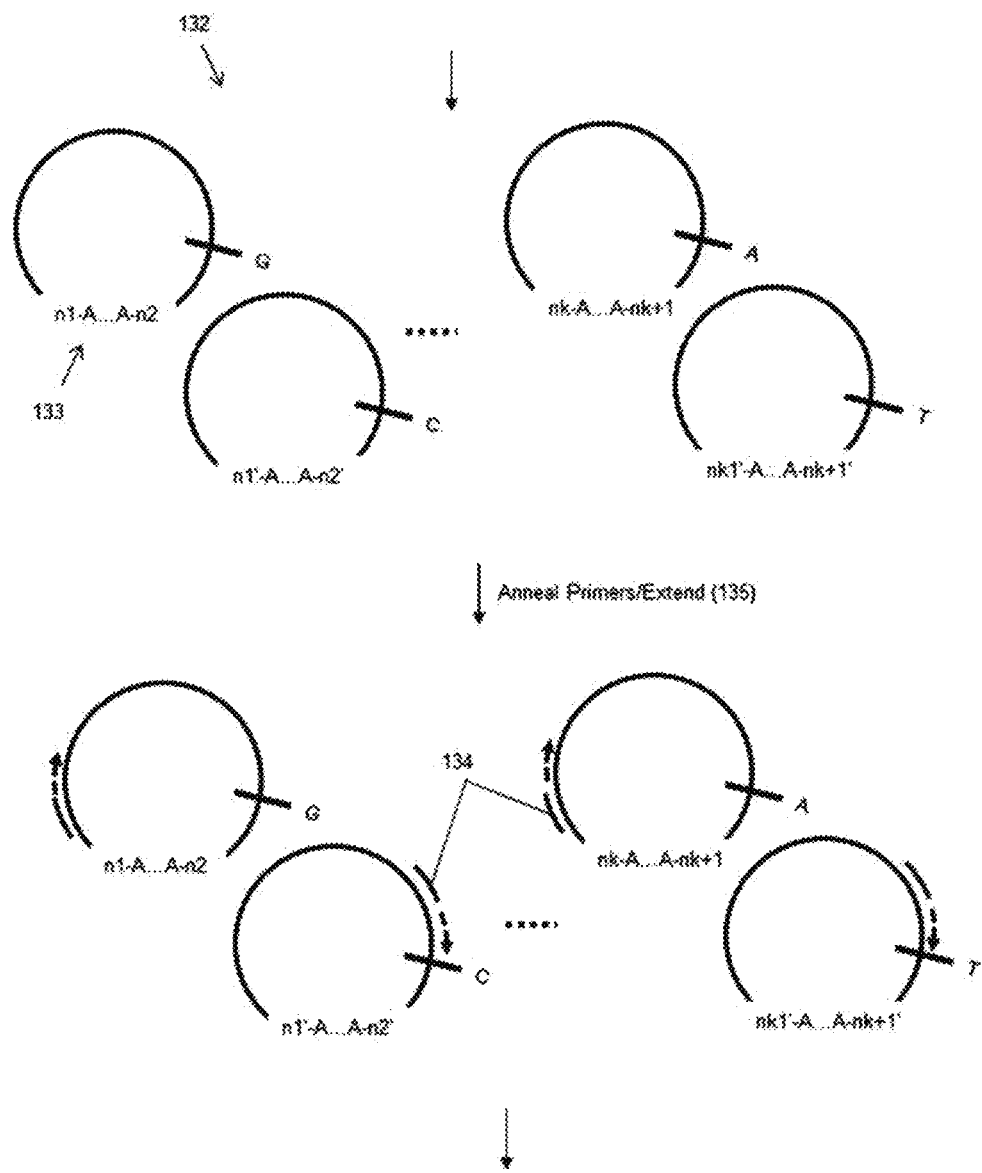

After tailing, and optional separation of the reaction products from the reaction mixture, individual strands are circularized, as shown in FIG. 36B, using a circularization reaction to produce circles (132), each comprising a sequence element of the form "$n_j$-A . . . A-$n_{j+1}$" (133). After circularization, and optional separation of circles (132) from the reaction mixture, primers (134) are annealed to one or more primer binding sites of circles (132), after which they are extended to produce concatemers each containing copies of their respective $n_j$-A . . . A-$n_{j+1}$ sequence element, as illustrated in FIG. 36E. After sequencing, complementary strands, such as (136) and (138), may be identified by matching sequence element components, $n_j$ and $n_{j+1}$, with their respective complements, $n_j'$ and $n_{j+1}'$. Selection of primer binding sites on circles (132) is a matter of design choice, or alternatively, random sequence primers may be used. In some embodiments, a single primer binding site is selected adjacent to genetic locus (100); in other embodiments, a plurality of primer binding sites are selected, each for a separate primer, to ensure amplification even if a boundary happens to occur in one of the primer binding sites. In some embodiments, two primers with separate primer binding sites are used to produce concatemers.

After identification of pairs of concatemers containing complementary strands, the concatemer sequences may be aligned and base calls at matching positions of the two strands may be compared. At some positions of concatemer pairs, as illustrated by (140) in FIG. 36F, a base called at a given position in one member of a pair may not be complementary to the base called on the other member of the pair, indicating that an incorrect call has been made due to, for example, amplification error, sequencing error, or the like. In this case, the indeterminacy at the given position may be resolve by examining the base calls at corresponding positions of other copies within the concatemer pair. For example, a base call at the given position may be taken to be a consensus, or a majority, of the base calls made for the individual copies in a pair of concatemers. Other methods for making such determinations would be available to one of ordinary skill in the art, which may be used in place of or in addition to these methods to supplement efforts to resolve base calls when sequence information between complementary strands are not complementary. In some cases, where bases at a specified position in complementary strands originating from the same double-stranded molecule (e.g. as identified by the 3' and 5' end sequences) are not complementary, a base call is resolved in favor of the reference sequence to which the sample sequence is compared, such that the difference is not identified as a true sequence variant with respect to such reference sequence.

Figure 36C:
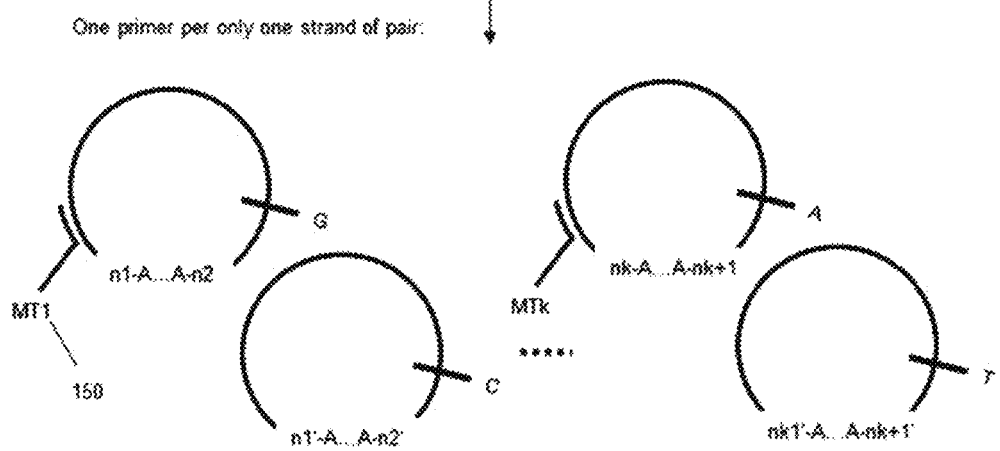
Figure 36D:
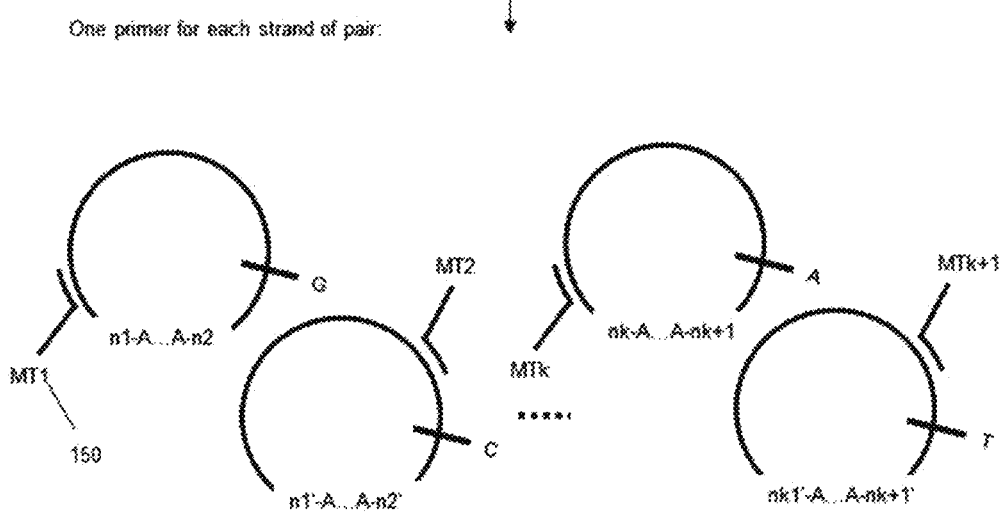
Figure 36E:
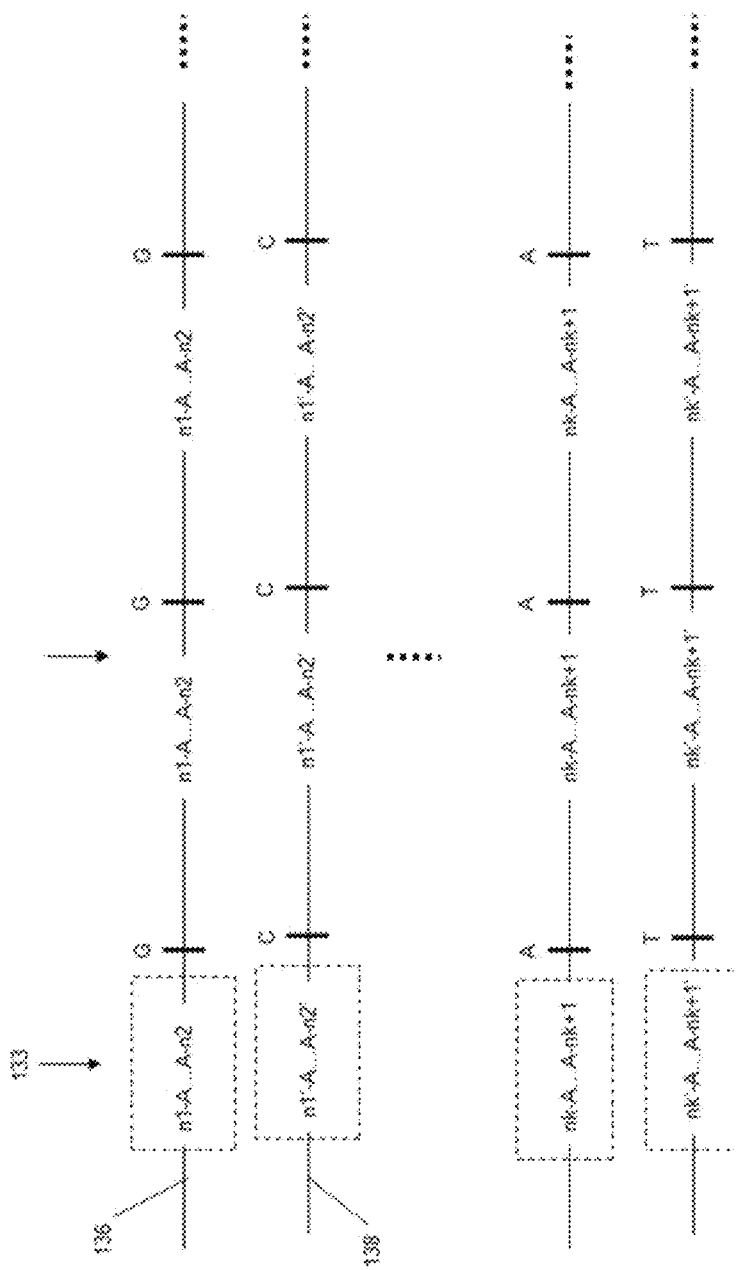
Figure 36F:
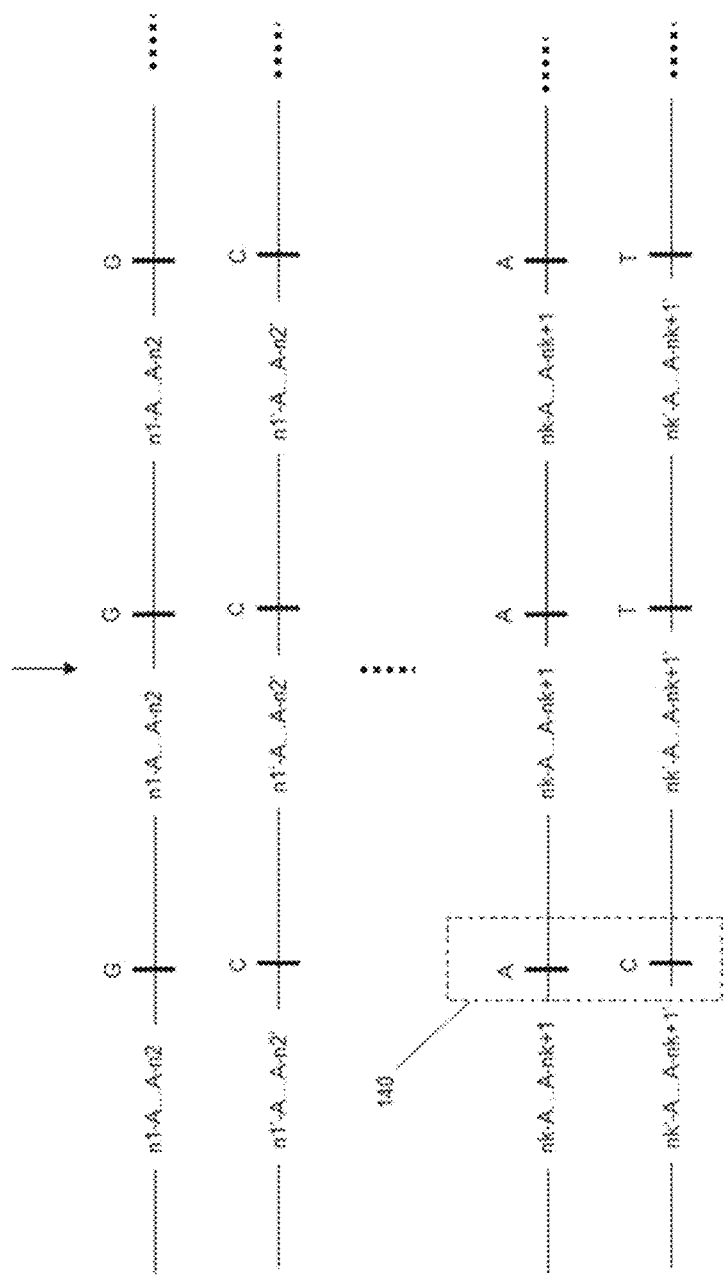
Figure 36G:
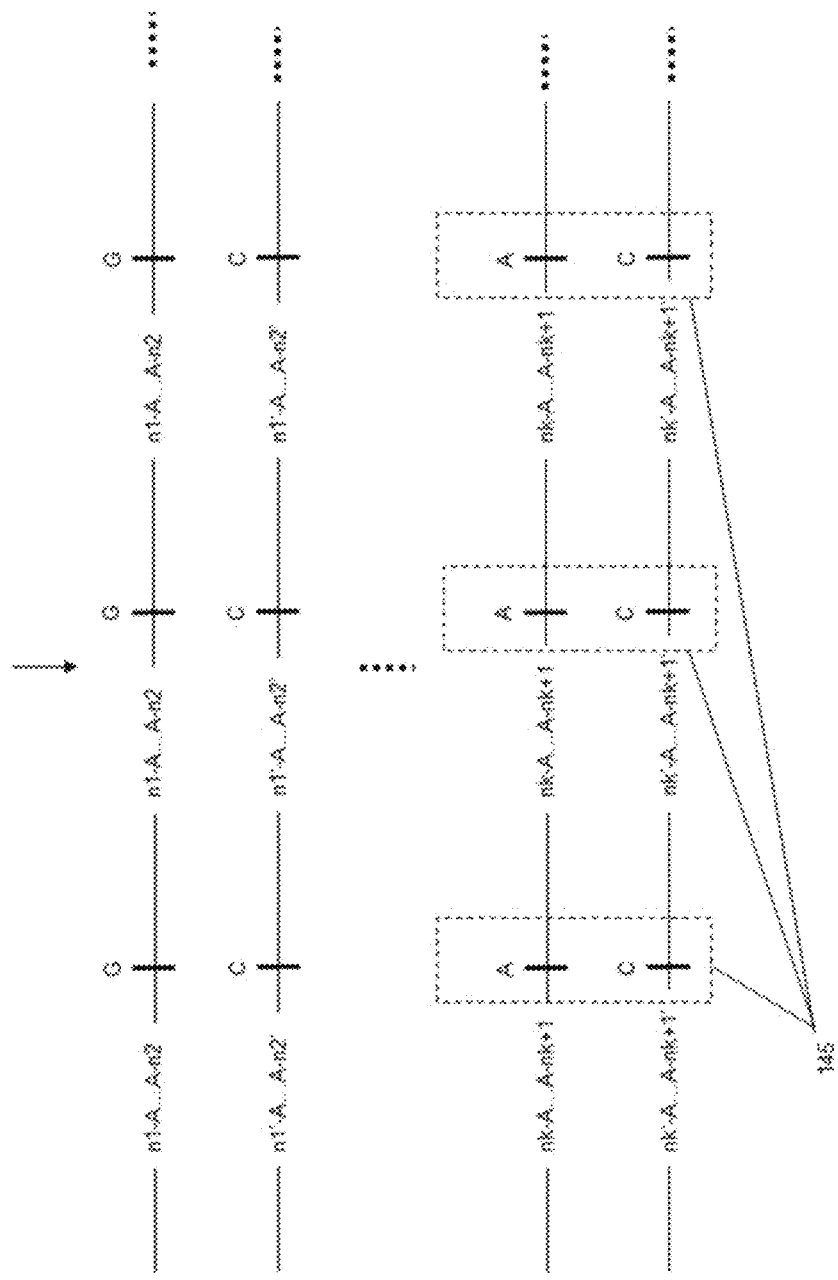
Figure 36H:
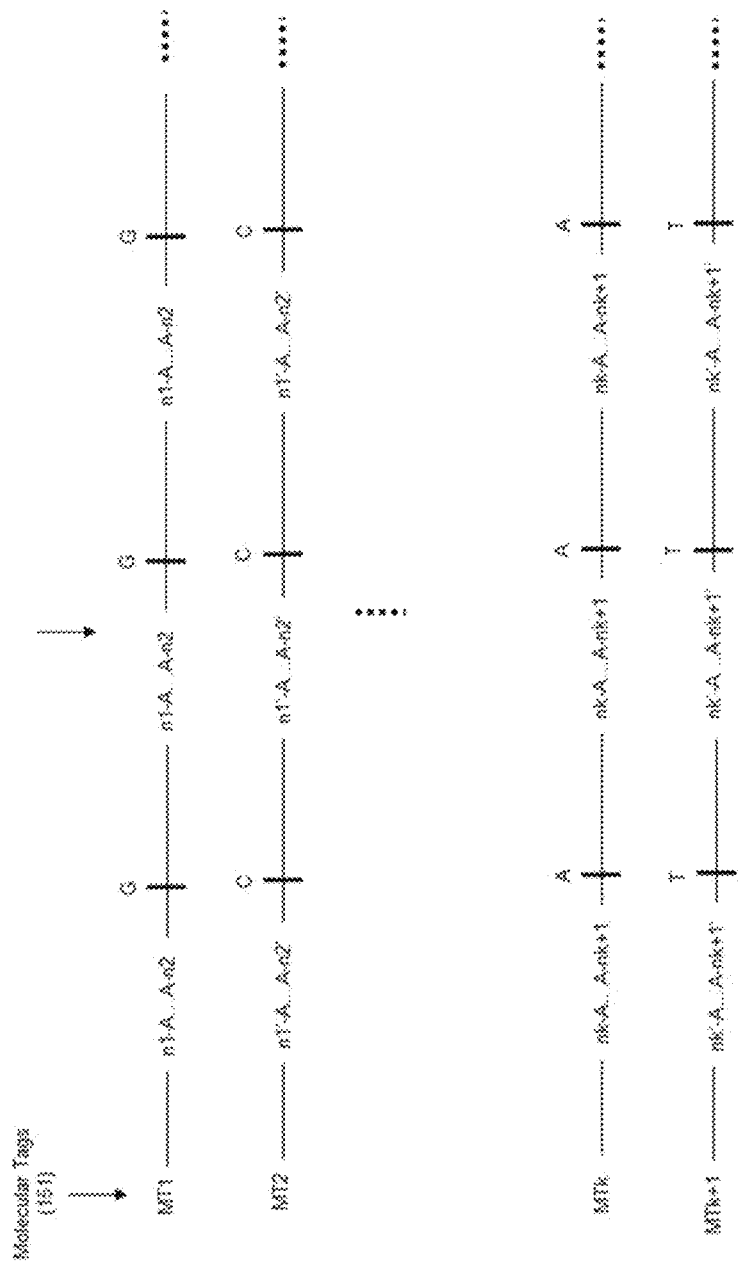

In other circumstances, the same error may appear in each copy of a target polynucleotide within a concatemer, as illustrated by (145) in FIG. 36G. Such data would suggest that the target polynucleotide was damaged before amplification or sequencing.

Figure 37A:
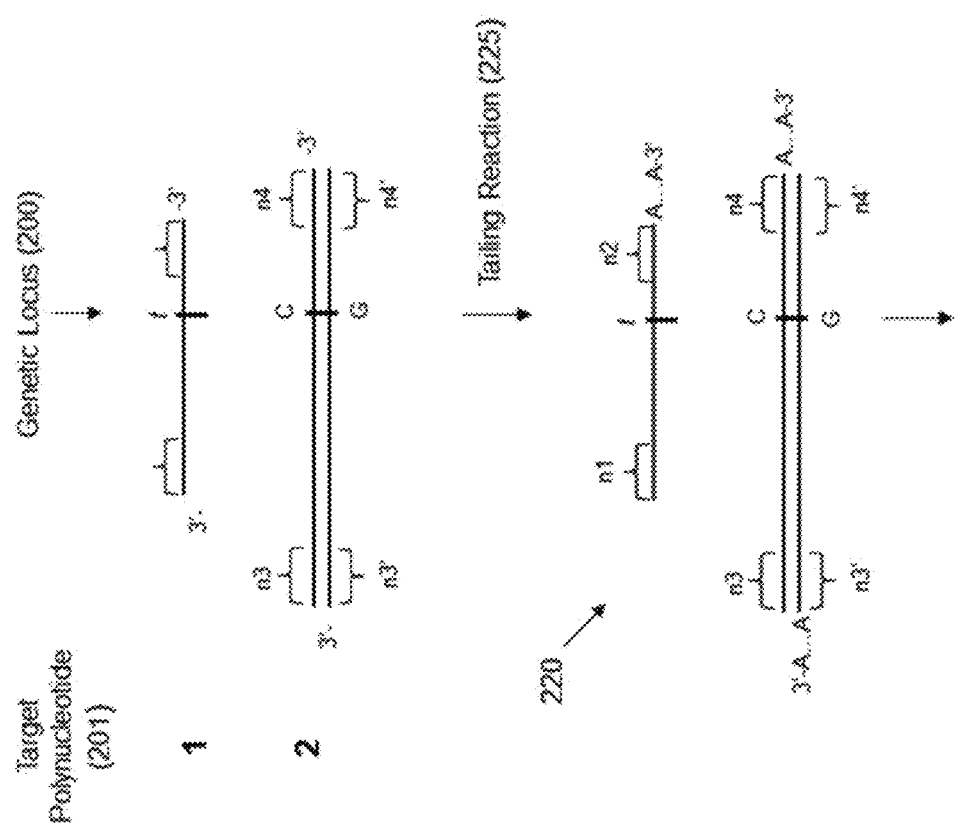
FIGS. 37A and 37B illustrate embodiments where target polynucleotides include single-stranded polynucleotides.
Figure 37B:
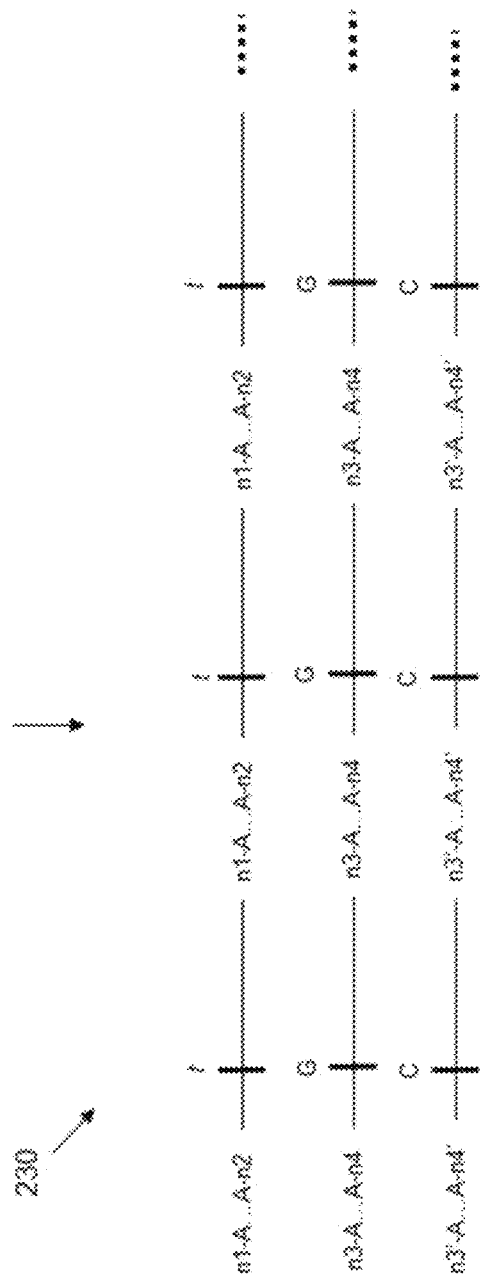

In still other circumstances, only a single concatemer may be identified; that is, a concatemer for which no match is found based on boundary information, such as, length of the segment of predetermined nucleotides, sequences of adjacent 3' and 5' ends, or the like. Such circumstances are illustrated in FIGS. 37A and 37B. There, target polynucleotides (201) comprise single stranded polynucleotide 1 and double stranded polynucleotide 2, each encompassing genetic locus (200). Predetermined nucleotides (for example, adenylates) may be attached to both polynucleotides 1 and 2 in tailing reaction (225) to form 3' tailed polynucleotides (220). As described above, polynucleotides (220) may then be circularized, amplified by RCA, and sequenced to give concatemer sequences (230), shown in FIG. 37B. In case an observed variant is common in DNA damage, for example, C to T or G to T, such information from an unpaired concatemer will still be helpful in deciding if it is a true mutation versus just a DNA damage.

In some embodiments, as illustrated in FIGS. 36C and 36D, primers each containing a molecular tag, e.g. MT1 (150), MT2, and so on, may be annealed to each single stranded circle at predetermined primer binding sites in order to produce concatemers each with a unique tag. The presence of unique molecular tags will distinguish products of single stranded circles that happen to have the same boundary, or $n_j$-A A-$n_{j+1}$ sequence element. Such tags may also be used for counting molecules to determine copy number variation at a genetic locus, for example, in accordance with methods described in Brenner et al, U.S. Pat. No. 7,537,897, or the like, which is incorporated herein by reference. In some embodiments, primers with molecular tags may be selected that have binding sites only on one strand of a target polynucleotide so that concatemers with molecular tags represent only one of the two strands of a target polynucleotide. In other embodiments, circles from complementary strands of a target polynucleotide may each be amplified using a primer having a molecular tag (as illustrated in FIG. 36C).

In some embodiments, the above steps for identifying complementary strands of target polynucleotides may be incorporated in a method for detecting rare variants at a genetic locus. In some embodiments, the method comprises the following steps: (a) extending by one or more predetermined nucleotides 3' ends of the polynucleotides; (b) circularizing individual strands of the polynucleotides to form single stranded polynucleotide circles, the one or more predetermined nucleotides defining a boundary between 3' sequences and 5' sequences of each single stranded polynucleotide circle; (c) amplifying by rolling circle replication (RCR) the single stranded polynucleotide circles to form concatemers; (d) sequencing the concatemers; (e) identifying pairs of concatemers containing complementary strands of polynucleotides by the identity of 3' sequences and 5' sequences adjacent to the one or more predetermined nucleotides; and (f) determining the sequence of the genetic locus from the sequences of the pairs of concatemers comprising complementary strands of the same polynucleotide. In other embodiments, the step of amplifying by RCR the single stranded circles includes annealing a primer having a 5'-noncomplementary tail to the single stranded circles wherein such primer includes a unique molecular tag in the 5'-noncomplementary tail and extending such primer in accordance with an RCR protocol. The resulting product is a concatemer containing a unique molecular tag, which may be counted along with other molecular tags attached to circles from the same locus to provide a copy number measurement for the locus.

In some embodiments, the step of extending may be implemented by tailing by one or more predetermined nucleotides 3' ends of the polynucleotides in a tailing reaction. In some embodiments, such tailing may be implemented by an untemplated 3' nucleotide addition activity, such as a TdT activity, an exo-polymerase activity, or the like.

Using the steps described above, concatemer sequences can be identified from polynucleotide sequences. In large-scale-parallel-sequencing (also referred to as "next generation sequencing" or NGS), reads containing concatemers can be identified and used to perform error correction and find sequence variants. Junctions of the original input molecules (the start and the end of the DNA/RNA sequence) can be reconstructed from the concatemers by aligning them to reference sequences; and the junctions can be used to identify the original input molecule and to remove sequencing duplicates for more accurate counting. The strand identity of each read which may contain a concatemer can be computed by aligning the reads to reference sequences and checking the sequence element components, $n_j$ and $n_{j+1}$ as described in FIG. 36A. Variants found in both concatemers labeled as complementary strands have a higher statistical confidence level, which can be used to perform further error correction. Variant confirmation using strand identity may be carried out by (but is not limited to) the following steps: a) variants found in reads with complementary strand identities are considered more confident; b) reads carrying variants can be grouped by its junction identification, the variants are more confident when complementary strand identities are found in reads within a group of reads having the same junction identification; c) reads carrying variants can be grouped by their molecular barcodes or the combination of molecular barcodes and junction identifications. The variants are more confident when the complement strand identities are found in reads within a group of reads having the same molecular barcodes and/or junction identifications.

Error correction using molecular barcodes and junction identification can be used independently, or combined with the error correction with concantemer sequencing as described in the previous steps. a) Reads with different molecular barcodes (or junction identifications) can be grouped into different read families which represents reads originated from different input molecules; b) consensus sequences can be built from the family of reads; c) consensus can be used for variant calling; d) molecular barcodes and junction identifications can be combined to form a composite ID for reads, which will help identify the original input molecules. In some embodiments, a base call (e.g. a sequence difference with respect to a reference sequence)

found in different read families are assigned a higher confidence. In some cases, a sequence difference is only identified as a true sequence variant representative of the original source polynucleotide (as opposed to an error of sample processing or analysis) if the sequence difference passes one or more filters that increase confidence of a base call, such as those described above. In some embodiments, a sequence difference is only identified as a true sequence variant if (a) it is identified on both strands of a double-stranded input molecule; (b) it occurs in the consensus sequence for the concatemer from which it originates (e.g. more than 50%, 80%, 90% or more of the repeats within the concatemer contain the sequence difference); and/or (c) it occurs in two different molecules (e.g. as identified by different 3' and 5' endpoints, and/or by an exogenous tag sequence).

Determining strand identity: 1) junctions of the original input molecules can be reconstructed from reads which may contain concatemer sequences by aligning the sequences to reference sequences; 2) the junctions can be located in the reads using the alignments; 3) the sequence element component, $n_j$ and $n_{j-1}$, as described in FIG. 36A, which represents the strand identity, can be extracted from the sequence based the junction locations in the reads; and in the case of concatemer, the sequence can be found between the junctions in the concatemer sequences; 4) the strand (positive or negative) of the reference sequence that the reads align to, combined with the strand identity sequences within the reads identified in step 3, can be used to identify the original strand that was incorporated into the sequence library and sequenced, and to identify which strand a sequence variant originated from. For example, suppose a strand identity sequence "AA" is added to the end of a strand of original input DNA fragment; after sequencing the read of the DNA fragment is aligned to the "+" strand of the reference and the strand identity sequence in the read is "AA", we know the original input strand is "+"; if the strand identity sequence is "TT", the read is reverse complementary to the original input strand and the original input strand is "−" strand. The strand identity determination allows a sequence variant to be distinguished from its reverse complementary counterpart, for example, C>T substitution from G>A substitution. The precise identification of allele changes can be used to carry out allele-specific error reduction in variant calling. For example, some DNA damage occurs more often as certain allele changes, and allele-specific error reduction can be carried out to suppress such damage; such error reduction can be done by various statistical methods, for example, 1) calculation of distribution of different allele changes in sequencing data (baseline), followed by 2) z-test or other statistical tests to determine if a observed allele change is different from the baseline distribution.

In some embodiments, the present disclosure provides a method of identifying a genetic variant on a particular strand at a genetic locus by comparing the frequency of a measured sequence, or one or more nucleotides, to a baseline frequency of nucleotide damage that results in the same sequence, or one or more nucleotides, as the measured sequence. In some embodiments, such a method may comprise the following steps: (a) extending by one or more predetermined nucleotides 3' ends of the polynucleotides; (b) amplifying individual strands of the extended polynucleotides; (c) sequencing the amplified individual strands of the extended polynucleotides; (d) identifying complementary strands of polynucleotides by the identity of 3' sequences and/or 5' sequences adjacent to the one or more predetermined nucleotides and identifying nucleotides of each strand at the genetic locus; (e) determining a frequency of each of one or more nucleotides at the genetic locus from the identified concatemers for identifying the genetic variant. In some embodiments, this method may be used to distinguish a genetic variant from nucleotide damage by the following step: calling at least one of said one or more nucleotides at said genetic locus on said strand identified by said one or more predetermined nucleotides as said genetic variant whenever said frequency of strands displaying the at least one nucleotide exceeds by a predetermined factor a baseline frequency of strands having nucleotide damage that gives rise to the same nucleotide.

As mentioned above, in some embodiments, the step of amplifying may be carried out by (i) circularizing individual strands of the polynucleotides to form single stranded polynucleotide circles, the one or more predetermined nucleotides defining a boundary between 3' sequences and 5' sequences of the polynucleotides in each single stranded polynucleotide circle; and (ii) amplifying by rolling circle replication the single stranded polynucleotide circles to form concatemers of the single stranded polynucleotide circles.

A baseline frequency of strands having nucleotide damage may be based on prior measurements on samples from the same individual who is being tested by the method, or a baseline frequency may be based on prior measurements on a population of individuals other than the individual being tested. A baseline frequency may also depend on and/or be specific for the kind of steps or protocol used in preparing a sample for analysis by a method of the disclosure. By comparing measured frequencies with baseline frequencies a statistical measure may be obtained of a likelihood (or confidence level) that a measured or determined sequence is a genuine genetic variant and not damage or error due to processing.

Typically, the sequencing data is acquired from large scale, parallel sequencing reactions. Many of the next generation high-throughput sequencing systems export data as FASTQ files, although other formats may be used. In some embodiments, sequences are analyzed to identify repeat unit length (e.g. the monomer length), the junction formed by circularization, and any true variation with respect to a reference sequence, typically through sequence alignment. Identifying the repeat unit length can include computing the regions of the repeated units, finding the reference loci of the sequences (e.g. when one or more sequences are particularly targeted for amplification, enrichment, and/or sequencing), the boundaries of each repeated region, and/or the number of repeats within each sequencing run. Sequence analysis can include analyzing sequence data for both strands of a duplex. As noted above, in some embodiments, an identical variant that appears the sequences of reads from different polynucleotides from the sample (e.g. circularized polynucleotides having different junctions) is considered a confirmed variant. In some embodiments, a sequence variant may also be considered a confirmed, or genuine, variant if it occurs in more than one repeated unit of the same polynucleotide, as the same sequence variation is likewise unlikely to occur at the same position in a repeated target sequence within the same concatemer. The quality score of a sequence may be considered in identifying variants and confirmed variants, for example, the sequence and bases with quality scores lower than a threshold may be filtered out. Other bioinformatics methods can be used to further increase the sensitivity and specificity of the variant calls.

In some embodiments, statistical analyses may be applied to determination of variants (mutations) and quantitate the ratio of the variant in total DNA samples. Total measurement of a particular base can be calculated using the sequencing data. For example, from the alignment results calculated in previous steps, one can calculate the number of "effective reads," that is, number of confirmed reads for each locus. The allele frequency of a variant can be normalized by the effective read count for the locus. The overall noise level, that is the average rate of observed variants across all loci, can be computed. The frequency of a variant and the overall noise level, combined with other factors, can be used to determine the confidence interval of the variant call. Statistical models such as Poisson distributions can be used to assess the confidence interval of the variant calls. The allele frequency of variants can also be used as an indicator of the relative quantity of the variant in the total sample.

In some embodiments, a microbial contaminant is identified based on the calling step. For example, a particular sequence variant may indicate contamination by a potentially infectious microbe. Sequence variants may be identified within a highly conserved polynucleotide for the purpose of identifying a microbe. Exemplary highly conserved polynucleotides useful in the phylogenetic characterization and identification of microbes comprise nucleotide sequences found in the 16S rRNA gene, 23S rRNA gene, 5S rRNA gene, 5.8S rRNA gene, 12S rRNA gene, 18S rRNA gene, 28S rRNA gene, gyrB gene, rpoB gene, fusA gene, recA gene, coxl gene and nifD gene. With eukaryotes, the rRNA gene can be nuclear, mitochondrial, or both. In some embodiments, sequence variants in the 16S-23S rRNA gene internal transcribed spacer (ITS) can be used for differentiation and identification of closely related taxa with or without the use of other rRNA genes. Due to structural constraints of 16S rRNA, specific regions throughout the gene have a highly conserved polynucleotide sequence although non-structural segments may have a high degree of variability. Identifying sequence variants can be used to identify operational taxonomic units (OTUs) that represent a subgenus, a genus, a subfamily, a family, a sub-order, an order, a sub-class, a class, a sub-phylum, a phylum, a sub-kingdom, or a kingdom, and optionally determine their frequency in a population. The detection of particular sequence variants can be used in detecting the presence, and optionally amount (relative or absolute), of a microbe indicative of contamination. Example applications include water quality testing for fecal or other contamination, testing for animal or human pathogens, pinpointing sources of water contamination, testing reclaimed or recycled water, testing sewage discharge streams including ocean discharge plumes, monitoring of aquaculture facilities for pathogens, monitoring beaches, swimming areas or other water related recreational facilities and predicting toxic algal blooms. Food monitoring applications include the periodic testing of production lines at food processing plants, surveying slaughter houses, inspecting the kitchens and food storage areas of restaurants, hospitals, schools, correctional facilities and other institutions for food borne pathogens such as *E. coli* strains O157:H7 or O111:B4, *Listeria monocytogenes*, or *Salmonella enterica* subsp. *enterica* serovar *Enteritidis*. Shellfish and shellfish producing waters can be surveyed for algae responsible for paralytic shellfish poisoning, neurotoxic shellfish poisoning, diarrhetic shellfish poisoning and amnesic shellfish poisoning. Additionally, imported foodstuffs can be screened while in customs before release to ensure food security. Plant pathogen monitoring applications include horticulture and nursery monitoring for instance the monitoring for *Phytophthora ramorum*, the microorganism responsible for Sudden Oak Death, crop pathogen surveillance and disease management and forestry pathogen surveillance and disease management. Manufacturing environments for pharmaceuticals, medical devices, and other consumables or critical components where microbial contamination is a major safety concern can be surveyed for the presence of specific pathogens like *Pseudomonas aeruginosa*, or *Staphylococcus aureus*, the presence of more common microorganisms associated with humans, microorganisms associated with the presence of water or others that represent the bioburden that was previously identified in that particular environment or in similar ones. Similarly, the construction and assembly areas for sensitive equipment including space craft can be monitored for previously identified microorganism that are known to inhabit or are most commonly introduced into such environments.

In some embodiments, the method comprises identifying a sequence variant in a nucleic acid sample comprising less than 50 ng of polynucleotides, each polynucleotide having a 5' end and a 3' end. In some embodiments, the method comprises: (a) circularizing with a ligase individual polynucleotides in said sample to form a plurality of circular polynucleotides; (b) upon separating said ligase from said circular polynucleotides, amplifying the circular polynucleotides to form concatemers; (c) sequencing the concatemers to produce a plurality of sequencing reads; (d) identifying sequence differences between the plurality of sequencing reads and a reference sequence; and (e) calling a sequence difference that occurs with a frequency of 0.05% or higher in said plurality of reads from said nucleic acid sample of less than 50 ng polynucleotides as the sequence variant.

The starting amount of polynucleotides in a sample may be small. In some embodiments, the amount of starting polynucleotides is less than 100 ng. In some embodiments, the amount of starting material is less than 75 ng. In some embodiments, the amount of starting material is less than 50 ng, such as less than 45 ng, 40 ng, 35 ng, 30 ng, 25 ng, 20 ng, 15 ng, 10 ng, 5 ng, 4 ng, 3 ng, 2 ng, ng, 0.5 ng, 0.1 ng, or less. In some embodiments, the amount of starting polynucleotides is in the range of 0.1-100 ng, such as between 1-75 ng, 5-50 ng, or 10-20 ng. In general, lower starting material increases the importance of increased recovery from various processing steps. Processes that reduce the amount of polynucleotides in a sample for participation in a subsequent reaction decrease the sensitivity with which rare mutations can be detected. For example, methods described by Lou et al. (PNAS, 2013, 110 (49)) are expected to recover only 10-20% of the starting material. For large amounts of starting material (e.g. as purified from lab-cultured bacteria), this may not be a substantial obstacle. However, for samples where the starting material is substantially lower, recovery in this low range can be a substantial obstacle to detection of sufficiently rare variants. Accordingly, in some embodiments, sample recovery from one step to another in a method of the disclosure (e.g. the mass fraction of input into a circularization step available for input into a subsequent amplification step or sequencing step) is about or more than about 50%, 60%, 75%, 80%, 85%, 90%, 95%, or more. Recovery from a particular step may be close to 100%. Recovery may be with respect to a particular form, such as recovery of circular polynucleotides from an input of non-circular polynucleotides.

The polynucleotides may be from any suitable sample, such as a sample described herein with respect to the various aspects of the disclosure. Polynucleotides from a sample may be any of a variety of polynucleotides, including but not limited to, DNA, RNA, ribosomal RNA (rRNA), transfer RNA (tRNA), micro RNA (miRNA), messenger RNA (mRNA), fragments of any of these, or combinations of any two or more of these. In some embodiments, samples comprise DNA. In some embodiments, the polynucleotides are single-stranded, either as obtained or by way of treatment (e.g. denaturation). Further examples of suitable polynucleotides are described herein, such as with respect to any of the various aspects of the disclosure. In some embodiments, polynucleotides are subjected to subsequent steps (e.g. circularization and amplification) without an extraction step, and/or without a purification step. For example, a fluid sample may be treated to remove cells without an extraction step to produce a purified liquid sample and a cell sample, followed by isolation of DNA from the purified fluid sample. A variety of procedures for isolation of polynucleotides are available, such as by precipitation or non-specific binding to a substrate followed by washing the substrate to release bound polynucleotides. Where polynucleotides are isolated from a sample without a cellular extraction step, polynucleotides will largely be extracellular or "cell-free" polynucleotides, such as cell-free DNA and cell-free RNA, which may correspond to dead or damaged cells. The identity of such cells may be used to characterize the cells or population of cells from which they are derived, such as in a microbial community. If a sample is treated to extract polynucleotides, such as from cells in a sample, a variety of extraction methods are available, examples of which are provided herein (e.g. with regard to any of the various aspects of the disclosure).

The sequence variant in the nucleic acid sample can be any of a variety of sequence variants. Multiple non-limiting examples of sequence variants are described herein, such as with respect to any of the various aspects of the disclosure. In some embodiments the sequence variant is a single nucleotide polymorphism (SNP). In some embodiments, the sequence variant occurs with a low frequency in the population (also referred to as a "rare" sequence variant). For example, the sequence variant may occur with a frequency of about or less than about 5%, 4%, 3%, 2%, 1.5%, 1%, 0.75%, 0.5%, 0.25%, 0.1%, 0.075%, 0.05%, 0.04%, 0.03%, 0.02%, 0.01%, 0.005%, 0.001%, or lower. In some embodiments, the sequence variant occurs with a frequency of about or less than about 0.1%.

According to some embodiments, polynucleotides of a sample are circularized, such as by use of a ligase. Circularization can include joining the 5' end of a polynucleotide to the 3' end of the same polynucleotide, to the 3' end of another polynucleotide in the sample, or to the 3' end of a polynucleotide from a different source (e.g. an artificial polynucleotide, such as an oligonucleotide adapter). In some embodiments, the 5' end of a polynucleotide is joined to the 3' end of the same polynucleotide (also referred to as "self-joining"). Non-limiting examples of circularization processes (e.g. with and without adapter oligonucleotides), reagents (e.g. types of adapters, use of ligases), reaction conditions (e.g. favoring self-joining), and optional additional processing (e.g. post-reaction purification) are provided herein, such as with regard to any of the various aspects of the disclosure.

As previously described, joining ends of a polynucleotide to one-another to form a circular polynucleotide (either directly, or with one or more intermediate adapter oligonucleotides) generally produces a junction having a junction sequence. Where the 5' end and 3' end of a polynucleotide are joined via an adapter polynucleotide, the term "junction" can refer to a junction between the polynucleotide and the adapter (e.g. one of the 5' end junction or the 3' end junction), or to the junction between the 5' end and the 3' end of the polynucleotide as formed by and including the adapter polynucleotide. Where the 5' end and the 3' end of a polynucleotide are joined without an intervening adapter (e.g. the 5' end and 3' end of a single-stranded DNA), the term "junction" refers to the point at which these two ends are joined. A junction may be identified by the sequence of nucleotides comprising the junction (also referred to as the "junction sequence"). In some embodiments, samples comprise polynucleotides having a mixture of ends formed by natural degradation processes (such as cell lysis, cell death, and other processes by which DNA is released from a cell to its surrounding environment in which it may be further degraded, such as in cell-free polynucleotides, such as cell-free DNA), fragmentation that is a byproduct of sample processing (such as fixing, staining, and/or storage procedures), and fragmentation by methods that cleave DNA without restriction to specific target sequences (e.g. mechanical fragmentation, such as by sonication; non-sequence specific nuclease treatment, such as DNase I, fragmentase). Where samples comprise polynucleotides having a mixture of ends, the likelihood that two polynucleotides will have the same 5' end or 3' end is low, and the likelihood that two polynucleotides will independently have both the same 5' end and 3' end is extremely low. Accordingly, in some embodiments, junctions may be used to distinguish different polynucleotides, even where the two polynucleotides comprise a portion having the same target sequence. Where polynucleotide ends are joined without an intervening adapter, a junction sequence may be identified by alignment to a reference sequence. For example, where the order of two component sequences appears to be reversed with respect to the reference sequence, the point at which the reversal appears to occur may be an indication of a junction at that point. Where polynucleotide ends are joined via one or more adapter sequences, a junction may be identified by proximity to the known adapter sequence, or by alignment as above if a sequencing read is of sufficient length to obtain sequence from both the 5' and 3' ends of the circularized polynucleotide. In some embodiments, the formation of a particular junction is a sufficiently rare event such that it is unique among the circularized polynucleotides of a sample.

After circularization, reaction products may be purified prior to amplification or sequencing to increase the relative concentration or purity of circularized polynucleotides available for participating in subsequent steps (e.g. by isolation of circular polynucleotides or removal of one or more other molecules in the reaction). For example, a circularization reaction or components thereof may be treated to remove single-stranded (non-circularized) polynucleotides, such as by treatment with an exonuclease. As a further example, a circularization reaction or portion thereof may be subjected to size exclusion chromatography, whereby small reagents are retained and discarded (e.g. unreacted adapters), or circularization products are retained and released in a separate volume. A variety of kits for cleaning up ligation reactions are available, such as kits provided by Zymo oligo purification kits made by Zymo Research. In some embodiments, purification comprises treatment to remove or degrade ligase used in the circularization reaction, and/or to purify circularized polynucleotides away from such ligase. In some embodiments, treatment to degrade ligase comprises treatment with a protease. Suitable proteases are available from prokaryotes, viruses, and eukaryotes. Examples of proteases include proteinase K (from Tritirachium album), pronase E (from *Streptomyces griseus*), *Bacillus polymyxa* protease, theromolysin (from thermophilic bacteria), trypsin, subtilisin, furin, and the like. In some embodiments, the protease is proteinase K. Protease treatment may follow manufacturer protocols, or subjected to standard conditions (e.g. as provided in Sambrook and Green, Molecular Cloning: A Laboratory Manual, 4th Edition (2012)). Protease treatment may also be followed by extraction and precipitation. In one example, circularized polynucleotides are purified by proteinase K (Qiagen) treatment in the presence of 0.1% SDS and 20 mM EDTA, extracted with 1:1 phenol/chloroform and chloroform, and precipitated with ethanol or isopropanol. In some embodiments, precipitation is in ethanol.

As described with respect to other aspects of the disclosure, circularization may be followed directly by sequencing the circularized polynucleotides. Alternatively, sequencing may be preceded by one or more amplification reactions. A variety of methods of amplifying polynucleotides (e.g. DNA and/or RNA) are available. Amplification may be linear, exponential, or involve both linear and exponential phases in a multi-phase amplification process. Amplification methods may involve changes in temperature, such as a heat denaturation step, or may be isothermal processes that do not require heat denaturation. Non-limiting examples of suitable amplification processes are described herein, such as with regard to any of the various aspects of the disclosure. In some embodiments, amplification comprises rolling circle amplification (RCA). As described elsewhere herein, a typical RCA reaction mixture comprises one or more primers, a polymerase, and dNTPs, and produces concatemers. Typically, the polymerase in an RCA reaction is a polymerase having strand-displacement activity. A variety of such polymerases are available, non-limiting examples of which include exonuclease minus DNA Polymerase I large (Klenow) Fragment, Phi29 DNA polymerase, Taq DNA Polymerase and the like. In general, a concatemer is a polynucleotide amplification product comprising two or more copies of a target sequence from a template polynucleotide (e.g. about or more than about 2, 3, 4, 5, 6, 7, 8, 9, 10, or more copies of the target sequence; in some embodiments, about or more than about 2 copies). Amplification primers may be of any suitable length, such as about or at least about 5, 10, 15, 20, 25, 30, 35, 40, 45, 50, 55, 60, 65, 70, 75, 80, 90, 100, or more nucleotides, any portion or all of which may be complementary to the corresponding target sequence to which the primer hybridizes (e.g. about, or at least about 5, 10, 15, 20, 25, 30, 35, 40, 45, 50, or more nucleotides). Examples of various RCA processes are described herein, such as the use of random primers, target-specific primers, and adapter-targeted primers, some of which are illustrated in FIGS. 7A-7C.

Where circularized polynucleotides are amplified prior to sequencing (e.g. to produce concatemers), amplified products may be subjected to sequencing directly without enrichment, or subsequent to one or more enrichment steps. Non-limiting examples of suitable enrichment processes are described herein, such as with respect to any of the various aspects of the disclosure (e.g. use of B2B primers for a second amplification step). According to some embodiments, circularized polynucleotides (or amplification products thereof, which may have optionally been enriched) are subjected to a sequencing reaction to generate sequencing reads. Sequencing reads produced by such methods may be used in accordance with other methods disclosed herein. A variety of sequencing methodologies are available, particularly high-throughput sequencing methodologies. Examples include, without limitation, sequencing systems manufactured by Illumina (sequencing systems such as HiSeq® and MiSeq®), Life Technologies (Ion Torrent®, SOLiD®, etc.), Roche's 454 Life Sciences systems, Pacific Biosciences systems, etc. In some embodiments, sequencing comprises use of HiSeq® and MiSeq® systems to produce reads of about or more than about 50, 75, 100, 125, 150, 175, 200, 250, 300, or more nucleotides in length. Additional non-limiting examples of amplification platforms and methodologies are described herein, such as with respect to any of the various aspects of the disclosure.

According to some embodiments, a sequence difference between sequencing reads and a reference sequence are called as a genuine sequence variant (e.g. existing in the sample prior to amplification or sequencing, and not a result of either of these processes) if it occurs in at least two different polynucleotides (e.g. two different circular polynucleotides, which can be distinguished as a result of having different junctions or two different polynucleotides having a different 5' end and/or a different 3' end). Because sequence variants that are the result of amplification or sequencing errors are unlikely to be duplicated exactly (e.g. position and type) on two different polynucleotides comprising the same target sequence, adding this validation parameter greatly reduces the background of erroneous sequence variants, with a concurrent increase in the sensitivity and accuracy of detecting actual sequence variation in a sample. In some embodiments, a sequence variant having a frequency of about or less than about 5%, 4%, 3%, 2%, 1.5%, 1%, 0.75%, 0.5%, 0.25%, 0.1%, 0.075%, 0.05%, 0.04%, 0.03%, 0.02%, 0.01%, 0.005%, 0.001%, or lower is sufficiently above background to permit an accurate call. In some embodiments, the sequence variant occurs with a frequency of about or less than about 0.1%. In some embodiments, the method comprises calling as a genuine sequence variant, those sequence differences having a frequency in the range of about 0.0005% to about 3%, such as between 0.001%-2%, or 0.01%-1%. In some embodiments, the frequency of a sequence variant is sufficiently above background when such frequency is statistically significantly above the background error rate (e.g. with a p-value of about or less than about 0.05, 0.01, 0.001, 0.0001, or lower). In some embodiments, the frequency of a sequence variant is sufficiently above background when such frequency is about or at least about 2-fold, 3-fold, 4-fold, 5-fold, 6-fold, 7-fold, 8-fold, 9-fold, 10-fold, 25-fold, 50-fold, 100-fold, or more above the background error rate (e.g. at least 5-fold higher). In some embodiments, the background error rate in accurately determining the sequence at a given position is about or less than about 1%, 0.5%, 0.1%, 0.05%, 0.01%, 0.005%, 0.001%, 0.0005%, or lower. In some embodiments, the error rate is lower than 0.001%. Methods for determining frequency and error rate are described herein, such as with regard to any of the various aspects of the disclosure.

In some embodiments, identifying a genuine sequence variant (also referred to as "calling" or "making a call") comprises optimally aligning one or more sequencing reads with a reference sequence to identify differences between the two, as well as to identify junctions. In general, alignment involves placing one sequence along another sequence, iteratively introducing gaps along each sequence, scoring how well the two sequences match, and preferably repeating for various positions along the reference. The best-scoring match is deemed to be the alignment and represents an inference about the degree of relationship between the sequences. A variety of alignment algorithms and aligners implementing them are available, non-limiting examples of which are described herein, such as with respect to any of the various aspects of the disclosure. In some embodiments, a reference sequence to which sequencing reads are compared is a known reference sequence, such as a reference genome (e.g. the genome of a member of the same species as the subject). A reference genome may be complete or incomplete. In some embodiments, a reference genome consists only of regions containing target polynucleotides, such as from a reference genome or from a consensus generated from sequencing reads under analysis. In some embodiments, a reference sequence comprises or consists of sequences of polynucleotides of one or more organisms, such as sequences from one or more bacteria, archaea, viruses, protists, fungi, or other organism. In some embodiments, the reference sequence consists of only a portion of a reference genome, such as regions corresponding to one or more target sequences under analysis (e.g. one or more genes, or portions thereof). For example, for detection of a pathogen (such as in the case of contamination detection), the reference genome is the entire genome of the pathogen (e.g. HIV, HPV, or a harmful bacterial strain, e.g. *E. coli*), or a portion thereof useful in identification, such as of a particular strain or serotype. In some embodiments, sequencing reads are aligned to multiple different reference sequences, such as to screen for multiple different organisms or strains. Additional non-limiting examples of reference sequences with respect to which sequence differences may be identified (and sequence variants called) are described herein, such as with respect to any of the various aspects of the disclosure.

In one aspect, the disclosure provides a method of amplifying in a reaction mixture a plurality of different concatemers comprising two or more copies of a target sequence, wherein the target sequence comprises sequence A and sequence B oriented in a 5' to 3' direction. In some embodiments, the method comprises subjecting the reaction mixture to a nucleic acid amplification reaction, wherein the reaction mixture comprises: (a) the plurality of concatemers, wherein individual concatemers in the plurality comprise different junctions formed by circularizing individual polynucleotides having a 5' end and a 3' end; (b) a first primer comprising sequence A', wherein the first primer specifically hybridizes to sequence A of the target sequence via sequence complementarity between sequence A and sequence A'; (c) a second primer comprising sequence B, wherein the second primer specifically hybridizes to sequence B' present in a complementary polynucleotide comprising a complement of the target sequence via sequence complementarity between sequence B and B'; and (d) a polymerase that extends the first primer and the second primer to produce amplified polynucleotides; wherein the distance between the 5' end of sequence A and the 3' end of sequence B of the target sequence is 75 nt or less.

In a related aspect, the disclosure provides a method of amplifying in a reaction mixture a plurality of different circular polynucleotides comprising a target sequence, wherein the target sequence comprises sequence A and sequence B oriented in a 5' to 3' direction. In some embodiments, the method comprises subjecting the reaction mixture to a nucleic acid amplification reaction, wherein the reaction mixture comprises: (a) the plurality of circular polynucleotides, wherein individual circular polynucleotides in the plurality comprise different junctions formed by circularizing individual polynucleotides having a 5' end and a 3' end; (b) a first primer comprising sequence A', wherein the first primer specifically hybridizes to sequence A of the target sequence via sequence complementarity between sequence A and sequence A'; (c) a second primer comprising sequence B, wherein the second primer specifically hybridizes to sequence B' present in a complementary polynucleotide comprising a complement of the target sequence via sequence complementarity between sequence B and B'; and (d) a polymerase that extends the first primer and the second primer to produce amplified polynucleotides; wherein sequence A and sequence B are endogenous sequences, and the distance between the 5' end of sequence A and the 3' end of sequence B of the target sequence is 75 nt or less.

Whether amplifying circular polynucleotides or concatemers, such polynucleotides may be from any suitable sample sources (either directly, or indirectly, such as by amplification). A variety of suitable sample sources, optional extraction processes, types of polynucleotides, and types of sequence variants are described herein, such as with respect to any of the various aspects of the disclosure. Circular polynucleotides may be derived from circularizing non-circular polynucleotides. Non-limiting examples of circularization processes (e.g. with and without adapter oligonucleotides), reagents (e.g. types of adapters, use of ligases), reaction conditions (e.g. favoring self-joining), optional additional processing (e.g. post-reaction purification), and the junctions formed thereby are provided herein, such as with regard to any of the various aspects of the disclosure. Concatemers may be derived from amplification of circular polynucleotides. A variety of methods of amplifying polynucleotides (e.g. DNA and/or RNA) are available, non-limiting examples of which have also been described herein. In some embodiments, concatemers are generated by rolling circle amplification of circular polynucleotides.

FIG. 10 illustrates an example arrangement of the first and second primer with respect to a target sequence in the context of a single repeat (which will typically not be amplified unless circular) and concatemers comprising multiple copies of the target sequence. As noted with regard to other aspects described herein, this arrangement of primers may be referred to as "back to back" (B2B) or "inverted" primers. Amplification with B2B primers facilitates enrichment of circular and/or concatemeric templates. Moreover, this orientation combined with a relatively smaller footprint (total distance spanned by a pair of primers) permits amplification of a wider variety of fragmentation events around a target sequence, as a junction is less likely to occur between primers than in the arrangement of primers found in a typical amplification reaction (facing one another, spanning a target sequence). In some embodiments, the distance between the 5' end of sequence A and the 3' end of sequence B is about or less than about 200, 150, 100, 75, 50, 40, 30, 25, 20, 15, or fewer nucleotides. In some embodiments, sequence A is the complement of sequence B. In some embodiments, multiple pairs of B2B primers directed to a plurality of different target sequences are used in the same reaction to amplify a plurality of different target sequences in parallel (e.g. about or at least about 10, 50, 100, 150, 200, 250, 300, 400, 500, 1000, 2500, 5000, 10000, 15000, or more different target sequences). Primers can be of any suitable length, such as described elsewhere herein. Amplification may comprise any suitable amplification reaction under appropriate conditions, such as an amplification reaction described herein. In some embodiments, amplification is a polymerase chain reaction.

Figure 15A:
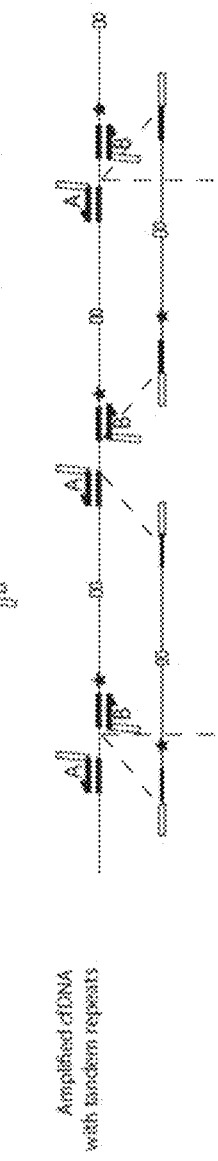
FIGS. 15A-15C illustrates a further implementation of amplification with tailed B2B primers, and implementing a "touch up" second phase of PCR at a higher temperature. The B2B primers contain a sequence-specific region (thick black line) and an adapter sequence (open box). With a lower, phase-one annealing temperature, the target-specific sequence anneals to the template to yield an initial monomer, and PCR products contain tandem repeats (FIG. 15A). In a second amplification phase at a higher temperature, both target-specific and adapter sequence hybridization is favored over target-specific sequence hybridizing alone, decreasing the degree to which short products are preferentially produced (FIG. 15B). Without favoring the whole primer, internal annealing with the target-specific sequences rapidly increases the fraction of monomers (FIG. 15C, left).
Figure 15B:
Figure 15C:
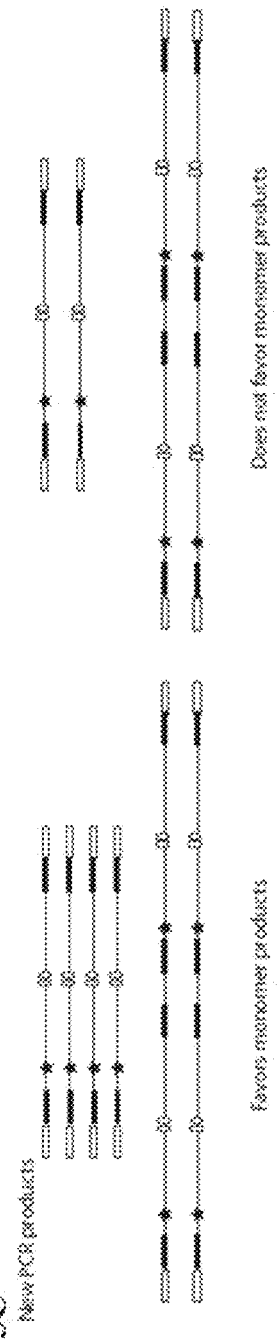

In some embodiments, B2B primers comprise at least two sequence elements, a first element that hybridizes to a target sequence via sequence complementarity, and a 5' "tail" that does not hybridize to the target sequence during a first amplification phase at a first hybridization temperature during which the first element hybridizes (e.g. due to lack of sequence complementarity between the tail and the portion of the target sequence immediately 3' with respect to where the first element binds). For example, the first primer comprises sequence C 5' with respect to sequence A', the second primer comprises sequence D 5' with respect to sequence B, and neither sequence C nor sequence D hybridize to the plurality of concatemers (or circular polynucleotides) during a first amplification phase at a first hybridization temperature. In some embodiments in which such tailed primers are used, amplification can comprise a first phase and a second phase; the first phase comprises a hybridization step at a first temperature, during which the first and second primers hybridize to the concatemers (or circular polynucleotides) and primer extension; and the second phase comprises a hybridization step at a second temperature that is higher than the first temperature, during which the first and second primers hybridize to amplification products comprising extended first or second primers, or complements thereof, and primer extension. The number of amplification cycles at each of the two temperatures can be adjusted based on the products desired. Typically, the first temperature will be used for a relatively low number of cycles, such as about or less than about 15, 10, 9, 8, 7, 6, 5, or fewer cycles. The number of cycles at the higher temperature can be selected independently of the number of cycles at the first temperature, but will typically be as many or more cycles, such as about or at least about 5, 6, 7, 8, 9, 10, 15, 20, 25, or more cycles. The higher temperature favors hybridization between the first element and tail element of the primer in primer extension products over shorter fragments formed by hybridization between only the first element in a primer and an internal target sequence within a concatemer. Accordingly, the two-phase amplification may be used to reduce the extent to which short amplification products might otherwise be favored, thereby maintaining a relatively higher proportion of amplification products having two or more copies of a target sequence. For example, after 5 cycles (e.g. at least 5, 6, 7, 8, 9, 10, 15, 20, or more cycles) of hybridization at the second temperature and primer extension, at least 5% (e.g. at least 5%, 6%, 7%, 8%, 9%, 10%, 15%, 20%, 25%, 30%, or more) of amplified polynucleotides in the reaction mixture comprise two or more copies of the target sequence. An illustration of an embodiment in accordance with this two-phase, tailed B2B primer amplification process is illustrated in FIGS. 11A-11D. Illustration of a further implementation is provided in FIGS. 15A-15C.

In some embodiments, amplification is under conditions that are skewed to increase the length of amplicons from concatemers. For example, the primer concentration can be lowered, such that not every priming site will hybridize a primer, thus making the PCR products longer. Similarly, decreasing the primer hybridization time during the cycles will similarly allow fewer primers to hybridize, thus also making the average PCR amplicon size increase. Furthermore, increasing the temperature and/or extension time of the cycles may similarly increase the average length of the PCR amplicons. Any combination of these techniques can be used.

In some embodiments, particularly where an amplification with B2B primers has been performed, amplification products are treated to filter the resulting amplicons on the basis of size to reduce and/or eliminate the number of monomers a mixture comprising concatemers. This can be done using a variety of available techniques, including, but not limited to, fragment excision from gels and gel filtration (e.g. to enrich for fragments larger than about 300, 400, 500, or more nucleotides in length); as well as SPRI beads (Agencourt AMPure XP) for size selection by fine-tuning the binding buffer concentration. For example, the use of 0.6× binding buffer during mixing with DNA fragments may be used to preferentially bind DNA fragments larger than about 500 base pairs (bp).

In some embodiments, the first primer comprises sequence C 5' with respect to sequence A', the second primer comprises sequence D 5' with respect to sequence B, and neither sequence C nor sequence D hybridize to the plurality of circular polynucleotides during a first amplification phase at a first hybridization temperature. Amplification may comprise a first phase and a second phase; wherein the first phase comprises a hybridization step at a first temperature, during which the first and second primer hybridize to the circular polynucleotides or amplification products thereof prior to primer extension; and the second phase comprises a hybridization step at a second temperature that is higher than the first temperature, during which the first and second primers hybridize to amplification products comprising extended first or second primers or complements thereof. For example, the first temperature may be selected as about or more than about the Tm of sequence A', sequence B, or the average of these, or a temperature that is greater than 1° C., 2° C., 3° C., 4° C., 5° C., 6° C., 7° C., 8° C., 9° C., 10° C., or higher than one of these Tm's. In this example, the second temperature may be selected to be about or more than about the Tm of the combined sequence (A'+C), the combine sequence (B+D), or the average of these, or a temperature that is greater than 1° C., 2° C., 3° C., 4° C., 5° C., 6° C., 7° C., 8° C., 9° C., 10° C., or higher than one of these Tm's. The term "Tm" is also referred to as the "melting temperature," and generally represents the temperature at which 50% of an oligonucleotide consisting of a reference sequence (which may in fact be a sub-sequence within a larger polynucleotide) and its complementary sequence are hybridized (or separated). In general, Tm increases with increasing length, and as such, the Tm of sequence A' is expected to be lower than the Tm of combination sequence (A'+C).

Figure 29:
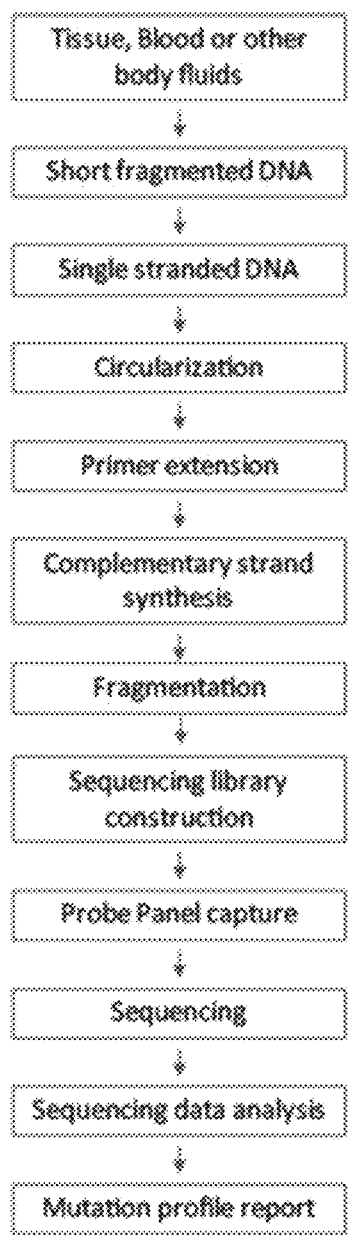
FIG. 29 illustrates an example workflow design of an amplification system for identifying sequence variants in accordance with methods of the disclosure, particularly with regard to circularized polynucleotides.
Figure 30:
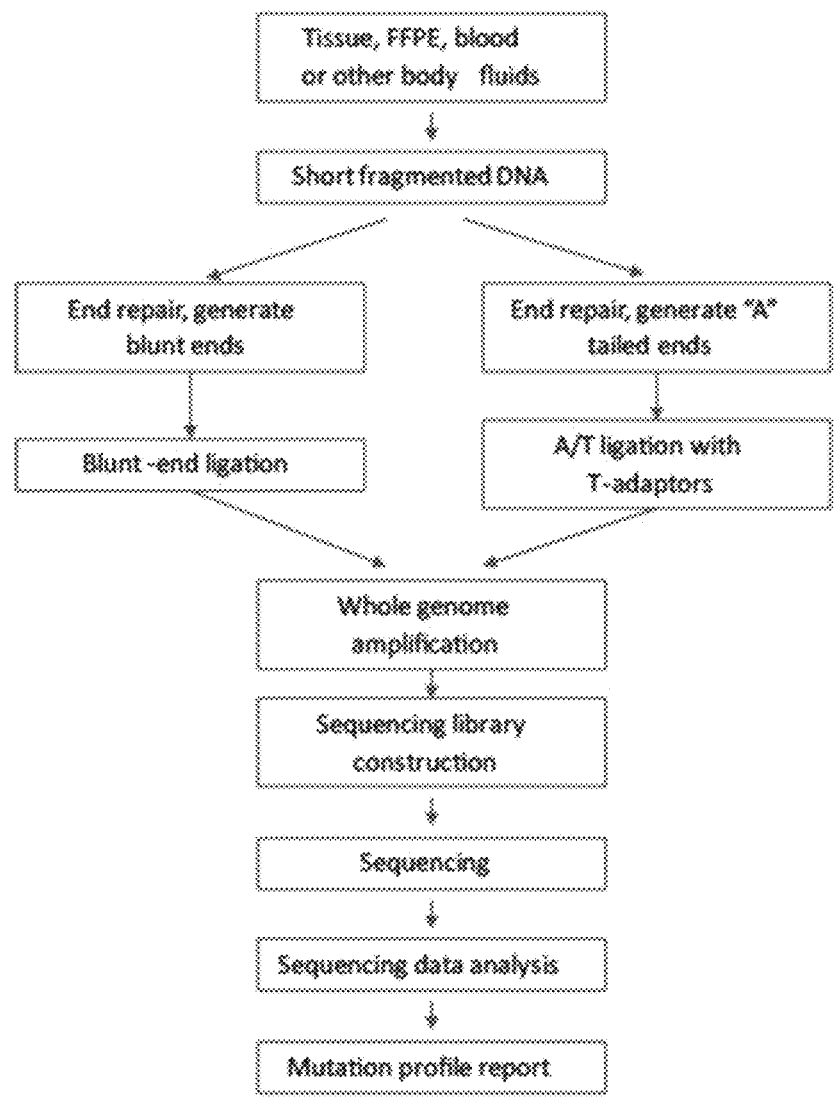
FIG. 30 illustrates an example workflow design of an amplification system for identifying sequence variants in accordance with methods of the disclosure, particularly with regard to linear polynucleotide inputs without a circularization step.
Figure 32:
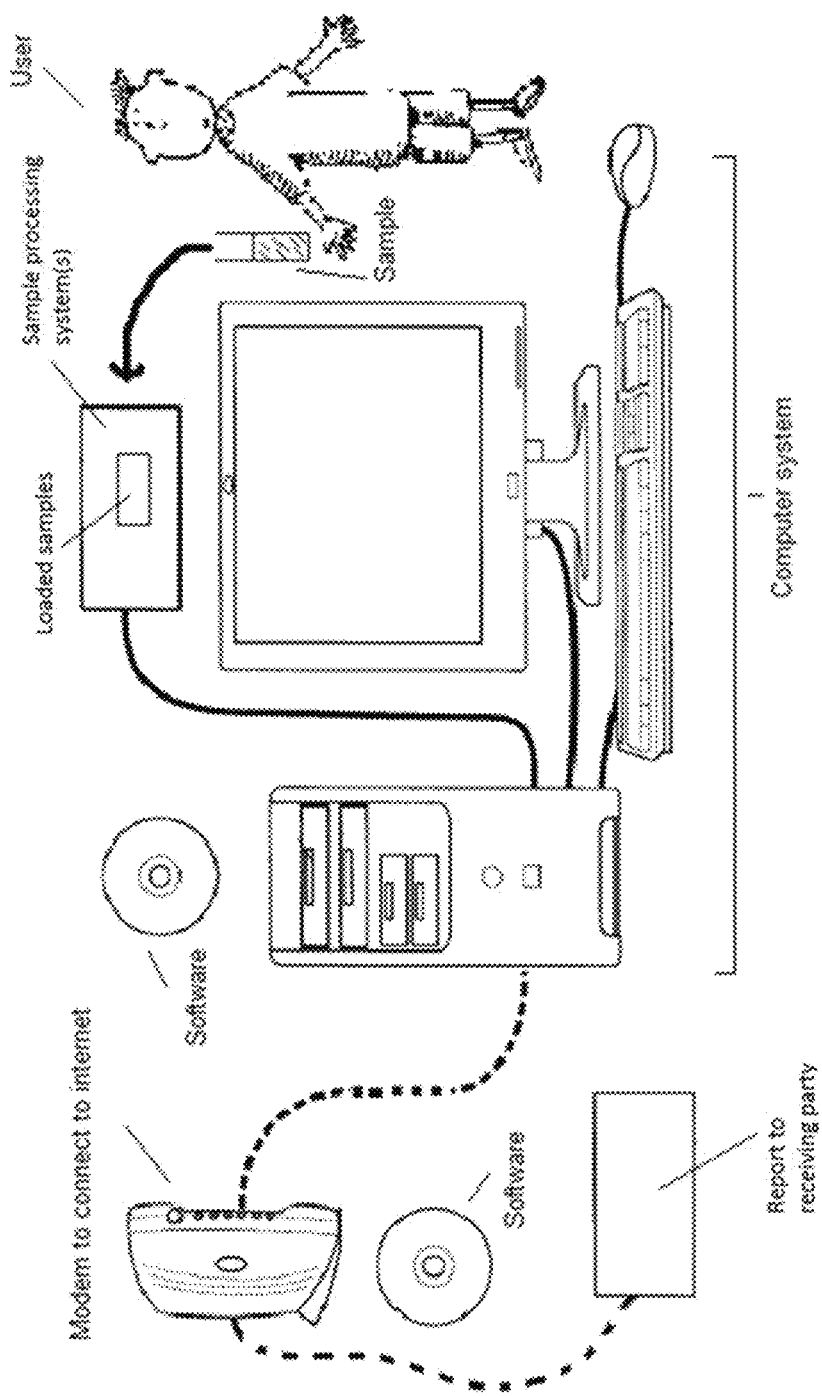
FIG. 32 is an illustration of a system according to an embodiment.

In one aspect, the disclosure provides a system for detecting a sequence variant. In some embodiments, the system comprises (a) a computer configured to receive a user request to perform a detection reaction on a sample; (b) an amplification system that performs a nucleic acid amplification reaction on the sample or a portion thereof in response to the user request, wherein the amplification reaction comprises the steps of (i) circularizing individual polynucleotides in a plurality of polynucleotides to form a plurality of circular polynucleotides using a ligase enzyme, each polynucleotide of the plurality having a junction between the 5' end and 3' end prior to ligation; (ii) degrading the ligase enzyme; and (ii) amplifying the circular polynucleotides after degrading the ligase enzyme to produce amplified polynucleotides; wherein polynucleotides are not purified or isolated between steps (i) and (iii); (c) a sequencing system that generates sequencing reads for polynucleotides amplified by the amplification system, identifies sequence differences between sequencing reads and a reference sequence, and calls a sequence difference that occurs in at least two circular polynucleotides having different junctions as the sequence variant; and (d) a report generator that sends a report to a recipient, wherein the report contains results for detection of the sequence variant. In some embodiments, the recipient is the user. FIG. 32 illustrates a non-limiting example of a system useful in the methods of the present disclosure. FIGS. 29 and 30 provide illustrative schematics of exemplary workflow design.

A computer for use in the system can comprise one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other suitable storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc. A client-server, relational database architecture can be used in embodiments of the system. A client-server architecture is a network architecture in which each computer or process on the network is either a client or a server. Server computers are typically powerful computers dedicated to managing disk drives (file servers), printers (print servers), or network traffic (network servers). Client computers include PCs (personal computers) or workstations on which users run applications, as well as example output devices as disclosed herein. Client computers rely on server computers for resources, such as files, devices, and even processing power. In some embodiments, the server computer handles all of the database functionality. The client computer can have software that handles all the front-end data management and can also receive data input from users.

The system can be configured to receive a user request to perform a detection reaction on a sample. The user request may be direct or indirect. Examples of direct request include those transmitted by way of an input device, such as a keyboard, mouse, or touch screen. Examples of indirect requests include transmission via a communication medium, such as over the internet (either wired or wireless).

The system can further comprise an amplification system that performs a nucleic acid amplification reaction on the sample or a portion thereof in response to the user request. A variety of methods of amplifying polynucleotides (e.g. DNA and/or RNA) are available. Amplification may be linear, exponential, or involve both linear and exponential phases in a multi-phase amplification process. Amplification methods may involve changes in temperature, such as a heat denaturation step, or may be isothermal processes that do not require heat denaturation. Non-limiting examples of suitable amplification processes are described herein, such as with regard to any of the various aspects of the disclosure. In some embodiments, amplification comprises rolling circle amplification (RCA). A variety of systems for amplifying polynucleotides are available, and may vary based on the type of amplification reaction to be performed. For example, for amplification methods that comprise cycles of temperature changes, the amplification system may comprise a thermocycler. An amplification system can comprise a real-time amplification and detection instrument, such as systems manufactured by Applied Biosystems, Roche, and Stratagene. In some embodiments, the amplification reaction comprises the steps of (i) circularizing individual polynucleotides to form a plurality of circular polynucleotides, each of which having a junction between the 5' end and 3' end; and (ii) amplifying the circular polynucleotides. Samples, polynucleotides, primers, polymerases, and other reagents can be any of those described herein, such as with regard to any of the various aspects. Non-limiting examples of circularization processes (e.g. with and without adapter oligonucleotides), reagents (e.g. types of adapters, use of ligases), reaction conditions (e.g. favoring self-joining), optional additional processing (e.g. post-reaction purification), and the junctions formed thereby are provided herein, such as with regard to any of the various aspects of the disclosure. Systems can be selected and or designed to execute any such methods.

Systems may further comprise a sequencing system that generates sequencing reads for polynucleotides amplified by the amplification system, identifies sequence differences between sequencing reads and a reference sequence, and calls a sequence difference that occurs in at least two circular polynucleotides having different junctions as the sequence variant. The sequencing system and the amplification system may be the same, or comprise overlapping equipment. For example, both the amplification system and sequencing system may utilize the same thermocycler. A variety of sequencing platforms for use in the system are available, and may be selected based on the selected sequencing method. Examples of sequencing methods are described herein. Amplification and sequencing may involve the use of liquid handlers. Several commercially available liquid handling systems can be utilized to run the automation of these processes (see for example liquid handlers from Perkin-Elmer, Beckman Coulter, Caliper Life Sciences, Tecan, Eppendorf, Apricot Design, Velocity 11 as examples). A variety of automated sequencing machines are commercially available, and include sequencers manufactured by Life Technologies (SOLiD platform, and pH-based detection), Roche (454 platform), Illumina (e.g. flow cell based systems, such as Genome Analyzer devices). Transfer between 2, 3, 4, 5, or more automated devices (e.g. between one or more of a liquid handler and a sequencing device) may be manual or automated.

Methods for identifying sequence differences and calling sequence variants with respect to a reference sequence are described herein, such as with regard to any of the various aspects of the disclosure. The sequencing system will typically comprise software for performing these steps in response to an input of sequencing data and input of desired parameters (e.g. selection of a reference genome). Examples of alignment algorithms and aligners implementing these algorithms are described herein, including but not limited to the Needleman-Wunsch algorithm (see e.g. the EMBOSS Needle aligner available at www.ebi.ac.uk/Tools/psa/emboss_needle/nucleotide.html, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa emboss_water/nucleotide.html, optionally with default settings). Optimal alignment may be assessed using any suitable parameters of a chosen algorithm, including default parameters. Such alignment algorithms may form part of the sequencing system.

The system can further comprise a report generator that sends a report to a recipient, wherein the report contains results for detection of the sequence variant. A report may be generated in real-time, such as during a sequencing read or while sequencing data is being analyzed, with periodic updates as the process progresses. In addition, or alternatively, a report may be generated at the conclusion of the analysis. The report may be generated automatically, such when the sequencing system completes the step of calling all sequence variants. In some embodiments, the report is generated in response to instructions from a user. In addition to the results of detection of the sequence variant, a report may also contain an analysis based on the one or more sequence variants. For example, where one or more sequence variants are associated with a particular contaminant or phenotype, the report may include information concerning this association, such as a likelihood that the contaminant or phenotype is present, at what level, and optionally a suggestion based on this information (e.g. additional tests, monitoring, or remedial measures). The report can take any of a variety of forms. It is envisioned that data relating to the present disclosure can be transmitted over such networks or connections (or any other suitable means for transmitting information, including but not limited to mailing a physical report, such as a print-out) for reception and/or for review by a receiver. The receiver can be but is not limited to an individual, or electronic system (e.g. one or more computers, and/or one or more servers).

In one aspect, the disclosure provides a computer-readable medium comprising codes that, upon execution by one or more processors, implement a method of detecting a sequence variant. In some embodiments, the implemented method comprises: (a) receiving a customer request to perform a detection reaction on a sample; (b) performing a nucleic acid amplification reaction on the sample or a portion thereof in response to the customer request, wherein the amplification reaction comprises the steps of (i) circularizing individual polynucleotides in a plurality of polynucleotides to form a plurality of circular polynucleotides using a ligase enzyme, wherein each polynucleotide of the plurality of polynucleotides has a 5' end and 3' end prior to ligation; (ii) degrading the ligase enzyme; and (ii) amplifying the circular polynucleotides after degrading the ligase enzyme to produce amplified polynucleotides; wherein polynucleotides are not purified or isolated between steps (i) and (iii); (c) performing a sequencing analysis comprising the steps of (i) generating sequencing reads for polynucleotides amplified in the amplification reaction; (ii) identifying sequence differences between sequencing reads and a reference sequence; and (iii) calling a sequence difference that occurs in at least two circular polynucleotides having different junctions as the sequence variant; and (d) generating a report that contains results for detection of the sequence variant.

A machine readable medium comprising computer-executable code may take many forms, including but not limited to, a tangible storage medium, a carrier wave medium or physical transmission medium. Non-volatile storage media include, for example, optical or magnetic disks, such as any of the storage devices in any computers) or the like, such as may be used to implement the databases, etc. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The subject computer-executable code can be executed on any suitable device comprising a processor, including a server, a PC, or a mobile device such as a smartphone or tablet. Any controller or computer optionally includes a monitor, which can be a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard, mouse, or touch-sensitive screen, optionally provide for input from a user. The computer can include appropriate software for receiving user instructions, either in the form of user input into a set of parameter fields, e.g., in a GUI, or in the form of preprogrammed instructions, e.g., preprogrammed for a variety of different specific operations.

In some embodiments of any of the various aspects disclosed herein, the methods, compositions, and systems have therapeutic applications, such as in the characterization of a patient sample and optionally diagnosis of a condition of a subject. Therapeutic applications may also include informing the selection of therapies to which a patient may be most responsive (also referred to as "theranostics"), and actual treatment of a subject in need thereof, based on the results of a method described herein. In particular, methods and compositions disclosed herein may be used to diagnose tumor presence, progression and/or metastasis of tumors, especially when the polynucleotides analyzed comprise or consist of cfDNA, ctDNA, cfRNA, or fragmented tumor DNA. In some embodiments, a subject is monitored for treatment efficacy. For example, by monitoring ctDNA over time, a decrease in ctDNA can be used as an indication of efficacious treatment, while increases can facilitate selection of different treatments or different dosages. Other uses include evaluations of organ rejection in transplant recipients (where increases in the amount of circulating DNA corresponding to the transplant donor genome is used as an early indicator of transplant rejection), and genotyping/ isotyping of pathogen infections, such as viral or bacterial infections. Detection of sequence variants in circulating fetal DNA may be used to diagnose a condition of a fetus.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested. Typically, prophylactic benefit includes reducing the incidence and/or worsening of one or more diseases, conditions, or symptoms under treatment (e.g. as between treated and untreated populations, or between treated and untreated states of a subject). Improving a treatment outcome may include diagnosing a condition of a subject in order to identify the subject as one that will or will not benefit from treatment with one or more therapeutic agents, or other therapeutic intervention (such as surgery). In such diagnostic applications, the overall rate of successful treatment with the one or more therapeutic agents may be improved, relative to its effectiveness among patients grouped without diagnosis according to a method of the present disclosure (e.g. an improvement in a measure of therapeutic efficacy by at least about 10%, 20%, 30%, 40%, 50%, 60%, 70%, 80%, 90%, 95%, or more).

The terms "subject," "individual," and "patient" are used interchangeably herein to refer to a vertebrate, preferably a mammal, more preferably a human Mammals include, but are not limited to, murines, simians, humans, farm animals, sport animals, and pets. Tissues, cells, and their progeny of a biological entity obtained in vivo or cultured in vitro are also encompassed.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

In some embodiments of the various methods described herein, the sample is from a subject. A subject can be any organism, non-limiting examples of which include plants, animals, fungi, protists, monerans, viruses, mitochondria, and chloroplasts. Sample polynucleotides can be isolated from a subject, such as a cell sample, tissue sample, bodily fluid sample, or organ sample (or cell cultures derived from any of these), including, for example, cultured cell lines, biopsy, blood sample, cheek swab, or fluid sample containing a cell (e.g. saliva). In some cases, the sample does not comprise intact cells, is treated to remove cells, or polynucleotides are isolated without a cellular extractions step (e.g. to isolate cell-free polynucleotides, such as cell-free DNA). Other examples of sample sources include those from blood, urine, feces, nares, the lungs, the gut, other bodily fluids or excretions, materials derived therefrom, or combinations thereof. The subject may be an animal, including but not limited to, a cow, a pig, a mouse, a rat, a chicken, a cat, a dog, etc., and is usually a mammal, such as a human. In some embodiments, the sample comprises tumor cells, such as in a sample of tumor tissue from a subject. In some embodiments, the sample is a blood sample or a portion thereof (e.g. blood plasma or serum). Serum and plasma may be of particular interest, due to the relative enrichment for tumor DNA associated with the higher rate of malignant cell death among such tissues. A sample may be a fresh sample, or a sample subjected to one or more storage processes (e.g. paraffin-embedded samples, particularly formalin-fixed paraffin-embedded (FFPE) sample). In some embodiments, a sample from a single individual is divided into multiple separate samples (e.g. 2, 3, 4, 5, 6, 7, 8, 9, 10, or more separate samples) that are subjected to methods of the disclosure independently, such as analysis in duplicate, triplicate, quadruplicate, or more. Where a sample is from a subject, the reference sequence may also be derived from the subject, such as a consensus sequence from the sample under analysis or the sequence of polynucleotides from another sample or tissue of the same subject. For example, a blood sample may be analyzed for ctDNA mutations, while cellular DNA from another sample (e.g. buccal or skin sample) is analyzed to determine the reference sequence.

Polynucleotides may be extracted from a sample, with or without extraction from cells in a sample, according to any suitable method. A variety of kits are available for extraction of polynucleotides, selection of which may depend on the type of sample, or the type of nucleic acid to be isolated. Examples of extraction methods are provided herein, such as those described with respect to any of the various aspects disclosed herein. In one example, the sample may be a blood sample, such as a sample collected in an EDTA tube (e.g. BD Vacutainer). Plasma can be separated from the peripheral blood cells by centrifugation (e.g. 10 minutes at 1900×g at 4° C.). Plasma separation performed in this way on a 6 mL blood sample will typically yield 2.5 to 3 mL of plasma. Circulating cell-free DNA can be extracted from a plasma sample, such as by using a QIAmp Circulating Nucleic Acid Kit (Qiagene), according the manufacturer's protocol. DNA may then be quantified (e.g. on an Agilent 2100 Bioanalyzer with High Sensitivity DNA kit (Agilent)). As an example, yield of circulating DNA from such a plasma sample from a healthy person may range from 1 ng to 10 ng per mL of plasma, with significantly more in cancer patient samples.

Polynucleotides can also be derived from stored samples, such frozen or archived samples. One common method for storing samples is to formalin-fix and paraffin-embed them. However, this process is also associated with degradation of nucleic acids. Polynucleotides processed and analyzed from an FFPE sample may include short polynucleotides, such as fragments in the range of 50-200 base pairs, or shorter. A number of techniques exist for the purification of nucleic acids from fixed paraffin-embedded samples, such as those described in WO2007133703, and methods described by Foss, et al Diagnostic Molecular Pathology, (1994) 3:148-155 and Paska, C., et al Diagnostic Molecular Pathology, (2004) 13:234-240. Commercially available kits may be used for purifying polynucleotides from FFPE samples, such as Ambion's Recoverall Total Nucleic acid Isolation kit. Typical methods start with a step that removes the paraffin from the tissue via extraction with Xylene or other organic solvent, followed by treatment with heat and a protease like proteinase K which cleaves the tissue and proteins and helps to release the genomic material from the tissue. The released nucleic acids can then be captured on a membrane or precipitated from solution, washed to removed impurities and for the case of mRNA isolation, a DNase treatment step is sometimes added to degrade unwanted DNA. Other methods for extracting FFPE DNA are available and can be used in the methods of the present disclosure.

In some embodiments, the plurality of polynucleotides comprise cell-free polynucleotides, such as cell-free DNA (cfDNA), cell-free RNA (cfRNA), circulating tumor DNA (ctDNA), or circulating tumor RNA (ctRNA). Cell-free DNA circulates in both healthy and diseased individuals. Cell-free RNA circulates in both healthy and diseased individuals. cfDNA from tumors (ctDNA) is not confined to any specific cancer type, but appears to be a common finding across different malignancies. According to some measurements, the free circulating DNA concentration in plasma is about 14-18 ng/ml in control subjects and about 180-318 ng/ml in patients with neoplasias. Apoptotic and necrotic cell death contribute to cell-free circulating DNA in bodily fluids. For example, significantly increased circulating DNA levels have been observed in plasma of prostate cancer patients and other prostate diseases, such as Benign Prostate Hyperplasia and Prostatits. In addition, circulating tumor DNA is present in fluids originating from the organs where the primary tumor occurs. Thus, breast cancer detection can be achieved in ductal lavages; colorectal cancer detection in stool; lung cancer detection in sputum, and prostate cancer detection in urine or ejaculate. Cell-free DNA may be obtained from a variety of sources. One common source is blood samples of a subject. However, cfDNA or other fragmented DNA may be derived from a variety of other sources. For example, urine and stool samples can be a source of cfDNA, including ctDNA. Cell-free RNA may be obtained from a variety of sources.

In some embodiments, polynucleotides are subjected to subsequent steps (e.g. circularization and amplification) without an extraction step, and/or without a purification step. For example, a fluid sample may be treated to remove cells without an extraction step to produce a purified liquid sample and a cell sample, followed by isolation of DNA from the purified fluid sample. A variety of procedures for isolation of polynucleotides are available, such as by precipitation or non-specific binding to a substrate followed by washing the substrate to release bound polynucleotides. Where polynucleotides are isolated from a sample without a cellular extraction step, polynucleotides will largely be extracellular or "cell-free" polynucleotides. For example, cell-free polynucleotides may include cell-free DNA (also called "circulating" DNA). In some embodiments, the circulating DNA is circulating tumor DNA (ctDNA) from tumor cells, such as from a body fluid or excretion (e.g. blood sample). Cell-free polynucleotides may include cell-free RNA (also called "circulating" RNA). In some embodiments, the circulating RNA is circulating tumor RNA (ctRNA) from tumor cells. Tumors frequently show apoptosis or necrosis, such that tumor nucleic acids are released into the body, including the blood stream of a subject, through a variety of mechanisms, in different forms and at different levels. Typically, the size of the ctDNA can range between higher concentrations of smaller fragments, generally 70 to 200 nucleotides in length, to lower concentrations of large fragments of up to thousands kilobases.

In some embodiments of any of the various aspects described herein, detecting a sequence variant comprises detecting mutations (e.g. rare somatic mutations) with respect to a reference sequence or in a background of no mutations, where the sequence variant is correlated with disease. In general, sequence variants for which there is statistical, biological, and/or functional evidence of association with a disease or trait are referred to as "causal genetic variants." A single causal genetic variant can be associated with more than one disease or trait. In some embodiments, a causal genetic variant can be associated with a Mendelian trait, a non-Mendelian trait, or both. Causal genetic variants can manifest as variations in a polynucleotide, such 1, 2, 3, 4, 5, 6, 7, 8, 9, 10, 20, 50, or more sequence differences (such as between a polynucleotide comprising the causal genetic variant and a polynucleotide lacking the causal genetic variant at the same relative genomic position). Non-limiting examples of types of causal genetic variants include single nucleotide polymorphisms (SNP), deletion/insertion polymorphisms (DIP), copy number variants (CNV), short tandem repeats (STR), restriction fragment length polymorphisms (RFLP), simple sequence repeats (SSR), variable number of tandem repeats (VNTR), randomly amplified polymorphic DNA (RAPD), amplified fragment length polymorphisms (AFLP), inter-retrotransposon amplified polymorphisms (IRAP), long and short interspersed elements (LINE/SINE), long tandem repeats (LTR), mobile elements, retrotransposon microsatellite amplified polymorphisms, retrotransposon-based insertion polymorphisms, sequence specific amplified polymorphism, and heritable epigenetic modification (for example, DNA methylation). A causal genetic variant may also be a set of closely related causal genetic variants. Some causal genetic variants may exert influence as sequence variations in RNA polynucleotides. At this level, some causal genetic variants are also indicated by the presence or absence of a species of RNA polynucleotides. Also, some causal genetic variants result in sequence variations in protein polypeptides. A number of causal genetic variants have been reported. An example of a causal genetic variant that is a SNP is the Hb S variant of hemoglobin that causes sickle cell anemia. An example of a causal genetic variant that is a DIP is the delta508 mutation of the CFTR gene which causes cystic fibrosis. An example of a causal genetic variant that is a CNV is trisomy 21, which causes Down's syndrome. An example of a causal genetic variant that is an STR is tandem repeat that causes Huntington's disease. Non-limiting examples of causal genetic variants and diseases with which they are associated are provided in Table 1. Additional non-limiting examples of causal genetic variants are described in WO2014015084. Further examples of genes in which mutations are associated with diseases, and in which sequence variants may be detected according to a method of the disclosure, are provided in Table 2.

TABLE 1

| Disease | Gene | Variant Name |
|---|---|---|
| 21-Hydroxylase Deficiency | CYP21A2 | F306 + t |
| 21-Hydroxylase Deficiency | CYP21A2 | F306 + t |
| 21-Hydroxylase Deficiency | CYP21A3 | g.655A/C > G |
| 21-Hydroxylase Deficiency | CYP21A4 | g.655A/C > G |
| 21-Hydroxylase Deficiency | CYP21A6 | G110del8nt |
| 21-Hydroxylase Deficiency | CYP21A5 | G110del8nt |
| 21-Hydroxylase Deficiency | CYP21A7 | I172N, rs34607927 |
| 21-Hydroxylase Deficiency | CYP21A2 | I236N |
| 21-Hydroxylase Deficiency | CYP21A2 | M239K, rs6476 |
| 21-Hydroxylase Deficiency | CYP21A2 | P30L |

TABLE 1-continued

| Disease | Gene | Variant Name |
|---|---|---|
| 21-Hydroxylase Deficiency | CYP21A2 | P453S |
| 21-Hydroxylase Deficiency | CYP21A2 | Q318X |
| 21-Hydroxylase Deficiency | CYP21A2 | R356W |
| 21-Hydroxylase Deficiency | CYP21A2 | V237E, rs12530380 |
| 21-Hydroxylase Deficiency | CYP21A2 | V281L, rs6471 |
| ABCC8-Related Hyperinsulinism | ABCC8 | 3992-9G > A |
| ABCC8-Related Hyperinsulinism | ABCC8 | delF1388 |
| ABCC8-Related Hyperinsulinism | ABCC8 | delF1388 |
| ABCC8-Related Hyperinsulinism | ABCC8 | V187D |
| Achondroplasia | FGFR3 | G375C |
| Achondroplasia | FGFR3 | G380R, rs28931614 |
| Achromatopsia | CNGB3 | c.1148delC |
| Achromatopsia | CNGB3 | c.1148delC |
| Achromatopsia | CNGB3 | c.819-826del8 |
| Achromatopsia | CNGB3 | c.819-826del8 |
| Achromatopsia | CNGB3 | c.886-896del11insT |
| Achromatopsia | CNGB3 | c.886-896del11insT |
| Achromatopsia | CNGB3 | c.991-3T > G |
| Achromatopsia | CNGB3 | p.Arg403Gln |
| Achromatopsia | CNGB3 | p.Glu336X |
| Adenosine Monophosphate Deaminase 1 | AMPD1 | P48L |
| Adenosine Monophosphate Deaminase 1 | AMPD1 | Q12X, rs17602729 |
| Agenesis of Corpus Callosum with Neuronopathy | SLC12A6 | c.2436delG |
| Agenesis of Corpus Callosum with Neuronopathy | SLC12A6 | c.2436delG |
| Alkaptonuria | HGD | c.174delA |
| Alkaptonuria | HGD | c.174delA |
| Alkaptonuria | HGD | c.457_458insG |
| Alkaptonuria | HGD | c.457_458insG |
| Alkaptonuria | HGD | G161R |
| Alkaptonuria | HGD | G270R |
| Alkaptonuria | HGD | IVS1-1G > A |
| Alkaptonuria | HGD | IVS5 + 1G > A |
| Alkaptonuria | HGD | Met368Val |
| Alkaptonuria | HGD | P230S |
| Alkaptonuria | HGD | S47L |
| Alkaptonuria | HGD | V300G |
| Alpha-1-Antitrypsin Deficiency | SERPINA1 | Arg101His, rs709932 |
| Alpha-1-Antitrypsin Deficiency | SERPINA1 | Glu264Val |

TABLE 1-continued

| Disease | Gene | Variant Name |
|---|---|---|
| Alpha-1-Antitrypsin Deficiency | SERPINA1 | Glu342Lys, rs28929474 |
| Alpha-1-Antitrypsin Deficiency | SERPINA1 | Glu376Asp, rs1303 |
| Alpha-Mannosidosis | MAN2B1 | IVS14 + 1G > C |
| Alpha-Mannosidosis | MAN2B1 | p.L809P |
| Alpha-Mannosidosis | MAN2B1 | p.R750W |
| Alpha-Sarcoglycanopathy | SGCA | R77C, rs28933693 |
| Alpha-Thalassemia | HBA2 | H19D |
| Alpha-Thalassemia | HBA1 | HbQ |
| Alpha-Thalassemia | HBA1, HBA2 | 3.7 kb (type I) deletion alpha-2 |
| Alpha-Thalassemia | HBA1, HBA2 | 3.7 kb (type I) deletion alpha-2 |
| Alpha-Thalassemia | HBA1, HBA2 | HbVar database id # 1086, --(SEA); deletion of ~20 kb including both alpha-globin genes alpha-Thal-1 |
| Alpha-Thalassemia | HBA1, HBA2 | HbVar database id # 1086, --(SEA); deletion of ~20 kb including both alpha-globin genes alpha-Thal-1 |
| Alpha-Thalassemia | HBA1, HBA2 | HbVar database id # 1087, --(MED-I); deletion of ~17.5 kb including both alpha-globin genes alpha-Thal-1 |
| Alpha-Thalassemia | HBA1, HBA2 | HbVar database id # 1087, --(MED-I); deletion of ~17.5 kb including both alpha-globin genes alpha-Thal-1 |
| Alpha-Thalassemia | HBA1, HBA2 | HbVar database id # 1088, -(alpha)20.5; this 20.5 kb deletion involves alpha2 and the 5' end of alpha1; alpha-Thal-1 |
| Alpha-Thalassemia | HBA1, HBA2 | HbVar database id # 1088, -(alpha)20.5; this 20.5 kb deletion involves alpha2 and the 5' end of alpha1; alpha-Thal-1 |
| Alpha-Thalassemia | HBA1, HBA2 | HbVar database id # 1094, --(FIL); a deletion of 30-34 kb involving the alpha1, alpha2, and zeta genes alpha-Thal-1 |
| Alpha-Thalassemia | HBA1, HBA2 | HbVar database id # 1094, --(FIL); a deletion of 30-34 kb involving the alpha1, alpha2, and zeta genes alpha-Thal-1 |
| Alpha-Thalassemia | HBA1, HBA2 | HbVar database id # 1095, --(THAI); a deletion of 34-38 kb involving the alpha1, alpha2, and zeta genes alpha-Thal-1 |
| Alpha-Thalassemia | HBA1, HBA2 | HbVar database id # 1095, --(THAI); a deletion of 34-38 kb involving the alpha1, alpha2, and zeta genes alpha-Thal-1 |
| Alpha-Thalassemia | HBA1, HBA2 | HbVar database id # 1097, --(MED-II); a deletion of 26.5 kb involving the two alpha and zeta genes alpha-Thal-1 |
| Alpha-Thalassemia | HBA1, HBA2 | HbVar database id # 1097, --(MED-II); a deletion of 26.5 kb |

TABLE 1-continued

| Disease | Gene | Variant Name |
|---|---|---|
| | | involving the two alpha and zeta genes alpha-Thal-1 |
| Alpha-Thalassemia | HBA2 | HbVar database id # 187 |
| Alpha-Thalassemia | HBA2 | HbVar database id # 2598, IVS I-5 (G > A) |
| Alpha-Thalassemia | HBA1, HBA2 | HbVar database id # 703 |
| Alpha-Thalassemia | HBA1, HBA2 | HbVar database id # 704 |
| Alpha-Thalassemia | HBA1, HBA2 | HbVar database id # 705, Hb Koya Dora |
| Alpha-Thalassemia | HBA1, HBA2 | HbVar database id # 707, rs41412046 |
| Alpha-Thalassemia | HBA1 | HbVar database id # 87 |
| Alpha-Thalassemia | HBA1, HBA2 | HbVar database id # 969, Poly A (A->G); AATAAA->AATGAA beta+ |
| Alpha-Thalassemia | HBA1, HBA2 | HbVar database id # 971, Poly A (A->G); AATAAA->AATAAG beta+ |
| Alpha-Thalassemia | HBA2 | M1T |
| Alpha-Thalassemia | HBA1 | W14X |
| Angiotensin II Receptor, Type 1 | AGTR1 | A1166C |
| Apolipoprotein E Genotyping | APOE | p.C112R, rs429358 |
| Apolipoprotein E Genotyping | APOE | p.R158C, rs7412 |
| Argininosuccinicaciduria | ASL | R385C |
| ARSACS | SACS | 5254C > T |
| ARSACS | SACS | 6594delT |
| ARSACS | SACS | 6594delT |
| Aspartylglycosaminuria | AGA | c.199_200delGA |
| Aspartylglycosaminuria | AGA | c.199_200delGA |
| Aspartylglycosaminuria | AGA | C163S |
| Ataxia with Vitamin E Deficiency | TTPA | 744delA |
| Ataxia with Vitamin E Deficiency | TTPA | 744delA |
| Ataxia-Telangiectasia | ATM | R35X |
| Autoimmune Polyendocrinopathy Syndrome Type 1 | AIRE | c.1163_1164insA |
| Autoimmune Polyendocrinopathy Syndrome Type 1 | AIRE | c.1163_1164insA |
| Autoimmune Polyendocrinopathy Syndrome Type 1 | AIRE | c.769C > T |
| Autoimmune Polyendocrinopathy Syndrome Type 1 | AIRE | c.967_979del |
| Autoimmune Polyendocrinopathy Syndrome Type 1 | AIRE | c.967_979del |
| Autoimmune Polyendocrinopathy Syndrome Type 1 | AIRE | Y85C |
| Bardet-Biedl Syndrome | BBS1 | M390R |

TABLE 1-continued

| Disease | Gene | Variant Name |
| --- | --- | --- |
| Bardet-Biedl Syndrome | BBS10 | p.C91LfsX4 |
| Bardet-Biedl Syndrome | BBS10 | p.C91LfsX4 |
| Best Vitelliform Macular Dystrophy | BEST1 | c.G383C |
| Beta-Sarcoglycanopathy | SGCB | S114F |
| Beta-Thalassemia | HBB | -28 (A->G) beta+ |
| Beta-Thalassemia | HBB | -29 (A->G) beta+ |
| Beta-Thalassemia | HBB | -29A > G |
| Beta-Thalassemia | HBB | -30 (T->A) beta+ |
| Beta-Thalassemia | HBB | -87 (C->G) beta+ |
| Beta-Thalassemia | HBB | -88C > T |
| Beta-Thalassemia | HBB | CAP + 1 (A->C) beta+ |
| Beta-Thalassemia | HBB | Codon 15 (G->A); TGG(Trp)->TAG(stop codon) beta0, rs34716011 |
| Beta-Thalassemia | HBB | Codon 15 (G->A); TGG(Trp)->TAG(stop codon) beta0, rs34716011 |
| Beta-Thalassemia | HBB | Codon 16 (-C); GGC(Gly)->GG- beta0 |
| Beta-Thalassemia | HBB | Codon 16 (-C); GGC(Gly)->GG- beta0 |
| Beta-Thalassemia | HBB | Codon 17 (A->T); AAG(Lys)->TAG(stop codon) beta0 |
| Beta-Thalassemia | HBB | Codon 24 (T->A); GGT(Gly)->GGA(Gly) beta+ |
| Beta-Thalassemia | HBB | Codon 39 (C->T); CAG(Gln)->TAG(stop codon) beta0 |
| Beta-Thalassemia | HBB | Codon 5 (-CT); CCT(Pro)->C-- beta0 |
| Beta-Thalassemia | HBB | Codon 5 (-CT); CCT(Pro)->C-- beta0 |
| Beta-Thalassemia | HBB | Codon 6 (-A); GAG(Glu)->G-G beta0 |
| Beta-Thalassemia | HBB | Codon 6 (-A); GAG(Glu)->G-G beta0 |
| Beta-Thalassemia | HBB | Codon 8 (-AA); AAG(Lys)->--G beta0 |
| Beta-Thalassemia | HBB | Codon 8 (-AA); AAG(Lys)->--G beta0 |
| Beta-Thalassemia | HBB | Codons 41/42 (-TTCT); TTCTTT(Phe-Phe)->----TT beta0 |
| Beta-Thalassemia | HBB | Codons 41/42 (-TTCT); TTCTTT(Phe-Phe)->----TT beta0 |
| Beta-Thalassemia | HBB | Codons 71/72 (+A); TTT AGT(Phe Ser)->TTT A AGT; beta0 |
| Beta-Thalassemia | HBB | Codons 71/72 (+A); TTT AGT(Phe Ser)->TTT A AGT; beta0 |

TABLE 1-continued

| Disease | Gene | Variant Name |
|---|---|---|
| Beta-Thalassemia | HBB | Codons 8/9 (+G); AAG TCT(Lys; Ser)->AAG G TCT beta0 |
| Beta-Thalassemia | HBB | Codons 8/9 (+G); AAG TCT(Lys; Ser)->AAG G TCT beta0 |
| Beta-Thalassemia | HBB | HbVar database id # 889, IVS-II-654 (C->T); AAGGCAATA-> AAG^GTAATA beta+(severe) |
| Beta-Thalassemia | HBB | HbVar database id # 890, IVS-II-705 (T->G); GATGTAAGA-> GAG^GTAAGA beta+ |
| Beta-Thalassemia | HBB | HbVar database id # 891, IVS-II-745 (C->G); CAGCTACCAT-> CAG^GTACCAT beta+ |
| Beta-Thalassemia | HBB | HbVar database id # 979, 619 bp deletion beta0 |
| Beta-Thalassemia | HBB | 619 bp deletion beta0 |
| Beta-Thalassemia | HBB | IVS-I-1 (G->A); AG^GTTGGT-> AGATTGGT beta0 |
| Beta-Thalassemia | HBB | IVS-I-1 (G->T); AG^GTTGGT-> AGTTTGGT beta0 |
| Beta-Thalassemia | HBB | IVS-I-110 (G->A) beta+; the mutation is 21 nucleotides 5' to the acceptor splice site AG^GC |
| Beta-Thalassemia | HBB | IVS-I-5 (G->C) beta+(severe) |
| Beta-Thalassemia | HBB | IVS-II-1 (G->A); beta0 |
| Beta-Thalassemia | HBB | IVS-II-844 (C->G); beta+ |
| Beta-Thalassemia | HBB | IVS1 + 6T > C |
| Beta-Thalassemia | HBB | IVS11-849A > C |
| Beta-Thalassemia | HBB | IVS11-849A > G |
| Biotinidase Deficiency | BTD | A171T, rs13073139 |
| Biotinidase Deficiency | BTD | D252G, rs28934601 |
| Biotinidase Deficiency | BTD | D444H, rs13078881 |
| Biotinidase Deficiency | BTD | F403V |
| Biotinidase Deficiency | BTD | G98:d7i3 |
| Biotinidase Deficiency | BTD | G98:d7i3 |
| Biotinidase Deficiency | BTD | Q456H |
| Biotinidase Deficiency | BTD | R157H |
| Biotinidase Deficiency | BTD | R538C |
| Blau Syndrome | NOD2 | E383K |
| Blau Syndrome | NOD2 | L469F |
| Blau Syndrome | NOD2 | R334Q |
| Blau Syndrome | NOD2 | R334W |
| Bloom Syndrome | BLM | 2407insT |
| Bloom Syndrome | BLM | 2407insT |

TABLE 1-continued

| Disease | Gene | Variant Name |
|---|---|---|
| Bloom Syndrome | BLM | 736delATCTGAinsTAGATTC (2281del6/ins7) |
| Bloom Syndrome | BLM | 736delATCTGAinsTAGATTC (2281del6/ins7) |
| BRCA1 Hereditary Breast/Ovarian Cancer | BRCA1 | 185delAG |
| BRCA1 Hereditary Breast/Ovarian Cancer | BRCA1 | 185delAG |
| BRCA1 Hereditary Breast/Ovarian Cancer | BRCA1 | 5382insC |
| BRCA1 Hereditary Breast/Ovarian Cancer | BRCA1 | 5382insC |
| BRCA1 Hereditary Breast/Ovarian Cancer | BRCA1 | Tyr978X |
| BRCA2 Hereditary Breast/Ovarian Cancer | BRCA2 | 6174delT |
| BRCA2 Hereditary Breast/Ovarian Cancer | BRCA2 | 6174delT |
| BRCA2 Hereditary Breast/Ovarian Cancer | BRCA2 | 8765delAG |
| BRCA2 Hereditary Breast/Ovarian Cancer | BRCA2 | 8765delAG |
| Canavan Disease | ASPA | A305E (914C > A), rs28940574 |
| Canavan Disease | ASPA | E285A (854A > C), rs28940279 |
| Canavan Disease | ASPA | IVS2 − 2A > G (433 − 2A > G) |
| Canavan Disease | ASPA | Y231X (693C > A) |
| Carnitine Palmitoyltransferase IA Deficiency | CPT1A | G710E |
| Carnitine Palmitoyltransferase IA Deficiency | CPT1A | P479L |
| Carnitine Palmitoyltransferase II Deficiency | CPT2 | G549D |
| Carnitine Palmitoyltransferase II Deficiency | CPT2 | L178F 534 ins/25 bp del |
| Carnitine Palmitoyltransferase II Deficiency | CPT2 | L178F 534 ins/25 bp del |
| Carnitine Palmitoyltransferase II Deficiency | CPT2 | P227L |
| Carnitine Palmitoyltransferase II Deficiency | CPT2 | P50H |
| Carnitine Palmitoyltransferase II Deficiency | CPT2 | P604S |
| Carnitine Palmitoyltransferase II Deficiency | CPT2 | Q413fs |
| Carnitine Palmitoyltransferase II Deficiency | CPT2 | Q413fs |
| Carnitine Palmitoyltransferase II Deficiency | CPT2 | Q550R |
| Carnitine Palmitoyltransferase II Deficiency | CPT2 | R124X |

TABLE 1-continued

| Disease | Gene | Variant Name |
|---|---|---|
| Carnitine Palmitoyltransferase II Deficiency | CPT2 | R503C |
| Carnitine Palmitoyltransferase II Deficiency | CPT2 | R631C |
| Carnitine Palmitoyltransferase II Deficiency | CPT2 | S113L |
| Carnitine Palmitoyltransferase II Deficiency | CPT2 | s38fs |
| Carnitine Palmitoyltransferase II Deficiency | CPT2 | s38fs |
| Carnitine Palmitoyltransferase II Deficiency | CPT2 | Y628S, rs28936673 |
| Cartilage-Hair Hypoplasia | RMRP | g.262G > T |
| Cartilage-Hair Hypoplasia | RMPR | g.70A > G |
| CFTR-Related Disorders | CFTR | 1811 + 1.6kbA->G |
| CFTR-Related Disorders | CFTR | 2183AA > G |
| CFTR-Related Disorders | CFTR | 2183AA > G |
| CFTR-Related Disorders | CFTR | 3849 + 10kbC > T |
| CFTR-Related Disorders | CFTR | A455E |
| CFTR-Related Disorders | CFTR | A559T |
| CFTR-Related Disorders | CFTR | C524X |
| CFTR-Related Disorders | CFTR | 574delA, 574delA |
| CFTR-Related Disorders | CFTR | 574delA, 574delA |
| CFTR-Related Disorders | CFTR | 2108delA, 2108delA |
| CFTR-Related Disorders | CFTR | 2108delA, 2108delA |
| CFTR-Related Disorders | CFTR | 3171delC, 3171delC |
| CFTR-Related Disorders | CFTR | 3171delC, 3171delC |
| CFTR-Related Disorders | CFTR | 621 + 1G->T |
| CFTR-Related Disorders | CFTR | 2105-2117del13insAGAAA |
| CFTR-Related Disorders | CFTR | 2105-2117del13insAGAAA |
| CFTR-Related Disorders | CFTR | 711 + 1G->T |
| CFTR-Related Disorders | CFTR | 711 + 5G->A |
| CFTR-Related Disorders | CFTR | 712 − 1G->T |
| CFTR-Related Disorders | CFTR | 1288insTA, 1288insTA |
| CFTR-Related Disorders | CFTR | 1288insTA, 1288insTA |
| CFTR-Related Disorders | CFTR | 936delTA |
| CFTR-Related Disorders | CFTR | 936delTA |
| CFTR-Related Disorders | CFTR | [delta]F311 |
| CFTR-Related Disorders | CFTR | [delta]F311 |
| CFTR-Related Disorders | CFTR | 1078delT, 1078delT |
| CFTR-Related Disorders | CFTR | 1078delT, 1078delT |
| CFTR-Related Disorders | CFTR | 1161delC, 1161delC |

TABLE 1-continued

| Disease | Gene | Variant Name |
|---|---|---|
| CFTR-Related Disorders | CFTR | 1161delC, 1161delC |
| CFTR-Related Disorders | CFTR | 1609delCA, 1609delCA |
| CFTR-Related Disorders | CFTR | 1609delCA, 1609delCA |
| CFTR-Related Disorders | CFTR | [delta]I507 |
| CFTR-Related Disorders | CFTR | [delta]I507 |
| CFTR-Related Disorders | CFTR | rs332, [delta]F508 |
| CFTR-Related Disorders | CFTR | rs332, [delta]F508 |
| CFTR-Related Disorders | CFTR | 1677delTA, 1677delTA |
| CFTR-Related Disorders | CFTR | 1677delTA, 1677delTA |
| CFTR-Related Disorders | CFTR | 1717 − 1G->A |
| CFTR-Related Disorders | CFTR | 1812 − 1G->A |
| CFTR-Related Disorders | CFTR | 1898 + 1G->A |
| CFTR-Related Disorders | CFTR | 1898 + 1G->T |
| CFTR-Related Disorders | CFTR | 1898 + 5G->T |
| CFTR-Related Disorders | CFTR | 1949del84, 1949del84 |
| CFTR-Related Disorders | CFTR | 1949del84, 1949del84 |
| CFTR-Related Disorders | CFTR | 2043delG, 2043delG |
| CFTR-Related Disorders | CFTR | 2043delG, 2043delG |
| CFTR-Related Disorders | CFTR | 2055del9->A |
| CFTR-Related Disorders | CFTR | 2055del9->A |
| CFTR-Related Disorders | CFTR | 2143delT, 2143delT |
| CFTR-Related Disorders | CFTR | 2143delT, 2143delT |
| CFTR-Related Disorders | CFTR | 2184delA, 2184delA |
| CFTR-Related Disorders | CFTR | 2184delA, 2184delA |
| CFTR-Related Disorders | CFTR | 2184insA, 2184insA |
| CFTR-Related Disorders | CFTR | 2184insA, 2184insA |
| CFTR-Related Disorders | CFTR | 2307insA, 2307insA |
| CFTR-Related Disorders | CFTR | 2307insA, 2307insA |
| CFTR-Related Disorders | CFTR | 296 + 12T->C |
| CFTR-Related Disorders | CFTR | 2789 + 5G->A |
| CFTR-Related Disorders | CFTR | 2869insG, 2869insG |
| CFTR-Related Disorders | CFTR | 2869insG, 2869insG |
| CFTR-Related Disorders | CFTR | 3120G->A |
| CFTR-Related Disorders | CFTR | 3120 + 1G->A |
| CFTR-Related Disorders | CFTR | 3272 − 26A->G |
| CFTR-Related Disorders | CFTR | 3659delC, 3659delC |
| CFTR-Related Disorders | CFTR | 3659delC, 3659delC |
| CFTR-Related Disorders | CFTR | 3667del4, 3667del4 |
| CFTR-Related Disorders | CFTR | 3667del4, 3667del4 |

TABLE 1-continued

| Disease | Gene | Variant Name |
|---|---|---|
| CFTR-Related Disorders | CFTR | 3791delC, 3791delC |
| CFTR-Related Disorders | CFTR | 3791delC, 3791delC |
| CFTR-Related Disorders | CFTR | 3821delT, 3821delT |
| CFTR-Related Disorders | CFTR | 3821delT, 3821delT |
| CFTR-Related Disorders | CFTR | 3905insT, 3905insT |
| CFTR-Related Disorders | CFTR | 3905insT, 3905insT |
| CFTR-Related Disorders | CFTR | 4016insT, 4016insT |
| CFTR-Related Disorders | CFTR | 4016insT, 4016insT |
| CFTR-Related Disorders | CFTR | 394delTT, 394delTT |
| CFTR-Related Disorders | CFTR | 394delTT, 394delTT |
| CFTR-Related Disorders | CFTR | 405 + 1G->A |
| CFTR-Related Disorders | CFTR | 405 + 3A->C |
| CFTR-Related Disorders | CFTR | 444delA |
| CFTR-Related Disorders | CFTR | 444delA |
| CFTR-Related Disorders | CFTR | 3876delA, 3876delA |
| CFTR-Related Disorders | CFTR | 3876delA, 3876delA |
| CFTR-Related Disorders | CFTR | 457TAT->G |
| CFTR-Related Disorders | CFTR | 457TAT->G |
| CFTR-Related Disorders | CFTR | 3199del6, 3199del6 |
| CFTR-Related Disorders | CFTR | 3199del6, 3199del6 |
| CFTR-Related Disorders | CFTR | 406 − 1G->A |
| CFTR-Related Disorders | CFTR | 663delT, 663delT |
| CFTR-Related Disorders | CFTR | 663delT, 663delT |
| CFTR-Related Disorders | CFTR | 935delA, 935delA |
| CFTR-Related Disorders | CFTR | 935delA, 935delA |
| CFTR-Related Disorders | CFTR | CFTR dele2,3 (21kb) |
| CFTR-Related Disorders | CFTR | CFTR dele2,3 (21kb) |
| CFTR-Related Disorders | CFTR | D1152H |
| CFTR-Related Disorders | CFTR | E60X |
| CFTR-Related Disorders | CFTR | E92X |
| CFTR-Related Disorders | CFTR | F508C, rs1800093 |
| CFTR-Related Disorders | CFTR | G178R |
| CFTR-Related Disorders | CFTR | G330X |
| CFTR-Related Disorders | CFTR | G480C |
| CFTR-Related Disorders | CFTR | G542X |
| CFTR-Related Disorders | CFTR | G551D |
| CFTR-Related Disorders | CFTR | G622D |
| CFTR-Related Disorders | CFTR | G85E |
| CFTR-Related Disorders | CFTR | G91R |

TABLE 1-continued

| Disease | Gene | Variant Name |
|---|---|---|
| CFTR-Related Disorders | CFTR | I148T, rs35516286 |
| CFTR-Related Disorders | CFTR | I506V |
| CFTR-Related Disorders | CFTR | IVS8-5T |
| CFTR-Related Disorders | CFTR | IVS8-7T |
| CFTR-Related Disorders | CFTR | IVS8-9T |
| CFTR-Related Disorders | CFTR | K710X |
| CFTR-Related Disorders | CFTR | L206W |
| CFTR-Related Disorders | CFTR | M1101K, rs36210737 |
| CFTR-Related Disorders | CFTR | N1303K |
| CFTR-Related Disorders | CFTR | P574H |
| CFTR-Related Disorders | CFTR | Q1238X |
| CFTR-Related Disorders | CFTR | Q359K/T360K_wt |
| CFTR-Related Disorders | CFTR | Q493X |
| CFTR-Related Disorders | CFTR | Q552X |
| CFTR-Related Disorders | CFTR | Q890X |
| CFTR-Related Disorders | CFTR | R1066C |
| CFTR-Related Disorders | CFTR | R1070Q |
| CFTR-Related Disorders | CFTR | R1158X |
| CFTR-Related Disorders | CFTR | R1162X |
| CFTR-Related Disorders | CFTR | R117C |
| CFTR-Related Disorders | CFTR | R117H |
| CFTR-Related Disorders | CFTR | R1283M |
| CFTR-Related Disorders | CFTR | R334W |
| CFTR-Related Disorders | CFTR | R347H |
| CFTR-Related Disorders | CFTR | R347P |
| CFTR-Related Disorders | CFTR | R352Q |
| CFTR-Related Disorders | CFTR | R553X |
| CFTR-Related Disorders | CFTR | R560T |
| CFTR-Related Disorders | CFTR | R709X |
| CFTR-Related Disorders | CFTR | R75X |
| CFTR-Related Disorders | CFTR | R764X |
| CFTR-Related Disorders | CFTR | S1196X |
| CFTR-Related Disorders | CFTR | S1235R, rs34911792 |
| CFTR-Related Disorders | CFTR | S1251N |
| CFTR-Related Disorders | CFTR | S1255X |
| CFTR-Related Disorders | CFTR | S364P |
| CFTR-Related Disorders | CFTR | S549I |
| CFTR-Related Disorders | CFTR | S549N |
| CFTR-Related Disorders | CFTR | S549R |

TABLE 1-continued

| Disease | Gene | Variant Name |
|---|---|---|
| CFTR-Related Disorders | CFTR | S549R |
| CFTR-Related Disorders | CFTR | T338I |
| CFTR-Related Disorders | CFTR | V520F |
| CFTR-Related Disorders | CFTR | W1089X |
| CFTR-Related Disorders | CFTR | W1204X |
| CFTR-Related Disorders | CFTR | W1204X |
| CFTR-Related Disorders | CFTR | W1282X |
| CFTR-Related Disorders | CFTR | Y1092X |
| CFTR-Related Disorders | CFTR | Y122X |
| Choroideremia | CHM | c.1609 + 2dupT |
| Choroideremia | CHM | c.1609 + 2dupT |
| CLN3-Related Neuronal Ceroid-Lipofuscinosis | CLN3 | c.461_677del |
| CLN3-Related Neuronal Ceroid-Lipofuscinosis | CLN3 | c.461_677del |
| CLN3-Related Neuronal Ceroid-Lipofuscinosis | CLN3 | c.791_1056del |
| CLN3-Related Neuronal Ceroid-Lipofuscinosis | CLN3 | c.791_1056del |
| CLN5-Related Neuronal Ceroid-Lipofuscinosis | CLN5 | c.1175_1176delAT |
| CLN5-Related Neuronal Ceroid-Lipofuscinosis | CLN5 | c.1175_1176delAT |
| CLN5-Related Neuronal Ceroid-Lipofuscinosis | CLN5 | c.225G > A |
| CLN8-Related Neuronal Ceroid-Lipofuscinosis | CLN8 | c.70C > G |
| Cohen Syndrome | VPS13B | c.3348_3349delCT |
| Cohen Syndrome | VPS13B | c.3348_3349delCT |
| Congenital Cataracts, Facial Dysmorphism, and Neuropathy | CTDP1 | IVS6 + 389C > T |
| Congenital Disorder of Glycosylation Ia | PMM2 | p.F119L |
| Congenital Disorder of Glycosylation Ia | PMM2 | p.R141H |
| Congenital Disorder of Glycosylation Ib | MPI | R295H, rs28928906 |
| Congenital Finnish Nephrosis | NPHS1 | c.121_122del |
| Congenital Finnish Nephrosis | NPHS1 | c.121_122del |
| Congenital Finnish Nephrosis | NPHS1 | c.3325C > T |
| Crohn Disease | NOD2 | 3020 ins C |
| Crohn Disease | NOD2 | 3020 ins C |
| Crohn Disease | NOD2 | G908R, rs2066845 |
| Crohn Disease | NOD2 | R702W, rs2066844 |
| Cystinosis | CTNS | 1035insC |
| Cystinosis | CTNS | 1035insC |
| Cystinosis | CTNS | 537del21 |

TABLE 1-continued

| Disease | Gene | Variant Name |
|---|---|---|
| Cystinosis | CTNS | 537del21 |
| Cystinosis | CTNS | 57kb deletion |
| Cystinosis | CTNS | 57kb deletion |
| Cystinosis | CTNS | D205N |
| Cystinosis | CTNS | L158P |
| Cystinosis | CTNS | W138X |
| DFNA 9 (COCH) | COCH | P51S |
| Diabetes and Hearing Loss | mtDNA | 3234A > G |
| Diabetes and Hearing Loss | mtDNA | 3271T > C |
| Diabetes and Hearing Loss | mtDNA | G8363A |
| Diabetes and Hearing Loss | mtDNA | T14709C |
| Early-Onset Primary Dystonia (DYT1) | TOR1A | 904_906delGAG |
| Early-Onset Primary Dystonia (DYT1) | TOR1A | 904_906delGAG |
| Epidermolysis Bullosa Junctional, Herlitz-Pearson Type | LAMB3 | 3024delT |
| Epidermolysis Bullosa Junctional, Herlitz-Pearson Type | LAMB3 | 3024delT |
| Epidermolysis Bullosa Junctional, Herlitz-Pearson Type | LAMB3 | p.Q243X |
| Epidermolysis Bullosa Junctional, Herlitz-Pearson Type | LAMB3 | R144X |
| Epidermolysis Bullosa Junctional, Herlitz-Pearson Type | LAMB3 | R42X |
| Epidermolysis Bullosa Junctional, Herlitz-Pearson Type | LAMB3 | R635X |
| Epidermolysis Bullosa Junctional, Herlitz-Pearson Type | LAMA3 | R650X |
| Epidermolysis Bullosa Junctional, Herlitz-Pearson Type | LAMC2 | R95X |
| Factor V Leiden Thrombophilia | F5 | H1299R |
| Factor V Leiden Thrombophilia | F5 | R506Q, rs6025 |
| Factor V R2 Mutation Thrombophilia | F5 | rs6027 |
| Factor XI Deficiency | F11 | E117X (576G > T) |
| Factor XI Deficiency | F11 | F283L (1074T > C) |
| Factor XI Deficiency | F11 | IVS14 + 1G > A |
| Factor XI Deficiency | F11 | IVS14del14 |
| Factor XI Deficiency | F11 | IVS14del14 |
| Factor XIII Deficiency | F13A1 | V34L, rs5985 |
| Familial Adenomatous Polyposis | APC | I1307K, rs1801155 |
| Familial Dysautonomia | IKBKAP | 2507 + 6T > C |
| Familial Dysautonomia | IKBKAP | P914L |
| Familial Dysautonomia | IKBKAP | R696P |
| Familial Hypercholesterolemia Type B | APOB | R3500Q, rs5742904 |

TABLE 1-continued

| Disease | Gene | Variant Name |
|---|---|---|
| Familial Hypercholesterolemia Type B | APOB | R3500W |
| Familial Hypercholesterolemia Type B | APOB | R3531C, rs12713559 |
| Familial Mediterranean Fever | MEFV | A744S (2230G > T) |
| Familial Mediterranean Fever | MEFV | delI692 (del2076_2078) |
| Familial Mediterranean Fever | MEFV | delI692 (del2076_2078) |
| Familial Mediterranean Fever | MEFV | E148Q (442 G > C), rs3743930 |
| Familial Mediterranean Fever | MEFV | E167D (501 G > C) |
| Familial Mediterranean Fever | MEFV | F479L (1437 C > G) |
| Familial Mediterranean Fever | MEFV | K695R (2084A > G) |
| Familial Mediterranean Fever | MEFV | M680I (2040G > C) |
| Familial Mediterranean Fever | MEFV | M694I (2082G > A), rs28940578 |
| Familial Mediterranean Fever | MEFV | M694V (2080A > G) |
| Familial Mediterranean Fever | MEFV | P369S (1105 C > T), rs11466023 |
| Familial Mediterranean Fever | MEFV | R408Q (1223G > A), rs11466024 |
| Familial Mediterranean Fever | MEFV | R653H (1958G > A) |
| Familial Mediterranean Fever | MEFV | R761H (2282G > A) |
| Familial Mediterranean Fever | MEFV | T267I (800 C > T) |
| Familial Mediterranean Fever | MEFV | V726A (2177T > C), rs28940579 |
| FANCC-Related Fanconi Anemia | FANCC | 322delG |
| FANCC-Related Fanconi Anemia | FANCC | 322delG |
| FANCC-Related Fanconi Anemia | FANCC | IVS4 + 4A > T (711 + 4A > T) |
| FANCC-Related Fanconi Anemia | FANCC | Q13X (37C > T) |
| FANCC-Related Fanconi Anemia | FANCC | R547X |
| FGFR1-Related Craniosynostosis | FGFR1 | P252R |
| FGFR2-Related Craniosynostosis | FGFR2 | P253R |
| FGFR2-Related Craniosynostosis | FGFR2 | S252W |
| FGFR3-Related Craniosynostosis | FGFR3 | A391E, rs28931615 |
| FGFR3-Related Craniosynostosis | FGFR3 | P250R, rs4647924 |
| Free Sialic Acid Storage Disorders | SLC17A5 | c.1007_1008delTA |
| Free Sialic Acid Storage Disorders | SLC17A5 | c.1007_1008delTA |
| Free Sialic Acid Storage Disorders | SLC17A5 | c.115C > T |
| Frontotemporal Dementia with Parkinsonism-17 | MAPT | IVS10 + 16 |
| Frontotemporal Dementia with Parkinsonism-17 | MAPT | P301L |
| Frontotemporal Dementia with Parkinsonism-17 | MAPT | P301S |
| Frontotemporal Dementia with Parkinsonism-17 | MAPT | R406W |
| Fumarase deficiency | FH | c.1431_1433dupAAA |
| Fumarase deficiency | FH | c.1431_1433dupAAA |

TABLE 1-continued

| Disease | Gene | Variant Name |
|---|---|---|
| Galactosemia | GALT | 5.0Kb gene deletion |
| Galactosemia | GALT | 5.0Kb gene deletion |
| Galactosemia | GALT | 5'UTR-119del |
| Galactosemia | GALT | 5'UTR-119del |
| Galactosemia | GALT | IVS2-2 A > G |
| Galactosemia | GALT | K285N |
| Galactosemia | GALT | L195P T > C |
| Galactosemia | GALT | L218L |
| Galactosemia | GALT | N314D, rs2070074 |
| Galactosemia | GALT | Phe171Ser |
| Galactosemia | GALT | Q169K |
| Galactosemia | GALT | Q188R |
| Galactosemia | GALT | S135L |
| Galactosemia | GALT | T138M C > T |
| Galactosemia | GALT | X380R |
| Galactosemia | GALT | Y209C A > G |
| Gaucher Disease | GBA | 1035insG |
| Gaucher Disease | GBA | 1035insG |
| Gaucher Disease | GBA | 84insG |
| Gaucher Disease | GBA | 84insG |
| Gaucher Disease | GBA | D409H, rs1064651 |
| Gaucher Disease | GBA | D409V |
| Gaucher Disease | GBA | IVS2(+1)G > A |
| Gaucher Disease | GBA | L444P (1448T > C), rs35095275 |
| Gaucher Disease | GBA | N370S |
| Gaucher Disease | GBA | R463C |
| Gaucher Disease | GBA | R463H |
| Gaucher Disease | GBA | R496H (1604G > A) |
| Gaucher Disease | GBA | V394L |
| GJB2-Related DFNA 3 Nonsyndromic Hearing Loss and Deafness | GJB2 | 167delT |
| GJB2-Related DFNA 3 Nonsyndromic Hearing Loss and Deafness | GJB2 | 167delT |
| GJB2-Related DFNA 3 Nonsyndromic Hearing Loss and Deafness | GJB2 | 235delC |
| GJB2-Related DFNA 3 Nonsyndromic Hearing Loss and Deafness | GJB2 | 235delC |
| GJB2-Related DFNA 3 Nonsyndromic Hearing Loss and Deafness | GJB2 | 35delG |
| GJB2-Related DFNA 3 Nonsyndromic | GJB2 | 35delG |

TABLE 1-continued

| Disease | Gene | Variant Name |
|---|---|---|
| Hearing Loss and Deafness | | |
| GJB2-Related DFNA 3 Nonsyndromic Hearing Loss and Deafness | GJB2 | IVS1 + 1G > A |
| GJB2-Related DFNB 1 Nonsyndromic Hearing Loss and Deafness | GJB2 | 101delAG |
| GJB2-Related DFNB 1 Nonsyndromic Hearing Loss and Deafness | GJB2 | 313del14 |
| GJB2-Related DFNB 1 Nonsyndromic Hearing Loss and Deafness | GJB2 | 313del14 |
| GJB2-Related DFNB 1 Nonsyndromic Hearing Loss and Deafness | GJB2 | delE120 |
| GJB2-Related DFNB 1 Nonsyndromic Hearing Loss and Deafness | GJB2 | delE120 |
| GJB2-Related DFNB 1 Nonsyndromic Hearing Loss and Deafness | GJB2 | M34T, rs35887622 |
| GJB2-Related DFNB 1 Nonsyndromic Hearing Loss and Deafness | GJB2 | Q124X |
| GJB2-Related DFNB 1 Nonsyndromic Hearing Loss and Deafness | GJB2 | R184P |
| GJB2-Related DFNB 1 Nonsyndromic Hearing Loss and Deafness | GJB2 | V37I |
| GJB2-Related DFNB 1 Nonsyndromic Hearing Loss and Deafness | GJB2 | W24X |
| GJB2-Related DFNB 1 Nonsyndromic Hearing Loss and Deafness | GJB2 | W77R |
| GJB2-Related DFNB 1 Nonsyndromic Hearing Loss and Deafness | GJB2 | W77X |
| Glucose-6-Phosphate Dehydrogenase Deficiency | G6PD | A335V |
| Glucose-6-Phosphate Dehydrogenase Deficiency | G6PD | R459L |
| Glucose-6-Phosphate Dehydrogenase Deficiency | G6PD | R459P |
| Glucose-6-Phosphate Dehydrogenase Deficiency | G6PD | rs1050828, rs1050828 |
| Glucose-6-Phosphate Dehydrogenase Deficiency | G6PD | rs1050829, rs1050829 |
| Glucose-6-Phosphate Dehydrogenase Deficiency | G6PD | rs5030868, rs5030868 |
| Glutaricacidemia Type 1 | GCDH | A421V |
| Glutaricacidemia Type 1 | GCDH | R402W |
| Glycogen Storage Disease Type 1a | G6PC | 459insTA |
| Glycogen Storage Disease Type 1a | G6PC | 459insTA |
| Glycogen Storage Disease Type 1a | G6PC | 727G/T |
| Glycogen Storage Disease Type 1a | G6PC | del F327 |
| Glycogen Storage Disease Type 1a | G6PC | del F327 |
| Glycogen Storage Disease Type 1a | G6PC | G188R |
| Glycogen Storage Disease Type 1a | G6PC | G270V |
| Glycogen Storage Disease Type 1a | G6PC | Q242X |

TABLE 1-continued

| Disease | Gene | Variant Name |
|---|---|---|
| Glycogen Storage Disease Type 1a | G6PC | Q27fsdelC |
| Glycogen Storage Disease Type 1a | G6PC | Q27fsdelC |
| Glycogen Storage Disease Type 1a | G6PC | Q347X |
| Glycogen Storage Disease Type 1a | G6PC | R83C |
| Glycogen Storage Disease Type 1a | G6PC | R83H |
| Glycogen Storage Disease Type 1b | G6PT1 | 1211delCT |
| Glycogen Storage Disease Type 1b | G6PT1 | A367T |
| Glycogen Storage Disease Type 1b | G6PT1 | G339C |
| Glycogen Storage Disease Type 1b | G6PT1 | G339D |
| Glycogen Storage Disease Type 1b | G6PT1 | W118R |
| Glycogen Storage Disease Type II | GAA | Arg854X |
| Glycogen Storage Disease Type II | GAA | Asp645Glu, rs28940868 |
| Glycogen Storage Disease Type II | GAA | IVS1(−13t > g) |
| Glycogen Storage Disease Type III | AGL | 1484delT |
| Glycogen Storage Disease Type III | AGL | 1484delT |
| Glycogen Storage Disease Type III | AGL | 17delAG |
| Glycogen Storage Disease Type III | AGL | 17delAG |
| Glycogen Storage Disease Type III | AGL | Q6X |
| Glycogen Storage Disease Type V | PYGM | G204S |
| Glycogen Storage Disease Type V | PYGM | K542T |
| Glycogen Storage Disease Type V | PYGM | K542X |
| Glycogen Storage Disease Type V | PYGM | R49X |
| GNE-Related Myopathies | GNE | M712T, rs28937594 |
| Gracile Syndrome | BCS1L | c.232A > G, rs28937590 |
| Hemoglobin S Beta-Thalassemia | HBB | c.19G > A |
| Hemoglobin S Beta-Thalassemia | HBB | c.20A > T |
| Hemoglobin S Beta-Thalassemia | HBB | c.79G > A |
| Hemoglobin S Beta-Thalassemia | HBB | Hb CS |
| Hemoglobin S Beta-Thalassemia | HBB | Hb D |
| Hemoglobin S Beta-Thalassemia | HBB | Hb O |
| Hereditary Fructose Intolerance | ALDOB | A149P, rs1800546 |
| Hereditary Fructose Intolerance | ALDOB | A174D |
| Hereditary Fructose Intolerance | ALDOB | Delta4E4 |
| Hereditary Fructose Intolerance | ALDOB | Delta4E4 |
| Hereditary Fructose Intolerance | ALDOB | N334K |
| Hereditary Fructose Intolerance | ALDOB | Y203X |
| Hereditary Pancreatitis | PRSS1 | A16V |
| Hereditary Pancreatitis | SPINK1 | M1T |
| Hereditary Pancreatitis | PRSS1 | N29I |

TABLE 1-continued

| Disease | Gene | Variant Name |
|---|---|---|
| Hereditary Pancreatitis | SPINK1 | N34S, rs17107315 |
| Hereditary Pancreatitis | PRSS1 | R122C |
| Hereditary Pancreatitis | PRSS1 | R122H |
| Hereditary Thymine-Uraciluria | DPYD | rs3918290 |
| Hexosaminidase A Deficiency | HEXA | 1278insTATC |
| Hexosaminidase A Deficiency | HEXA | 1278insTATC |
| Hexosaminidase A Deficiency | HEXA | G269S (805G > A) |
| Hexosaminidase A Deficiency | HEXA | IVS12 + 1G > C |
| Hexosaminidase A Deficiency | HEXA | IVS7 + 1G > A |
| Hexosaminidase A Deficiency | HEXA | IVS9 + 1G > A |
| Hexosaminidase A Deficiency | HEXA | R178C |
| Hexosaminidase A Deficiency | HEXA | R178H |
| Hexosaminidase A Deficiency | HEXA | R247W (739C > T) |
| Hexosaminidase A Deficiency | HEXA | R249W (745C > T) |
| HFE-Associated Hereditary Hemochromatosis | HFE | E168Q |
| HFE-Associated Hereditary Hemochromatosis | HFE | E168X |
| HFE-Associated Hereditary Hemochromatosis | HFE | HM971246, H63H |
| HFE-Associated Hereditary Hemochromatosis | HFE | P160delC |
| HFE-Associated Hereditary Hemochromatosis | HFE | P160delC |
| HFE-Associated Hereditary Hemochromatosis | HFE | Q127H, rs28934595 |
| HFE-Associated Hereditary Hemochromatosis | HFE | Q283P |
| HFE-Associated Hereditary Hemochromatosis | HFE | rs1799945, rs1799945 |
| HFE-Associated Hereditary Hemochromatosis | HFE | rs1800562, rs1800562 |
| HFE-Associated Hereditary Hemochromatosis | HFE | rs1800730, rs1800730 |
| HFE-Associated Hereditary Hemochromatosis | HFE | V53M |
| HFE-Associated Hereditary Hemochromatosis | HFE | V59M |
| HFE-Associated Hereditary Hemochromatosis | HFE | W169X |
| Hidrotic Ectodermal Dysplasia 2 | GJB6 | A88V, rs28937872 |
| Hidrotic Ectodermal Dysplasia 2 | GJB6 | G11R |
| Hidrotic Ectodermal Dysplasia 2 | GJB6 | V37E |
| Homocystinuria Caused by Cystathionine Beta-Synthase Deficiency | CBS | G307S 919G->A |

TABLE 1-continued

| Disease | Gene | Variant Name |
|---|---|---|
| Homocystinuria Caused by Cystathionine Beta-Synthase Deficiency | CBS | I278T 833T->C, rs5742905 |
| Hyperkalemic Periodic Paralysis Type 1 | SCN4A | I693T |
| Hyperkalemic Periodic Paralysis Type 1 | SCN4A | L689I |
| Hyperkalemic Periodic Paralysis Type 1 | SCN4A | L689V |
| Hyperkalemic Periodic Paralysis Type 1 | SCN4A | M1360V |
| Hyperkalemic Periodic Paralysis Type 1 | SCN4A | M1592V |
| Hyperkalemic Periodic Paralysis Type 1 | SCN4A | p.A1156T |
| Hyperkalemic Periodic Paralysis Type 1 | SCN4A | p.M1370V |
| Hyperkalemic Periodic Paralysis Type 1 | SCN4A | p.R1448C |
| Hyperkalemic Periodic Paralysis Type 1 | SCN4A | p.T1313M |
| Hyperkalemic Periodic Paralysis Type 1 | SCN4A | R675G |
| Hyperkalemic Periodic Paralysis Type 1 | SCN4A | R675Q |
| Hyperkalemic Periodic Paralysis Type 1 | SCN4A | R675W |
| Hyperkalemic Periodic Paralysis Type 1 | SCN4A | T704M |
| Hyperkalemic Periodic Paralysis Type 1 | SCN4A | V781I |
| Hyperornithinemia-Hyperammonemia-Homocitrullinuria Syndrome | SLC25A15 | F188del |
| Hyperornithinemia-Hyperammonemia-Homocitrullinuria Syndrome | SLC25A15 | F188del |
| Hyperoxaluria, Primary, Type 1 | AGXT | 33insC |
| Hyperoxaluria, Primary, Type 1 | AGXT | 33insC |
| Hyperoxaluria, Primary, Type 1 | AGXT | F152I |
| Hyperoxaluria, Primary, Type 1 | AGXT | G170R |
| Hyperoxaluria, Primary, Type 1 | AGXT | I244T |
| Hyperoxaluria, Primary, Type 2 | GRHPR | 103delG |
| Hyperoxaluria, Primary, Type 2 | GRHPR | 103delG |
| Hypochondroplasia | FGFR3 | Asn328Ile |
| Hypochondroplasia | FGFR3 | I538V |
| Hypochondroplasia | FGFR3 | K650M |
| Hypochondroplasia | FGFR3 | K650N 1950G > T |
| Hypochondroplasia | FGFR3 | K650Q |
| Hypochondroplasia | FGFR3 | N540K 1620C > A |
| Hypochondroplasia | FGFR3 | N540S |
| Hypochondroplasia | FGFR3 | N540T |
| Hypokalemic Periodic Paralysis Type 1 | CACNA1S | R528G |
| Hypokalemic Periodic Paralysis Type 1 | CACNA1S | R528H |
| Hypokalemic Periodic Paralysis Type 1 | CACNA1S | rs28930068, rs28930068 |
| Hypokalemic Periodic Paralysis Type 1 | CACNA1S | rs28930069, rs28930069 |
| Hypokalemic Periodic Paralysis Type 2 | SCN4A | R669H |

TABLE 1-continued

| Disease | Gene | Variant Name |
|---|---|---|
| Hypokalemic Periodic Paralysis Type 2 | SCN4A | R672C |
| Hypokalemic Periodic Paralysis Type 2 | SCN4A | R672G |
| Hypokalemic Periodic Paralysis Type 2 | SCN4A | R672H |
| Hypokalemic Periodic Paralysis Type 2 | SCN4A | R672S |
| Hypophosphatasia | ALPL | Asp361Val |
| Hypophosphatasia | ALPL | c.1559delT |
| Hypophosphatasia | ALPL | c.1559delT |
| Hypophosphatasia | ALPL | E174K |
| Hypophosphatasia | ALPL | G317D |
| Hypophosphatasia | ALPL | Phe310Leu |
| Isovaleric Acidemia | IVD | A282V |
| Isovaleric Acidemia | IVD | rs28940889 |
| Krabbe Disease | GALC | EX11-17DEL |
| Krabbe Disease | GALC | EX11-17DEL |
| Krabbe Disease | GALC | G270D |
| Krabbe Disease | GALC | rs1805078, rs1805078 |
| Krabbe Disease | GALC | rs398607 |
| Leber Hereditary Optic Neuropathy | mtDNA | 14484T > C |
| Leber Hereditary Optic Neuropathy | mtDNA | 15257G > A |
| Leber Hereditary Optic Neuropathy | mtDNA | G14459A |
| Leber Hereditary Optic Neuropathy | mtDNA | G3460A |
| Leber Hereditary Optic Neuropathy | mtDNA | m.11778G > A |
| Leber Hereditary Optic Neuropathy | mtDNA | m.13708G > A |
| Leber Hereditary Optic Neuropathy | mtDNA | m.15812G > A |
| Leber Hereditary Optic Neuropathy | mtDNA | m.3394T > C |
| Leber Hereditary Optic Neuropathy | mtDNA | m.4216T > C |
| Leber Hereditary Optic Neuropathy | mtDNA | m.4917A > G |
| Leigh Syndrome, French-Canadian Type | LRPPRC | A354V |
| LGMD2I | FKRP | L276I, rs28937900 |
| Long Chain 3-Hydroxyacyl-CoA Dehydrogenase Deficiency | HADHA | E474Q c.1528G > C |
| Long Chain 3-Hydroxyacyl-CoA Dehydrogenase Deficiency | HADHA | Q342X 1132C > T |
| Maple Syrup Urine Disease Type 1A | BCKDHA | Y438N |
| Maple Syrup Urine Disease Type 1B | BCKDHB | E372X |
| Maple Syrup Urine Disease Type 1B | BCKDHB | G278S |
| Maple Syrup Urine Disease Type 1B | BCKDHB | R183P |
| McCune-Albright Syndrome | GNAS | R201C |
| McCune-Albright Syndrome | GNAS | R201G |
| McCune-Albright Syndrome | GNAS | R201H |

TABLE 1-continued

| Disease | Gene | Variant Name |
|---|---|---|
| Medium Chain Acyl-Coenzyme A Dehydrogenase Deficiency | ACADM | 244insT |
| Medium Chain Acyl-Coenzyme A Dehydrogenase Deficiency | ACADM | 244insT |
| Medium Chain Acyl-Coenzyme A Dehydrogenase Deficiency | ACADM | 250C > T |
| Medium Chain Acyl-Coenzyme A Dehydrogenase Deficiency | ACADM | 583G > A |
| Medium Chain Acyl-Coenzyme A Dehydrogenase Deficiency | ACADM | 616C > T |
| Medium Chain Acyl-Coenzyme A Dehydrogenase Deficiency | ACADM | 617G > A |
| Medium Chain Acyl-Coenzyme A Dehydrogenase Deficiency | ACADM | 799G > A |
| Medium Chain Acyl-Coenzyme A Dehydrogenase Deficiency | ACADM | K304E |
| Medium Chain Acyl-Coenzyme A Dehydrogenase Deficiency | ACADM | Y42H |
| Megalencephalic Leukoencephalopathy with Subcortical Cysts | MLC1 | 135insC |
| Megalencephalic Leukoencephalopathy with Subcortical Cysts | MLC1 | 135insC |
| MELAS | mtDNA | 3243A > G |
| MELAS | mtDNA | 3250T > C |
| MELAS | mtDNA | 3252A > G |
| MELAS | mtDNA | A12770G |
| MELAS | mtDNA | C3256T |
| MELAS | mtDNA | G13513A |
| MELAS | mtDNA | T3291C |
| MELAS | mtDNA | T8356C |
| MELAS | mtDNA | T9957C |
| MERRF | mtDNA | 8361G > A |
| MERRF | mtDNA | A8296G |
| MERRF | mtDNA | m.8344A > G |
| Metachromatic Leukodystrophy | ARSA | c.459 + 1G > A |
| Metachromatic Leukodystrophy | ARSA | p.P426L, rs28940893 |
| Metachromatic Leukodystrophy | ARSA | p.T274M |
| Metachromatic Leukodystrophy | ARSA | P377L |
| Mitochondrial Cardiomyopathy | mtDNA | A3260T |
| Mitochondrial Cardiomyopathy | mtDNA | A4300G |
| Mitochondrial Cardiomyopathy | mtDNA | C3303T |
| Mitochondrial Cardiomyopathy | mtDNA | T9997C |
| Mitochondrial DNA-Associated Leigh Syndrome and NARP | mtDNA | 5537insT |
| Mitochondrial DNA-Associated Leigh Syndrome and NARP | mtDNA | 5537insT |

TABLE 1-continued

| Disease | Gene | Variant Name |
|---|---|---|
| Mitochondrial DNA-Associated Leigh Syndrome and NARP | mtDNA | 8993T > C |
| Mitochondrial DNA-Associated Leigh Syndrome and NARP | mtDNA | 8993T > G |
| Mitochondrial DNA-Associated Leigh Syndrome and NARP | mtDNA | C11777A |
| Mitochondrial DNA-Associated Leigh Syndrome and NARP | mtDNA | T10158C |
| Mitochondrial DNA-Associated Leigh Syndrome and NARP | mtDNA | T10191C |
| Mitochondrial DNA-Associated Leigh Syndrome and NARP | mtDNA | T8851C |
| Mitochondrial DNA-Associated Leigh Syndrome and NARP | mtDNA | T9176C |
| Mitochondrial DNA-Associated Leigh Syndrome and NARP | mtDNA | T9176G |
| MTHFR Deficiency | MTHFR | 1298A > C |
| MTHFR Deficiency | MTHFR | rs1801133, rs1801133 |
| MTRNR1-Related Hearing Loss and Deafness | mtDNA | 1095T > C |
| MTRNR1-Related Hearing Loss and Deafness | mtDNA | 1494C > T |
| MTRNR1-Related Hearing Loss and Deafness | mtDNA | 1555A > G |
| MTRNR1-Related Hearing Loss and Deafness | mtDNA | 961T > G |
| MTRNR1-Related Hearing Loss and Deafness | mtDNA | A7445G |
| MTTS1-Related Hearing Loss and Deafness | mtDNA | 7443A > G |
| MTTS1-Related Hearing Loss and Deafness | mtDNA | 7444G > A |
| MTTS1-Related Hearing Loss and Deafness | mtDNA | 7472insC |
| MTTS1-Related Hearing Loss and Deafness | mtDNA | 7472insC |
| MTTS1-Related Hearing Loss and Deafness | mtDNA | 7510T > C |
| MTTS1-Related Hearing Loss and Deafness | mtDNA | 7511T > C |
| MTTS1-Related Hearing Loss and Deafness | mtDNA | 7512T > C |
| Mucolipidosis IV | MCOLN1 | delEx1 3 Ex7 (511 > 6944del) |
| Mucolipidosis IV | MCOLN1 | delEx1 3 Ex7 (511 > 6944del) |
| Mucolipidosis IV | MCOLN1 | IVS-2A > G |
| Mucopolysaccharidosis Type I | IDUA | c.46_57del |
| Mucopolysaccharidosis Type I | IDUA | c.46_57del |
| Mucopolysaccharidosis Type I | IDUA | p.A327P |
| Mucopolysaccharidosis Type I | IDUA | p.P533R |

TABLE 1-continued

| Disease | Gene | Variant Name |
|---|---|---|
| Mucopolysaccharidosis Type I | IDUA | Q70X |
| Mucopolysaccharidosis Type I | IDUA | W402X |
| Mucopolysaccharidosis Type IIIA | SGSH | p.R245H |
| Mucopolysaccharidosis Type IIIA | SGSH | p.R74C |
| Mucopolysaccharidosis Type IIIA | SGSH | p.S66W |
| Mucopolysaccharidosis Type VII | GUSB | p.D152N |
| Multiple Endocrine Neoplasia Type 2 | RET | 2047T > A |
| Multiple Endocrine Neoplasia Type 2 | RET | 2047T > A |
| Multiple Endocrine Neoplasia Type 2 | RET | 2047T > C |
| Multiple Endocrine Neoplasia Type 2 | RET | 2047T > G |
| Multiple Endocrine Neoplasia Type 2 | RET | 2048G > A |
| Multiple Endocrine Neoplasia Type 2 | RET | A883F 2647 G > T |
| Multiple Endocrine Neoplasia Type 2 | RET | Glu768Asp G > C |
| Multiple Endocrine Neoplasia Type 2 | RET | M918T |
| Muscle-Eye-Brain Disease | POMGNT1 | c.1539 + 1G > A |
| MYH-Associated Polyposis | MUTYH | c.1376C > A |
| MYH-Associated Polyposis | MUTYH | c.494A > G, rs34612342 |
| MYH-Associated Polyposis | GENE_SYMBOL_TBD | rs36053993, rs36053993 |
| Niemann-Pick Disease Due to Sphingomyelinase Deficiency | SMPD1 | c.990delC |
| Niemann-Pick Disease Due to Sphingomyelinase Deficiency | SMPD1 | c.990delC |
| Niemann-Pick Disease Due to Sphingomyelinase Deficiency | SMPD1 | fsP330 |
| Niemann-Pick Disease Due to Sphingomyelinase Deficiency | SMPD1 | fsP330 |
| Niemann-Pick Disease Due to Sphingomyelinase Deficiency | SMPD1 | L302P |
| Niemann-Pick Disease Due to Sphingomyelinase Deficiency | SMPD1 | R496L |
| Niemann-Pick Disease Due to Sphingomyelinase Deficiency | SMPD1 | R608del |
| Niemann-Pick Disease Type C1 | NPC1 | I1061T |
| Nijmegen Breakage Syndrome | NBN | 657del5 |
| Nijmegen Breakage Syndrome | NBN | 657del5 |
| Pallister-Hall Syndrome | GLI3 | 2012delG |
| Pallister-Hall Syndrome | GLI3 | 2012delG |
| Pallister-Hall Syndrome | GLI3 | 2023delG |
| Pallister-Hall Syndrome | GLI3 | 2023delG |
| Pendred Syndrome | SLC26A4 | 1197delT |
| Pendred Syndrome | SLC26A4 | 1197delT |
| Pendred Syndrome | SLC26A4 | E384G |

TABLE 1-continued

| Disease | Gene | Variant Name |
|---|---|---|
| Pendred Syndrome | SLC26A4 | IV58 + 1(G->A) |
| Pendred Syndrome | SLC26A4 | L236P |
| Pendred Syndrome | SLC26A4 | T416P |
| Peroxisomal Bifunctional Enzyme Deficiency | HSD17B4 | c.302 + 1G > C |
| Peroxisomal Bifunctional Enzyme Deficiency | HSD17B4 | c.303-1G > A |
| Pervasive Developmental Disorders | NLGN4X | D396X |
| Pervasive Developmental Disorders | NLGN4X | D396X |
| Pervasive Developmental Disorders | NLGN4X | NLGN4X:1253delAG |
| Pervasive Developmental Disorders | NLGN4X | NLGN4X:1253delAG |
| Pervasive Developmental Disorders | NLGN3 | R451C |
| Phenylalanine Hydroxylase Deficiency | PAH | G272X |
| Phenylalanine Hydroxylase Deficiency | PAH | I65T |
| Phenylalanine Hydroxylase Deficiency | PAH | IVS12 + 1G > T |
| Phenylalanine Hydroxylase Deficiency | PAH | L48S, rs5030841 |
| Phenylalanine Hydroxylase Deficiency | PAH | R158Q, rs5030843 |
| Phenylalanine Hydroxylase Deficiency | PAH | R252W, rs5030847 |
| Phenylalanine Hydroxylase Deficiency | PAH | R261Q, rs5030849 |
| Phenylalanine Hydroxylase Deficiency | PAH | R408Q, rs5030859 |
| Phenylalanine Hydroxylase Deficiency | PAH | R408W, rs5030858 |
| Phenylalanine Hydroxylase Deficiency | PAH | rs5030855 |
| Phenylalanine Hydroxylase Deficiency | PAH | rs5030861 |
| Phenylalanine Hydroxylase Deficiency | PAH | Y414C, rs5030860 |
| Plasminogen Activator Inhibitor I | SERPINE1 | -844 G > A |
| Plasminogen Activator Inhibitor I | SERPINE1 | 4G/5G |
| Polycystic Kidney Disease, Autosomal Recessive | PKHD1 | c.10412T > G |
| Polycystic Kidney Disease, Autosomal Recessive | PKHD1 | c.107C > T |
| Polycystic Kidney Disease, Autosomal Recessive | PKHD1 | c.1486C > T |
| Polycystic Kidney Disease, Autosomal Recessive | PKHD1 | c.5895dupA |
| Polycystic Kidney Disease, Autosomal Recessive | PKHD1 | c.5895dupA |
| Polycystic Kidney Disease, Autosomal Recessive | PKHD1 | c.9689delA |
| Polycystic Kidney Disease, Autosomal Recessive | PKHD1 | c.9689delA |
| PPT1-Related Neuronal Ceroid-Lipofuscinosis | PPT1 | c.364A > T |
| PPT1-Related Neuronal Ceroid-Lipofuscinosis | PPT1 | p.L10X |

TABLE 1-continued

| Disease | Gene | Variant Name |
|---|---|---|
| PPT1-Related Neuronal Ceroid-Lipofuscinosis | PPT1 | p.R151X |
| PPT1-Related Neuronal Ceroid-Lipofuscinosis | PPT1 | T75P |
| PROP1-related pituitary hormome deficiency | PROP1 | 301-302delAG |
| PROP1-related pituitary hormome deficiency | PROP1 | 301-302delAG |
| Prothrombin Thrombophilia | F2 | rs1799963 |
| Prothrombin Thrombophilia | F2 | rs6025, rs6025 |
| Pseudovitamin D Deficiency Rickets | CYP27B1 | 7bp duplication in exon8 |
| Pseudovitamin D Deficiency Rickets | CYP27B1 | 7bp duplication in exon8 |
| Pseudovitamin D Deficiency Rickets | CYP27B1 | 958delG |
| Pseudovitamin D Deficiency Rickets | CYP27B1 | 958delG |
| Rett Syndrome | MECP2 | 806delG |
| Rett Syndrome | MECP2 | 806delG |
| Rett Syndrome | MECP2 | A140V, rs28934908 |
| Rett Syndrome | MECP2 | P152R |
| Rett Syndrome | MECP2 | P225R |
| Rett Syndrome | MECP2 | R106W, rs28934907 |
| Rett Syndrome | MECP2 | R133C |
| Rett Syndrome | MECP2 | R168X |
| Rett Syndrome | MECP2 | R255X |
| Rett Syndrome | MECP2 | R270X |
| Rett Syndrome | MECP2 | R294X |
| Rett Syndrome | MECP2 | R306C, rs28935468 |
| Rett Syndrome | MECP2 | S134C |
| Rett Syndrome | MECP2 | T158M, rs28934906 |
| Rhizomelic Chondrodysplasia Punctata Type 1 | PEX7 | p.A218V |
| Rhizomelic Chondrodysplasia Punctata Type 1 | PEX7 | p.G217R |
| Rhizomelic Chondrodysplasia Punctata Type 1 | PEX7 | p.L292X, rs1805137 |
| Short Chain Acyl-CoA Dehydrogenase Deficiency | ACADS | c.511C > T, rs1800556 |
| Short Chain Acyl-CoA Dehydrogenase Deficiency | ACADS | c.625G > A |
| Short Chain Acyl-CoA Dehydrogenase Deficiency | ACADS | R107C |
| Shwachman-Diamond Syndrome | SBDS | 183_184TA > CT |
| Shwachman-Diamond Syndrome | SBDS | 183_184TA > CT |
| Shwachman-Diamond Syndrome | SBDS | 258 + 2T > C |
| Sjogren-Larsson Syndrome | ALDH3A2 | c.943C > T |

TABLE 1-continued

| Disease | Gene | Variant Name |
|---|---|---|
| Smith-Lemli-Opitz Syndrome | DHCR7 | C380Y |
| Smith-Lemli-Opitz Syndrome | DHCR7 | IVS8-1G > C |
| Smith-Lemli-Opitz Syndrome | DHCR7 | L109P |
| Smith-Lemli-Opitz Syndrome | DHCR7 | L157P |
| Smith-Lemli-Opitz Syndrome | DHCR7 | R352Q |
| Smith-Lemli-Opitz Syndrome | DHCR7 | R352W |
| Smith-Lemli-Opitz Syndrome | DHCR7 | R404C |
| Smith-Lemli-Opitz Syndrome | DHCR7 | R446Q |
| Smith-Lemli-Opitz Syndrome | DHCR7 | T93M |
| Smith-Lemli-Opitz Syndrome | DHCR7 | V326L |
| Smith-Lemli-Opitz Syndrome | DHCR7 | W151X |
| Smith-Lemli-Opitz Syndrome | DHCR7 | W151X |
| Spastic Paraplegia 13 | HSPD1 | V72I |
| Sulfate Transporter-Related Osteochondrodysplasia | SLC26A2 | 340delV |
| Sulfate Transporter-Related Osteochondrodysplasia | SLC26A2 | 340delV |
| Sulfate Transporter-Related Osteochondrodysplasia | SLC26A2 | c.837C > T |
| Sulfate Transporter-Related Osteochondrodysplasia | SLC26A2 | C653S |
| Sulfate Transporter-Related Osteochondrodysplasia | SLC26A2 | IVS1 + 2T > C |
| Sulfate Transporter-Related Osteochondrodysplasia | SLC26A2 | R178X |
| TFR2-Related Hereditary Hemochromatosis | TFR2 | AVAQ594-597del |
| TFR2-Related Hereditary Hemochromatosis | TFR2 | AVAQ594-597del |
| TFR2-Related Hereditary Hemochromatosis | TFR2 | E60X |
| TFR2-Related Hereditary Hemochromatosis | TFR2 | E60X |
| TFR2-Related Hereditary Hemochromatosis | TFR2 | M172K |
| TFR2-Related Hereditary Hemochromatosis | TFR2 | Y250X |
| Thanatophoric Dysplasia | FGFR3 | G370C |
| Thanatophoric Dysplasia | FGFR3 | K650E |
| Thanatophoric Dysplasia | FGFR3 | R248C |
| Thanatophoric Dysplasia | FGFR3 | S249C |
| Thanatophoric Dysplasia | FGFR3 | S371C |
| Thanatophoric Dysplasia | FGFR3 | X807C A > T |
| Thanatophoric Dysplasia | FGFR3 | X807G |
| Thanatophoric Dysplasia | FGFR3 | X807L |

TABLE 1-continued

| Disease | Gene | Variant Name |
|---|---|---|
| Thanatophoric Dysplasia | FGFR3 | X807R |
| Thanatophoric Dysplasia | FGFR3 | X807S |
| Thanatophoric Dysplasia | FGFR3 | X807W |
| Thanatophoric Dysplasia | FGFR3 | Y373C |
| TPP1-Related Neuronal Ceroid-Lipofuscinosis | TPP1 | c.509-1G > A |
| TPP1-Related Neuronal Ceroid-Lipofuscinosis | TPP1 | c.509-1G > C |
| TPP1-Related Neuronal Ceroid-Lipofuscinosis | TPP1 | G284V |
| TPP1-Related Neuronal Ceroid-Lipofuscinosis | TPP1 | p.R208X |
| Transthyretin Amyloidosis | TTR | c.148G > A |
| Tyrosine Hydroxylase-Deficient DRD | TH | L205P |
| Tyrosine Hydroxylase-Deficient DRD | TH | R202H |
| Tyrosinemia Type I | FAH | E357X |
| Tyrosinemia Type I | FAH | IVS12 + 5 G > A |
| Tyrosinemia Type I | FAH | IVS7-6 T > G |
| Tyrosinemia Type I | FAH | IVS8-1G > C |
| Tyrosinemia Type I | FAH | p.W262X |
| Tyrosinemia Type I | FAH | P261L |
| Tyrosinemia Type I | FAH | Q64H |
| Wilson Disease | ATP7B | 1340del4 |
| Wilson Disease | ATP7B | 3402delC |
| Wilson Disease | ATP7B | 3402delC |
| Wilson Disease | ATP7B | H1069Q |
| Wilson Disease | ATP7B | R778G |
| Wilson Disease | ATP7B | W779X |
| Wilson Disease | ATP7B | W779X |
| X-Linked Juvenile Retinoschisis | RS1 | E72K |
| X-Linked Juvenile Retinoschisis | RS1 | G109R |
| X-Linked Juvenile Retinoschisis | RS1 | G74V |
| Zellweger Syndrome Spectrum | PEX1 | c.2097_2098insT |
| Zellweger Syndrome Spectrum | PEX1 | c.2097_2098insT |
| Zellweger Syndrome Spectrum | PEX1 | c.2916delA |
| Zellweger Syndrome Spectrum | PEX1 | c.2916delA |
| Zellweger Syndrome Spectrum | PEX1 | p.G843D |

TABLE 2

| Disease/Disorder | Gene(s) |
|---|---|
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc |
| Age-related Macular Degeneration | Abcr; Ccl2; Cc2; cp (ceruloplasmin); Timp3; cathepsinD; Vldlr; Ccr2 |
| Schizophrenia | Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b |
| Trinucleotide Repeat Disorders | HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn1 (DRPLA Dx); CBP (Creb-BP - global instability); VLDLR (Alzheimer's); Atxn7; Atxn10 |
| Fragile X Syndrome | FMR2; FXR1; FXR2; mGLUR5 |
| Secretase Related Disorders | APH-1 (alpha and beta); Presenilin (Psen1); nicastrin (Ncstn); PEN-2 |
| Prion - related disorders | Prp |
| ALS | SOD1; ALS2; STEX; FUS; TARDBP; VEGF (VEGF-a; VEGF-b; VEGF-c) |
| Drug addiction | Prkce (alcohol); Drd2; Drd4; ABAT (alcohol); GRIA2; Grm5; Grin1; Htr1b; Grin2a; Drd3; Pdyn; Gria1 (alcohol) |
| Autism | Mecp2; BZRAP1; MDGA2; Sema5A; Neurexin 1; Fragile X (FMR2 (AFF2); FXR1; FXR2; Mglur5) |
| Alzheimer's Disease | E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1; Uchl3; APP |
| Inflammation | IL-10; IL-1 (IL-1a; IL-1b); IL-13; IL-17 (IL-17a (CTLA8); IL-17b; IL-17c; IL-17d; IL-17f); Il-23; Cx3cr1; ptpn22; TNFa; NOD2/CARD15 for IBD; IL-6; IL-12 (IL-12a; IL-12b); CTLA4; Cx3cl1 |
| Parkinson's Disease | x-Synuclein; DJ-1; LRRK2; Parkin; PINK1 |

In some embodiments, a method further comprises the step of diagnosing a subject based on a calling step, such as diagnosing the subject with a disease associated with a detected causal genetic variant, or reporting a likelihood that the patient has or will develop such disease. Examples of diseases, associated genes, and associated sequence variants are provided herein. In some embodiments, a result is reported via a report generator, such as described herein.

In some embodiments, one or more causal genetic variants are sequence variants associated with a particular type or stage of cancer, or of cancer having a particular characteristic (e.g. metastatic potential, drug resistance, drug responsiveness). In some embodiments, the disclosure provides methods for the determination of prognosis, such as where certain mutations are known to be associated with patient outcomes. For example, ctDNA has been shown to be a better biomarker for breast cancer prognosis than the traditional cancer antigen 53 (CA-53) and enumeration of circulating tumor cells (see e.g. Dawson, et al., N Engl J Med 368:1199 (20 13)). Additionally, the methods of the present disclosure can be used in therapeutic decisions, guidance and monitoring, as well as development and clinical trials of cancer therapies. For example, treatment efficacy can be monitored by comparing patient ctDNA samples from before, during, and after treatment with particular therapies such as molecular targeted therapies (monoclonal drugs), chemotherapeutic drugs, radiation protocols, etc. or combinations of these. For example, the ctDNA can be monitored to see if certain mutations increase or decrease, new mutations appear, etc., after treatment, which can allow a physician to alter a treatment (continue, stop or change treatment, for example) in a much shorter period of time than afforded by methods of monitoring that track patient symptoms. In some embodiments, a method further comprises the step of diagnosing a subject based on a calling step, such as diagnosing the subject with a particular stage or type of cancer associated with a detected sequence variant, or reporting a likelihood that the patient has or will develop such cancer.

For example, for therapies that are specifically targeted to patients on the basis of molecular markers (e.g. Herceptin and her2/neu status), patients are tested to find out if certain mutations are present in their tumor, and these mutations can be used to predict response or resistance to the therapy and guide the decision whether to use the therapy. Therefore, detecting and monitoring ctDNA during the course of treatment can be very useful in guiding treatment selections. Some primary (before treatment) or secondary (after treatment) cancer mutations are found to be responsible for the resistance of cancers to some therapies (Misale et al., Nature 486(7404):532 (2012)).

A variety of sequence variants that are associated with one or more kinds of cancer that may be useful in diagnosis, prognosis, or treatment decisions are known. Suitable target sequences of oncological significance that find use in the methods of the disclosure include, but are not limited to, alterations in the TP53 gene, the ALK gene, the KRAS gene, the PIK3CA gene, the BRAF gene, the EGFR gene, and the KIT gene. A target sequence may be specifically amplified, and/or specifically analyzed for sequence variants may be all or part of a cancer-associated gene. In some embodiments, one or more sequence variants are identified in the TP53 gene. TP53 is one of the most frequently mutated genes in human cancers, for example, TP53 mutations are found in 45% of ovarian cancers, 43% of large intestinal cancers, and 42% of cancers of the upper aerodigestive track (see e.g. M. Olivier, et, al. TP53Mutations in Human Cancers: Origins, Consequences, and Clinical Use. Cold Spring Harb Perspect Biol. 2010 January; 2(1). Characterization of the mutation status of TP53 can aid in clinical diagnosis, provide prognostic value, and influence treatment for cancer patients. For example, TP53 mutations may be used as a predictor of a poor prognosis for patients in CNS tumors derived from glial cells and a predictor of rapid disease progression in patients with chronic lymphocytic leukemia (see e.g. McLendon R E, et al. Cancer. 2005 Oct. 15; 1 04(8): 1693-9; Dicker F, et al. Leukemia. 2009 January; 23(1):117-24). Sequence variation can occur anywhere within the gene. Thus, all or part of the TP53 gene can be evaluated herein. That is, as described elsewhere herein, when target specific components (e.g. target specific primers) are used, a plurality of TP53 specific sequences can be used, for example to amplify and detect fragments spanning the gene, rather than just one or more selected subsequences (such as mutation "hot spots") as may be used for selected targets. Alternatively, target-specific primers may be designed that hybridize upstream or downstream of one or more selected subsequences (such a nucleotide or nucleotide region associated with an increased rate of mutation among a class of subjects, also encompassed by the term "hot spot"). Standard primers spanning such a subsequence may be designed, and/or B2B primers that hybridize upstream or downstream of such a subsequence may be designed.

In some embodiments, one or more sequence variants are identified in the all or part of the ALK gene. ALK fusions have been reported in as many as 7% of lung tumors, some of which are associated with EGFR tyrosine kinase inhibitor (TKI) resistance (see e.g. Shaw et al., J Clin Oncol. Sep. 10, 2009; 27(26): 4247-4253). Up to 2013, several different point mutations spanning across the entire ALK tyrosine kinase domain have been found in patients with secondary resistance to the ALK tyrosine kinase inhibitor (TKI) (Katayama R 2012 Sci Transl Med. 2012 Feb. 8; 4(120)). Thus, mutation detection in ALK gene can be used to aid cancer therapy decisions.

In some embodiments, one or more sequence variants are identified in the all or part of the KRAS gene. Approximately 15-25% of patients with lung adenocarcinoma and 40% of patients with colorectal cancer have been reported as harboring tumor associated KRAS mutations (see e.g. Neuman 2009, Pathol Res Pract. 2009; 205(12):858-62). Most of the mutations are located at codons 12, 13, and 61 of the KRAS gene. These mutations activate KRAS signaling pathways, which trigger growth and proliferation of tumor cells. Some studies indicate that patients with tumors harboring mutations in KRAS are unlikely to benefit from anti-EGFR antibody therapy alone or in combination with chemotherapy (see e.g. Amado et al. 2008 J Clin On col. 2008 Apr. 1; 26(1 0): 1626-34, Bokemeyer et al. 2009 J Clin Oncol. 2009 Feb. 10; 27(5):663-71). One particular "hot spot" for sequence variation that may be targeted for identifying sequence variation is at position 35 of the gene. Identification of KRAS sequence variants can be used in treatment selection, such as in treatment selection for a subject with colorectal cancer.

In some embodiments, one or more sequence variants are identified in the all or part of the PIK3CA gene. Somatic mutations in PIK3CA have been frequently found in various type of cancers, for example, in 10-30% of colorectal cancers (see e.g. Samuels et al. 2004 Science. 2004 Apr. 23; 304(5670):554.). These mutations are most commonly located within two "hotspot" areas within exon 9 (the helical domain) and exon 20 (the kinase domain), which may be specifically targeted for amplification and/or analysis for the detection sequence variants. Position 3140 may also be specifically targeted.

In some embodiments, one or more sequence variants are identified in the all or part of the BRAF gene. Near 50% of all malignant melanomas have been reported as harboring somatic mutations in BRAF (see e.g. Maldonado et al., J Natl Cancer Inst. 2003 Dec. 17; 95(24):1878-90). BRAF mutations are found in all melanoma subtypes but are most frequent in melanomas derived from skin without chronic sun-induced damage. Among the most common BRAF mutations in melanoma are missense mutations V600E, which substitutes valine at position 600 with glutamine. BRAF V600E mutations are associated with clinical benefit of BRAF inhibitor therapy. Detection of BRAF mutation can be used in melanoma treatment selection and studies of the resistance to the targeted therapy.

In some embodiments, one or more sequence variants are identified in the all or part of the EGFR gene. EGFR mutations are frequently associated with Non-Small Cell Lung Cancer (about 10% in the US and 35% in East Asia; see e.g. Pao et al., Proc Natl Acad Sci US A. 2004 Sep. 7; 101(36):13306-11). These mutations typically occur within EGFR exons 18-21, and are usually heterozygous. Approximately 90% of these mutations are exon 19 deletions or exon 21 L858R point mutations.

In some embodiments, one or more sequence variants are identified in the all or part of the KIT gene. Near 85% of Gastrointestinal Stromal Tumor (GIST) have been reported as harboring KIT mutations (see e.g. Heinrich et al. 2003 J Clin Oncol. 2003 Dec. 1; 21 (23):4342-9). The majority of KIT mutations are found in juxtamembrane domain (exon 11, 70%), extracellular dimerization motif (exon 9, 10-15%), tyrosine kinase I (TKI) domain (exon 13, 1-3%), and tyrosine kinase 2 (TK2) domain and activation loop (exon 17, 1-3%). Secondary KIT mutations are commonly identified after target therapy imatinib and after patients have developed resistance to the therapy.

Additional non-limiting examples of genes associated with cancer, all or a portion of which may be analyzed for sequence variants according to a method described herein include, but are not limited to PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR; (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; and Apc. Further examples are provided elsewhere herein. Examples of cancers that may be diagnosed based on calling one or more sequence variants in accordance with a method disclosed herein include, without limitation, Acanthoma, Acinic cell carcinoma, Acoustic neuroma, Acral lentiginous melanoma, Acrospiroma, Acute eosinophilic leukemia, Acute lymphoblastic leukemia, Acute megakaryoblastic leukemia, Acute monocytic leukemia, Acute myeloblastic leukemia with maturation, Acute myeloid dendritic cell leukemia, Acute myeloid leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Hairy cell leukemia, Head and Neck Cancer, Head and neck cancer, Heart cancer, Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplastic Disease, Myelodysplastic Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, and combinations thereof. Non-limiting examples of specific sequence variants associated with cancer are provided in Table 3.

TABLE 3

| Gene | Mutation Amino acid Nucleotide | COSMIC mutation % in melanoma | Clinical relevance |
|---|---|---|---|
| BRAF | V600E<br>1799T > A | 50% (80-90% among BRAF mutations) | Increase sensitivity to BRAF inhibitors<br>Increase sensitivity to MEK inhibitors |
| BRAF | V600E<br>1799_1800delTGinsAA | 50% (80-90% among BRAF mutations) | Increase sensitivity to BRAF inhibitors<br>Increase sensitivity to MEK inhibitors |
| BRAF | V600R<br>1798_1799delGTinsAG | 50% (<5% among BRAF mutations) | Increase sensitivity to BRAF inhibitors<br>Respond to MEK inhibitors |
| BRAF | V600M<br>1798G > A | 50% (<1% among BRAF mutations) | Increase sensitivity to BRAF inhibitors<br>Respond to MEK inhibitors |
| BRAF | V600K<br>1798_1799delGTinsAA | 50% (5% among BRAF mutations) | Increase sensitivity to BRAF inhibitors<br>Increase sensitivity to MEK inhibitors |
| BRAF | V600G<br>1799T > G | 50% (<1% among BRAF mutations) | Increase sensitivity BRAF inhibitors<br>Respond to MEK inhibitors |
| BRAF | V600D<br>1799-800delTGinsAT | 50% (<5% among BRAF mutations) | Increase sensitivity to BRAF inhibitors<br>Respond to MEK inhibitors |
| BRAF | L597V<br>1789C > G | 50% (1% among BRAF mutations) | Respond to BRAF inhibitors<br>Respond to MEK inhibitors |
| BRAF | L597S<br>1789_1790delCTinsTC | 50% (<1% among BRAF mutations) | Respond to BRAF inhibitors<br>Respond to MEK inhibitors |
| BRAF | L597Q<br>1790T > A | 50% (<1% among BRAF mutations) | Respond to BRAF inhibitors<br>Respond to MEK inhibitors |
| BRAF | L597R<br>1790T > G | 50% (<1% among BRAF mutations) | Respond to BRAF inhibitors<br>Respond to MEK inhibitors |
| BRAF | D594N<br>1799_1780delTGinsGA | 50% (<1% among BRAF mutations) | Not to BRAF inhibitors<br>May respond to MEK inhibitors |
| BRAF | D594H<br>1780C > G | 50% (<1% among BRAF mutations) | Not to BRAF inhibitors<br>May respond to MEK inhibitors |
| BRAF | D594E<br>1782T > A | 50% (<1% among BRAF mutations) | Not to BRAF inhibitors<br>May respond to MEK inhibitors |
| BRAF | D594E<br>1782T > G | 50% (<1% among BRAF mutations) | Not to BRAF inhibitors<br>May respond to MEK inhibitors |
| BRAF | D594G<br>1781A > G | 50% (<1% among BRAF mutations) | Not to BRAF inhibitors<br>May respond to MEK inhibitors |
| BRAF | D594V<br>1781A > T | 50% (<1% among BRAF mutations) | Not to BRAF inhibitors<br>May respond to MEK inhibitors |
| NRAS | G12D<br>35G > A | 13-25% (4% among NRAS mutations) | cytotoxic chemotherapy |
| NRAS | G13R<br>37G > C | 13-25% (2% among NRAS mutations) | cytotoxic chemotherapy<br>Not to BRAF inhibitors<br>May respond to MEK inhibitors |
| NRAS | G13D<br>38G > A | 13-25% (2% among NRAS mutations) | cytotoxic chemotherapy<br>Not to BRAF inhibitors<br>May respond to MEK inhibitors |
| NRAS | G13V<br>38G > T | 13-25% (2% among NRAS mutations) | cytotoxic chemotherapy<br>Not to BRAF inhibitors<br>May respond to MEK inhibitors |
| NRAS | Q61K<br>181C > A | 13-25% (34% among NRAS mutations) | Respond to MEK inhibitors |
| NRAS | Q61L<br>182A > T | 13-25% (8% among NRAS mutations) | Respond to MEK inhibitors |
| NRAS | Q61R<br>182A > G | 13-25% (35% among NRAS mutations) | Respond to MEK inhibitors |
| NRAS | Q61H<br>183A > C | 13-25% (2% among NRAS mutations) | Respond to MEK inhibitors |
| NRAS | Q61H<br>183A > T | 13-25% (2% among NRAS mutations) | Respond to MEK inhibitors |
| CTNNB1 | S37F<br>110C > T | ~2-3% in primary uveal melanoma (46% among CTNNB1 mutations) | |
| CNA11 | Q209L<br>626A > T | 34% in primary uveal melanoma (92% among CNA11 mutations) | |
| CNA11 | Q209P<br>626A > C | 34% in primary uveal melanoma (1% among CNA11 mutations) | |
| GNAQ | Q209L<br>626A > T | ~50% in primary uveal melanoma | Sensitive to MEK inhibitors |

TABLE 3-continued

| Gene | Mutation Amino acid Nucleotide | COSMIC mutation % in melanoma | Clinical relevance |
| --- | --- | --- | --- |
| | | (~33% among CNAQ mutations) | |
| GNAQ | Q209P 626A > C | ~50% in primary uveal melanoma (~64% among CNAQ mutations) | Sensitive to MEK inhibitors Sensitive to MEK inhibitors |
| GNAQ | Q209R 626A > G | ~50% in primary uveal melanoma (~2% among CNAQ mutations) | |
| KIT | K624E 1924A > G | ~20% among KIT mutant malignant melanomas | Increase sensitivity to KIT inhibitor |
| KIT | D816H 2446G > C | ~5% among KIT mutant malignant melanomas | Increase sensitivity to KIT inhibitor |
| KIT | L567P 1727T > C | ~25% among KIT mutant malignant melanomas | Increase sensitivity to KIT inhibitor |
| KIT | V559A 1676T > C | ~20% among KIT mutant malignant melanomas | Increase sensitivity to KIT inhibitor |
| KIT | V559D 1676T > A | ~5% among KIT mutant malignant melanomas | Increase sensitivity to KIT inhibitor |
| KIT | W557R 1669T > C | ~10% among KIT mutant malignant melanomas | Increase sensitivity to KIT inhibitor |
| KIT | W557R 1669T > A | ~10% among KIT mutant malignant melanomas | Increase sensitivity to KIT inhibitor |

In addition, the methods and compositions disclosed herein may be useful in discovering new, rare mutations that are associated with one or more cancer types, stages, or cancer characteristics. For example, populations of individuals sharing a characteristic under analysis (e.g. a particular disease, type of cancer, stage of cancer, etc.) may be subjected to a method of detection sequence variants according to the disclosure so as to identify sequence variants or types of sequence variants (e.g. mutations in particular genes or parts of genes). Sequence variants identified as occurring with a statistically significantly greater frequency among the group of individuals sharing the characteristic than in individuals without the characteristic may be assigned a degree of association with that characteristic. The sequence variants or types of sequence variants so identified may then be used in diagnosing or treating individuals discovered to harbor them.

Other therapeutic applications include use in non-invasive fetal diagnostics. Fetal DNA can be found in the blood of a pregnant woman Methods and compositions described herein can be used to identify sequence variants in circulating fetal DNA, and thus may be used to diagnose one or more genetic diseases in the fetus, such as those associated with one or more causal genetic variants. Non-limiting examples of causal genetic variants are described herein, and include trisomies, cystic fibrosis, sickle-cell anemia, and Tay-Saks disease. In this embodiment, the mother may provide a control sample and a blood sample to be used for comparison. The control sample may be any suitable tissue, and will typically be process to extract cellular DNA, which can then be sequenced to provide a reference sequence. Sequences of cfDNA corresponding to fetal genomic DNA can then be identified as sequence variants relative to the maternal reference. The father may also provide a reference sample to aid in identifying fetal sequences, and sequence variants.

Still further therapeutic applications include detection of exogenous polynucleotides, such as from pathogens (e.g. bacteria, viruses, fungi, and microbes), which information may inform a diagnosis and treatment selection. For example, some HIV subtypes correlate with drug resistance (see e.g. hivdb.stanford.edu/pages/genotype-rx). Similarly, HCV typing, subtyping and isotype mutations can also be done using the methods and compositions of the present disclosure. Moreover, where an HPV subtype is correlated with a risk of cervical cancer, such diagnosis may further inform an assessment of cancer risk. Further non-limiting examples of viruses that may be detected include Hepadnavirus hepatitis B virus (HBV), woodchuck hepatitis virus, ground squirrel (Hepadnaviridae) hepatitis virus, duck hepatitis B virus, heron hepatitis B virus, Herpesvirus herpes simplex virus (HSV) types 1 and 2, varicella-zoster virus, cytomegalovirus (CMV), human cytomegalovirus (HCMV), mouse cytomegalovirus (MCMV), guinea pig cytomegalovirus (GPCMV), Epstein-Barr virus (EBV), human herpes virus 6 (HHV variants A and B), human herpes virus 7 (HHV-7), human herpes virus 8 (HHV-8), Kaposi's sarcoma-associated herpes virus (KSHV), B virus Poxvirus vaccinia virus, variola virus, smallpox virus, monkeypox virus, cowpox virus, camelpox virus, ectromelia virus, mousepox virus, rabbitpox viruses, raccoonpox viruses, molluscum contagiosum virus, orf virus, milker's nodes virus, bovin papullar stomatitis virus, sheeppox virus, goatpox virus, lumpy skin disease virus, fowlpox virus, canarypox virus, pigeonpox virus, sparrowpox virus, myxoma virus, hare fibroma virus, rabbit fibroma virus, squirrel fibroma viruses, swinepox virus, tanapox virus, Yabapox virus, Flavivirus dengue virus, hepatitis C virus (HCV), GB hepatitis viruses (GBV-A, GBV-B and GBV-C), West Nile virus, yellow fever virus, St. Louis encephalitis virus, Japanese encephalitis virus, Powassan virus, tick-borne encephalitis virus, Kyasanur Forest disease virus, Togavirus, Venezuelan equine encephalitis (VEE) virus, chikungunya virus, Ross River virus, Mayaro virus, Sindbis virus, rubella virus, Retrovirus human immunodeficiency virus (HIV) types 1 and 2, human T cell leukemia virus (HTLV) types 1, 2, and 5, mouse mammary tumor virus (MMTV), Rous sarcoma virus (RSV), lentiviruses, Coronavirus, severe acute respiratory syndrome (SARS) virus, Filovirus Ebola virus, Marburg virus, Metapneumoviruses (MPV) such as human metapneumovirus (HMPV), Rhabdovirus rabies virus, vesicular stomatitis virus, Bunyavirus, Crimean-Congo hemorrhagic fever virus, Rift Valley fever virus, La Crosse virus, Hantaan virus, Orthomyxovirus, influenza virus (types A, B, and C), Paramyxovirus, parainfluenza virus (PIV types 1, 2 and 3), respiratory syncytial virus (types A and B), measles virus, mumps virus, Arenavirus, lymphocytic choriomeningitis virus, Junin virus, Machupo virus, Guanarito virus, Lassa virus, Ampari virus, Flexal virus, Ippy virus, Mobala virus, Mopeia virus, Latino virus, Parana virus, Pichinde virus, Punta toro virus (PTV), Tacaribe virus and Tamiami virus.

Examples of bacterial pathogens that may be detected by methods of the disclosure include, without limitation, Specific examples of bacterial pathogens include without limitation any one or more of (or any combination of) *Acinetobacter baumanii*, *Actinobacillus* sp., *Actinomycetes*, *Actinomyces* sp. (such as *Actinomyces israelii* and *Actinomyces naeslundii*), *Aeromonas* sp. (such as *Aeromonas hydrophila*, *Aeromonas veronii biovar sobria* (*Aeromonas sobria*), and *Aeromonas caviae*), *Anaplasma phagocytophilum*, *Alcaligenes xylosoxidans*, *Acinetobacter baumanii*, *Actinobacillus actinomycetemcomitans*, *Bacillus* sp. (such as *Bacillus anthracis*, *Bacillus cereus*, *Bacillus subtilis*, *Bacillus thuringiensis*, and *Bacillus stearothermophilus*), *Bacteroides* sp. (such as *Bacteroides fragilis*), *Bartonella* sp. (such as *Bartonella bacilliformis* and *Bartonella henselae*, *Bifidobacterium* sp., *Bordetella* sp. (such as *Bordetella pertussis*, *Bordetella parapertussis*, and *Bordetella bronchiseptica*), *Borrelia* sp. (such as *Borrelia recurrentis*, and *Borrelia burgdorferi*), *Brucella* sp. (such as *Brucella abortus*, *Brucella canis*, *Brucella melintensis* and *Brucella suis*), *Burkholderia* sp. (such as *Burkholderia pseudomallei* and *Burkholderia cepacia*), *Campylobacter* sp. (such as *Campylobacter jejuni*, *Campylobacter coli*, *Campylobacter lari* and *Campylobacter fetus*), *Capnocytophaga* sp., *Cardiobacterium hominis*, *Chlamydia trachomatis*, *Chlamydophila pneumoniae*, *Chlamydophila psittaci*, *Citrobacter* sp. *Coxiella burnetii*, *Corynebacterium* sp. (such as, *Corynebacterium diphtheriae*, *Corynebacterium jeikeum* and *Corynebacterium*), *Clostridium* sp. (such as *Clostridium perfringens*, *Clostridium difficile*, *Clostridium botulinum* and *Clostridium tetani*), *Eikenella corrodens*, *Enterobacter* sp. (such as *Enterobacter aerogenes*, *Enterobacter agglomerans*, *Enterobacter cloacae* and *Escherichia coli*, including opportunistic *Escherichia coli*, such as enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* sp. (such as *Enterococcus faecalis* and *Enterococcus faecium*) *Ehrlichia* sp. (such as *Ehrlichia chafeensia* and *Ehrlichia canis*), *Erysipelothrix rhusiopathiae*, *Eubacterium* sp., *Francisella tularensis*, *Fusobacterium nucleatum*, *Gardnerella vaginalis*, *Gemella morbillorum*, *Haemophilus* sp. (such as *Haemophilus influenzae*, *Haemophilus ducreyi*, *Haemophilus aegyptius*, *Haemophilus parainfluenzae*, *Haemophilus haemolyticus* and *Haemophilus parahaemolyticus*, *Helicobacter* sp. (such as *Helicobacter pylori*, *Helicobacter cinaedi* and *Helicobacter fennelliae*), *Kingella kingii*, *Klebsiella* sp. (such as *Klebsiella pneumoniae*, *Klebsiella granulomatis* and *Klebsiella oxytoca*), *Lactobacillus* sp., *Listeria monocytogenes*, *Leptospira interrogans*, *Legionella pneumophila*, *Leptospira interrogans*, *Peptostreptococcus* sp., *Moraxella catarrhalis*, *Morganella* sp., *Mobiluncus* sp., *Micrococcus* sp., *Mycobacterium* sp. (such as *Mycobacterium leprae*, *Mycobacterium tuberculosis*, *Mycobacterium intracellulare*, *Mycobacterium avium*, *Mycobacterium bovis*, and *Mycobacterium marinum*), *Mycoplasm* sp. (such as *Mycoplasma pneumoniae*, *Mycoplasma hominis*, and *Mycoplasma genitalium*), *Nocardia* sp. (such as *Nocardia asteroides*, *Nocardia cyriacigeorgica* and *Nocardia brasiliensis*), *Neisseria* sp. (such as *Neisseria gonorrhoeae* and *Neisseria meningitidis*), *Pasteurella multocida*, *Plesiomonas shigelloides*. *Prevotella* sp., *Porphyromonas* sp., *Prevotella melaminogenica*, *Proteus* sp. (such as *Proteus vulgaris* and *Proteus mirabilis*), *Providencia* sp. (such as *Providencia alcalifaciens*, *Providencia rettgeri* and *Providencia stuartii*), *Pseudomonas aeruginosa*, *Propionibacterium acnes*, *Rhodococcus equi*, *Rickettsia* sp. (such as *Rickettsia rickettsii*, *Rickettsia akari* and *Rickettsia prowazekii*, *Orientia tsutsugamushi* (formerly: *Rickettsia tsutsugamushi*) and *Rickettsia typhi*), *Rhodococcus* sp., *Serratia marcescens*, *Stenotrophomonas maltophilia*, *Salmonella* sp. (such as *Salmonella enterica*, *Salmonella typhi*, *Salmonella paratyphi*, *Salmonella enteritidis*, *Salmonella cholerasuis* and *Salmonella typhimurium*), *Serratia* sp. (such as *Serratia marcesans* and *Serratia liquifaciens*), *Shigella* sp. (such as *Shigella dysenteriae*, *Shigella flexneri*, *Shigella boydii* and *Shigella sonnei*), *Staphylococcus* sp. (such as *Staphylococcus aureus*, *Staphylococcus epidermidis*, *Staphylococcus hemolyticus*, *Staphylococcus saprophyticus*), *Streptococcus* sp. (such as *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae*, *Streptococcus mutans*, *Streptococcus pyogenes*, Group A streptococci, *Streptococcus pyogenes*, Group B streptococci, *Streptococcus agalactiae*, Group C streptococci, *Streptococcus anginosus*, *Streptococcus equismilis*, Group D streptococci, *Streptococcus bovis*, Group F streptococci, and *Streptococcus anginosus* Group G streptococci), *Spirillum minus*, *Streptobacillus moniliformi*, *Treponema* sp. (such as *Treponema carateum*, *Treponema petenue*, *Treponema pallidum* and *Treponema endemicum*, *Tropheryma whippelii*, *Ureaplasma urealyticum*, *Veillonella* sp., *Vibrio* sp. (such as *Vibrio cholerae*, *Vibrio parahemolyticus*, *Vibrio vulnificus*, *Vibrio parahaemolyticus*, *Vibrio vulnificus*, *Vibrio alginolyticus*, *Vibrio mimicus*, *Vibrio hollisae*, *Vibrio fiuvialis*, *Vibrio metchnikovii*, *Vibrio damsela* and *Vibrio furnish*), *Yersinia* sp. (such as *Yersinia enterocolitica*, *Yersinia pestis*, and *Yersinia pseudotuberculosis*) and *Xanthomonas maltophilia* among others.

In some embodiments, the methods and compositions of the disclosure are used in monitoring organ transplant recipients. Typically, polynucleotides from donor cells will be found in circulation in a background of polynucleotides from recipient cells. The level of donor circulating DNA will generally be stable if the organ is well accepted, and the rapid increase of donor DNA (e.g. as a frequency in a given sample) can be used as an early sign of transplant rejection. Treatment can be given at this stage to prevent transplant failure. Rejection of the donor organ has been shown to result in increased donor DNA in blood; see Snyder et al., PNAS 108(15):6629 (2011). The present disclosure provides significant sensitivity improvements over prior techniques in this area. In this embodiment, a recipient control sample (e.g. cheek swab, etc.) and a donor control sample can be used for comparison. The recipient sample can be used to provide that reference sequence, while sequences corresponding to the donor's genome can be identified as sequence variants relative to that reference. Monitoring may comprise obtaining samples (e.g. blood samples) from the recipient over a period of time. Early samples (e.g. within the first few weeks) can be used to establish a baseline for the fraction of donor cfDNA. Subsequent samples can be compared to the baseline. In some embodiments %, an increase in the fraction of donor cfDNA of about or at least about 10%, 20%, 30%, 40%, 50%, 60%, 70%, 80%, 90%, 95%, 100%, 250%, 500%, 1000%, or more may serve as an indication that a recipient is in the process of rejecting donor tissue.

In some embodiments, there are provided methods of detection.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Preparing Tandem Repetitive Sequencing Library for Mutation Detection Starting with >10 ng of ~150 bp DNA fragments in 12 µL water or 10 mM Tris-HCl pH 8.0, 2 µL 10× CircLigase buffer mix was added and mixture heated to 95° C. for 2 minutes and chilled on ice for 5 minutes. To this was added 4 µL 5M Betaine, 1 µL 50 mM $MnCl_2$, and 1 µL CircLigase II. The reaction was incubated at 60° C. for at least 12 hours. Next was added 2 µL RCA primer mix (50 nM each, to a 5 nM final concentration), and mixed. The mixture was heated to 95° C. for 2 minutes and cooled down to 42° C. for 2 hours. The CirLigation product was purified with Zymo oligo nucleotide purification kit. According to the manufacturer's instructions, 28 µL water was added into 22 µL CircLigation product for a total volume of 50 µL. This was mixed with 100 µL Oligo binding buffer and 400 µL ethanol. This was spun for 30 seconds at >10,000×g, and the flow-through was discarded. 750 µL DNA wash buffer was added, then spun for 30 seconds at >10,000×g, flow-through discarded, and spun for another 1 minute at top speed. The column was moved to a new Eppendorf tube and eluted with 17 µL water (final eluted volume was approximately 15 µL).

Rolling circle amplification was conducted in a volume of about 50 µL. Into the 15 µL elution sample, was added 5 µL 10× RepliPHI buffer (Epicentre), 1 µL 25 mM dNTPs, 2 µL 100 mM DTT, 1 µL 100U/µL RepliPHI Phi29, and 26 µL water. The reaction mix was incubated at 30° C. for 1 hour. RCA products were purified by adding 80 µL of Ampure beads, following the manufacturer's instructions for the remaining wash steps. For elution, 22.5 µL elution buffer was added, and the beads were incubated at 65° C. for 5 minutes. After spinning briefly, the tube was returned to the magnets.

About 20 µL of eluted product from the RCA reaction was mixed with 25 µL 2× Phusion Master mix, 2.5 µL DMSO, and 0.5 µL of 10 µM of each B2B primer mix. Amplification used the following PCR program: 95° C. for 1 minute, 5 cycles of extension (95° C. for 15 seconds, 55° C. for 15 seconds, 72° C. for 1 minute), 13-18 cycles of replication (95° C. for 15 seconds, 68° C. for 15 seconds, 72° C. for 1 minute), and 72° C. for 7 minutes of final extension. PCR product size was checked by running an E-gel. If the range was from 100-500 bp, a 0.6× Ampure bead purification was performed to enrich 300-500 bp and take 1-2 ng for another round of PCR with small RNA library adaptor primers. If the product size range was >1000 bp, products were purified with 1.6× Ampure beads, and 2-3 ng taken for Nextera XT amplicon library prep to enrich sizes in the range of 400-1000 bp by 0.6× Ampure bead purification.

For performing bioinformatics on sequencing data, FASTQ files were obtained from a MiSeq run. The sequences were aligned in FASTQ files to reference genomic sequences containing targeted sequences (e.g. KRAS and EGFR) using BWA. The regions and lengths of repeat units and its reference position were found for each sequence (both reads) using the alignment results. Variants in all loci were found using the alignment results and information of repeat units of each sequence. Results from two reads were combined. The normalized frequency of variants and the noise level were computed. Multiple additional criteria in variant calls from confirmed variants were applied, including qscore >30 and p-value <0.0001. The confirmed variants that passed these criteria were reported as true variants (mutations). The process can be automated by computer languages (e.g. python).

Example 2: Making Tandem Repetitive Sequencing Library for Detection of Sequence Variants 10 ng of DNA fragments with 150 bp average length in a 12 µL volume were used for tandem repetitive sequencing library construction. The DNA was previously processed with T4 Polynucleotide Kinase (New England Biolabs) to add phosphate group at the 5' terminus and leaving a hydroxyl group at the 3' terminus. For DNA fragments generated from DNase I or enzymatic fragmentation or extracted from serum or plasma, the terminus processing step was skipped. The DNA was mixed with 2 µL 10× CircLigase buffer (Epicentre CL9021K). The mixture was heated to 95° C. for 2 minutes and chilled on ice for 5 minutes, then 4 µL Betaine, 1 µL 50 mM $MnCl_2$, and 1 µL CircLigase II (Epicentre CL9021K) were added. The ligation reaction was performed at 60° C. for at least 12 hours. 1 µL of each RCA primer mix at 200 nM (to final of 10 nM final concentration) was added to the ligation products and mixed, heated to 96° C. for 1 minute, cooled to 42° C., and incubated at 42° C. for 2 hours.

The CircLigation product with hybridized RCA primers were purified with Zymo oligo nucleotide purification kit (Zymo Research, D4060). To do this, the 21 µL of product was diluted to 50 µL with 28 µL water and 1 µL of carrier RNA (Sigma-Aldrich, R5636, diluted at 200 ng/µL with 1×TE buffer). The diluted sample was mixed with 100 µL Oligo binding buffer and 400 µL of 100% ethanol. The mixture was loaded on the column and centrifuged for 30 seconds at >10,000×g. The flow-through was discarded. The column was washed with 750 µL DNA wash buffer by centrifuging for 30 seconds at >10,000×g, discarding the flow-through and centrifuging for another 1 minute at top speed. The column was moved to a new 1.5 mL Eppendorf tube and the DNA was eluted with 17 µL elution buffer (10 mM Tris-Cl pH 8.0, final eluted volume about 15 µL).

5 µL 10× RepliPHI buffer, 2 µL 25 mM dNTPs, 2 µL 100 mM DTT, 1 µL 100 U/µL RepliPHI Phi29, and 25 µL water (Epicentre, RH040210) were added to the 15 µL eluted sample from the column, for a total reaction volume of 50 µL. The reaction mix was incubated at 30° C. for 2 hours. The RCA products were purified by adding 80 µL of Ampure XP beads (Beckman Coulter, A63881). The manufacturer's instructions were followed for the washing steps. RCA products were eluted after 5 minutes of 65° C. incubation in 22.5 µL elution buffer. The tube was briefly centrifuged before returned to magnets.

About 20 µL of eluted product from the RCA reaction were mixed with 25 µL 2× Phusion Master mix (New England Biolabs M0531S), 2.5 µL water, 2.5 µL DMSO, and 0.5 µL of B2B primer mix (10 µM each). Amplification was performed with the following thermocycling program: 95° C. for 2 minutes, 5 cycles of extension (95° C. for 30 seconds, 55° C. for 15 seconds, 72° C. for 1 minute), 18 cycles of replication (95° C. for 15 seconds, 68° C. for 15 seconds, 72° C. for 1 minute), and 72° C. for 7 minutes of final extension. The PCR product size was checked by electrophoresis. Once the long PCR products were confirmed by electrophoresis, the PCR products were mixed with 30 µL Ampure beads (0.6× volume) for purification to enrich >500 bp PCR products. The purified products were quantified with Qubit 2.0 Quantification Platform (Invitrogen). About 1 ng purified DNA was used for Nextera XT Amplicon library preparation (Illumina FC-131-1024). Library elements with an insert size of >500 bp were enriched by purification with 0.6× Ampure beads.

The concentration and size distribution of the amplified libraries were analyzed using the Agilent DNA High Sensitivity Kit for the 2100 Bioanalyzer (Agilent Technologies Inc., Santa Clara, Calif.). Sequencing was performed using Illumina MiSeq with 2-250 bp MiSeq sequencing kit. According to the MiSeq manual, 12 pM denatured library was loaded on the sequencing run.

In a variation on this procedure, Illumina adapters were used in library preparation in place of Nextera preparation. To do this, about 1 ng of similarly purified DNA was used for PCR amplification with a pair of primers containing the universal part of B2B primers and Illumina Adapter sequence (P5 and P7; 5'CAAGCAGAAGACGGCAT-ACGA3' (SEQ ID NO: 1) and 5'ACACTCTTTCCCTA-CACGACGCTCTTCCGATCT3' (SEQ ID NO: 2)). Using Phusion Master Mix, 12 cycles of replication steps (95° C. for 30 seconds, 55° C. for 15 seconds, 72° C. for 60 seconds) were performed. The purpose of this amplification step was to add Illumina adapters for amplicon sequencing. Amplicons >500 bp in length were enriched with 0.6× Ampure beads. The concentration and size distribution of the amplicon library were analyzed using the Agilent DNA High Sensitivity Kit for the 2100 Bioanalyzer (Agilent technologies Inc., Santa Clara, Calif.). Sequencing was performed using Illumina MiSeq with 2×250 bp MiSeq sequencing kit. The universal part of B2B primers also served as sequencing primer sequences and custom sequencing primer was added if the primer was not contained in the Illumina kit. 12 pM denatured library was loaded on the sequencing run.

Figure 33:
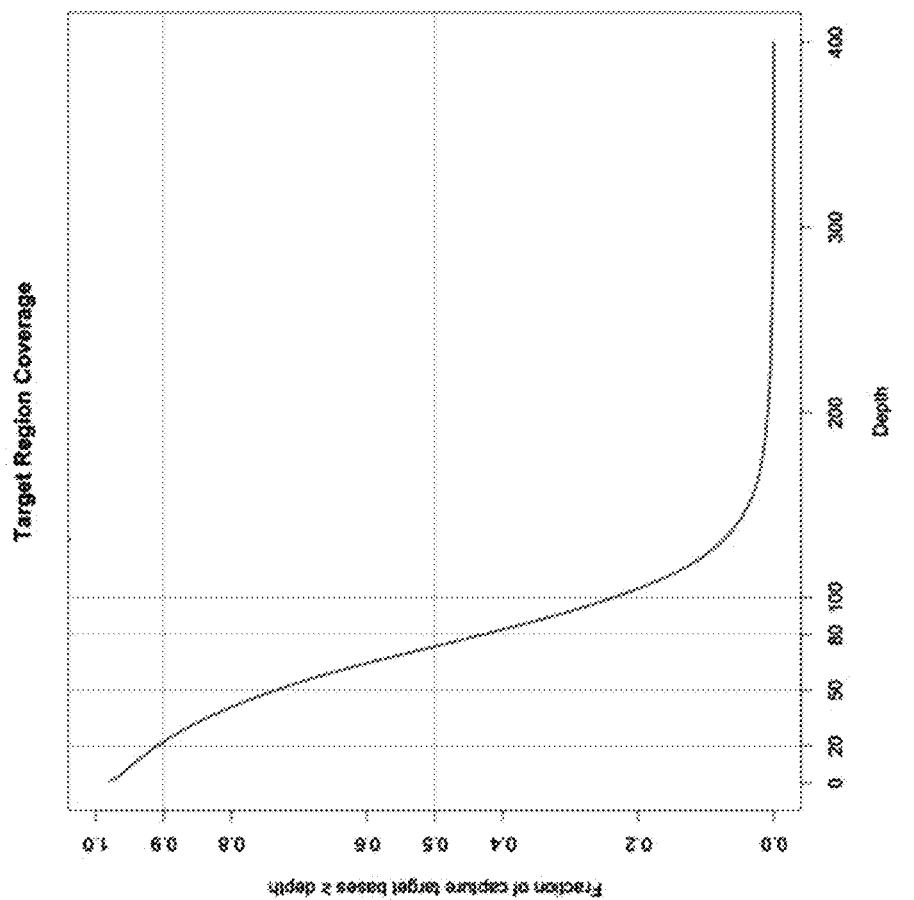
FIG. 33 illustrates efficiency of the capture and the coverage along the target regions according to an example. >90% of the targeting bases are covered more than 20×, and >50% of the targeted bases have >50× coverage.

The target region coverage in one example analysis is illustrated in FIG. 33. Table 6 below describes results for the analysis of the targeted regions.

Table 4 provides examples of RCA primers useful in methods of the disclosure. Table 5 provides examples of B2B primers useful in methods of the disclosure.

TABLE 4

| Gene Name | RCA primerA name | RCA PrimerA Sequence | SEQ ID NO | RCA primerB name | RCA Primer B Sequence | SEQ ID NO |
|---|---|---|---|---|---|---|
| PIK3CA | PIK3CA-E1a | GCTTTGAGCTGT TCTTTGTCATT | 3 | PIK3CA-E1b | AAAGCAATTTCTA CACGAGATCC | 45 |
| PIK3CA | PIK3CA-E2a | TTTAATTGTGTG GAAGATCCAATC | 4 | PIK3CA-E2b | ATTAAACAGCATG CATTGAACTG | 46 |
| EGFR | EGFR-E1a | CTTTCTCACCTTC TGGGATCC | 5 | EGFR-E1b | AAATTCCCGTCGC TATCAAG | 47 |
| EGFR | EGFR-E2a | CCATCACGTAGG CTTCCTG | 6 | EGFR-E2b | ATGGCCAGCGTGG ACAAC | 48 |
| EGFR | EGFR-E3a | GACATAGTCCAG GAGGCAGC | 7 | EGFR-E3b | TGTCCGGGAACAC AAAGAC | 49 |
| EGFR | EGFR-E4a | AAGCGACGGTCC TCCAAG | 8 | EGFR-E4b | TGGCAGCCAGGAA CGTAC | 50 |
| EGFR | EGFR-E5a | AGTACGTTCCTG GCTGCC | 9 | EGFR-E5b | AACACCGCAGCAT GTCAAG | 51 |
| EGFR | EGFR-E6a | ATCCACTTGATA GGCACCTTG | 10 | EGFR-E6b | AAGTGGATGGCAT TGGAATC | 52 |
| EGFR | EGFR-E7a | TCTCGCTGGCAG GGATTC | 11 | EGFR-E7b | CCTGGAGAAAGGA GAACGC | 53 |

TABLE 4-continued

| Gene Name | RCA primerA name | RCA PrimerA Sequence | SEQ ID NO | RCA primerB name | RCA Primer B Sequence | SEQ ID NO |
|---|---|---|---|---|---|---|
| EGFR | EGFR-E9a | AACTTTGGGCGACTATCTGC | 12 | EGFR-E9b | AGTTCCGTGAGTTGATCATCG | 54 |
| EGFR | EGFR-E10a | TTGGAGTCTGTAGGACTTGGC | 13 | EGFR-E10b | ACTTCTACCGTGCCCTGATG | 55 |
| EGFR | EGFR-E11a | CTGCTGTGGGATGAGGTACTC | 14 | EGFR-E11b | CACAGCAGGGCTTCTTCAG | 56 |
| EGFR | EGFR-E12a | CATGGAATGCTTGTACCACATC | 15 | EGFR-E12b | CATGGGCAACTTCTCTGTTTC | 57 |
| BRAF | BRAF-E1a | CAGTTTGAACAGTTGTCTGGATC | 16 | BRAF-E1b | AAACTGATGGGACCCACTCC | 58 |
| PTEN | PTEN-E1a | TGTTTCTGCTAACGATCTCTTTG | 17 | PTEN-E1b | AGGAGATATCAAGAGGATGGATTC | 59 |
| PTEN | PTEN-E2a | CAGGAAATCCCATAGCAATAATG | 18 | PTEN-E2b | TCCTGCAGAAAGACTTGAAGG | 60 |
| PTEN | PTEN-E3a | GCTTTGAATCCAAAAACCTTAAAAC | 19 | PTEN-E3b | GGATTCAAAGCATAAAAACCATTAC | 61 |
| PTEN | PTEN-E4a | TACAGTACATTCATACCTACCTCTGC | 20 | PTEN-E4b | TATGTTGTATAACTTAAACCCGATAGAC | 62 |
| PTEN | PTEN-E5a | AAAGGATATTGTGCAACTGTGG | 21 | PTEN-E5b | TTGAAGACCATAACCCACCAC | 63 |
| PTEN | PTEN-E6a | CCATAGAAATCTAGGGCCTCTTG | 22 | PTEN-E6b | AAGTAAGGACCAGAGACAAAAGG | 64 |
| PTEN | PTEN-E7a | CCAGATGATTCTTTAACAGGTAGC | 23 | PTEN-E7b | GGATTATAGACCAGTGGCACTG | 65 |
| PTEN | PTEN-E9a | GAACTTGTCTTCCCGTCGTG | 24 | PTEN-E9b | CATGTACTTTGAGTTCCCTCAGC | 66 |
| PTEN | PTEN-E12a | TCTGGTCCTGGTATGAAGAATG | 25 | PTEN-E12b | CAGGACCAGAGGAAACCTCAG | 67 |
| PTEN | PTEN-E13a | GCTCTATACTGCAAATGCTATCG | 26 | PTEN-E13b | CGTGCAGATAATGACAAGGAATATC | 68 |
| PTEN | PTEN-E14a | TTGGAGAAAAGTATCGGTTGG | 27 | PTEN-E14b | GGTCAGTTAAATTAAACATTTTGTGG | 69 |
| PTEN | PTEN-E15a | TGGTGTTACAGAAGTTGAACTGC | 28 | PTEN-E15b | GATGTTAGTGACAATGAACCTGATC | 70 |
| KRAS | KRAS-E1a | AAGAGTGCCTTGACGATACAGC | 29 | KRAS-E1b | TCTTGCCTACGCCACCAG | 71 |
| TP53 | TP53-E1a | CCTGACTCAGACTGACATTCTCC | 30 | TP53-E1b | CAGGCCCTTCTGTCTTGAAC | 72 |
| TP53 | TP53-E2a | ATGTTCCGAGAGCTGAATGAG | 31 | TP53-E2b | GAACATCTCGAAGCGCTCAC | 73 |
| TP53 | TP53-E3a | TTAAAGGACCAGACCAGCTTTC | 32 | TP53-E3b | TTATGGTATAAGTTGGTGTTCTGAAG | 74 |
| TP53 | TP53-E4a | CTTGGGACCTCTTATCAAGTGG | 33 | TP53-E4b | AGAGGTCCCAAGACTTAGTACCTG | 75 |
| TP53 | TP53-E5a | AAGCAAGCAGGACAAGAAGC | 34 | TP53-E5b | GCTTGCTTACCTCGCTTAGTG | 76 |
| TP53 | TP53-E6a | GGGACGGAACAGCTTTGAG | 35 | TP53-E6b | TTCCGTCCCAGTAGATTACCAC | 77 |
| TP53 | TP53-E7a | CAACTACATGTGTAACAGTTCCTGC | 36 | TP53-E7b | CATGTAGTTGTAGTGGATGGTGG | 78 |

TABLE 4-continued

| Gene Name | RCA primerA name | RCA PrimerA Sequence | SEQ ID NO | RCA primerB name | RCA Primer B Sequence | SEQ ID NO |
|---|---|---|---|---|---|---|
| TP53 | TP53-E8a | GTGGAGTATTTGGATGACAGAAAC | 37 | TP53-E8b | ATACTCCACACGCAAATTTCC | 79 |
| TP53 | TP53-E9a | TGCTCAGATAGCGATGGTGAG | 38 | TP53-E9b | CTATCTGAGCAGCGCTCATG | 80 |
| TP53 | TP53-E10a | CTGTGCAGCTGTGGGTTGA | 39 | TP53-E10b | GCAGGTCTTGGCCAGTTG | 81 |
| TP53 | TP53-E12a | AAGTCTGTGACTTGCACGGTC | 40 | TP53-E12b | TGTCCCAGAATGCAAGAAGC | 82 |
| TP53 | TP53-E13a | CCTGTCATCTTCTGTCCCTTC | 41 | TP53-E13b | GATGACAGGGGCCAGGAG | 83 |
| TP53 | TP53-E14a | AAGACCCAGGTCCAGATGAAG | 42 | TP53-E14b | TGGGTCTTCAGTGAACCATTG | 84 |
| TP53 | TP53-E15a | CTGCTCTTGTCTTTCAGACTTCC | 43 | TP53-E15b | GAGCAGAAAGTCAGTCCCATG | 85 |
| TP53 | TP53-E16a | CTCTGAGTCAGGAAACATTTTCAG | 44 | TP53-E16b | GCTCGACGCTAGGATCTGAC | 86 |

TABLE 5

| Gene Name | B2B primerA | PrimerA Sequence | SEQ ID NO | B2B primerB | PrimerB Sequence | SEQ ID NO |
|---|---|---|---|---|---|---|
| PIK3CA | PIK3CA-BX1a | GTTCAGAGTTCTACAGTCCGACGATCGCTTTGAGCTGTTCTTTGTCATT | 87 | PIK3CA-BX1b | CCTTGGCACCCGAGAATTCCAAAAGCAATTTCTACACGAGATCC | 129 |
| PIK3CA | PIK3CA-BX2a | GTTCAGAGTTCTACAGTCCGACGATCTTTAATTGTGTGGAAGATCCAATC | 88 | PIK3CA-BX2b | CCTTGGCACCCGAGAATTCCAATTAAACAGCATGCATTGAACTG | 130 |
| EGFR | EGFR-BX1a | GTTCAGAGTTCTACAGTCCGACGATCCTTTCTCACCTTCTGGGATCC | 89 | EGFR-BX1b | CCTTGGCACCCGAGAATTCCAAAATTCCCGTCGCTATCAAG | 131 |
| EGFR | EGFR-BX2a | GTTCAGAGTTCTACAGTCCGACGATCCCATCACGTAGGCTTCCTG | 90 | EGFR-BX2b | CCTTGGCACCCGAGAATTCCAATGGCCAGCGTGGACAAC | 132 |
| EGFR | EGFR-BX3a | GTTCAGAGTTCTACAGTCCGACGATCGACATAGTCCAGGAGGCAGC | 91 | EGFR-BX3b | CCTTGGCACCCGAGAATTCCATGTCCGGGAACACAAAGAC | 133 |
| EGFR | EGFR-BX4a | GTTCAGAGTTCTACAGTCCGACGATCAAGCGACGGTCCTCCAAG | 92 | EGFR-BX4b | CCTTGGCACCCGAGAATTCCATGGCAGCCAGGAACGTAC | 134 |
| EGFR | EGFR-BX5a | GTTCAGAGTTCTACAGTCCGACGATCAGTACGTTCCTGGCTGCC | 93 | EGFR-BX5b | CCTTGGCACCCGAGAATTCCAAACACCGCAGCATGTCAAG | 135 |
| EGFR | EGFR-BX6a | GTTCAGAGTTCTACAGTCCGACGATCATCCACTTGATAGGCACCTTG | 94 | EGFR-BX6b | CCTTGGCACCCGAGAATTCCAAAGTGGATGGCATTGGAATC | 136 |
| EGFR | EGFR-BX7a | GTTCAGAGTTCTACAGTCCGACGATCTC | 95 | EGFR-BX7b | CCTTGGCACCCGAGAATTCCACCTGGAG | 137 |

TABLE 5-continued

| Gene Name | B2B primerA | PrimerA Sequence | SEQ ID NO | B2B primerB | PrimerB Sequence | SEQ ID NO |
| --- | --- | --- | --- | --- | --- | --- |
| | | TCGCTGGCAGGGATTC | | | AAAGGAGAACGC | |
| EGFR | EGFR-BX9a | GTTCAGAGTTCTACAGTCCGACGATCAACTTTGGGCGACTATCTGC | 96 | EGFR-BX9b | CCTTGGCACCCGAGAATTCCAAGTTCCGTGAGTTGATCATCG | 138 |
| EGFR | EGFR-BX10a | GTTCAGAGTTCTACAGTCCGACGATCTTGGAGTCTGTAGGACTTGGC | 97 | EGFR-BX10b | CCTTGGCACCCGAGAATTCCAACTTCTACCGTGCCCTGATG | 139 |
| EGFR | EGFR-BX11a | GTTCAGAGTTCTACAGTCCGACGATCCTGCTGTGGGATGAGGTACTC | 98 | EGFR-BX11b | CCTTGGCACCCGAGAATTCCACACAGCAGGGCTTCTTCAG | 140 |
| EGFR | EGFR-BX12a | GTTCAGAGTTCTACAGTCCGACGATCCATGGAATGCTTGTACCACATC | 99 | EGFR-BX12b | CCTTGGCACCCGAGAATTCCACATGGGCAACTTCTCTGTTTC | 141 |
| BRAF | BRAF-BX1a | GTTCAGAGTTCTACAGTCCGACGATCCAGTTTGAACAGTTGTCTGGATC | 100 | BRAF-BX1b | CCTTGGCACCCGAGAATTCCAAAACTGATGGGACCCACTCC | 142 |
| PTEN | PTEN-BX1a | GTTCAGAGTTCTACAGTCCGACGATCTGTTTCTGCTAACGATCTCTTTG | 101 | PTEN-BX1b | CCTTGGCACCCGAGAATTCCAAGGAGATATCAAGAGGATGGATTC | 143 |
| PTEN | PTEN-BX2a | GTTCAGAGTTCTACAGTCCGACGATCCAGGAAATCCCATAGCAATAATG | 102 | PTEN-BX2b | CCTTGGCACCCGAGAATTCCATCCTGCAGAAAGACTTGAAGG | 144 |
| PTEN | PTEN-BX3a | GTTCAGAGTTCTACAGTCCGACGATCGCTTTGAATCCAAAAACCTTAAAAC | 103 | PTEN-BX3b | CCTTGGCACCCGAGAATTCCAGGATTCAAAGCATAAAAACCATTAC | 145 |
| PTEN | PTEN-BX4a | GTTCAGAGTTCTACAGTCCGACGATCTACAGTACATTCATACCTACCTCTGC | 104 | PTEN-BX4b | CCTTGGCACCCGAGAATTCCATATGTTGTATAACTTAAACCCGATAGAC | 146 |
| PTEN | PTEN-BX5a | GTTCAGAGTTCTACAGTCCGACGATCAAAGGATATTGTGCAACTGTGG | 105 | PTEN-BX5b | CCTTGGCACCCGAGAATTCCATTGAAGACCATAACCCACCAC | 147 |
| PTEN | PTEN-BX6a | GTTCAGAGTTCTACAGTCCGACGATCCCATAGAAATCTAGGGCCTCTTG | 106 | PTEN-BX6b | CCTTGGCACCCGAGAATTCCAAAGTAAGGACCAGAGACAAAAAGG | 148 |
| PTEN | PTEN-BX7a | GTTCAGAGTTCTACAGTCCGACGATCCCAGATGATTCTTTAACAGGTAGC | 107 | PTEN-BX7b | CCTTGGCACCCGAGAATTCCAGGATTATAGACCAGTGGCACTG | 149 |
| PTEN | PTEN-BX9a | GTTCAGAGTTCTACAGTCCGACGATCGAACTTGTCTTCCCGTCGTG | 108 | PTEN-BX9b | CCTTGGCACCCGAGAATTCCACATGTACTTTGAGTTCCCTCAGC | 150 |
| PTEN | PTEN-BX12a | GTTCAGAGTTCTACAGTCCGACGATCTCTGGTCCTGGTATGAAGAATG | 109 | PTEN-BX12b | CCTTGGCACCCGAGAATTCCACAGGACCAGAGGAAACCTCAG | 151 |
| PTEN | PTEN-BX13a | GTTCAGAGTTCTACAGTCCGACGATCGC | 110 | PTEN-BX13b | CCTTGGCACCCGAGAATTCCACGTGCAG | 152 |

TABLE 5-continued

| Gene Name | B2B primerA | PrimerA Sequence | SEQ ID NO | B2B primerB | PrimerB Sequence | SEQ ID NO |
|---|---|---|---|---|---|---|
| | | TCTATACTGCAAAT GCTATCG | | | ATAATGACAAGGA ATATC | |
| PTEN | PTEN-BX14a | GTTCAGAGTTCTAC AGTCCGACGATCTT GGAGAAAAGTATCG GTTGG | 111 | PTEN-BX14b | CCTTGGCACCCGAG AATTCCAGGTCAGT TAAATTAAACATTT TGTGG | 153 |
| PTEN | PTEN-BX15a | GTTCAGAGTTCTAC AGTCCGACGATCTG GTGTTACAGAAGTT GAACTGC | 112 | PTEN-BX15b | CCTTGGCACCCGAG AATTCCAGATGTTA GTGACAATGAACCT GATC | 154 |
| KRAS | KRAS-BX1a | GTTCAGAGTTCTAC AGTCCGACGATCAA GAGTGCCTTGACGA TACAGC | 113 | KRAS-BX1b | CCTTGGCACCCGAG AATTCCATCTTGCC TACGCCACCAG | 155 |
| TP53 | TP53-BX1a | GTTCAGAGTTCTAC AGTCCGACGATCCC TGACTCAGACTGAC ATTCTCC | 114 | TP53-BX1b | CCTTGGCACCCGAG AATTCCACAGGCCC TTCTGTCTTGAAC | 156 |
| TP53 | TP53-BX2a | GTTCAGAGTTCTAC AGTCCGACGATCAT GTTCCGAGAGCTGA ATGAG | 115 | TP53-BX2b | CCTTGGCACCCGAG AATTCCAGAACATC TCGAAGCGCTCAC | 157 |
| TP53 | TP53-BX3a | GTTCAGAGTTCTAC AGTCCGACGATCTT AAAGGACCAGACCA GCTTTC | 116 | TP53-BX3b | CCTTGGCACCCGAG AATTCCATTATGGT ATAAGTTGGTGTTC TGAAG | 158 |
| TP53 | TP53-BX4a | GTTCAGAGTTCTAC AGTCCGACGATCCT TGGGACCTCTTATC AAGTGG | 117 | TP53-BX4b | CCTTGGCACCCGAG AATTCCAAGAGGTC CCAAGACTTAGTAC CTG | 159 |
| TP53 | TP53-BX5a | GTTCAGAGTTCTAC AGTCCGACGATCAA GCAAGCAGGACAAG AAGC | 118 | TP53-BX5b | CCTTGGCACCCGAG AATTCCAGCTTGCT TACCTCGCTTAGTG | 160 |
| TP53 | TP53-BX6a | GTTCAGAGTTCTAC AGTCCGACGATCGG GACGGAACAGCTTT GAG | 119 | TP53-BX6b | CCTTGGCACCCGAG AATTCCATTCCGTC CCAGTAGATTACCAC | 161 |
| TP53 | TP53-BX7a | GTTCAGAGTTCTAC AGTCCGACGATCCA ACTACATGTGTAAC AGTTCCTGC | 120 | TP53-BX7b | CCTTGGCACCCGAG AATTCCACATGTAG TTGTAGTGGATGGT GG | 162 |
| TP53 | TP53-BX8a | GTTCAGAGTTCTAC AGTCCGACGATCGT GGAGTATTTGGATG ACAGAAAC | 121 | TP53-BX8b | CCTTGGCACCCGAG AATTCCAATACTCC ACACGCAAATTTCC | 163 |
| TP53 | TP53-BX9a | GTTCAGAGTTCTAC AGTCCGACGATCTG CTCAGATAGCGATG GTGAG | 122 | TP53-BX9b | CCTTGGCACCCGAG AATTCCACTATCTG AGCAGCGCTCATG | 164 |
| TP53 | TP53-BX10a | GTTCAGAGTTCTAC AGTCCGACGATCCT GTGCAGCTGTGGGT TGA | 123 | TP53-BX10b | CCTTGGCACCCGAG AATTCCAGCAGGTC TTGGCCAGTTG | 165 |
| TP53 | TP53-BX12a | GTTCAGAGTTCTAC AGTCCGACGATCAA GTCTGTGACTTGCA CGGTC | 124 | TP53-BX12b | CCTTGGCACCCGAG AATTCCATGTCCCA GAATGCAAGAAGC | 166 |
| TP53 | TP53-BX13a | GTTCAGAGTTCTAC AGTCCGACGATCCC | 125 | TP53-BX13b | CCTTGGCACCCGAG AATTCCAGATGACA | 167 |

TABLE 5-continued

| Gene Name | B2B primerA | PrimerA Sequence | SEQ ID NO | B2B primerB | PrimerB Sequence | SEQ ID NO |
|---|---|---|---|---|---|---|
| | | TGTCATCTTCTGTCC CTTC | | | GGGGCCAGGAG | |
| TP53 | TP53-BX14a | GTTCAGAGTTCTAC AGTCCGACGATCAA GACCCAGGTCCAGA TGAAG | 126 | TP53-BX14b | CCTTGGCACCCGAG AATTCCATGGGTCT TCAGTGAACCATTG | 168 |
| TP53 | TP53-BX15a | GTTCAGAGTTCTAC AGTCCGACGATCCT GCTCTTGTCTTTCAG ACTTCC | 127 | TP53-BX15b | CCTTGGCACCCGAG AATTCCAGAGCAG AAAGTCAGTCCCATG | 169 |
| TP53 | TP53-BX16a | GTTCAGAGTTCTAC AGTCCGACGATCCT CTGAGTCAGGAAAC ATTTTCAG | 128 | TP53-BX16b | CCTTGGCACCCGAG AATTCCAGCTCGAC GCTAGGATCTGAC | 170 |

TABLE 6

| | Results |
|---|---|
| reads | 1.5M |
| % target base w/1x | 97.8% |
| % on target | 63.4% |
| % duplicates | 18.2% |
| mean coverage | 74.5x |
| s.d of coverage | 0.21 |

Example 3: Fragmentation of Genomic DNA for Sequencing Library Construction

1 µL of genomic DNA was processed using a NEBNext dsDNA Fragmentase kit (New England Biolabs) by following the manufacturer's protocol. Incubation time was extended to 45 minutes at 37° C. The fragmentation reaction was stopped by adding 5 µL of 0.5M EDTA pH 8.0, and was purified by adding 2× volumes of Ampure XP beads (Beckman Coulter, A63881) according to the manufacturer's protocol. Fragmented DNA was analyzed on a Bioanalyzer with a High Sensitivity DNA kit (Agilent). The size range of fragmented DNA was typically from about 100 bp to about 200 bp with a peak of about 150 bp.

Example 4: Library Preparation Procedures

In this example, a KAPA Library Prep Kit (KK8230) was used for illustration purposes.

For steps involving bead purification, AMPure XP Beads (cat # A63881) were equilibrated to room temperature and thoroughly resuspended before mixing with the sample. After mixing thoroughly with the sample on a vortex mixer, it was incubated at room temperature for 15 minutes to allow DNA to bind to the beads. Beads were then put over a magnetic stand until the liquid was clear. The beads were then washed twice with 200 ul 80% ethanol and dried at room temperature for 15 minutes.

For performing the end-repair reaction, up to 50 µL (2-10 ng) of cell-free DNA was mixed with 20 µL of end repair master mix (8 µL water, 7 µL 10×KAPA end repair buffer, and 5 µL KAPA end repair enzyme mix), and incubated for 30 minutes at 20° C. 120 µL of AMPure XP Beads were then added to the 70 µL end repair reaction. The sample was then purified as above.

For performing A-tailing reactions, dried beads containing the end-repaired DNA fragment were mixed with A-tailing master mix (42 µL water, 5 µL 10×KAPA A tailing buffer, and KAPA A-tailing enzyme). The reaction was incubated at 30° C. for 30 minutes. After adding 90 µL of PEG solution (20% PEG 8000, 2.5M NaCl), the mixture was washed according the bead purification protocol above. This A-tailing step was skipped for blunt-end ligation reactions.

For linker ligation, two oligos having the following sequences (5' to 3') were used to form an adapter polynucleotide duplex: /5Phos/CCATTTCATTACCTCTTTCTCCG-CACCCGACA TAGAT*T (SEQ ID NO: 171) and /5Phos/ATCTAT-GTCGGGTGCGGAGAAAGAGGTAATGA AATGG*T (SEQ ID NO: 172). The dried beads containing end-repaired (for blunt ligation) or a-tailed (for linker-based ligation) was mixed with 45 µL of ligation master mix (30 µL water, 10 µL 5×KAPA ligation buffer, and 5 µL KAPA T4 DNA ligase), and 5 µL water (for blunt end ligation) or 5 µL of an equal molar mix of linker oligonucleotides (for linker-based ligation). The beads were thoroughly resuspended, and incubated at 20° C. for 15 minutes. After adding 50 µL of PEG solution (see above), the mixture was washed according to the above bead purification protocol.

Multiple displacement amplification (MDA) was performed using Illustra Genomiphi V2 DNA Amplification Kits. The dried beads containing the ligated fragment chain were resuspended in 9 µl of random hexamer-containing buffer and heated to 3 minutes at 95° C., followed by rapid cooling on ice. After adding 1 µL of enzyme mix, the cooled sample was incubated at 30° C. for 90 minutes. The reaction was then stopped by heating at 65° C. for 10 minutes. After adding 30 µL of PEG solution (see above), the mixture was washed according to the purification protocol described above, and resuspended in 200 µL TE (with an incubation at 65° C. for 5 minutes). If desired, the purified product could be quantitated with quantitative PCR, digital droplet PCR (ddPCR), or put forward to next generation sequencing (NGS).

After MDA, long ligated fragment chains (e.g. >2 kb) were sonicated to ~300 bp using a Covaris 5220 in 130 µL total volume. The manufacturer's protocol indicated 140 W peak power, 10% duty factor, 200 cycles per burst, and 80 seconds of treatment time. The fragment length of ~300 bp was selected to increase the chance of keeping an intact original cell free DNA fragment. A standard library preparation protocol can be used to put adaptors on sonicated DNA fragments for sequencing if desired. A variety of read compositions were returned from pair-end sequencing runs on Illumina sequencers (either HiSeq or MiSeq). Those in which the junction (either self-junction, or adapter junction in the case where adapters were included in the ligation step) was internal to the read (flanked 5' and 3' by non-adapter sequence) were used to barcode sequences of interest.

Example 5: Circularization and Amplification

This provides an example illustration of a circularization and amplification procedure according to methods herein. The procedure used the following supplies: PCR Machine (e.g. MJ research PTC-200 Peltier thermal cycler); Circligase II, ssDNA ligase Epicentre cat # CL9025K; Exonuclease (e.g. ExoI, NEB Biolabs cat # M0293S; ExoIII, NEB biolabs cat # M0206S); T4 Polynucleotide Kinase (NEB Biolab cat # M0201S); Whole Genome Amplification kit (e.g. GE Healthcare, Illustra, Ready-To-Go, Genomiphi, V3 DNA amplification kit); GlycoBlue (e.g. Ambion cat # AM9515); Micro centrifuge (e.g. Eppendrof 5415D); DNA purification beads (e.g. Agencourt, AMpure XP, Beckman Coulter cat # A63881); Magnetic stand (e.g. The MagnaRack™ Invitrogen cat # CS15000); Qubit® 2.0 Fluorometer (Invitrogen, cat # Q32866); molecular probes ds DNA HS assay kit (Life Technology cat #032854); and a Bioanalyzer (Agilent 2100), and high sensitivity DNA reagents (cat #5067-4626).

For amplification of DNA fragments lacking a 5' terminal phosphate (e.g. cell-free DNA), the first step was end-repair and formation of single strands. DNA was denatured at 96° C. for 30 seconds (e.g. on a PCR machine). A polynucleotide kinase (PNK) reaction was prepared by combining 40 μL of DNA and 5 μL 10×PNK reaction buffer, followed by incubation at 37° C. for 30 minutes. 1 mM ATP and the PNK enzyme were added to the reaction, and incubated for 37° C. for 45 minutes. A buffer exchange was conducted by precipitating and resuspending the DNA. 50 μL DNA from the PNK reaction, 5 μL sodium acetate 0.5M pH 5.2, 1 μL GlycoBlue, 1 μL oligo (100 ng/μL), and 150 μL 100% ethanol were combined. The mixture was incubated at −80° C. for 30 minutes, and centrifuged at 16 k rpm for 5 minutes to pellet the DNA. The DNA pellet was washed with 500 μL of 70% ethanol, air dried for 5 minutes at room temperature, and DNA was suspended in 12 μL 10 mM Tris-Cl pH 8.0.

Resuspended DNA was then circularized by ligation. The DNA was denatured at 96° C. for 30 seconds, the sample was chilled on ice for 2 minutes, and ligase mix (2 μL 10× CircLigase buffer, 4 μL 5M Betaine, 1 μL 50 mM $MnCl_2$, 1 μL CircLigase II) was added. The ligation reaction was incubated at 60° C. for 16 hours on a PCR machine. Unligated polynucleotides were degraded by exonuclease digestion. For this, DNA was denatured at 80° C. for 45 seconds, and 1 μL Exo nuclease mix (ExoI 20U/μL: ExoIII 100U/μL=1:2) was added to each tube. This was mixed by pipetting up and down 5 times, and spun briefly. The digestion mix was incubated at 37° C. for 45 minutes. The volume was brought to 50 μL with 30 μL of water, and a further buffer exchange was conducted by precipitation and resuspension as above.

For conducting whole genome amplification (WGA), purified DNA was first denatured at 65° C. for 5 minutes. 10 μL of denature buffer from GE WGA kit was added to 10 μL of purified DNA. The DNA was cooled on a cool block or ice for 2 minutes. 20 μL of DNA was added to the Ready-To-Go GenomiPhi V3 cake (WGA). The WGA reaction was incubated at 30° C. for 1.5 hours, followed by heat inactivation at 65° C. for 10 minutes.

The sample was purified using AmpureXP magnetic beads (1.6×). The beads were vortexed, and 80 μL aliquoted in 1.5 mL tubes. 30 μL water, 20 μL amplified DNA, and the 80 μL of beads were then combined, and incubated at room temperature for 3 minutes. The tubes were placed on a magnetic stand for 2 minutes, and the clear solution was pipetted out. The beads were washed twice with 80% ethanol. DNA was eluted by adding 200 μL of 10 mM Tris-Cl pH 8.0. The DNA bead mixture was incubated at 65° C. for 5 minutes. The tubes were placed back on the magnetic stand for 2 minutes. 195 μL of DNA was transferred to a new tube. 1 μL was used for quantification by Qubit. Finally, 130 μL WGA product was sonicated using Covaris S220 to reach a size of around 400 bp.

Figures 18A, 18B:
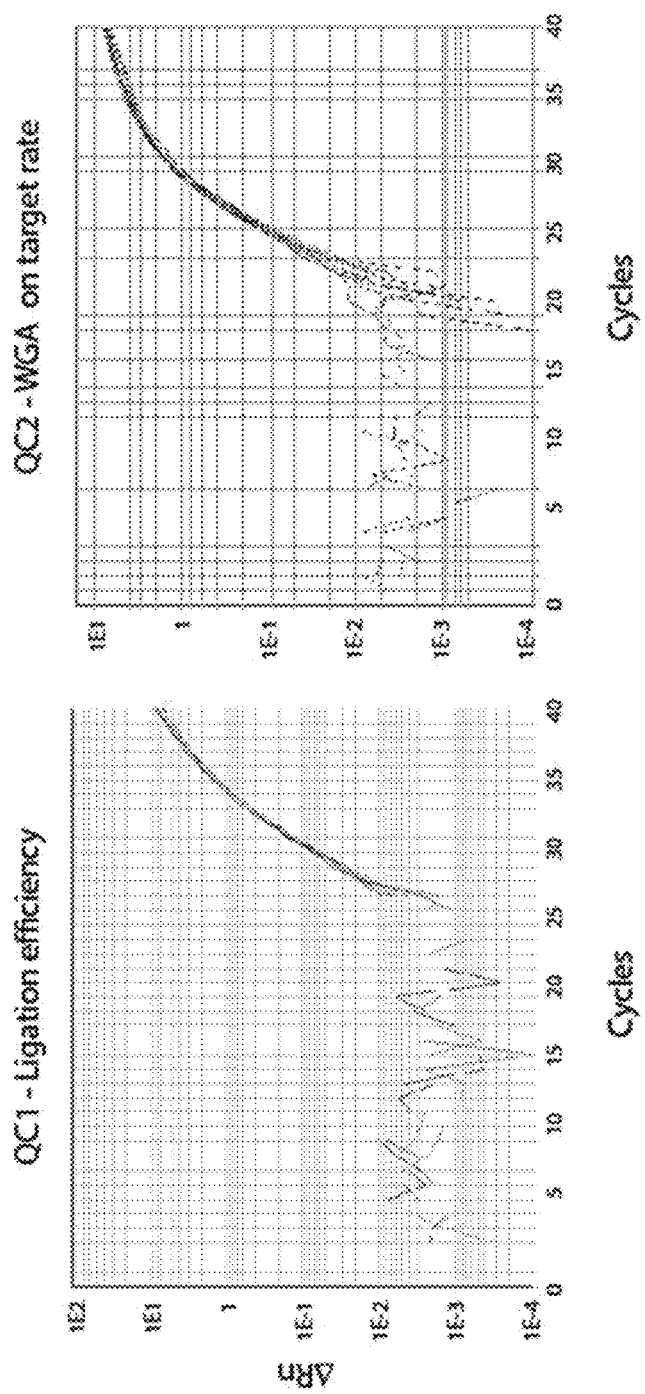
FIGS. 18A and 18B illustrate results of an analysis of ligation efficiency and on-target rate of an embodiment of the disclosure.

Example 6: Analysis of Ligation Efficiency and On-Target Rates cfDNA that was circularized and subjected to whole genome application as in the above examples was analyzed by quantitative PCR (qPCR). The qPCR amplification curve results for a sample target (using KRAS primers) are shown in FIGS. 18A and 18B. As shown in FIG. 18A, qPCR amplification of $\frac{1}{10}^{th}$ of input cfDNA gave an average Ct (cycle threshold) of 31.75, and $\frac{1}{10}^{th}$ of the same sample's ligation product gave an average Ct of 31.927, indicating a high ligation efficiency of about 88%. Ligation efficiency may range from about or more than about 70%, 80%, 90%, 95%, or more, such as about 100%. The linear DNA that was not circularized is removed in some examples, such that about all DNA can be amplified from circular forms. Each sample was run three times, in duplicate. As shown in FIG. 18B, the amplification curves of 10 ng of WGA product and reference genomic DNA (gDNA) (12878, 10 ng) virtually overlap with each other. The average Ct for the WGA sample was 26.655, while that of the gDNA sample was 26.605, indicating a high on-target rate of over 96%. The number of KRAS in a given amount of amplified DNA was comparable with the un-amplified gDNA, indicating an unbiased amplification process. Each sample was tested three times, in duplicate. As a point of contrast, the circularization protocol provided in Lou et al. (PNAS, 2013, 110 (49)) was also tested. Using the Lou method, which lacked the precipitation and purification steps of the examples described above, only 10-30% of linear input DNA was converted to circular DNA. Such low recovery presents a challenge to downstream sequencing and variant detection.

Example 7: Analysis of Amplified Circularized DNA by ddPCR

Droplet digital PCR (ddPCR) was used to assess allele frequency preservation and bias in whole genome amplification products generated from circularized polynucleotides. In general, ddPCR refers to a digital PCR assay that measures absolute quantities by counting nucleic acid molecules encapsulated in discrete, volumetrically defined, water-in-oil droplet partitions that support PCR amplification (Hinson et al, 2011, Anal. Chem. 83:8604-8610; Pinheiro et al, 2012, Anal. Chem. 84: 1003-1011). A single ddPCR reaction may be comprised of at least 20,000 partitioned droplets per well. Droplet digital PCR may be performed using any platform that performs a digital PCR assay that measures absolute quantities by counting nucleic acid molecules encapsulated in discrete, volumetrically defined, water-in-oil droplet partitions that support PCR amplification. A typical strategy for droplet digital PCR may be summarized as follows: a sample is diluted and partitioned into thousands to millions of separate reaction chambers (water-in-oil droplets) so that each contains one or no copies of the nucleic acid molecule of interest. The number of "positive" droplets detected, which contain the target amplicon (i.e., nucleic acid molecule of interest), versus the number of "negative" droplets, which do not contain the target amplicon (nucleic acid molecule of interest), may be used to determine the number of copies of the nucleic acid molecule of interest that were in the original sample. Examples of droplet digital PCR systems include the QX100TM Droplet Digital PCR System by Bio-Rad, which partitions samples containing nucleic acid template into 20,000 nanoliter-sized droplets; and the RainDrop™ digital PCR system by RainDance, which partitions samples containing nucleic acid template into 1,000,000 to 10,000,000 pico liter-sized droplets. Additional examples of methods for ddPCR are provided in WO2013181276A1.

Figure 19:
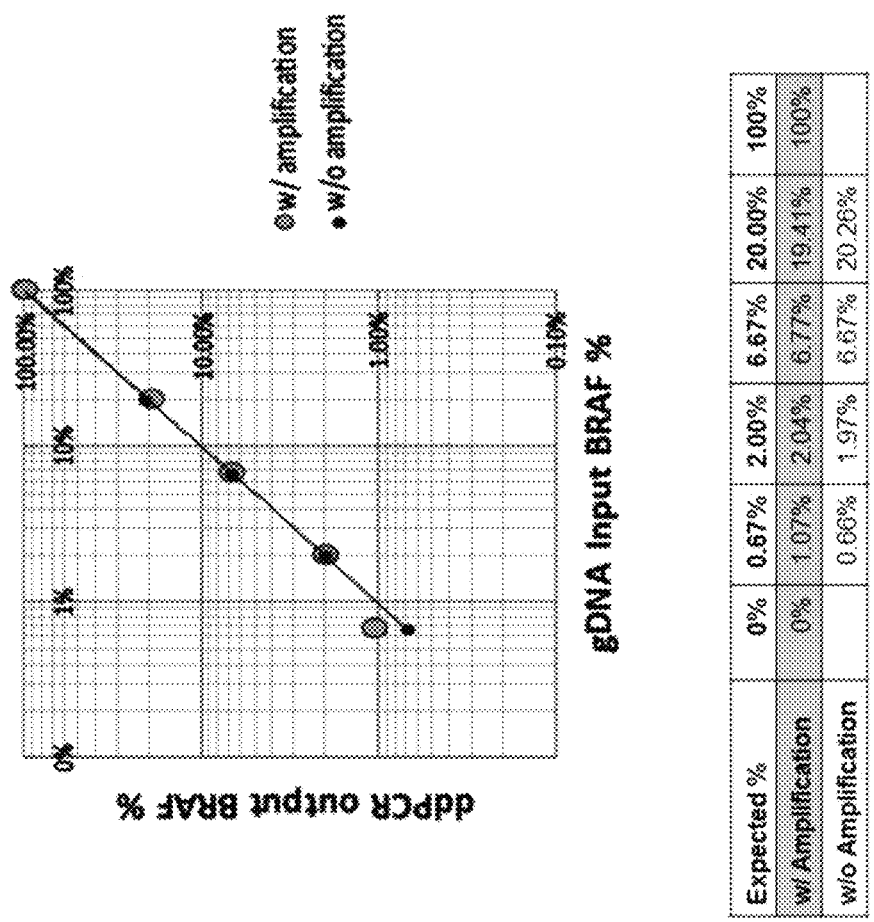
FIG. 19 illustrates the preservation of allele frequencies, and substantial absence of bias, in a method in accordance with an embodiment of the disclosure.

In this example, BRAF V600E genomic DNA (gDNA) from a melanoma cell line was mixed in with reference genome DNA 12878 at specific proportions (0%, 0.67%, 2.0%, 6.67%, 20%, or 100%), and fragmented to generate fragments of a size resembling those found in cfDNA (in this case, about 150 bp). The mixed DNA samples (10 ng) were circularized and amplified according to Example 2. 40 ng of amplified DNA was subjected to ddPCR for BRAF V600E and wild type. The observed mutation allele frequencies are illustrated graphically and tabulated in FIG. 19. As shown, the observed mutation allele frequency with amplification (middle row of FIG. 19 table) reflects the input mutant allele frequency (top row), as well as the ddPCR result from 100 ng of genomic DNA without amplification (bottom row). The allele frequency by ddPCR output is calculated as the number of BRAF mutation containing droplets over the sum of both mutant and wild type containing droplets. DNA with amplification is indicated as an open circle, and without amplification is indicated as a small filled circle. With the exception of a small deviation at 0.67%, the two data sets overlap completely. This demonstrates preservation of true representation of the mutant allele frequency, substantially without bias.

Figure 20:
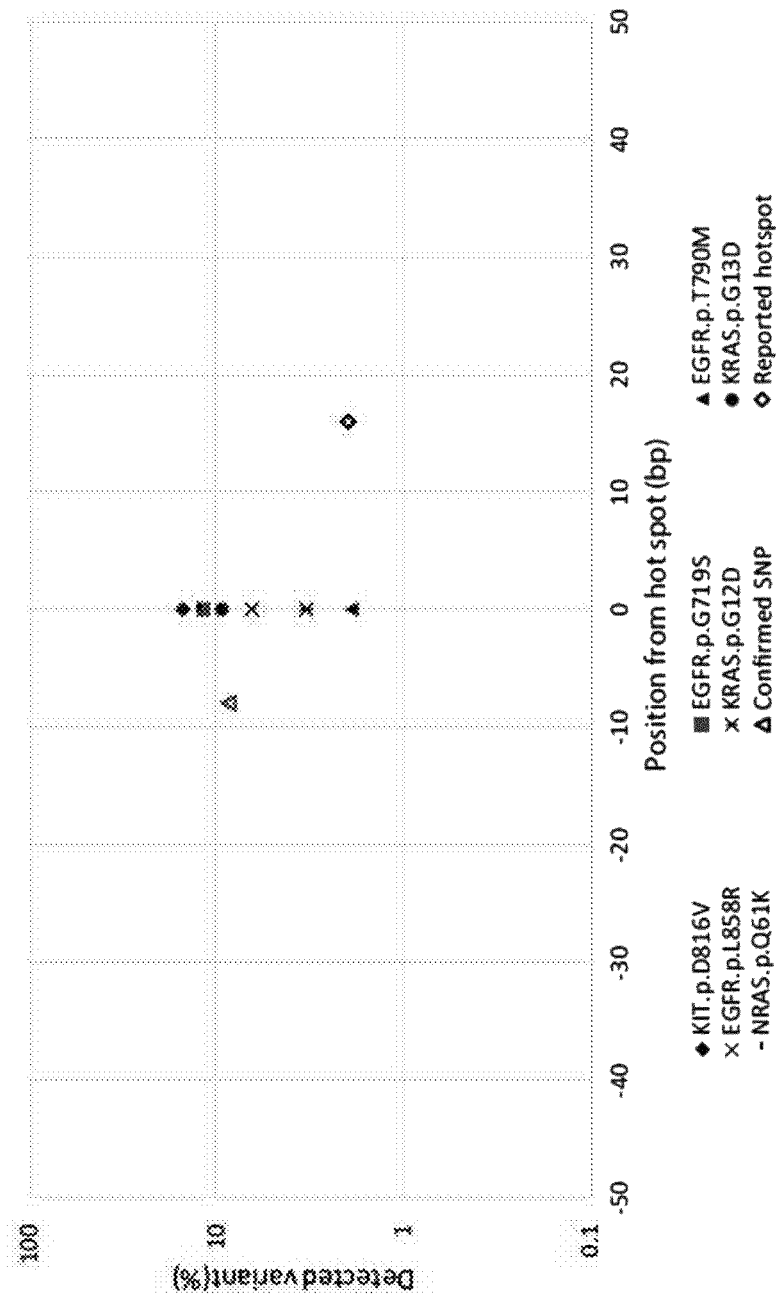
FIG. 20 illustrates results for detection of sequence variants in a small input sample, in accordance with an embodiment.

Example 8: Detection of Sequence Variants Above Background 10 ng of sonicated gDNA (150 bp, Multi-Gene Multiplex reference DNA, Horizon) was circularized and amplified as described in Example 2, and followed by sonication. Fragmented DNA was then subjected to Rubicon sequencing library construction. After capture sequencing, variants within 50 bp from reference hotspots were plotted. Results for variant detection, where calling a variant required detection in two different polynucleotides distinguished by different junctions, are shown in FIG. 20. The seven expected reference hotspots (KIT D816V, EGFR G719S, EGFR T790M, EGFR L858R, KRAS G13D, KRAS G12D, NRAS Q61K) are plotted at position 0. Two other variants were also confirmed, illustrated as the open triangle and diamond in FIG. 20.

Figure 21:
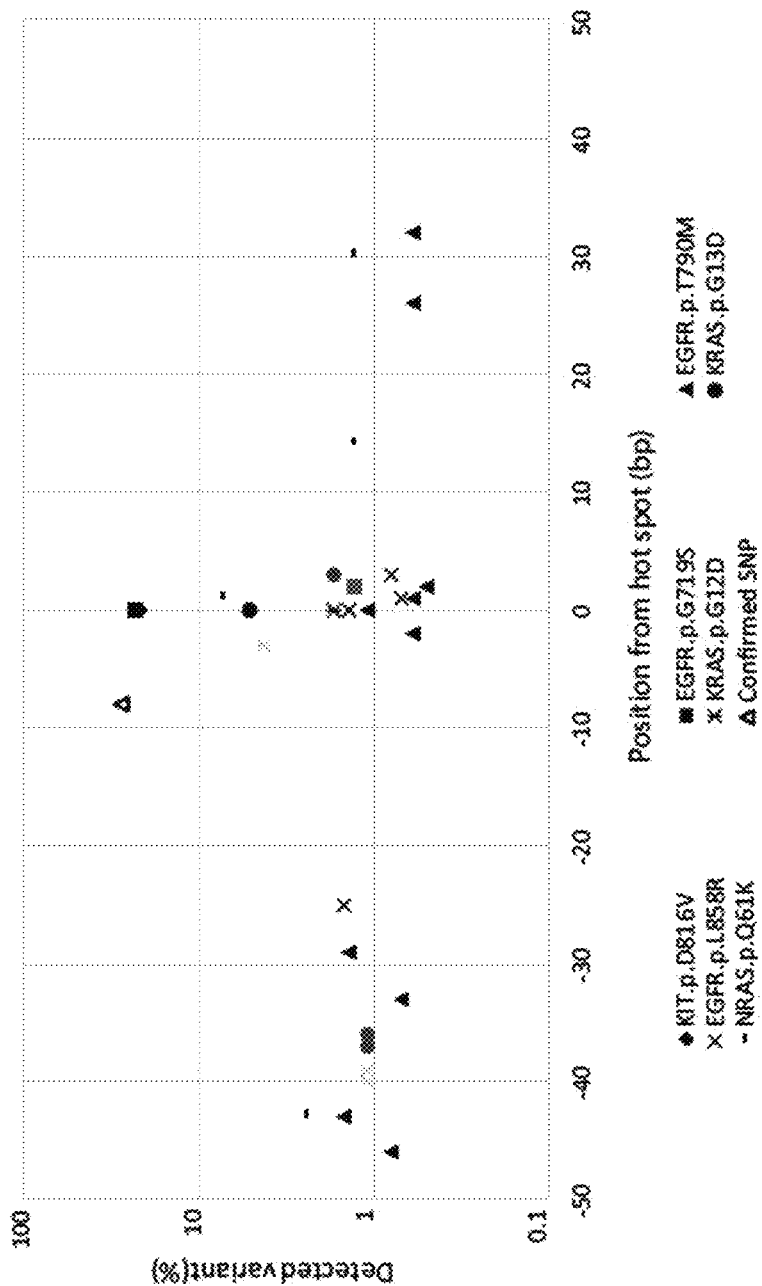
FIG. 21 illustrates an example of high background in results for detection of sequence variants obtained without requiring that a sequence difference occur on two different polynucleotides, according to standard sequencing methods.

For comparison, gDNA was sonicated as above, but 10 ng of the sonicated gDNA was directly subjected to Rubicon sequencing library construction according to common practice, without circularization and without requiring confirmation of a sequence variants on two different polynucleotides. After capture sequencing, variants within 50 bp from reference hotspots were again plotted, with results in FIG. 21. The seven expected reference hotspots (KIT D816V, EGFR G719S, EGFR T790M, EGFR L858R, KRAS G13D, KRAS G12D, NRAS Q61K) are plotted at position 0. The variants at other positions were not expected, and are most likely due to sequencing errors. By contrast with results of the method employed in generating FIG. 20, the results in FIG. 21 indicate that standard sequencing methods have a much higher random error rate that can mask true mutation signal when allele frequency is low (such as below 5%).

Figure 16:
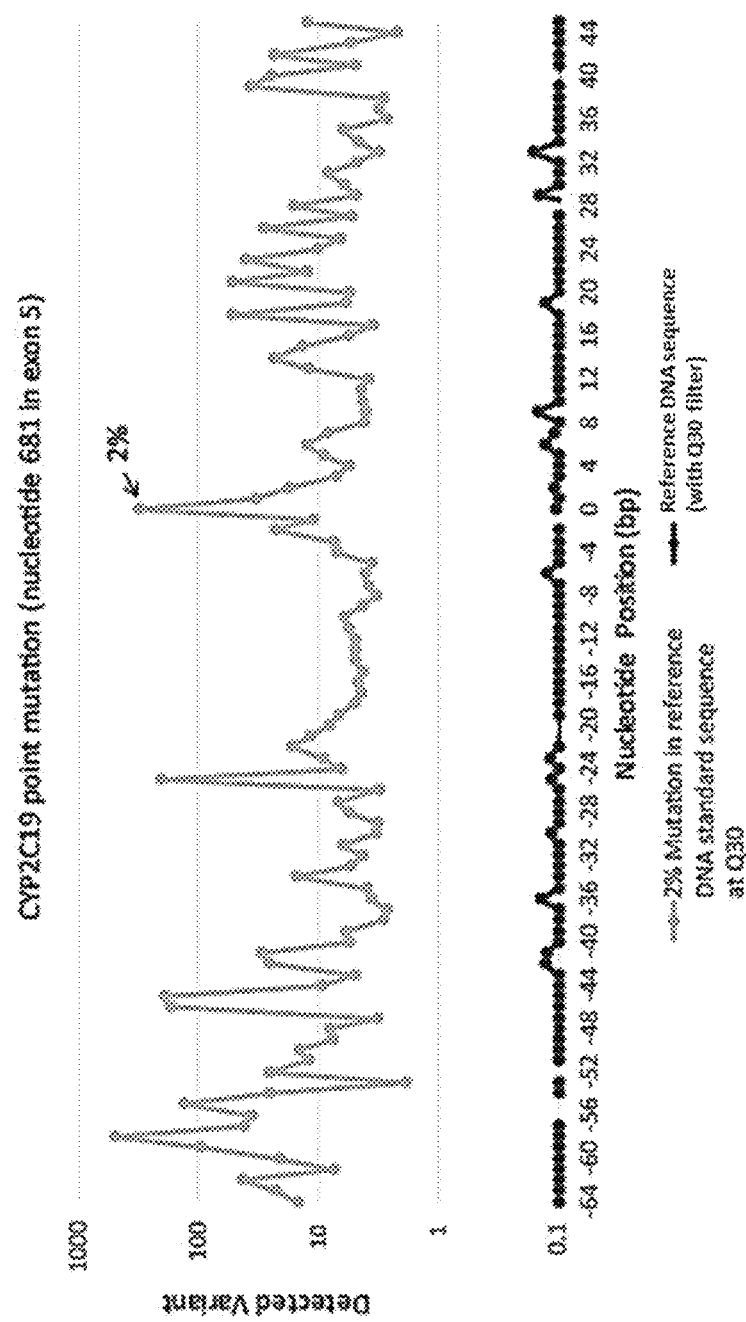
FIG. 16 illustrates a comparison between the background noise (frequency of variants) detected by target sequencing methods using a Q30 filter with (bottom line) and without (top line) requiring that a sequence difference occur on two different polynucleotides (e.g. identified by different junctions) to be counted as a variant. Human genomic DNA (12878, Coriell Institute) was fragmented to 100-200 bp, and included a 2% spike-in of genomic DNA (19240, Coriell Institute) containing a known SNP (CYP2C19). The true variant signal (marked peak) was not significantly above background (top, light grey plot). Background noise was decreased to about 0.1 by applying the validation filter (lower, black plot).
Figure 17:
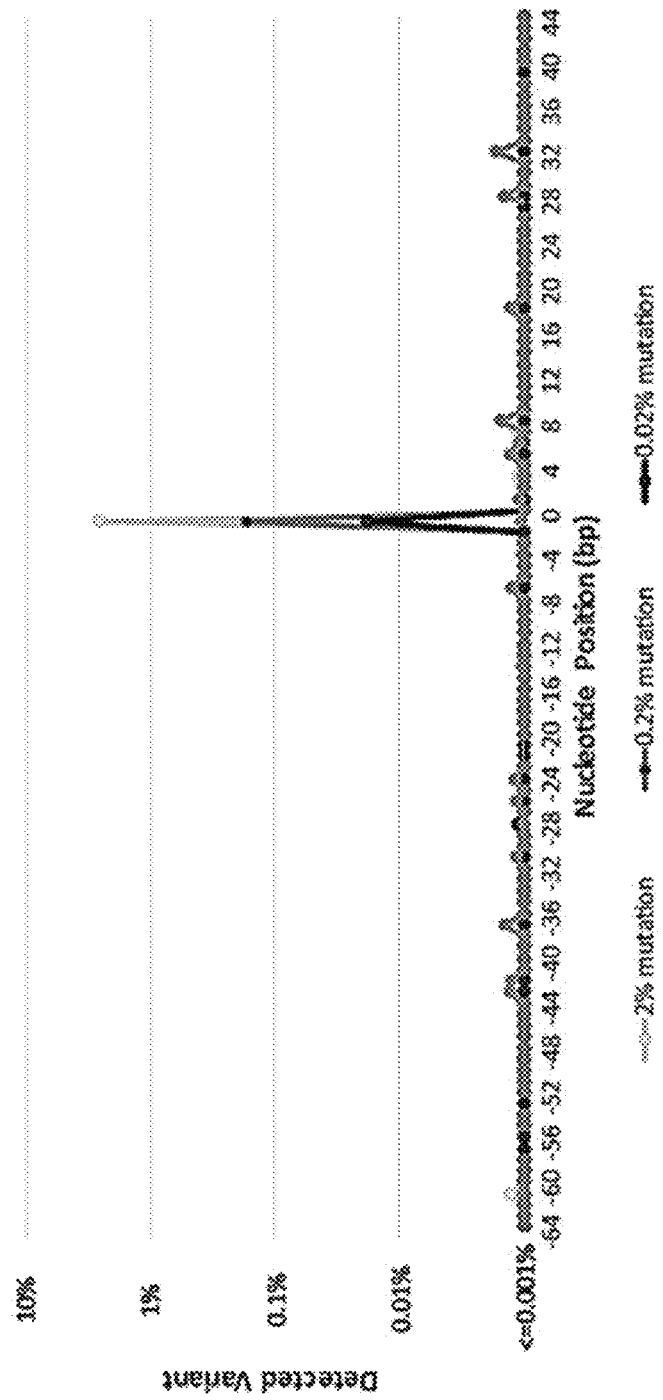
FIG. 17 illustrates detection of sequence variants spiked in at various low frequencies in the population of polynucleotides (2%, 0.2%, and 0.02%), which are nonetheless significantly above background, when applying a method of the disclosure.

Results of a separate analysis of sensitivity and background noise detected by sequencing methods with and without requiring detection in two different polynucleotides are illustrated in FIGS. 16-17. As these figures illustrate, the validation requirement greatly reduces background noise and increases sensitivity.

Figure 22:
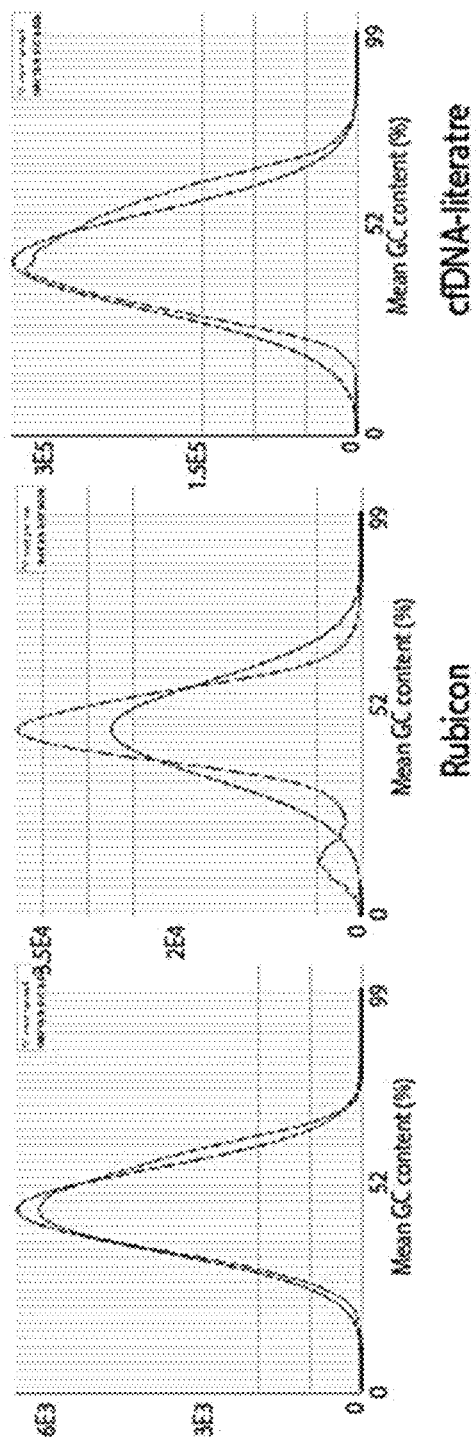
FIG. 22 provides graphs illustrating comparisons between GC content distributions of the genome and GC content distributions of sequencing results produced in accordance with a method in accordance with an embodiment of the disclosure (methods disclosed herein; left), sequencing results using an alternative sequencing library construction kit (Rubicon, Rubicon Genomics; middle), and cell-free DNA (cfDNA) generally as reported in the literature for 32 ng (right).

Example 9: Analysis of GC Composition and Size Distribution 10 ng of sonicated gDNA (150 bp, Multi-Gene Multiplex reference DNA, Horizon) was amplified circularized and amplified as in Example 5, sequenced, and analyzed with the variant-calling two-polynucleotide verification filter (left). The number of sequences with a range of CG percentages were tabulated and plotted graphically, as shown in FIG. 22. As shown in the far left plot, sequences for samples prepared according to Example 5 largely resemble the theoretical distribution except the central peak (corresponds to the overall GC content of the underlying genome). By contrast, when the same amount of gDNA was used directly to construct a sequencing library without amplification using a Rubicon sequencing library construction kit, the difference between the sequencing result and theoretical distribution is very apparent (see the middle plot). The central peak of this direct Rubicon sequencing is higher than the theoretical distribution. Newman et al. (2014; Nature Medicine, (20): 548-54) reported that the cfDNA sequencing GC content distribution was similar with theoretical distribution when 32 ng of cfDNA was used. This is illustrated in the far right plot.

Figure 23:
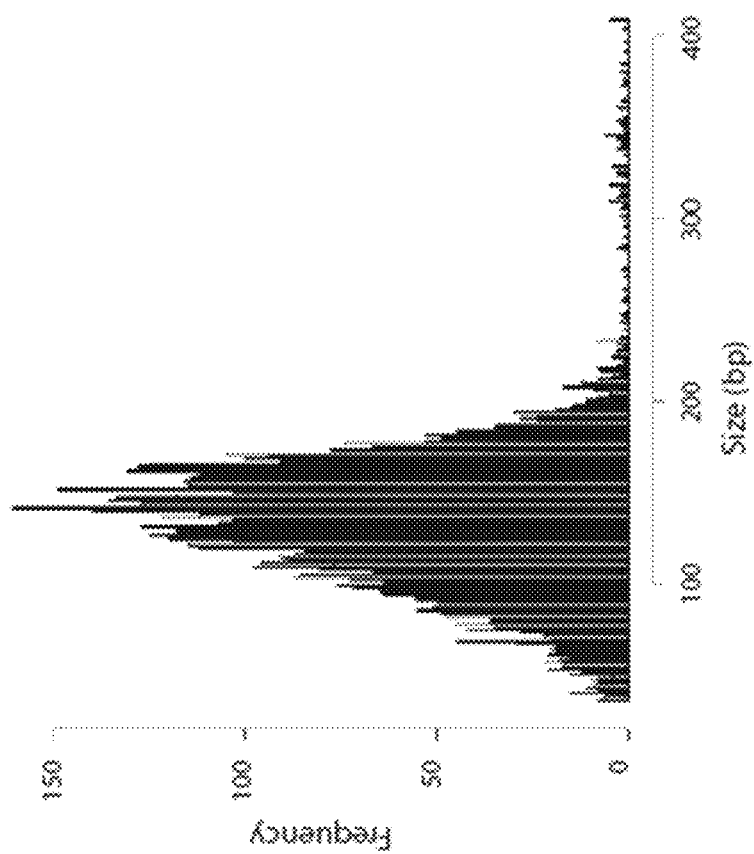
FIG. 23 provides a graph illustrating the size distribution of input DNA obtained from sequencing reads of a method in accordance with an embodiment.

DNA size distribution was assessed for cfDNA that had been circularized, amplified, and sequenced as in Example 5. As shown in FIG. 23, the peak of the distribution of fragment lengths indicated by the sequencing results is at about 150-180 bp, which resembles the typical distribution pattern of cfDNA.

Example 10: Assessment of Amplification Uniformity

Figure 24:
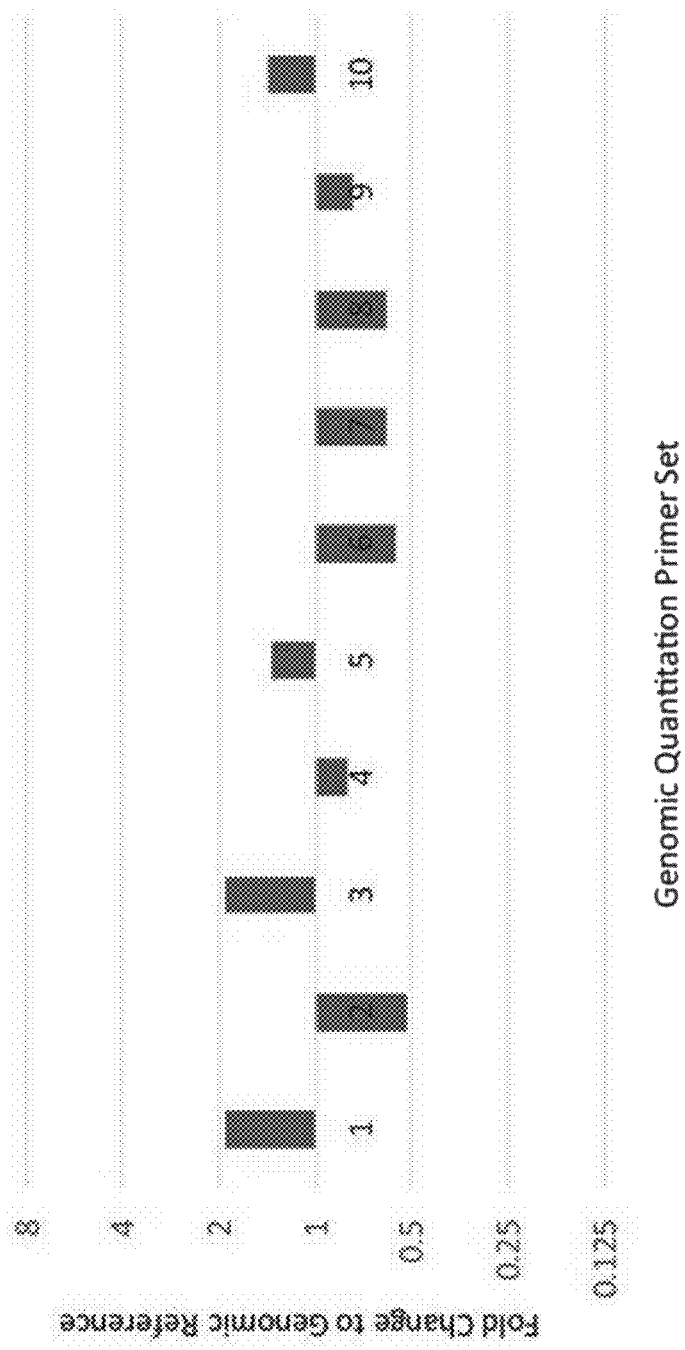
FIG. 24 provides a graph illustrating uniform amplification across multiple targets by a random-priming method in accordance with an embodiment.

The qPCR results of 10 products circularized and amplified according to Example 5 were compared to unamplified reference DNA (gDNA from 12878 cell line, Coriell Institute). 10 ng of genomic reference DNA or amplification product were used for each real-time qPCR reaction, and ratios were generated by relative quantification of amplification product over genomic reference. As shown in FIG. 24, the ratio of each PCR is within a 2-fold change, suggesting that the copy number of these targets in the amplified DNA pool are very similar to the un-amplified reference DNA. The 10 pairs of PCR primers from 6 genes (BRAF, cKIT, EGFR, KRAS, NRAS, PI3KCA) were designed and previously validated.

Example 11: Quantification of Amplification Yield of DNA Fragments cfDNA was isolated from four patients (patient 1-4) and one healthy control. Genomic DNA (gDNA, Multi-Gene Multiplex Horizon) was sonicated to approximately 150 bp fragments. DNA was circularized and amplified with random primers. Table 7 shows the amount of DNA input into the amplification reaction, and the amount of DNA produced by amplification. Significant amplification was obtained for even the smallest sample (0.4 ng), and all samples were amplified at least 600-fold.

TABLE 7

| Sample Type | Input (ng) | Yield (ng) |
|---|---|---|
| gDNA | 10 | 6100 |
| gDNA | 4 | 6880 |
| gDNA | 2 | 5700 |
| gDNA | 1 | 5760 |
| gDNA | 0.5 | 3280 |
| cfDNA healthy control | 0.4 | 6240 |
| cfDNA patient1 | 4 | 13800 |
| cfDNA patient2 | 3 | 9480 |
| cfDNA patient3 | 3 | 7840 |
| cfDNA patient4 | 1 | 3180 |

Example 12: Detecting Low-Frequency Mutations from cfDNA of Cancer Patients

In step 1, cfDNA was circularized. The circle ligation mix was prepared in a PCR tube at room temperature. 4 ng-10 ng cfDNA were pipetted in a 12 µl of volume to the PCR tube. DNA was denatured at 96° C. for 30 seconds, then PCR tubes were chilled on ice for 2 minutes. Ligation mix (2 td of 10× CircLigase buffer, 4 µl 5 M betaine, 1 µl 50 mM MnCl2, 1 µl CircLigase II) was added to each tube, and the reaction proceeded at 60° C. for 16 hours on a PCR machine.

In step 2, the ligation reactions were treated to remove unligated linear DNA. 1 µl Exonuclease mix (NEB M0206S, M0293S; ExoI 20u/µl: ExoIII 100u/µl=1:2) was added to each tube, mixed, and incubated at 37° C. for 30 minutes in PCR machine.

In step 3, the ligation reaction was purified for buffer exchange. The ligation product was purified with Oligo Clean & Concentrator (Zymo Research). Binding mix (30 µl of 10 mM Tris, 100 td of Oligo binding buffer, 400 µl of 100% Ethanol) was added to the ligation reaction after Exonuclease treatment, mixed, and briefly spun down. Zymo-spin columns were loaded, and spun at greater than 10,000×g for 30 seconds. Columns were washed with 750 µl of DNA wash buffer, and centrifuged at 14,000×g for 1 minute. DNA was eluted with 15 µl of 10 mM Tris by centrifugation at greater than 10,000×g for 30 seconds.

In step 4, the DNA was amplified by random priming Whole genome amplification (WGA) was performed with Ready-To-Go Genomiphi V3 DNA amplification Kit (GE Healthcare). 10 µl of purified ligation was mixed with 10 µl of 2× denaturation buffer, incubated at 95° C. for 3 minutes, then cooled to 4° C. on ice. 20 µl of denatured DNA was added to WGA pre-mix, samples were incubated at 30° C. for 1.5 hours followed by inactivation at 65° C. for 10 minutes.

In step 5, the amplification products were cleaned up using Agencourt AMPure XP Purification (1.6×) (Beckman Coulter). 30 µl of 10 mM Tris and 80 µl of AMpure beads were added to 20 µl of WGA reaction. The mixture was incubated at room temperature for 2 minutes. The tubes were placed on a magnet stand, and incubated for 2 minutes. The supernatants were removed and discarded. Samples were washed with 200 µl of ethanol (80%) twice, air dried for 5 minutes, and DNA eluted with 200 µl of 10 mM Tris pH 8.0.

In step 6, WGA DNA was fragmented. 130 µl WGA product was sonicated using a Covaris 5220 sonicator to obtain a fragment size of approximately 400 bp. Covaris 5220 settings were as follows: peak incident power=140 W, duty factor=10%, cycles per burst=200, treatment time=55 seconds.

In step 7, samples were quantified by qPCR. 1/10 of the ligation input and ligation product were used for qPCR reactions with three replications to measure ligation efficiency. 10 ng of the fragmented WGA product along with 10 ng of reference gDNA (12878 cell line) were used for qPCR to measure on target rate. Reactions comprised 5 µl of 2× master mix (TaqMan Fast Universal PCR master mix (2×), Applied Biosystems; Evagreen dye, Biotium), 0.5 µl of primer (5 µM), 1.2 µl of H2O, 10 µl of DNA. Amplification proceeded according to the following program: 95° C. 2 minutes; and 40 cycles of [95° C., 10 seconds; 60° C., 20 seconds].

In step 8, sequencing libraries were constructed. Sequencing libraries were prepared from 500-1000 ng of sonicated amplified DNA using KAPA Hyper Prep Kit (KK8500) or KAPA Library Preparation Kit with Standard PCR Library (KK8200). Adaptor ligations (with 1 uM adaptor final concentration) were prepared according to manufacturer's protocol. Adaptor ligated wash of the ligated product, 30 µl (0.3×) of 20% PEG 8000/2.5M NaCl solution was added to 100 µl of the resuspended ligated product. Beads were mixed thoroughly with the ligated product and incubated at room temperature for 15 minutes. Beads were then captured on a magnet until the liquid was clear. 130 µl of supernatant was then subjected to size selection using Ampure XP beads. Samples were transferred to a new plate followed by an addition of 20 µl of Ampure XP beads (0.5×). Ligated product was now captured in the beads and washed two times with 200 µl 80% ethanol. Ligated product was then resuspended and eluted in 20 µl EB buffer. After size selection and purification, 20 ligated product was added to 25 µl 2×KAPA HiFi Hotstart ready mix and 5 µl 10 µM P5+P7 primers (5'CAAGCAGAAGACGGCATACGA3' (SEQ ID NO: 1), 5'ACACTCTTTCCCTACAC-GACGCTCTTCCGATCT3' (SEQ ID NO: 2)) to amplify the library using the following cycling program: 98° C., 45 seconds; 5 cycles of (98° C., 15 seconds; 60° C., 30 seconds; 72° C., 30 seconds); 72° C., 60 seconds. Amplified library was diluted 20× before loading on a fragment analyzer or bioanalyzer (high sensitivity chip) for quantitation. Further size selection was done via gel size selector (Blue Pippin prep from Sage Science).

In step 9, the sequencing library was enriched by probe capture enrichment using probes from xGEN Pan-Cancer Panel v1.5, 127908597 (IDT). In step 10, the library was sequenced in a HiSeq 2500, with an average depth of 1000×.

In step 11, sequencing data was analyzed to make variant calls. Variant calling included a step requiring that a sequence difference occur on two different polynucleotides (e.g. identified by different junctions) to be counted as a variant. Several somatic mutations were detected and they were also reported in a public databases (COSMIC (Catalog of Somatic Mutations in Cancer)). Among the mutations identified was BRAF V600M with a 0.05% allele frequency, which demonstrate the high sensitivity of this system even when the input is low. Results for the detection of various mutations, including their frequency in the sample, are shown in Table 8.

TABLE 8

| Cancer type | Mutated gene | Mutation | Frequency in sample |
|---|---|---|---|
| Melanoma | FGFR2 | V191I | 0.20% |
| Melanoma | NRAS | Q61K | 0.20% |
| Melanoma | CTNNB1 | S37F | 0.10% |
| Melanoma | BRAF | V600E | 0.10% |
| Melanoma | BRAF | V600M | 0.05% |
| Breast cancer | PIK3CA | H1407L | 53% |
| Breast cancer | LIFR | S679L | 0.60% |
| Breast cancer | KRAS | G12D | 0.60% |
| Breast cancer | ATM | R2993* | 0.30% |
| Breast cancer | ATRX | S618F | 0.10% |
| Prostate | AR | T346A | 6.40% |
| Prostate | SPOP | F133L | 3.30% |
| Prostate | BRAF | V600M | 1.10% |
| Prostate | NSD1 | R1557C | 1.00% |
| Prostate | SF3B1 | K700E | 1.60% |
| Pancreatic | KRAS | G12V | 1.70% |
| Pancreatic | TP53 | 7578176C > T (splice donor variant) | 0.5% |

Example 13: Accurate Mutation Detection from Multiplex Reference DNA from FFPE Sample DNA was extracted from sample Horizon FFPE-multiplex (HD200) by following the manufacturer's protocol (Covaris truXTRAC™ FFPE DNA Kit). 130 µl FFPE gDNA was sonicated using a Covaris 5220 sonicator to obtain a fragment size of approximately 150 bp (Covaris 5220 settings: peak incident power=175 W, duty factor=10%, cycles per burst=200, treatment time=430 seconds). 50 ng DNA in 11 µl volume was denatured at 95° C. for 30 seconds. 10.5 µl H$_2$O, 2.5 ligase buffer (NEB B0202S), and 1 µl T4 Polynucleotide Kinase (NEB M0201S) were added. Reactions were incubated at 37° C. for 30 minutes for phosphorylate.

Samples were ligated, then purified with Oligo Clean & Concentrator (Zymo Research). Binding mix (30 µl of 10 mM Tris, 100 µl of Oligo binding buffer, 400 µl of 100% Ethanol) was added to the ligation reaction after Exonuclease treatment, mixed by vortex, and spun briefly. Samples were load on a Zymo-spin column, and spun at greater than 10,000×g for 30 seconds. Columns were washed with 750 µl of DNA wash buffer, and centrifuged at 14,000×g for 1 minute. DNA was eluted with 15 µl of 10 mM Tris by centrifugation at greater than 10,000×g for 30 seconds.

Samples were further processed and analyzed according to steps 5-11 in Example 13. Results are summarized in Table 9. The representation of nine mutations in Horizon's multiple mutation standard DNA were roughly retained by this process, while the quantity of DNA increased at least 600-fold.

TABLE 9

| Gene | Mutations | Allele Frequency | Measured Allele Frequency |
|---|---|---|---|
| BRAF | p.V600E | 10.5% | 8% |
| KIT | p.D816V | 10% | 9.4% |
| EGFR | p.L858R | 3% | 4% |
| EGFR | p.T790M | 1% | 1% |
| EGFR | p.G719S | 24.5% | 14% |
| KRAS | p.G13D | 15% | 9.1% |
| KRAS | p.G12D | 6% | 5.4% |
| NRAS | p.Q61K | 12.5% | 8.3% |
| PIK3CA | p.H1047R | 17.5% | 14% |

Figure 31:
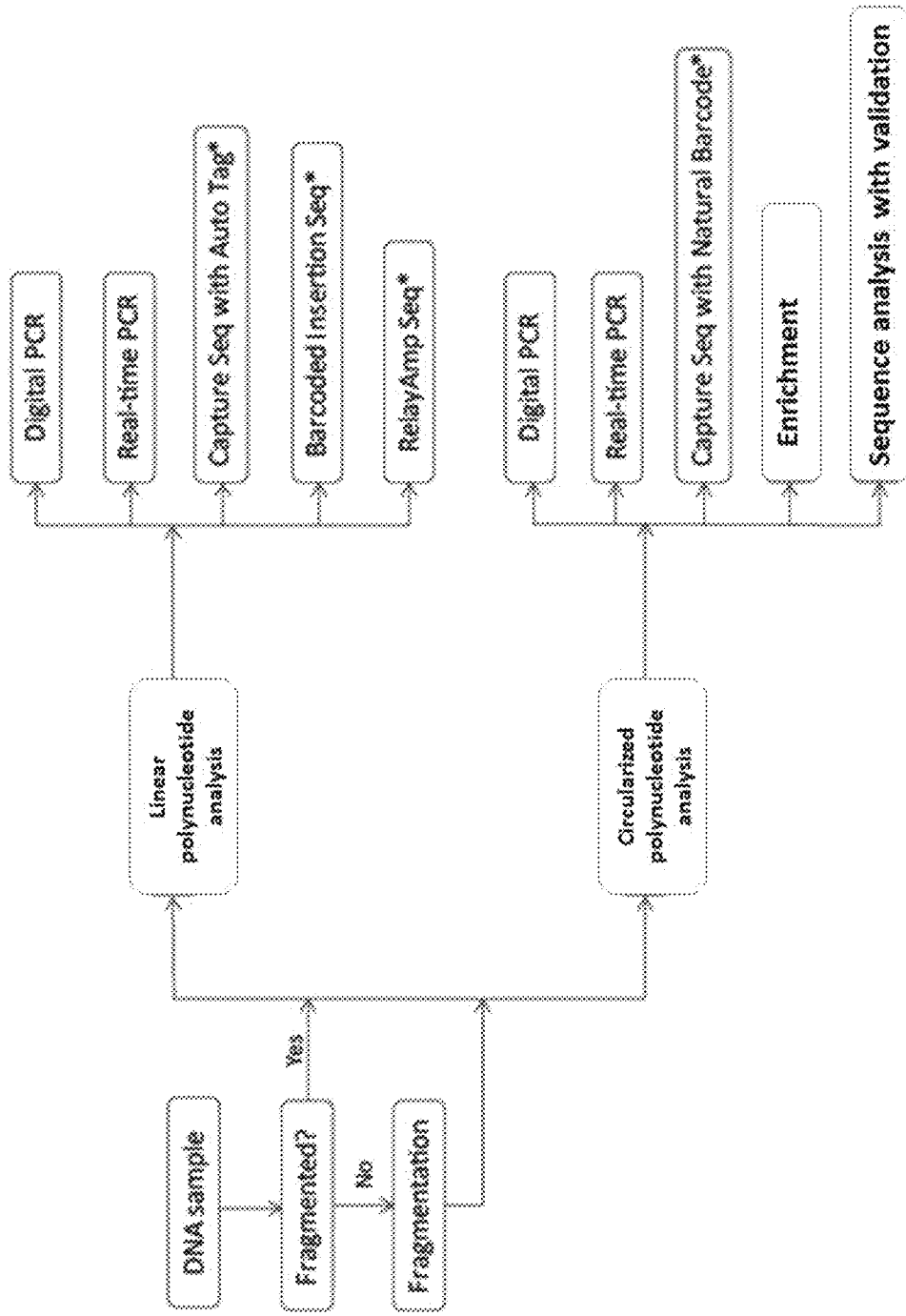
FIG. 31 provides a summary illustration of example workflows for identifying sequence variants in accordance with methods of the disclosure. Along the "linear polynucleotide analysis" (upper) branch, analysis may include digital PCR (e.g. digital droplet PCR, ddPCR), real-time PCR, enrichment by probe capture (capture seq) with analysis of junction sequences (auto tag), sequencing based on inserted adapter sequences (barcoded insertion), or Relay Amp sequencing. Along the "circularized polynucleotide analysis" (lower) branch, analysis may include digital PCR (e.g. digital droplet PCR, ddPCR), real-time PCR, enrichment by probe capture (capture seq) with analysis of junction sequences (natural barcode), enrichment by probe capture or targeted amplification (e.g. B2B amplification), and sequence analysis with a validation step of identifying a sequence variant as a difference occurring in two different polynucleotides (e.g. polynucleotides having different junctions).

Example 14: Detecting Low-Frequency Mutation from Cancer Mutation Cell Line gDNA Multimers In this example, sonicated genomic DNA was ligated to form multimers, which were then subjected to amplification, fragmentation, and analysis. FIGS. 25A and 25B illustrate an example of this process. An illustrative workflow is provided in FIG. 31.

gDNA from a melanoma cell line SK-mel-28 (ATCC) containing BRAF V600E mutation was mixed with reference gDNA (12878 Coriell Institute) to achieve 1% BRAF V600E. DNA was sonicated as in Example 14 to obtain a fragment size of approximately 150 bp. 100 ng of DNA in 11 µl volume was denature at 95° C. for 30 sec. 10.5 µl H2O, 2.5 µl ligase buffer (NEB B0202S), and 1 µl T4 Polynucleotide Kinase (NEB M0201S) were added, followed by incubation at 37° C. for 30 minutes to phosphorylate the DNA.

Samples were purified with Oligo Clean & Concentrator (Zymo Research). This included adding binding mix (25 µl of 10 mM Tris, 100 µl of Oligo binding buffer, 400 µl of 100% Ethanol) to the ligation reaction after Exonuclease treatment. This was mixed by vortex and spun briefly. A Zymo-spin column was loaded, and spun at greater than 10,000×g for 30 seconds, washed with 750 µl of DNA wash buffer, and centrifuged at 14,000×g for 1 minute. DNA was eluted with 15 µl of 10 mM Tris by centrifugation at greater than 10,000×g for 30 seconds.

To ligate, 6 ng DNA in 4 µl volume, was mixed with 0.45 µl 10× end repair buffer (Enyzymatics), 0.05 µl dNTP 25 mM, 0.5 µl ATP 10 mM, End repair enzyme mix (Enyzymatics), and T4 ligase 2000 unit/µl. The reaction was incubated at 25° C. for 30 minutes, and followed by 75° C. for 20 minutes.

Whole genome amplification was performed with Ready-To-Go Genomiphi V3 DNA amplification Kit (GE Healthcare). 8 µl of H$_2$O and 10 µl of purified ligation were mixed with 10 µl of 2× denaturation buffer. DNA was denatured at 95° C. for 3 minutes, and then cooled to 4° C. on ice. 20 µl of denatured DNA was added to WGA pre-mix, and incubated at 30° C. for 1.5 hours followed by inactivation at 65° C. for 10 minutes.

The amplification reaction was then cleaned up using Agencourt AMPure XP Purification (1.6×) (Beckman Coulter). 30 µl of 10 mM Tris and 80 µl of AMpure beads were added to 20 µl of WGA reaction. This was incubated at room temperature for 2 minutes. The tube was placed on a magnet stand, and incubated for 2 minutes. Supernatant was removed and discarded. Beads were washed with 200 µl of ethanol (80%) twice, then air dried for 5 minutes. DNA was eluted with 200 µl of 10 mM Tris pH 8.0. 130 µl WGA product was then fragmented using the Covaris 5220 sonicator to obtain a fragment size of approximately 400 bp (Covaris 5220 settings: peak incident power=140 W, duty factor=10%, cycles per burst=200, treatment time=55 seconds).

Mutations were detected by ddPCR using BioRad Prime PCR ddPCR mutation detection assays. Mutation-detection ddPCR reaction was assembled in a PCR tube at room temperature (80 ng of amplified DNA, 10 µl of 2×ddPCR supermix for probes, 1 µl of 20× target (BRAF V600E, BioRad) primers (9 µM)/probe (FAM; 5 µM), 1 µl of 20× wild-type primers (9 µM)/probe (HEX; 5 µM), 8 µl of DNA sample (50 ng). The reaction was mixed by pipetting up and down 5 times, and then transferred to droplet generator cartridge. Droplets were generated using the QX200 droplet generator, transferred into a 96-well PCR plate, and amplified using the following PCR program: 95° C., 10 minutes; 40 cycles of [94° C., 30 seconds, 55° C. 1 minute]; 98° C., 10 minutes. PCR reaction plate was transferred into a QX200 droplet reader to quantify the result. Based on the input DNA, the expected frequency of the BRAF V600E mutation was 1%. By this ligation and amplification procedure, this frequency was roughly maintained (1.41% according to the ddPCR analysis) while the quantity of DNA increased about 200-fold.

Figure 26:
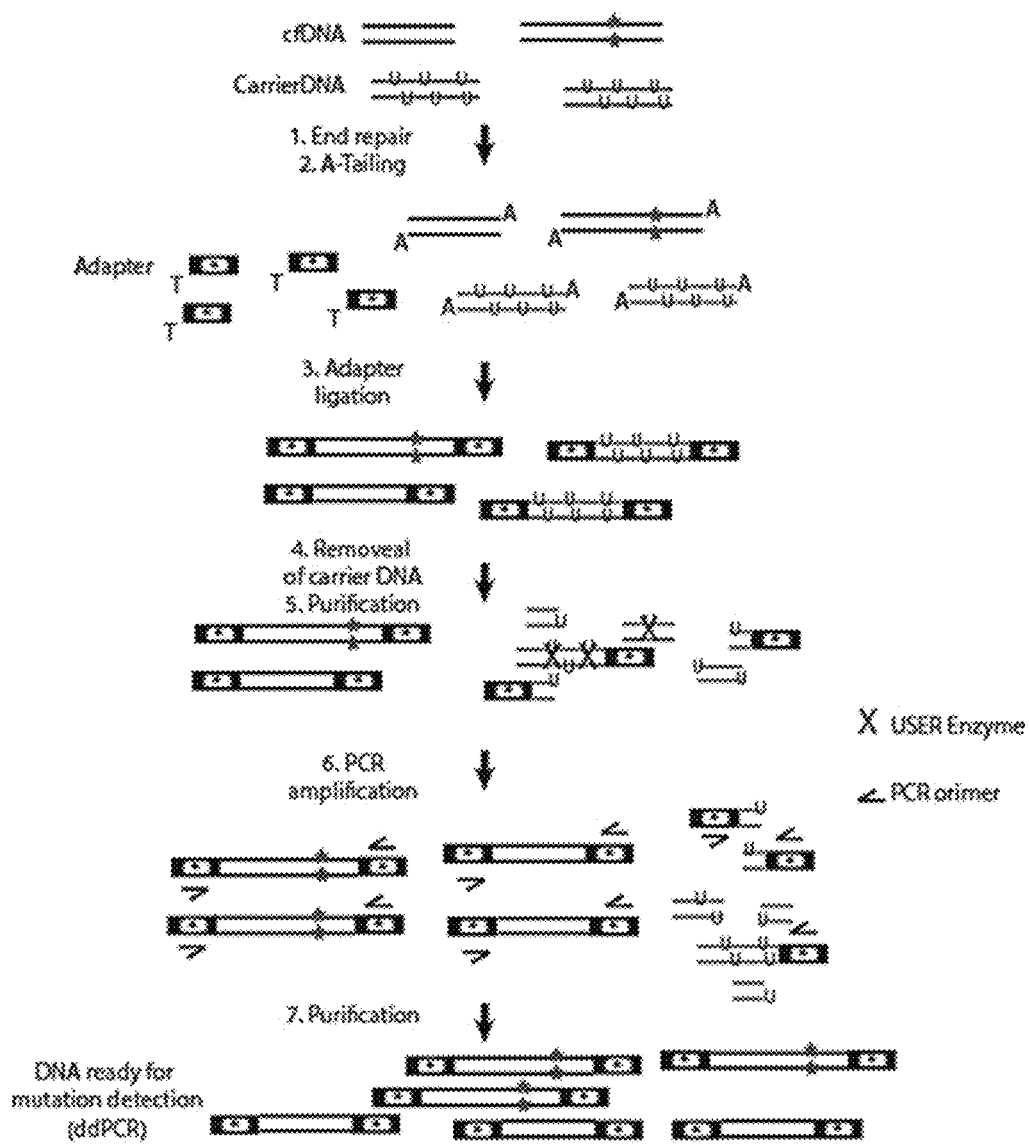
FIG. 26 illustrates an example variation on the process FIG. 25. Polynucleotides (e.g. cfDNA, or other polynucleotide fragments) are end-repaired, A-tailed, and adapter ligated (e.g. using a standard kit, such as kits by KAPA Biosystems). Carrier DNA labeled with internal uracil (U) can be supplemented to raise total DNA input to desired levels (e.g. to about or more than about 20 ng). A sequence variant to be detected is indicated by a "star". When ligation is complete, carrier DNA can be degraded by addition of Uracil-Specific Excision Reagent (USER) enzyme, which is a mixture of Uracil DNA glycosylase (UDG) and the DNA glycosylase-lyase Endonuclease VIII. Products are purified to eliminate fragments of carrier DNA. Purified products are amplified (e.g. by PCR, using primers directed to adapter sequences). Any residual carrier DNA is not likely to be amplified due to degradation, and separation from an adapter on at least one end. Amplified products can be purified to remove short DNA fragments.

FIGS. 26 and 27 illustrate exemplary variations on the process of FIG. 25.

Example 15: Detection of Rare Mutations in a Single Reaction Assay

The ability to detect rare mutations in circulating cell-free DNA using NGS is limited by two factors: first is accuracy of the sequencing technology; second is the overall conversion rate of the assay. Described herein is a method for sensitive detection of rare variants in a targeted region using a single reaction assay workflow and an algorithm for accurate variant calling. An exemplary workflow for a single reaction assay is provided in FIGS. 34A and 34B.

Linear single stranded polynucleotides are circularized by end-joining. Where single-stranded circles are desired, the polynucleotide may be a single-stranded polynucleotide as originally isolated, or may be treated to render the polynucleotide single-stranded (e.g. by denaturation). In this example, a method for circularizing a polynucleotide involves an enzyme, such as use of a ligase (e.g., an RNA ligase or a DNA ligase). Reaction conditions are those specified by the manufacturer of the selected enzyme. Joining the ends of a polynucleotide to form a circular polynucleotide (either directly to itself or to one or more other polynucleotides, e.g., a circular target polynucleotide comprising two target polynucleotides) produces a junction having a junction sequence.

After circularization, an exonuclease step is included to digest any unligated nucleic acids after the circularization reaction. That is, closed circles do not contain a free 5' or 3' end, and thus the introduction of a 5' or 3' exonuclease will not digest the closed circles but will digest the unligated components. In some cases, this finds particular use in multiplex systems.

Figure 34A:
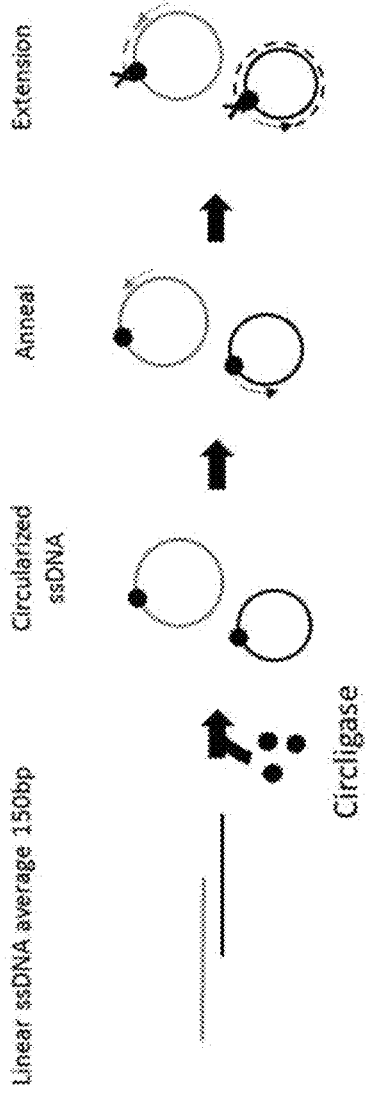
FIGS. 34A and 34B illustrate exemplary single reaction assay workflows.
Figure 34B:
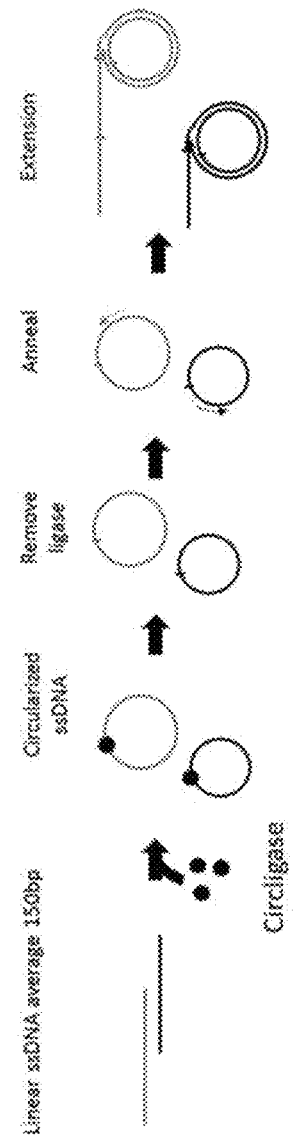

After circularization, ligase may remain bound on the ligated molecules. The presence of ligase at the ligation junction may block primer extension during polymerization reaction and reduce amplification efficiency (as illustrated in FIG. 34A). Removal of ligase used in the circularization reaction by degradation allows polymerase to extend through the junction and amplify the circularized target molecules as concatemers effectively. Degradation of ligase comprises treatment with a heat-labile protease, such as Qiagen protease, which can be head-inactivated by incubation at 70° C. for 15 minutes.

After removal of ligase, circularized DNA molecules can be amplified by random primers for whole genome amplification or specific primers for targeted amplification. The amplified concatemers will be randomly sonicated to create fragments at size range ~500 bp-1000 bp for NGS library construction and sequencing.

Figure 35:
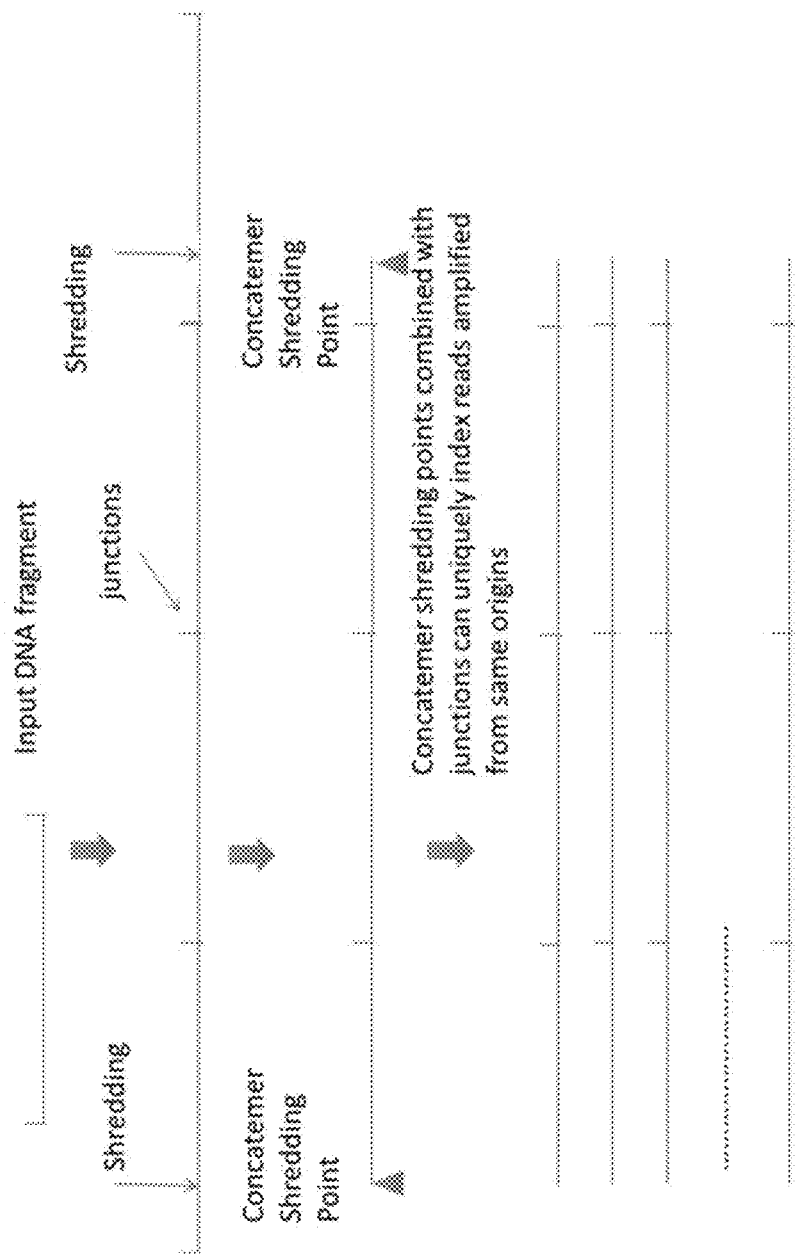
FIG. 35 illustrates a sequence variant call using junction information.

Improvements to the algorithm in this example are illustrated in FIG. 35. The junctions (characterized by the start and end positions in the reference) in the concatemer sequences can be identified through alignment to reference sequences and can be used as tags for the original input DNA fragments. However, the number of junction types (combinations of the start and ends in reference) may be limited in a given targeted region; and when there are a large number of input DNA fragments present, there is relatively high chance of collision in the junction from two independent input DNA fragments. Consequently, the "junction tags" may not be treated as a unique tag in many applications, and error correction and molecular counting based on this kind of tags may not be uniquely distinguishing.

By combining concatemer shredding points with the junction in the concatemer sequences, more distinct tags can be created for the input molecules. Illustrated in FIG. 35, a long string of concatemers, which can be generated after circle-ligation and RCA, is shredded using sonication or other methods of fragmentation (e.g., enzymatic cleavage) to form shorter concatemers. These results in many concatemers with different structures: for example, different numbers of repeats or different starting/ending positions in reads relative to the junctions—the concatemer shredding points at two ends.

By incorporating the concatemer shredding points to create distinct tags, it will be possible to effectively perform additional error correction based on the consensus sequences built from the read families identified by the distinct tags. Various voting schemes are used to build consensus sequences from the families of reads and to do variant calling, e.g. a variant is called only if all the reads in the family report the same variant. Second, the distinct tags can be used to help count input molecules and compute allele frequencies.

An example algorithm to identify the concatemer shredding points are as follows. 1) identify in the concatemer sequences (reads), the repeat length, repeat regions and junctions, which can be done with self-alignment, alignment to reference sequences or other computational methods; 2) determine the positions of the junctions within the reads by aligning the read to the reference sequence; 3) calculate the positions of the concatemer shredding points (at both ends) by shifting position from the reference start or end positions of the junction while the number of bases to shift is determined by the read positions of the adjacent junctions.

Example 16: qPCR Analysis of Ligase Treated cfDNA Molecules with or without Ligase Removal Ligase treated cfDNA samples circularized and purified under various conditions were analyzed by qPCR. Three purification conditions were included in the test: 1. Circ-ligated DNA purified by chromatography columns; 2. Circ-ligated DNA purified by phenol chloroform; and 3. Circ-ligated DNA treated with proteinase K to remove ligase before purification by chromatography column 10 ng of cfDNA was used for each condition (1, 2, and 3). cfDNA was denatured at 96° C. for 30 seconds, and chilled on an ice block for 2 minutes followed by addition of ligation mix (2 µL of 10× Circligase buffer, 4 µL of 5M Betaine, 1 µL of 50 mM MnCl$_2$, 1 µL of Circligase II (Epicentre # CL9025K). A 'no ligase control' (4) and a 'no DNA control' (5) were setup at the same time. The 'no ligase control' contained 10 ng of cfDNA mixed with 2 µL of 10× Circligase buffer, 4 µL of 5M Betaine, 1 µL of 50 mM MnCl$_2$ but no ligase. The 'no DNA control' contained all the ligation reagents but no cfDNA. All reactions were incubated at 60° C. for 1 hour.

After ligation, the 'no ligase control' (4), 'no DNA control' (5) and condition 1 (Circ-ligated DNA purified by chromatography columns) were purified by chromatography columns Each reaction was loaded on a micro bio-spin P-6 column pre-washed with 10 mM Tris-Cl pH 8.0 and eluted by centrifuge the columns for 4 minutes at 1,000×(g).

Condition 2 (Circ-ligated DNA purified by phenol chloroform) was purified by phenol chloroform extraction and ethanol precipitation. 180 µL of 10 mM Tris was added to 20 µL of DNA from the exonuclease treatment to make a volume of 200 µL, and 200 µL of phenol was used to extract DNA. The aqueous layer was collected, and the DNA was recovered by ethanol precipitation. The ethanol coprecipitant mix (200 µL of DNA solution after phenol extraction, 20 µL sodium acetate 0.5M pH 5.2, 1 µL GlycoBlue, 1 µL carrier oligo (100 ng/µL), 600 µL of 100% ethanol was incubated at −80° C. for 30 minutes, and centrifuged at 16 k rpm for 5 minutes to precipitate the DNA. The DNA pellet was washed with 500 µL of 70% ethanol. The DNA pellet was air dried for 5 minutes at room temperature, and resuspended with 11 µL 10 mM Tris-Cl pH 8.0.

Condition 3 (Circ-ligated DNA treated with proteinase K) was first treated with proteinase K at 37° C. for 30 minutes, followed by purification using a chromatography column. The reaction was loaded on a micro bio-spin P-6 column pre-washed with 10 mM Tris-Cl pH 8.0 and eluted by centrifuge the columns for 4 minutes at 1,000×(g).

Products from each condition (1-5) were then analyzed by quantitative PCR (qPCR). 3 replicate qPCR reactions were setup for each sample and average Ct was calculated. As shown in Table 10, qPCR amplification of no DNA control (5) gave an average Ct (cycle threshold) of 40, no ligase control (4) product gave an average Ct of 30.79, indicating a high recovery of the input DNA under a condition without ligase treatment. Conditions 1 and 2 gave average Ct at 34.80 and 35.18 respectively. Comparing to the no ligase control (4), conditions 1 and 2 showed significant loss of amplifiable DNA after ligase treatment, even though both products were purified to remove free enzyme. Products from condition 3, in which ligase was removed through enzyme degradation before purification, showed an average Ct of 30.42, which was comparable to no ligase control (4), indicating that removal of ligase is critical for efficient recovery of amplifiable DNA.

TABLE 10

| Sample | Avg Ct |
| --- | --- |
| 1. Ligated DNA purified by column | 34.80 |
| 2. Ligated DNA purified by phenol-chloroform extraction | 35.18 |
| 3. Ligated DNA treated with protease and purified by column | 30.42 |
| 4. No Ligase Control DNA purified by column | 30.79 |
| 5. No DNA Control | 40.00 |

Example 17: Comparison of NGS Library Complexity

This example compares complexity of NGS libraries prepared by different workflows. Workflows compared in this example include:
1. Library prepared through circularization and purification through a phenol chlorophorm extraction step before amplification;
2. Library prepared through circularization and direct amplification without purification;
3. Library prepared through circularization and protease treatment for 15 minutes, followed by amplification without purification;
4. Library prepared through circularization and protease treatment for 20 minutes, followed by amplification without purification;
5. Library prepared through circularization and protease treatment for 30 minutes, followed by amplification without purification;
6. Library prepared through circularization and protease treatment for 60 minutes, followed by amplification without purification;

For each condition, 12 µL of 20 ng cfDNA was used as input for library construction. DNA samples were denatured at 96° C. for 30 seconds, and chilled on an ice block for 2 minutes. The addition of ligation mix (12 µL cfDNA, 2 µL of 10× Circligase buffer, 4 µL 5M Betaine, 1 µL of 50 mM $MnCl_2$, 1 µL of Circligase II (Epicentre # CL9025K) was set up on a cool block, and ligation was performed at 60° C. for 3 hours. Ligation DNA mixture was incubated at 80° C. for 45 seconds on a PCR machine, followed by an Exonuclease treatment. 1 µL Exo nuclease mix (ExoI 20U/µL: ExoIII 100U/µL=1:2) was added to each tube, and reactions were incubated at 37° C. for 30 minutes.

For workflow 1, ligation product was phenol chloroform extracted and precipitated with salt and ethanol. 180 µL of 10 mM Tris was added to 20 µL of DNA from the exonuclease treatment to make a volume of 200 µL, and 200 µL of phenol was used to extract DNA. The aqueous layer was collected, and the DNA was recovered by ethanol precipitation. The ethanol co-precipitant mix (200 µL of DNA solution after phenol extraction, 20 µL sodium acetate 0.5M pH 5.2, 1 µL GlycoBlue, 1 µL carrier oligo (100 ng/µL), 600 µL of 100% ethanol was incubated at −80° C. for 30 minutes, and centrifuged at 16 k rpm for 5 minutes to precipitate the DNA. The DNA pellet was washed with 500 µL of 70% ethanol.

The DNA pellet was air dried for 5 minutes at room temperature, and resuspended with 11 µL of 10 mM Tris-Cl pH 8.0. For conducting whole genome amplification (WGA), purified DNA was first denatured at 65° C. for 5 minutes. 10 µL of denature buffer from GE WGA kit was added to 10 µL of purified DNA. The DNA was cooled on a cool block or ice for 2 minutes. 20 µL of DNA was added to the Ready-To-Go GenomiPhi V3 cake (WGA). The WGA reaction was incubated at 30° C. for 1.5 hours, followed by heat inactivation at 65° C. for 10 minutes.

For workflow 2, 0.12 µL of 0.5M EDTA and 0.58 µL of 1M KCl were added to the exonuclease treated ligation product and mixed well. Ligation mix was denatured at 95° C. for 2 minutes and cooled to 4° C. on ice before added to the Ready-To-Go GenomiPhi V3 cake (WGA). The WGA reaction was incubated at 30° C. for 4.5 hours, followed by heat inactivation at 65° C. for 10 minutes.

For workflows 3-6, the exonuclease treated ligation products were first treated with protease to remove circligase II. 1 µL of serine protease was added to each reaction and incubation time at 55° C. was titrated from 15 minutes to 60 minutes (condition 3: 15 minutes; condition 4: 20 minutes; condition 5: 30 minutes; condition 6: 60 minutes), followed by heat inactivation at 70° C. for 15 minutes, and 0.12 µL of 0.5M EDTA and 0.58 µL of 1M KCl were added to the treated ligation product. Ligation mix was then denatured at 95° C. for 2 minutes and cooled to 4° C. on ice before added to the Ready-To-Go GenomiPhi V3 cake (WGA). The WGA reaction was incubated at 30° C. for 4.5 hours, followed by heat inactivation at 65° C. for 10 minutes.

Figure 38:
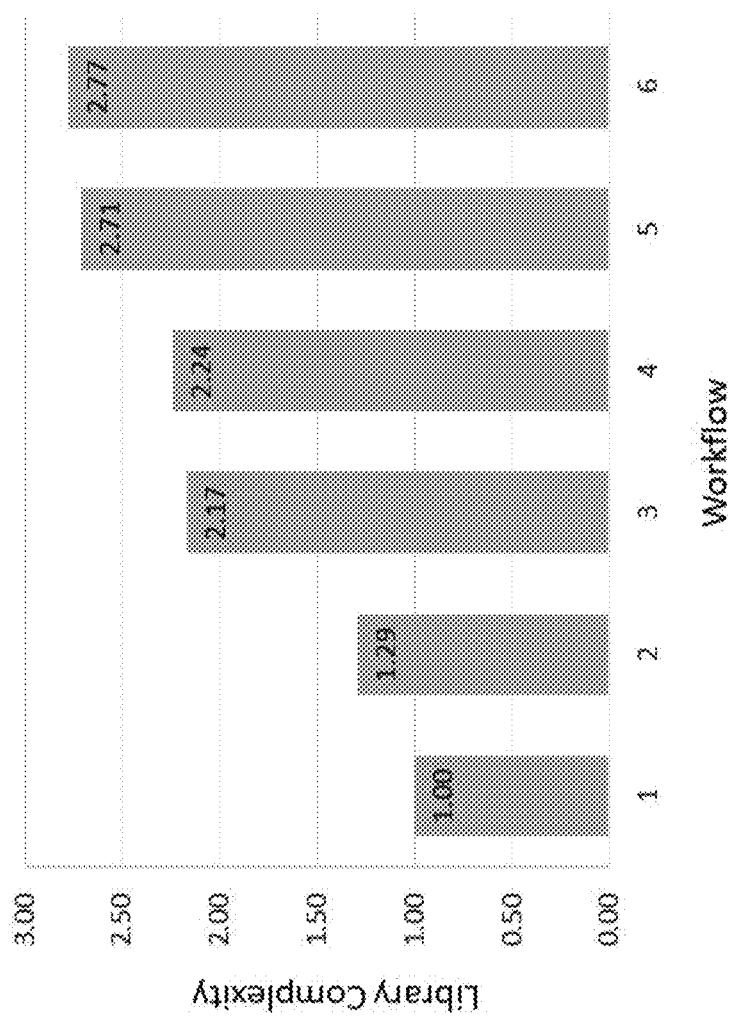
FIG. 38 shows library complexity from various workflows described herein.

For all conditions, WGA products were bead purification using AmpureXP magnetic beads and sonicated to average size of 800 bp. The sonicated DNA samples were then used as input for standard sequencing library construction using KAPA library preparation kit. Libraries were then sequenced by Illumina HiSeq2500 and library complexity was evaluated by calculating the number of unique molecules detected in each library. Comparison of library complexities are shown in the figure below, with the number of unique molecules scaled on a relative basis. Workflow 1 showed lowest complexity; workflow 2 had slightly higher library complexity than workflow 1, indicating less molecule loss by skipping purification; removal of ligase (workflows 3-6) significantly increased the number of unique molecules in the libraries, with longer protease treatment time lead to more unique molecules detected. The increase of molecules detected started to plateau after 30 minutes incubation in this experiment. The results are presented in FIG. 38.

Example 18: Variant Calling

This example evaluates variant calling using methods described herein wherein a sequence variant occurring in at least two different sheared polynucleotides is identified as a true sequence variant.

Genomic DNA from 9 cell lines were fragmented to an average size of ~150 bp and mixed to produce a DNA mix. The DNA mix covers 8 cancer hotspots (Table 11) at 0.1% allele frequency (AF). 12 µL of 20 ng the DNA mix was used as input for library construction for each reaction. DNA samples were denatured at 96° C. for 30 seconds, and chilled on an ice block for 2 minutes. After the addition of ligation mix (12 µL cfDNA, 2 µL of 10× Circligase buffer, 4 µL 5M Betaine, 1 µL of 50 mM $MnCl_2$, 1 µL of Circligase II (Epicentre # CL9025K)), the reaction was set up on a cool block, and ligation was performed at 60° C. for 3 hours. Ligation DNA mixture was incubated at 80° C. for 45 seconds on a PCR machine, followed by an Exonuclease treatment. 1 µL Exo nuclease mix (ExoI 20U/µL: ExoIII 100U/µL=1:2) was added to each tube, and reactions were incubated at 37° C. for 30 minutes. Circligase II was removed by protease treatment and 0.12 µL of 0.5M EDTA/ 0.58 µL of 1M KCl was added to the reactions. Ligation mix was then denatured at 95° C. for 2 minutes and cooled to 4° C. on ice before adding to the Ready-To-Go GenomiPhi V3 cake (whole genome amplification, WGA). The WGA reaction was incubated at 30° C. for 4.5 hours, followed by heat inactivation at 65° C. for 10 minutes.

Figure 39:
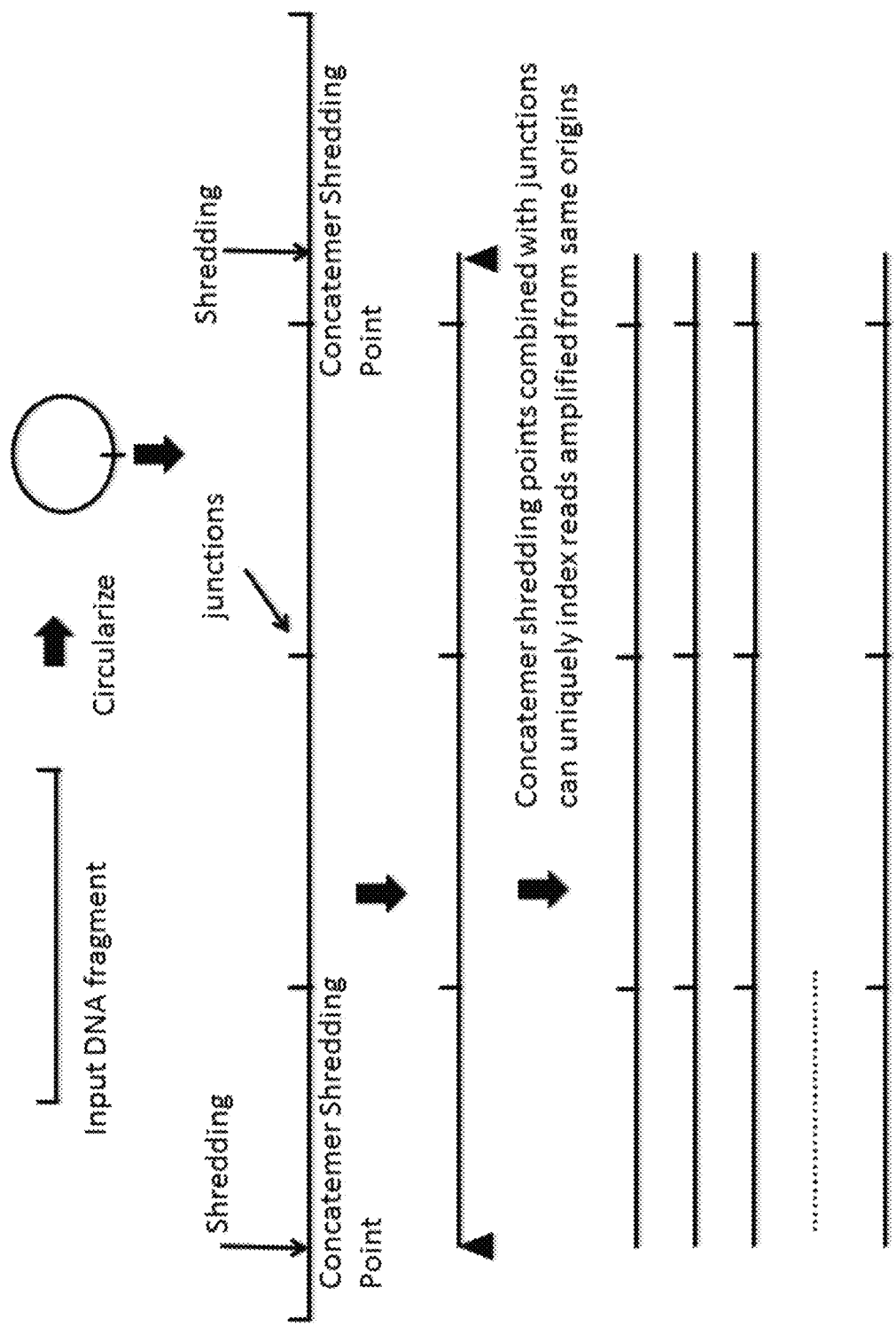
FIG. 39 illustrates an exemplary schematic in which concatemer shredding points and junction sequences are used to uniquely index reads amplified from the same origins.
Figure 40:
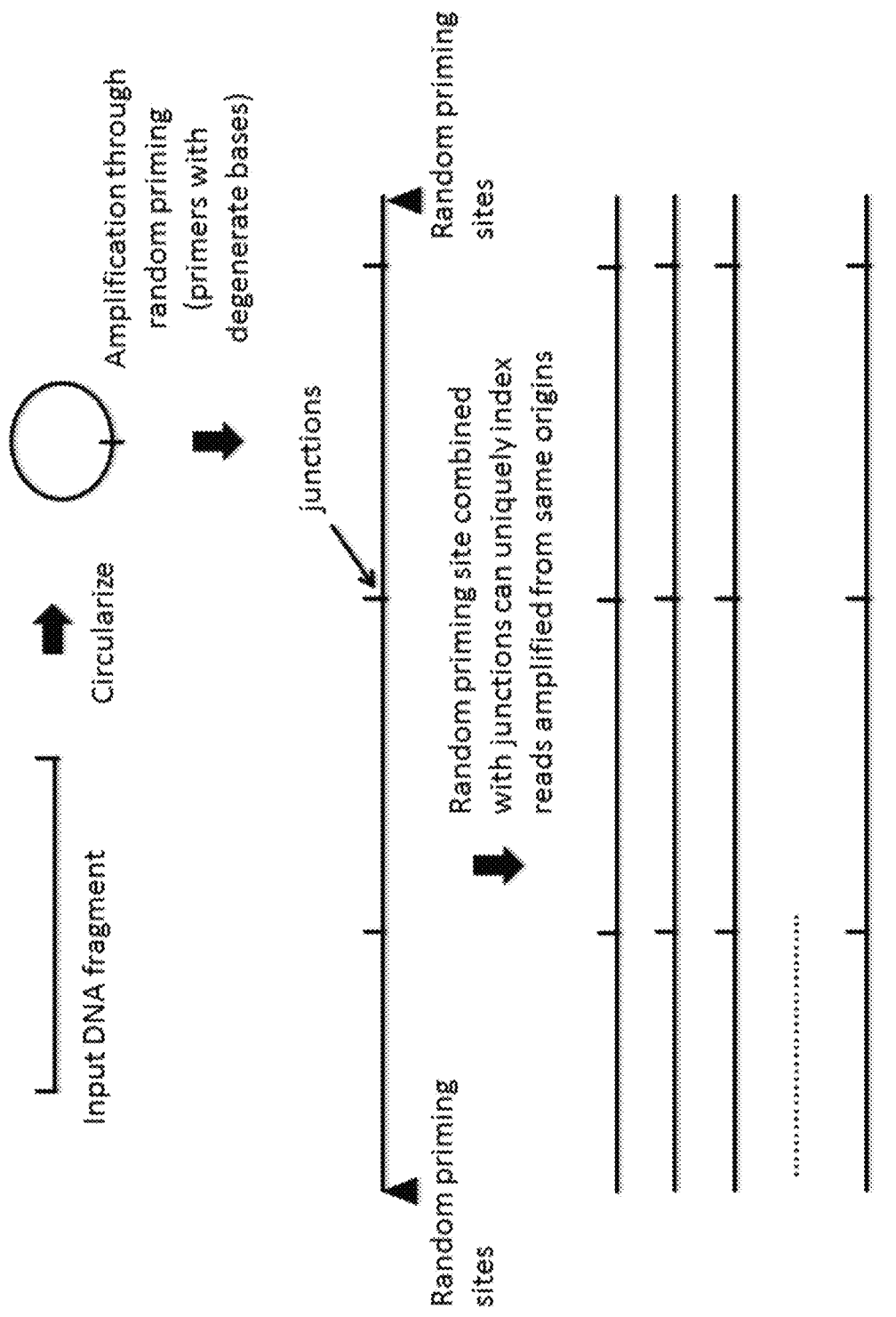
FIG. 40 illustrates an exemplary schematic in which concatemer 5' and 3' sequences resulting from random priming during amplification and junction sequences are used to uniquely index reads amplified from the same origins.

WGA products were bead purified using AmpureXP magnetic beads and sonicated to an average size of ~800 bp. The sonicated DNA samples were then used as input for standard sequencing library construction using KAPA library preparation kit. As illustrated in FIG. 39, sonication or other methods of fragmentation (e.g., enzymatic cleavage) can be used to generate shorter concatemers from a long string of concatemers resulting from RCA. The resulting concatemers can have a variety of structures. The shorter concatemers formed may have different numbers of repeats, or copies of the input DNA sequence, and/or different starting/ending positions in reads relative to the junctions (e.g., concatemer shredding points). In some cases, concatemers having a variety of structures are produced by random priming (FIG. 40).

Libraries were sequenced by Illunima HiSeq2500 and sequencing reads were subjected to sequence analysis. In sequence analysis, the concatemer shredding points can be combined with the junction sequences of sequencing reads to create unique tags that can be associated with sequencing reads. Consensus sequences built from read families identified by the unique tags can be used to perform additional error correction.

Various voting schemes may be used to build consensus sequences from the families of reads and to perform variant calling. A consensus, for example, can be built based on the majority of the reads in the family reporting the same variant. Sequence differences can be indentified between a read family consensus and a reference sequence, and a variant is called, in some cases, when the same sequence difference occurs in at least two different read families. The unique tags can also be used to help count input molecules and compute allele frequencies.

Figure 41A:
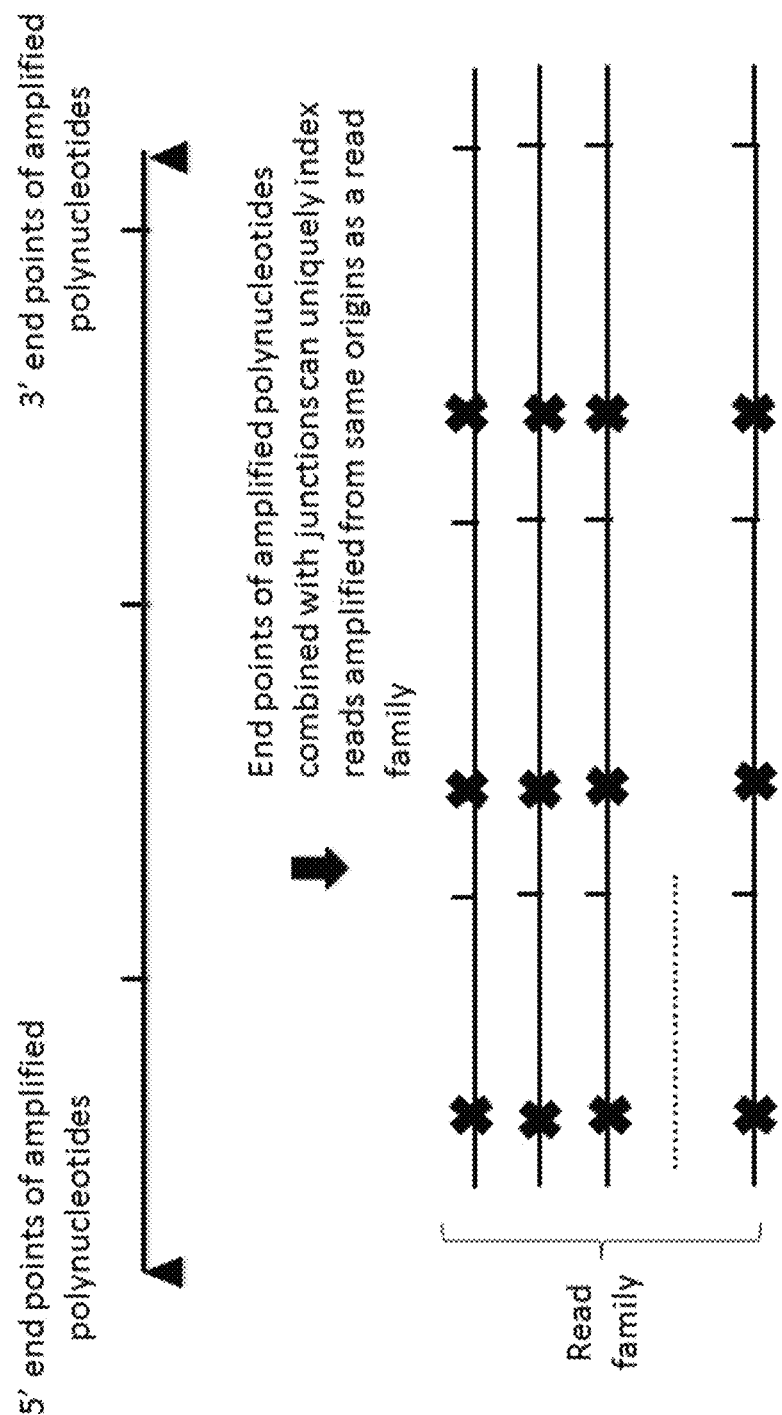
FIGS. 41A-41C illustrate an exemplary schematic in which junction sequences and 5'/3' ends of amplified polynucleotides are used to generate read families.
Figure 41B:
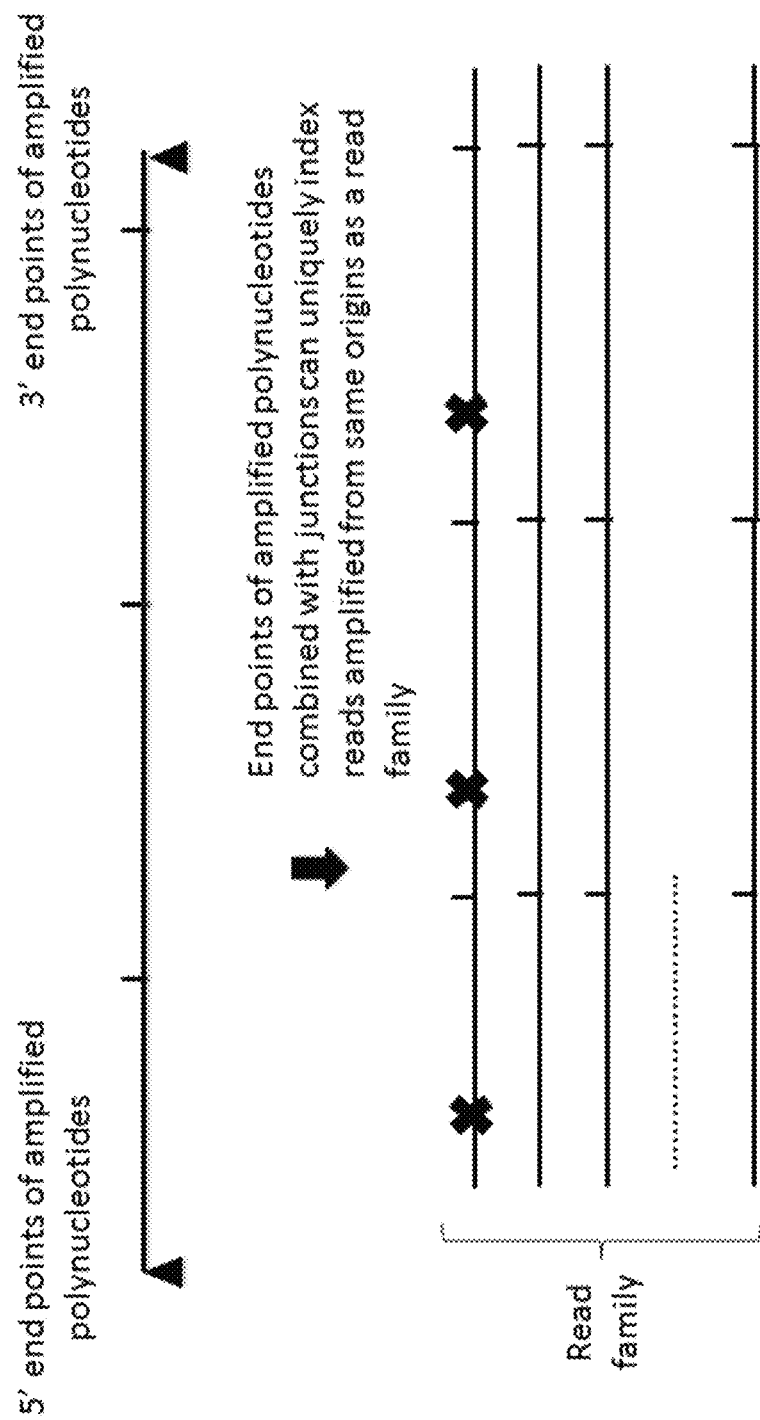
Figure 41C:
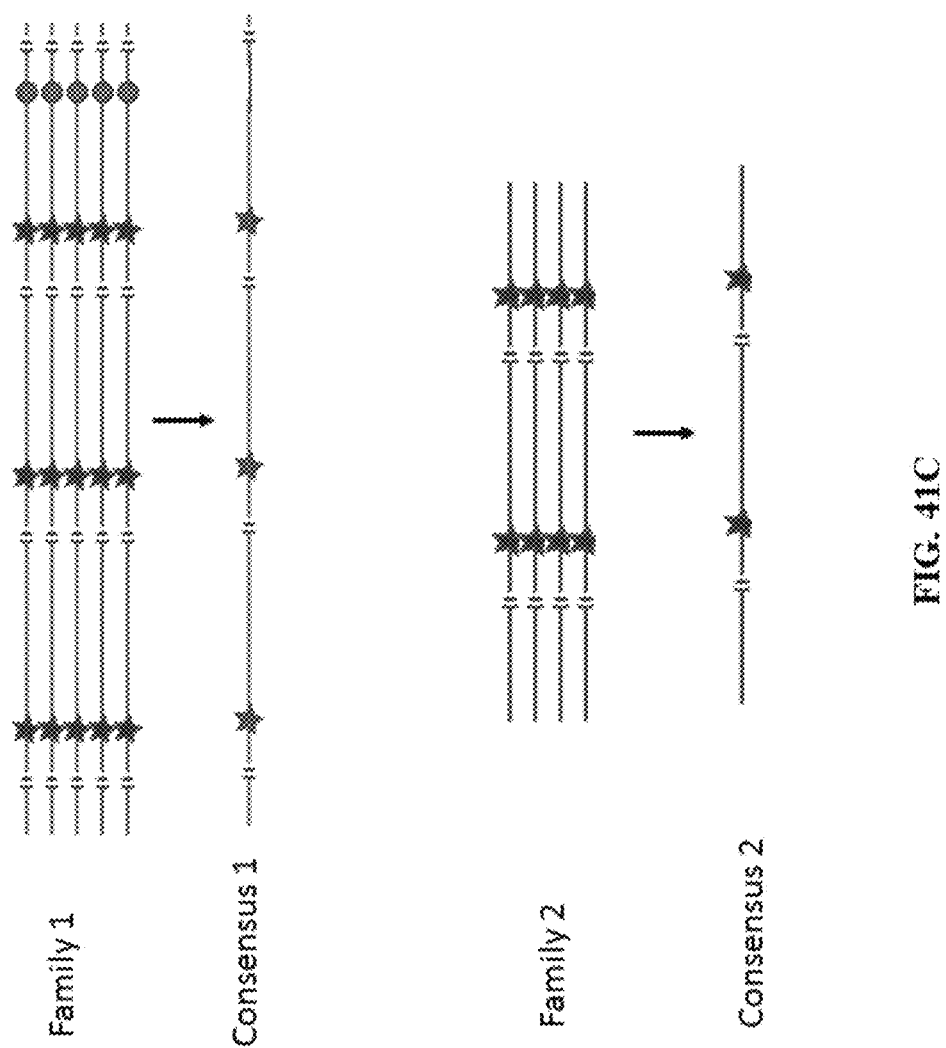

In an exemplary algorithm to identify the concatemer shredding points and perform variant calling,
1) Identify in the concatemer sequences (read) the repeat length, repeat regions and junctions, for example, by self-alignment, alignment to reference sequences or other computational methods.
2) Determine the positions of the junctions within the reads by aligning the read to the reference sequence.
3) Calculate the positions of the concatemer shredding points (at both ends) by shifting position from the reference start or end positions of the junction while the number of bases to shift is determined by the read positions of the adjacent junctions.
4) Group reads based on their shredding points in combination with their "junction tag" (e.g., unique tag), and create different read families of reads, each of which has a unique tag.
5) If a majority of the reads in the read family vote unanimously for the variants, that is, all the reads report the variant with concatemer confirmation, this family will be counted as a variant family (FIG. 41A); otherwise this family will not be counted as a variant family (FIG. 41B).
6) The number of the variant families can be used to determine whether an input molecule identified by "junction tag" can be counted as "variant molecule," where various cutoff may apply. For example, in FIG. 41C, a variant is called when the same sequence difference (start) occurred in at least two different read families. In some cases, the number of "variant molecules" can be used to determine whether a variant should be called and can be used to calculated allele frequency.

To determine the improvements to variant detection using the methods described herein, the number of variants identified by calling a sequence difference detected in sequencing reads as the variant when the sequence difference occurs in a majority of the sequencing reads from a first sheared polynucleotide and a majority of sequencing reads from a second sheared polynucleotide was compared to variants identified by methods without such requirements. As shown in Table 12, the requirement of a sequence variant occurring in at least two different sheared polynucleotides reduced non-specific false positive variants by ~23.39% while none of the true positive calls were removed (0% of the specific true variants was removed), indicating a significant improvement of specificity without affecting sensitivity.

TABLE 11

List of caner hotspots in the mixed cell line DNA

| Gene | Variants |
|---|---|
| PIK3CA | H1047R |
| KRAS | G12D |
| EGFR | L747-E749delA750P |
| EGFR | T790M |
| EGFR | L858R |
| NRAS | Q61R |
| BRAF | V600E |
| EGFR | G719S |

TABLE 12

| | Variant detection using methods described herein | | | | | |
|---|---|---|---|---|---|---|
| | total variants before filtering | total variants after filtering | % non-specific variants removed | # spike-in cancer hotspots detected before filtering | # spike-in cancer hotspots detected after filtering | % specific variants removed |
| Replicate 1 | 1260 | 945 | 25.00% | 6 | 6 | 0.00% |
| Replicate 2 | 1194 | 934 | 21.78% | 7 | 7 | 0.00% |
| Average | 1227 | 939.5 | 23.39% | 6.5 | 6.5 | 0.00% |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of identifying a sequence variant in a nucleic acid sample comprising a plurality of polynucleotides, each polynucleotide of the plurality having a 5' end and a 3' end, the method comprising:

(a) in a reaction mixture, circularizing individual polynucleotides of said plurality to form a plurality of circular polynucleotides using a ligase, each of which having a junction between the 5' end and 3' end;

(b) adding a heat labile protease to said reaction mixture to degrade the ligase enzyme;

(c) amplifying the circular polynucleotides after step (b) without isolating the circular polynucleotides from said reaction mixture between steps (a) and (c) to produce amplified polynucleotides;

(d) sequencing the polynucleotides to produce a plurality of sequencing reads;

(e) identifying sequence differences between sequencing reads and a reference sequence; and (f) calling a sequence difference as the sequence variant when the sequence difference occurs in at least two different amplified polynucleotides, wherein the amplifying yields a higher level of recovery of the plurality of polynucleotides as compared to performing a rolling circle amplification comprising steps (a) and (c) alone, wherein the higher level of recovery is evidenced by an increased library complexity, and wherein the increased library complexity is represented by an increased number of unique sequences amplified from said plurality of polynucleotides.

2. The method of claim 1, wherein calling the sequence difference as the sequence variant occurs further when (i) the sequence difference occurs in at least two circular polynucleotides having different junctions; and/or (ii) the sequence difference is identified on both strands of a double-stranded input molecule; and/or (iii) the sequence difference occurs in a consensus sequence for a concatemer formed by amplification comprising rolling circle amplification.

3. The method of claim 1, wherein the plurality of polynucleotides are single-stranded.

4. The method of claim 1, wherein the sequence variant is a single nucleotide polymorphism.

5. The method of claim 1, wherein the reference sequence is a consensus sequence formed by aligning the sequencing reads with one another.

6. The method of claim 1, wherein the reference sequence is a sequencing read.

7. The method of claim 1, wherein circularizing comprises the step of joining an adapter polynucleotide to the 5' end, the 3' end, or both the 5' end and the 3' end of a polynucleotide in the plurality of polynucleotides.

8. The method of claim 1, wherein amplifying is effected by using a polymerase having strand-displacement activity.

9. The method of claim 1, wherein amplifying comprises subjecting the circular polynucleotides to an amplification reaction mixture comprising random primers.

10. The method of claim 1, wherein amplifying comprises subjecting the circular polynucleotides to an amplification reaction mixture comprising one or more primers, each of which specifically hybridizes to a different target sequence via sequence complementarity.

11. The method of claim 1, wherein the amplified polynucleotides are subjected to the sequencing step without enrichment.

12. The method of claim 1, further comprising enriching one or more target polynucleotides among the amplified polynucleotides by performing an enrichment step prior to sequencing.

13. The method of claim 1, wherein a microbial contaminant is identified based on the calling step.

14. The method of claim 1, wherein the nucleic acid sample is obtained from a sample from a subject.

15. The method of claim 14, wherein the sample is urine, stool, blood, saliva, tissue, or bodily fluid.

16. The method of claim 14, wherein the sample comprises tumor cells.

17. The method of claim 14, wherein the sample is a formalin-fixed paraffin embedded (FFPE) sample.

18. The method of claim 1, wherein the sequence variant is associated with a type or stage of cancer.

19. The method of claim 1, wherein the plurality of polynucleotides comprises cell-free polynucleotides.

20. The method of claim 19, wherein the cell-free polynucleotides comprise circulating tumor DNA.

21. The method of claim 1, wherein the method comprises following step (c) and prior to step (d) shearing the amplified polynucleotides to produce sheared polynucleotides, each sheared polynucleotide comprising one or more shear points at a 5' end and/or a 3' end.

22. A method of identifying a sequence variant in a nucleic acid sample comprising a plurality of polynucleotides, each polynucleotide of the plurality having a 5' end and a 3' end, the method comprising:
  (a) in a reaction mixture, circularizing individual polynucleotides of said plurality to form a plurality of circular polynucleotides using a ligase, each of which having a junction between the 5' end and 3' end;
  (b) adding a heat labile protease to said reaction mixture to degrade the ligase enzyme;
  (c) amplifying the circular polynucleotides after step (b) without isolating the circular polynucleotides from said reaction mixture between steps (a) and (c) to produce amplified polynucleotides;
  (d) shearing the amplified polynucleotides to produce sheared polynucleotides, each sheared polynucleotide comprising one or more shear points at a 5' end and/or a 3' end;
  (e) sequencing the sheared polynucleotides to produce a plurality of sequencing reads;
  (f) identifying sequence differences between sequencing reads and a reference sequence; and
  (g) calling a sequence difference as the sequence variant when the sequence difference occurs in at least two different sheared polynucleotides,
  wherein the amplifying yields a higher level of recovery of the plurality of polynucleotides as compared to performing a rolling circle amplification comprising steps (a) and (c) alone,
  wherein the higher level of recovery is evidenced by an increased library complexity, and
  wherein the increased library complexity is represented by an increased number of unique sequences amplified from said plurality of polynucleotides.

23. The method of claim 22, wherein calling the sequence difference as the sequence variant occurs further when (i) the sequence difference occurs in at least two circular polynucleotides having different junctions; and/or (ii) the sequence difference is identified on both strands of a double-stranded input molecule; and/or (iii) the sequence difference occurs in a consensus sequence for a concatemer formed by amplification comprising rolling circle amplification.

* * * * *

SEQUENCE LISTING

<160> NUMBER OF SEQ ID NOS: 172

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
caagcagaag acggcatacg a                                                   21

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acactctttc cctacacgac gctcttccga tct                                      33

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gctttgagct gttctttgtc att                                                 23

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tttaattgtg tggaagatcc aatc                                          24

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ctttctcacc ttctgggatc c                                             21

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccatcacgta ggcttcctg                                                19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gacatagtcc aggaggcagc                                               20

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aagcgacggt cctccaag                                                 18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
agtacgttcc tggctgcc                                                 18

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atccacttga taggcacsctt g                                          21

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tctcgctggc agggattc                                               18

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aactttgggc gactatctgc                                             20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ttggagtctg taggacttgg c                                           21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctgctgtggg atgaggtact c                                           21

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
catggaatgc ttgtaccaca tc                                          22

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cagtttgaac agttgtctgg atc                                         23

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgtttctgct aacgatctct ttg                                    23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
caggaaatcc catagcaata atg                                    23

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gctttgaatc caaaaacctt aaaac                                  25

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tacagtacat tcatacctac ctctgc                                 26

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aaaggatatt gtgcaactgt gg                                     22

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccatagaaat ctagggcctc ttg                                    23

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccagatgatt ctttaacagg tagc                                          24

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gaacttgtct tcccgtcgtg                                               20

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tctggtcctg gtatgaagaa tg                                            22

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gctctatact gcaaatgcta tcg                                           23

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ttggagaaaa gtatcggttg g                                             21

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tggtgttaca gaagttgaac tgc                                           23

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aagagtgcct tgacgataca gc                                              22

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cctgactcag actgacattc tcc                                             23

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
atgttccgag agctgaatga g                                               21

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ttaaaggacc agaccagctt tc                                              22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cttgggacct cttatcaagt gg                                              22

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aagcaagcag gacaagaagc                                                 20

<210> SEQ ID NO 35

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gggacggaac agctttgag                                                    19

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
caactacatg tgtaacagtt cctgc                                             25

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gtggagtatt tggatgacag aaac                                              24

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tgctcagata gcgatggtga g                                                 21

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ctgtgcagct gtgggttga                                                    19

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
aagtctgtga cttgcacggt c                                                 21

<210> SEQ ID NO 41
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
cctgtcatct tctgtccctt c                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aagacccagg tccagatgaa g                                              21

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ctgctcttgt ctttcagact tcc                                            23

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ctctgagtca ggaaacattt tcag                                           24

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
aaagcaattt ctacacgaga tcc                                            23

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
attaaacagc atgcattgaa ctg                                            23

<210> SEQ ID NO 47
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 47
aaattcccgt cgctatcaag                                              20

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
atggccagcg tggacaac                                                18

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tgtccgggaa cacaaagac                                               19

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tggcagccag gaacgtac                                                18

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
aacaccgcag catgtcaag                                               19

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
aagtggatgg cattggaatc                                              20

<210> SEQ ID NO 53
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 53
cctggagaaa ggagaacgc                                                    19

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
agttccgtga gttgatcatc g                                                 21

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
acttctaccg tgccctgatg                                                   20

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cacagcaggg cttcttcag                                                    19

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
catgggcaac ttctctgttt c                                                 21

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
aaactgatgg gacccactcc                                                   20

<210> SEQ ID NO 59
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 59
aggagatatc aagaggatgg attc                                             24

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tcctgcagaa agacttgaag g                                                21

<210> SEQ ID NO 61
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ggattcaaag cataaaaacc attac                                            25

<210> SEQ ID NO 62
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tatgttgtat aacttaaacc cgatagac                                         28

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ttgaagacca taacccacca c                                                21

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
aagtaaggac cagagacaaa aagg                                             24

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 65
ggattataga ccagtggcac tg                                           22

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
catgtacttt gagttccctc agc                                          23

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
caggaccaga ggaaacctca g                                            21

<210> SEQ ID NO 68
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
cgtgcagata atgacaagga atatc                                        25

<210> SEQ ID NO 69
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ggtcagttaa attaaacatt ttgtgg                                       26

<210> SEQ ID NO 70
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gatgttagtg acaatgaacc tgatc                                        25

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
tcttgcctac gccaccag                                                 18

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
caggcccttc tgtcttgaac                                               20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gaacatctcg aagcgctcac                                               20

<210> SEQ ID NO 74
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ttatggtata agttggtgtt ctgaag                                        26

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
agaggtccca agacttagta cctg                                          24

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gcttgcttac ctcgcttagt g                                             21

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 77
ttccgtccca gtagattacc ac                                              22

<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
catgtagttg tagtggatgg tgg                                             23

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
atactccaca cgcaaatttc c                                               21

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ctatctgagc agcgctcatg                                                 20

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gcaggtcttg gccagttg                                                   18

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tgtcccagaa tgcaagaagc                                                 20

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
```
gatgacaggg gccaggag                                                     18

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tgggtcttca gtgaaccatt g                                                 21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gagcagaaag tcagtcccat g                                                 21

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gctcgacgct aggatctgac                                                   20

<210> SEQ ID NO 87
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gttcagagtt ctacagtccg acgatcgctt tgagctgttc tttgtcatt                   49

<210> SEQ ID NO 88
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gttcagagtt ctacagtccg acgatcttta attgtgtgga agatccaatc                  50

<210> SEQ ID NO 89
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89

```
gttcagagtt ctacagtccg acgatccttt ctcaccttct gggatcc                47
```

<210> SEQ ID NO 90
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90

```
gttcagagtt ctacagtccg acgatcccat cacgtaggct tcctg                  45
```

<210> SEQ ID NO 91
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91

```
gttcagagtt ctacagtccg acgatcgaca tagtccagga ggcagc                 46
```

<210> SEQ ID NO 92
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92

```
gttcagagtt ctacagtccg acgatcaagc gacggtcctc caag                   44
```

<210> SEQ ID NO 93
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93

```
gttcagagtt ctacagtccg acgatcagta cgttcctggc tgcc                   44
```

<210> SEQ ID NO 94
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94

```
gttcagagtt ctacagtccg acgatcatcc acttgatagg caccttg                47
```

<210> SEQ ID NO 95
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95

```
gttcagagtt ctacagtccg acgatctctc gctggcaggg attc                   44
```

<210> SEQ ID NO 96
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
gttcagagtt ctacagtccg acgatcaact ttgggcgact atctgc                    46

<210> SEQ ID NO 97
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
gttcagagtt ctacagtccg acgatcttgg agtctgtagg acttggc                   47

<210> SEQ ID NO 98
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
gttcagagtt ctacagtccg acgatcctgc tgtgggatga ggtactc                   47

<210> SEQ ID NO 99
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
gttcagagtt ctacagtccg acgatccatg gaatgcttgt accacatc                  48

<210> SEQ ID NO 100
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
gttcagagtt ctacagtccg acgatccagt ttgaacagtt gtctggatc                 49

<210> SEQ ID NO 101
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
gttcagagtt ctacagtccg acgatctgtt tctgctaacg atctctttg                 49

<210> SEQ ID NO 102
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 102
gttcagagtt ctacagtccg acgatccagg aaatcccata gcaataatg                49

<210> SEQ ID NO 103
<211> LENGTH: 51
<212> TYPE: DNA
<213> ORGANISM: Artificial Sequence
<220> FEATURE:
<223> OTHER INFORMATION: Description of Artificial Sequence: Synthetic primer

<400> SEQUENCE: 103
gttcagagtt ctacagtccg acgatcgctt tgaatccaaa aaccttaaaa c              51

<210> SEQ ID NO 104
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 104
gttcagagtt ctacagtccg acgatctaca gtacattcat acctacctct gc             52

<210> SEQ ID NO 105
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 105
gttcagagtt ctacagtccg acgatcaaag gatattgtgc aactgtgg                  48

<210> SEQ ID NO 106
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 106
gttcagagtt ctacagtccg acgatcccat agaaatctag ggcctcttg                 49

<210> SEQ ID NO 107
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 107
gttcagagtt ctacagtccg acgatcccag atgattcttt aacaggtagc                50

```
<210> SEQ ID NO 108
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
gttcagagtt ctacagtccg acgatcgaac ttgtcttccc gtcgtg                    46

<210> SEQ ID NO 109
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gttcagagtt ctacagtccg acgatctctg gtcctggtat gaagaatg                  48

<210> SEQ ID NO 110
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
gttcagagtt ctacagtccg acgatcgctc tatactgcaa atgctatcg                 49

<210> SEQ ID NO 111
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gttcagagtt ctacagtccg acgatcttgg agaaaagtat cggttgg                   47

<210> SEQ ID NO 112
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
gttcagagtt ctacagtccg acgatctggt gttacagaag ttgaactgc                 49

<210> SEQ ID NO 113
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
gttcagagtt ctacagtccg acgatcaaga gtgccttgac gatacagc                  48

<210> SEQ ID NO 114
```

```
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gttcagagtt ctacagtccg acgatccctg actcagactg acattctcc            49

<210> SEQ ID NO 115
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
gttcagagtt ctacagtccg acgatcatgt tccgagagct gaatgag              47

<210> SEQ ID NO 116
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
gttcagagtt ctacagtccg acgatcttaa aggaccagac cagctttc             48

<210> SEQ ID NO 117
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
gttcagagtt ctacagtccg acgatccttg ggacctctta tcaagtgg             48

<210> SEQ ID NO 118
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gttcagagtt ctacagtccg acgatcaagc aagcaggaca agaagc               46

<210> SEQ ID NO 119
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
gttcagagtt ctacagtccg acgatcggga cggaacagct ttgag                45

<210> SEQ ID NO 120
<211> LENGTH: 51
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
gttcagagtt ctacagtccg acgatccaac tacatgtgta acagttcctg c        51

<210> SEQ ID NO 121
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
gttcagagtt ctacagtccg acgatcgtgg agtatttgga tgacagaaac           50

<210> SEQ ID NO 122
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
gttcagagtt ctacagtccg acgatctgct cagatagcga tggtgag              47

<210> SEQ ID NO 123
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
gttcagagtt ctacagtccg acgatcctgt gcagctgtgg gttga                45

<210> SEQ ID NO 124
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
gttcagagtt ctacagtccg acgatcaagt ctgtgacttg cacggtc              47

<210> SEQ ID NO 125
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gttcagagtt ctacagtccg acgatccctg tcatcttctg tcccttc              47

<210> SEQ ID NO 126
<211> LENGTH: 47
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 126
gttcagagtt ctacagtccg acgatcaaga cccaggtcca gatgaag                    47

<210> SEQ ID NO 127
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gttcagagtt ctacagtccg acgatcctgc tcttgtcttt cagacttcc                  49

<210> SEQ ID NO 128
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
gttcagagtt ctacagtccg acgatcctct gagtcaggaa acattttcag                 50

<210> SEQ ID NO 129
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
ccttggcacc cgagaattcc aaaagcaatt tctacacgag atcc                       44

<210> SEQ ID NO 130
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
ccttggcacc cgagaattcc aattaaacag catgcattga actg                       44

<210> SEQ ID NO 131
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
ccttggcacc cgagaattcc aaaattcccg tcgctatcaa g                          41

<210> SEQ ID NO 132
<211> LENGTH: 39
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 132
ccttggcacc cgagaattcc aatggccagc gtggacaac                          39

<210> SEQ ID NO 133
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
ccttggcacc cgagaattcc atgtccggga acacaaagac                         40

<210> SEQ ID NO 134
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
ccttggcacc cgagaattcc atggcagcca ggaacgtac                          39

<210> SEQ ID NO 135
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
ccttggcacc cgagaattcc aaacaccgca gcatgtcaag                         40

<210> SEQ ID NO 136
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
ccttggcacc cgagaattcc aaagtggatg gcattggaat c                       41

<210> SEQ ID NO 137
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
ccttggcacc cgagaattcc acctggagaa aggagaacgc                         40

<210> SEQ ID NO 138
<211> LENGTH: 42
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 138
ccttggcacc cgagaattcc aagttccgtg agttgatcat cg                          42

<210> SEQ ID NO 139
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
ccttggcacc cgagaattcc aacttctacc gtgccctgat g                           41

<210> SEQ ID NO 140
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
ccttggcacc cgagaattcc acacagcagg gcttcttcag                             40

<210> SEQ ID NO 141
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
ccttggcacc cgagaattcc acatgggcaa cttctctgtt tc                          42

<210> SEQ ID NO 142
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
ccttggcacc cgagaattcc aaaactgatg ggacccactc c                           41

<210> SEQ ID NO 143
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
ccttggcacc cgagaattcc aaggagatat caagaggatg gattc                       45

<210> SEQ ID NO 144
<211> LENGTH: 42
<212> TYPE: DNA
<213> ORGANISM: Artificial Sequence
<220> FEATURE:
<223> OTHER INFORMATION: Description of Artificial Sequence: Synthetic
```

```
                                  primer

<400> SEQUENCE: 144
ccttggcacc cgagaattcc atcctgcaga aagacttgaa gg                    42

<210> SEQ ID NO 145
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
ccttggcacc cgagaattcc aggattcaaa gcataaaaac cattac               46

<210> SEQ ID NO 146
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
ccttggcacc cgagaattcc atatgttgta taacttaaac ccgatagac            49

<210> SEQ ID NO 147
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
ccttggcacc cgagaattcc attgaagacc ataacccacc ac                   42

<210> SEQ ID NO 148
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
ccttggcacc cgagaattcc aaagtaagga ccagagacaa aaagg                45

<210> SEQ ID NO 149
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
ccttggcacc cgagaattcc aggattatag accagtggca ctg                  43

<210> SEQ ID NO 150
<211> LENGTH: 44
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 150
ccttggcacc cgagaattcc acatgtactt tgagttccct cagc        44

<210> SEQ ID NO 151
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
ccttggcacc cgagaattcc acaggaccag aggaaacctc ag          42

<210> SEQ ID NO 152
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
ccttggcacc cgagaattcc acgtgcagat aatgacaagg aatatc      46

<210> SEQ ID NO 153
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
ccttggcacc cgagaattcc aggtcagtta aattaaacat tttgtgg     47

<210> SEQ ID NO 154
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
ccttggcacc cgagaattcc agatgttagt gacaatgaac ctgatc      46

<210> SEQ ID NO 155
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
ccttggcacc cgagaattcc atcttgccta cgccaccag             39

<210> SEQ ID NO 156
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 156
ccttggcacc cgagaattcc acaggcccctt ctgtcttgaa c                    41

<210> SEQ ID NO 157
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
ccttggcacc cgagaattcc agaacatctc gaagcgctca c                     41

<210> SEQ ID NO 158
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
ccttggcacc cgagaattcc attatggtat aagttggtgt tctgaag               47

<210> SEQ ID NO 159
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
ccttggcacc cgagaattcc aagaggtccc aagacttagt acctg                 45

<210> SEQ ID NO 160
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
ccttggcacc cgagaattcc agcttgctta cctcgcttag tg                    42

<210> SEQ ID NO 161
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
ccttggcacc cgagaattcc attccgtccc agtagattac cac                   43

<210> SEQ ID NO 162
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
```
ccttggcacc cgagaattcc acatgtagtt gtagtggatg gtgg                44

<210> SEQ ID NO 163
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
ccttggcacc cgagaattcc aatactccac acgcaaattt cc                  42

<210> SEQ ID NO 164
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
ccttggcacc cgagaattcc actatctgag cagcgctcat g                   41

<210> SEQ ID NO 165
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
ccttggcacc cgagaattcc agcaggtctt ggccagttg                      39

<210> SEQ ID NO 166
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
ccttggcacc cgagaattcc atgtcccaga atgcaagaag c                   41

<210> SEQ ID NO 167
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
ccttggcacc cgagaattcc agatgacagg ggccaggag                      39

<210> SEQ ID NO 168
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168

```
ccttggcacc cgagaattcc atgggtcttc agtgaaccat tg                           42

<210> SEQ ID NO 169
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
ccttggcacc cgagaattcc agagcagaaa gtcagtccca tg                           42

<210> SEQ ID NO 170
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
ccttggcacc cgagaattcc agctcgacgc taggatctga c                            41

<210> SEQ ID NO 171
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
ccatttcatt acctctttct ccgcacccga catagatt                                38

<210> SEQ ID NO 172
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
atctatgtcg ggtgcggaga aagaggtaat gaaatggt                                38
```